US009345719B2

(12) United States Patent
Cha et al.

(10) Patent No.: US 9,345,719 B2
(45) Date of Patent: May 24, 2016

(54) FUSED PYRIMIDINE DERIVATIVES FOR INHIBITION OF TYROSINE KINASE ACTIVITY

(71) Applicant: HANMI SCIENCE CO., LTD, Hwaseong-si (KR)

(72) Inventors: Mi Young Cha, Seongnam-si (KR); Seok Jong Kang, Okcheon-gun (KR); Mi Ra Kim, Seoul (KR); Ju Yeon Lee, Gwangju (KR); Ji Young Jeon, Gunpo-si (KR); Myoung Gi Jo, Anyang-si (KR); Eun Joo Kwak, Seogwipo-si (KR); Kwang Ok Lee, Yongin-si (KR); Tae Hee Ha, Hwaseong-si (KR); Kwee Hyun Suh, Suwon-si (KR); Maeng Sup Kim, Seoul (KR)

(73) Assignee: Hanmi Science Co., Ltd., Hwaseong-Si (KR)

( * ) Notice: Subject to any disclaimer, the term of this patent is extended or adjusted under 35 U.S.C. 154(b) by 0 days.

(21) Appl. No.: 14/521,766

(22) Filed: Oct. 23, 2014

(65) Prior Publication Data

US 2015/0045324 A1 Feb. 12, 2015

Related U.S. Application Data

(62) Division of application No. 13/805,183, filed as application No. PCT/KR2011/004482 on Jun. 20, 2011, now Pat. No. 8,957,065.

(30) Foreign Application Priority Data

Jun. 23, 2010 (KR) .................. 10-2010-0059686

(51) Int. Cl.

| | |
|---|---|
| *C07D 491/04* | (2006.01) |
| *A61K 31/519* | (2006.01) |
| *A61K 31/675* | (2006.01) |
| *A61K 31/5377* | (2006.01) |
| *A61K 31/541* | (2006.01) |
| *A61K 31/55* | (2006.01) |
| *A61K 31/553* | (2006.01) |
| *C07D 495/04* | (2006.01) |
| *C07D 491/048* | (2006.01) |
| *C07F 9/6561* | (2006.01) |
| *A61K 31/538* | (2006.01) |
| *A61K 45/06* | (2006.01) |
| *C07D 493/04* | (2006.01) |
| *C07D 519/00* | (2006.01) |
| *C07F 9/38* | (2006.01) |
| *A61P 25/28* | (2006.01) |
| *A61P 25/16* | (2006.01) |
| *A61P 19/02* | (2006.01) |
| *A61P 11/06* | (2006.01) |
| *A61P 35/04* | (2006.01) |
| *A61K 35/02* | (2015.01) |
| *A61P 37/06* | (2006.01) |

(52) U.S. Cl.
CPC ............. *A61K 31/675* (2013.01); *A61K 31/519* (2013.01); *A61K 31/538* (2013.01); *A61K 31/5377* (2013.01); *A61K 31/541* (2013.01); *A61K 31/55* (2013.01); *A61K 31/553* (2013.01); *A61K 45/06* (2013.01); *C07D 491/048* (2013.01); *C07D 493/04* (2013.01); *C07D 495/04* (2013.01); *C07D 519/00* (2013.01); *C07F 9/3834* (2013.01); *C07F 9/6561* (2013.01)

(58) Field of Classification Search
CPC ........................... C07D 491/04; A61K 31/519
See application file for complete search history.

(56) References Cited

FOREIGN PATENT DOCUMENTS

| | | |
|---|---|---|
| JP | 2008-13527 A | 1/2008 |
| WO | 98/02438 A1 | 1/1998 |
| WO | 2009/062258 A1 | 5/2009 |
| WO | 2009/126515 A1 | 10/2009 |
| WO | 2009/158571 A1 | 12/2009 |
| WO | 2010/054285 A2 | 5/2010 |
| WO | 2010/129053 A2 | 11/2010 |
| WO | 2011/079231 A1 | 6/2011 |

OTHER PUBLICATIONS

European Search Report dated Dec. 4, 2013, issued in European Patent Application No. 11798350.2.
H.D. Hollis Showalter, "Tyrosine Kinase Inhibitors. 16. 6,5,6-Tricyclic Benzothieno [3,2-d] pyrimidines and Pyrimido [5,4-b]- and -[4,5-b] indoles as Potent Inhibitors of the Epidermal Growth Factor Receptor Tyrosine Kinase", J. Med. Chem. 1999, pp. 5464-5474, vol. 42, No. 11.
Susanne Trumpp-Kallmeyer, et al., Development of a Binding Model to Protein Tyrosine Kinases for Substituted Pyrido [2,3-d] pyrimidine Inhibitors, J. Med. Chem. 1998, pp. 1752-1763, vol. 41, No. 11.
Peter Traxler, et al., "Use of a Pharmacophore Model for the Design of EGF-R Tyrosine Kinase Inhibitors: 4-(Phenylamino) Pyrazolo [3,4-d] pyrimidines", J. Med. Chem., 1997, pp. 3601-3616, vol. 40, No. 22.
International Searching Authority, International Search Report, PCT/KR2011/004482, Feb. 29, 2012.
Japanese Patent Office, Communication dated Mar. 3, 2015, issued in corresponding Japanese application No. 2013-516501.
European Patent Office, Applicant Reply to Communication, dated Jun. 26, 2014, filed in counterpart European Patent Application No. 11798350.2.
European Patent Office, Communication Pursuant to Article 94(3) EPC, dated Apr. 13, 2015, issued in counterpart European Patent Application No. 11798350.2.
European Patent Office, Applicant Reply to Communication, dated Oct. 21, 2015, filed in counterpart European Patent Application No. 11798350.2.
United States Patent Office, Examiner Search Strategy and Results, from parent U.S. Appl. No. 13/805,183, dated Oct. 15, 2014.
Zhou, W. et al., Discovery of selective irreversible inhibitors for EGFR-T790M., 2011, Bioorganic & Medicinal Chemistry Letters 21(2011) 638-643.

*Primary Examiner* — Susanna Moore
(74) *Attorney, Agent, or Firm* — Dan L. Wood

(57) ABSTRACT

The present invention relates to a novel fused pyrimidine derivative having an inhibitory activity for tyrosine kinases, and a pharmaceutical composition for preventing or treating cancers, tumors, inflammatory diseases, autoimmune diseases, or immunologically mediated diseases comprising same as an active ingredient.

31 Claims, 3 Drawing Sheets

FUSED PYRIMIDINE DERIVATIVES FOR INHIBITION OF TYROSINE KINASE ACTIVITY

The present application is a divisional of U.S. application Ser. No. 13/805,183 filed Dec. 18, 2012, which is a National Stage of International Application No. PCT/KR2011/004482, filed on Jun. 20, 2011, which claims the benefit of priority from Korean Patent Application No. KR 10-2010-0059686, filed on Jun. 23, 2010, the contents of which are herein incorporated by reference in their entirety.

FIELD OF THE INVENTION

The present invention relates to a novel fused pyrimidine derivative having an inhibitory activity for tyrosine kinases, and a pharmaceutical composition comprising same as an active ingredient.

BACKGROUND OF THE INVENTION

There are many signal transduction systems in cells which are functionally linked to each other to control the proliferation, growth, metastasis and apoptosis of cells (William G. Kaelin Jr., *Nature Reviews Cancer* 5, 689, 2005). The breakdown of the intracellular controlling system by genetic and environmental factors causes abnormal amplification or destruction of the signal transduction system leading to tumor cell generation (Douglas Hanahan and Robert A. Weinberg, *Cell* 100, 57, 2000).

Protein tyrosine kinases play important roles in such cellular regulation (Irena Melnikova and James Golden, *Nature Reviews Drug Discovery* 3, 993, 2004), and their abnormal expression or mutation has been observed in cancer cells or autoimmune diseases. The protein tyrosine kinase is an enzyme which catalyzes the transportation of phosphate groups from ATP to tyrosines located on protein substrates. Many growth factor receptor proteins function as tyrosine kinases to transport cellular signals. The interaction between growth factors and their receptors normally controls the cellular growth, but abnormal signal transduction caused by the mutation or overexpression of any of the receptors often induces various cancers or autoimmune diseases such as rheumatoid arthritis.

With regard to the roles of these tyrosine kinases, a variety growth factors and receptors thereof have been investigated, and among them, epidermal growth factors (EGF) and EGF receptor (EGFR) tyrosine kinases have been intensely studied (Nancy E. Hynes and Heidi A. Lane, *Nature Reviews Cancer* 5, 341, 2005). An EGFR tyrosine kinase is composed of a receptor and tyrosine kinase, and delivers extracellular signals to cell nucleus through the cellular membrane. Various EGFR tyrosine kinases are classified based on their structural differences into four subtypes, i.e., EGFR (Erb-B1), Erb-B2, Erb-B3 and Erb-B4, and it is known that EGFR activating mutations, such as L858R point mutation in exon 21 and in-frame deletions in exon 19 of the EGFR tyrosine kinase domain, are the important cause of non-small cell lung cancer.

Gefitinib (AstraZeneca) was initially developed as a small molecule for the inhibition of EGFR tyrosine kinases, which selectively and reversibly inhibits EGFR (Erb-B1). Erlotinib (Roche) has also similar characteristics. These EGFR-targeted drugs are efficacious for non-small cell lung cancer (NSCLC) and provide therapeutic convenience for patients with EGFR activating mutations.

However, it has been reported that the development of resistance lowers the activity of a particular drug used in EGFR-targeted therapies. It has been already reported that about half of the patients administered with Gefitinib or Erlotinib exhibited the resistance to the drugs due to the induction of the secondary EGFR T790M mutation (William Pao et al., *Public Library of Science Medicine*, 2(3), 225, 2005, *Cancer Res*, 67(24), 11924, 2007). Further, it has been recently found that irreversible inhibitors to target for EGFR are more beneficial in securing excellent efficacy and overcoming the resistance development, as compared to the conventional reversible inhibitors such as Gefitinib and Erlotinib (Danan Li et al., *Cancer Cell* 12, 81, 2007; and Anja Michalczyk et al., *Bioorganic & Medicinal Chemistry* 16, 3482, 2008). Hence, irreversible inhibitors such as BIBW-2992 (Afatinib, Boeringer Ingelheim) (C H Mom et al., *British Journal of Cancer* 98, 80, 2007), PF00299804 (Dacomitinib, Pfizer) (Engelman J A, et al., *Cancer Res*. 67, 11924, 2007), and AV-412 (AVEO Pharmaceuticals) (Tsuyoshi Suzuki et al., *Cancer Sci*. 98(12), 1977, 2007) have been developed and are currently in the clinical stage. The compounds have been known to form a covalent bond with Cystein773 (Cys773) positioned at an ATP domain of EGFR, thereby irreversibly blocking the autophosphorylation of EGFR and thus efficiently inhibiting the signal transduction of cancer cells (David W. Fry et al., *Proc. Natl. Acad. Sci. U.S.A*. 95, 12022, 1998), and exhibit higher inhibitory activities compared to the reversible inhibitors commercially available as dual inhibitors of EGFR/HER-2, or pan-HER inhibitors in in vitro activities and in various in vivo models of carcinomas (Jeff B. Smaill et al., *J. Med. Chem*. 42, 1803, 1999). However, the compounds may cause serious side effects such as skin rashes, diarrhea and weight loss due to high activities to EGFR WT (wild type) present in normal cells, when they are administered in a dose sufficient to overcome the resistance induced by EGFR T790M mutations, and this has been limited their clinical application, (Martin L. Sos, et al., *Cancer Res*. 70, 868, 2010).

As evidenced by clinical tests of the irreversible inhibitors in non-small cell lung cancer, the compounds have exhibited improved activities but still weak therapeutic effects in the resistance development of cancer patients, compared to the conventional reversible inhibitors. Accordingly, there has been a continued need to develop a novel drug that is effective in drug-resistant cancers and has no adverse side effects.

Meanwhile, there are various evidences that B-cells (B-lymphocytes) and T-cells (T-lymphocytes) play a key role in the pathogenesis of inflammatory diseases, autoimmune diseases and/or immunity mediated diseases.

For instance, aberrant signaling can induce deregulated B-cell proliferation and differentiation to cause all sorts of lymphoma including various acute or chronic lymphoid leukemia and can cause formation of autoantibodies that lead to multiple inflammatory diseases, autoimmune diseases and/or immunity mediated diseases.

Bruton's tyrosine kinase (BTK) is a member of the TEC family of tyrosine kinases, and plays an important role in B-cell activation and signal transduction. BTK plays an essential role in B-cell signaling pathway which links the B-cell receptor (BCR) stimuli on the surface of B-cells to the response in downstream cells. Further, BTK has been known to be a critical regulator of B-cell development and mature B-cell activation and survival (Khan et al., *Immunity* 3, 283, 1995; Ellmeier et al., *J. Exp. Med*. 192, 1611, 2000; Kurosaki, *Current Opinion in Immunology* 12, 276, 2000; Schaeffer and Schwartzberg, *Current Opinion in Immunology* 12, 282, 2000). Thus, inhibition of BTK could be a therapeutic approach to block B-cell mediated disease processes.

For example, it has been known that BTK-deficient mice are resistant to collagen-induced arthritis and BTK inhibitors have been demonstrated dose-dependent efficacies in a mouse model of arthritis (Jansson and Holmdahl, Clin. Exp. Immunol. 94, 459, 1993; Pan et al., Chem. Med. Chem. 2, 58, 2007). Thus, effective BTK inhibitors may be useful in the treatment of rheumatoid arthritis.

In addition, BTK is also expressed by cells other than B-cells that may be involved in disease processes, i.e., bone marrow-derived mast cells. It has been reported that the antigen-induced degranulation is suppressed in BTK-deficient bone marrow-derived mast cells (Iwaki et al., J. Biol. Chem. 280, 40261, 2005). This shows that BTK could be useful to treat pathological mast cell responses such as allergy and asthma.

Also, monocytes, in which BTK activity is absent, showed decreased TNF-α production following stimulation (Horwood et al. J Exp Med. 197, 1603, 2003). Therefore, TNF-α mediated inflammation could be modulated by BTK inhibitors.

Furthermore, BTK has been reported to play a role in apoptosis as some of regulators (Islam and Smith, Immunol. Rev. 178, 49, 2000). Thus, BTK inhibitors would be useful for the treatment of certain B-cell lymphomas and leukemias (Feldhahn et al., J. Exp. Med. 201, 1837, 2005).

Meanwhile, T-cells play a role in transmitting signals delivered through the T-cell receptor (TCR) on the cell surface from antigen presenting cells into downstream effectors by the activation of intercellular various kinases such as janus kinases. At this time, they secrete various interleukin (IL) or interferon-γ to activate various leukocytes as well as the B-cells. Protein kinases involved in signal transduction in T-cells are Janus kinases (JAK) such as JAK1, JAK2, JAK3 and TYK2, IL-2 inducible T-cell kinases (ITK), and TEC family of kinases such as resting lymphocyte kinases (RLK).

Janus kinases involving JAK3 have been widely investigated as a target for autoimmune and/or inflammatory diseases. Among them, unlike JAK2 involved in hematosis and erythrocyte homeostasis or JAK1 expressed in various tissues, JAK3 is expressed in lymphocytes and plays a very important role in signal transduction via various cytokines, i.e., IL-2, IL-4, IL-7, IL-9 and IL-15, which is more attractive (Flanagan et al, Journal of medicinal Chemistry, 53, 8468, 2010). According to animal studies, JAK3 plays a role in the maturation of B-cells and T-cells as well as in maintaining T-cell functions.

Therefore, JAK3 inhibitors may be useful in the treatment of rheumatoid arthritis, psoriasis, atopic dermatitis, lupus, multiple sclerosis, Type I diabetes and complications from diabetes, cancer, asthma, autoimmune thyroid disorders, ulcerative colitis, Crohn's disease, Alzheimer's disease, leukemia, and other indications where immunosuppression would be desirable, such as organ transplants or xeno transplantation (Pesu M, Laurence A, Kishore N, et al., Immunol Rev 223, 132, 2008.; Kawahara A, Minami Y, Miyazaki T, et al., Proc Natl Acad Sci USA 92, 8724, 1995; Nosaka T, van Deursen J M A, Tripp R A, et al., Science 270, 800, 1995; Papageorgiou Ac, Wikman L E K., et al., Trends Pharm Sci 25, 558, 2004).

Meanwhile, other TEC family of kinases also play an important role in T-cell activation (Pamela L. Schwartzberg, et al., Nature Reviews Immunology 5, 284, 2005). For example, deletion of ITK which is characteristically expressed in T-cells in mice led to decreased cell proliferation which is induced by stimulation via T-cell receptors and decreased secretion of various cytokines such as IL-2, IL-4, IL-5, IL-10 and IFN-γ (Schaeffer et al., Science 284, 638, 1999; Fowell et al., Immunity 11, 399, 1999; Schaffer et al., Nature Immunology 2, 1183, 2001).

In addition, in ITK-deficient mice, immune symptoms of allergic asthma were attenuated and lung inflammation, eosinophil infiltration, and mucous production in response to challenge with the allergen ovalbumin were drastically reduced (Muller et al., Journal of Immunology 170, 5056, 2003). This shows that ITK inhibitors would be useful in the treatment of asthma.

Further, ITK has also been implicated in atopic dermatitis. This gene has been reported to be more highly expressed in peripheral blood T-cells from patients with severe atopic dermatitis, compared with controls or patients with mild atopic dermatitis (Matsumoto et al., International archives of Allergy and Immunology 129, 327, 2002).

Meanwhile, RLK functions to activate the secretion of IL-2 which is produced by signal transduction of T-cell receptors of splenocytes. Thus, the inhibition of RLK may reduce various responses by T-cells (Schaeffer et al., Nature Immunology 2, 1183, 2001; Schaeffer et al., Science 284, 638, 1999).

In addition, bone marrow tyrosine kinase (BMX) has been known to be involved in epithelial and endothelial cell migration (Pan et al., Mol. Cell. Biol. 2002, 22, 7512). Therefore, BMK inhibitors may be developed as anticancer agents for inhibiting the metastasis of cancer cells and angiogenesis.

As above, since TEC family kinases such as BTK, ITK, RLK, BMX and others and Janus kinases such as JAK3 play a critical role in the activation of B-cells and/or T-cells which is implicated in the pathogenesis of inflammatory diseases, autoimmune diseases, and immunologically mediated diseases, a compound for effectively inhibiting the kinases may be useful as a therapeutic agent for various inflammatory diseases, autoimmune diseases, and immunity mediated diseases.

Furthermore, a compound for inhibiting BTK involved in B-cell activation inducing B-cell lymphoma, and BMX involved in metastasis of cancer cells may be useful as an anticancer or antitumor agent.

Therefore, the development of a compound, which can inhibit above kinases and selectively inhibit variant EGFRs such as secondary T790M mutations as well as L858R point mutation at exon 21 or in-frame deletion at exon 19, is one of very important challenges.

Even though it was suggested that EGFR irreversible inhibitors, which form a covalent bond with Cystein773 (Cys773) positioned at an ATP domain of EGFR, may show inhibitory effects on the activities of TEC family of kinases such as BTK, ITK, RLK and BMX in which cysteine is present in a same position of the amino acid sequence, as well as kinases such as JAK3 or BLK (Wooyoung Hur, et al., Bioorg. Med. Chem. Lett. 18, 5916, 2008), there has been no developed for a compound which can inhibit irreversibly, selectively and effectively variant EGFR, BTK, JAK3, ITK, RLK, BMX and/or BLK.

SUMMARY OF THE INVENTION

Therefore, it is an object of the present invention to provide a novel fused pyrimidine derivative which selectively and effectively inhibits cancers or tumors induced by an epidermal growth factor receptor (EGFR) tyrosine kinase or a mutant thereof with reduced adverse side effects.

It is another object of the present invention to provide a novel fused pyrimidine derivative which can treat cancers, tumors, inflammatory diseases, autoimmune diseases, or immunologically mediated diseases mediated by abnormally activated B-lymphocytes, T-lymphocytes or both, by repressing non-receptor tyrosine kinases such as TEC family kinases (e.g. BTK, ITK, BMX or RLK) and janus kinases (e.g. JAK3).

It is still another object of the present invention to provide a pharmaceutical composition for preventing or treating cancers, tumors, inflammatory diseases, autoimmune diseases, or immunologically mediated diseases which comprises said novel fused pyrimidine derivative.

In accordance with one aspect of the present invention, there is provided a compound of formula (I) or a pharmaceutically acceptable salt thereof:

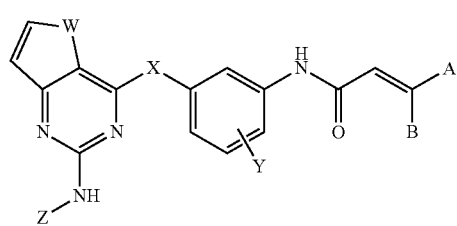

(I)

wherein,
W is O or S;
X is O, NH, S, SO or SO$_2$;
Y is hydrogen atom, halogen atom, C$_{1-6}$alkyl or C$_{1-6}$alkoxy;
A and B are each independently hydrogen atom, halogen atom, or di(C$_{1-6}$alkyl)aminomethyl;
Z is aryl or heteroaryl having one or more substituents selected from the group consisting of: hydrogen atom, halogen atom, hydroxy, nitro, cyano, C$_{1-6}$alkyl, C$_{1-6}$alkoxy, C$_{1-6}$alkylcarbonyl, C$_{1-6}$alkoxycarbonyl, di(C$_{1-6}$alkyl)aminoC$_{2-6}$alkoxycarbonyl, amino, C$_{1-6}$alkylamino, di(C$_{1-6}$alkyl)amino, carbamoyl, C$_{1-6}$alkylcarbamoyl, di(C$_{1-6}$alkyl)carbamoyl, di(C$_{1-6}$alkyl)aminoC$_{2-6}$alkylcarbamoyl, sulfamoyl, C$_{1-6}$alkylsulfamoyl, di(C$_{1-6}$alkyl)sulfamoyl, di(C$_{1-6}$alkyl)aminoC$_{2-6}$alkylsulfamoyl, C$_{1-6}$alkylsulfonyl, C$_{1-6}$alkylsulfinyl, di(C$_{1-6}$alkyl)phosphonyl, hydroxyC$_{1-6}$alkyl, hydroxycarbonylC$_{1-6}$alkyl, C$_{1-6}$alkoxyC$_{1-6}$alkyl, C$_{1-6}$alkylsulfonylC$_{1-6}$alkyl, C$_{1-6}$alkylsulfinylC$_{1-6}$alkyl, di(C$_{1-6}$alkyl)phosphonylC$_{1-6}$alkyl, hydroxyC$_{2-6}$alkoxy, C$_{1-6}$alkoxyC$_{2-6}$alkoxy, aminoC$_{1-6}$alkoxy, C$_{1-6}$alkylaminoC$_{1-6}$alkyl, di(C$_{1-6}$alkyl)aminoC$_{1-6}$alkyl, di(C$_{1-6}$alkyl)aminoacetyl, aminoC$_{2-6}$alkoxy, C$_{1-6}$alkylaminoC$_{2-6}$alkoxy, di(C$_{1-6}$alkyl)aminoC$_{2-6}$alkoxy, hydroxyC$_{2-6}$alkylamino, C$_{1-6}$alkoxyC$_{2-6}$alkylamino, aminoC$_{2-6}$alkylamino, C$_{1-6}$alkylaminoC$_{2-6}$alkylamino, di(C$_{1-6}$alkyl)aminoC$_{2-6}$alkylamino, heteroaryl, heterocycle, heterocyclic oxy, heterocyclic thio, heterocyclic sulfinyl, heterocyclic sulfonyl, heterocyclic sulfamoyl, heterocyclic C$_{1-6}$alkyl, heterocyclic C$_{1-6}$alkoxy, heterocyclic amino, heterocyclic C$_{1-6}$alkylamino, heterocyclic aminoC$_{1-6}$alkyl, heterocyclic carbonyl, heterocyclic C$_{1-6}$alkylcarbonyl, heterocyclic carbonylC$_{1-6}$alkyl, heterocyclic C$_{1-6}$alkylthio, heterocyclic C$_{1-6}$alkylsulfinyl, heterocyclic C$_{1-6}$alkylsulfonyl, heterocyclic aminocarbonyl, heterocyclic C$_{1-6}$alkylaminocarbonyl, heterocyclic aminocarbonylC$_{1-6}$alkyl, heterocyclic carboxamido, and heterocyclic C$_{1-6}$alkylcarboxamido;
the aryl refers to a C$_{6-12}$ cyclic or bicyclic aromatic ring;
the heteroaryls each independently refer to a 5- to 12-membered cyclic or bicyclic aromatic hetero ring having one or more N, O or S;
the heterocycles each independently refer to a saturated or partially unsaturated 3- to 12-membered cyclic or bicyclic hetero ring having one or more N, O, S, SO or SO$_2$, in which a carbon atom forming the heterocycle optionally has one or more substituents selected from the group consisting of C$_{1-6}$alkyl, hydroxy, hydroxyC$_{1-6}$alkyl, hydroxycarbonyl, C$_{1-6}$alkoxy, amino, C$_{1-6}$alkylamino, di(C$_{1-6}$alkyl)amino, di(C$_{1-6}$alkyl)aminoC$_{1-6}$alkyl, di(C$_{1-6}$alkyl)aminocarbonyl, heterocycle, heterocyclic C$_{1-6}$alkyl, and heteroaryl, and in which, provided that the heterocycle optionally comprises a nitrogen atom, the nitrogen atom optionally has a substituent selected from the group consisting of hydrogen atom, C$_{1-6}$alkyl, monohalogenoC$_{1-6}$alkyl, dihalogenoC$_{1-6}$alkyl, trihalogenoC$_{1-6}$alkyl, C$_{3-6}$cycloalkyl, hydroxyC$_{2-6}$alkyl, C$_{1-6}$alkoxyC$_{2-6}$alkyl, C$_{1-6}$alkylcarbonyl, hydroxyC$_{1-6}$alkylcarbonyl, C$_{1-6}$alkoxycarbonyl, carbamoyl, C$_{1-6}$alkylcarbamoyl, di(C$_{1-6}$alkyl)carbamoyl, sulfamoyl, C$_{1-6}$alkylsulfamoyl, di(C$_{1-6}$alkyl)sulfamoyl, C$_{1-6}$alkylsulfonyl, aminoC$_{2-6}$alkyl, C$_{1-6}$alkylaminoC$_{2-6}$alkyl, di(C$_{1-6}$alkyl)aminoC$_{2-6}$alkyl, di(C$_{1-6}$alkyl)aminoC$_{1-6}$alkylcarbonyl, heterocycle, heterocyclic oxy, heterocyclic thio, heterocyclic sulfinyl, heterocyclic sulfonyl, heterocyclic C$_{1-6}$alkyl, heterocyclic carbonyl, heterocyclic C$_{1-6}$alkylcarbonyl, heterocyclic C$_{1-6}$alkylsulfinyl, and heterocyclic C$_{1-6}$alkylsulfonyl (wherein, when the nitrogen atom forms tertiary amine, it is optionally of an N-oxide form); and optionally, the C$_{1-6}$alkyl is partially unsaturated or has a C$_{3-6}$cycloalkyl moiety, and a carbon atom in the heterocycle exists in a carbonyl form.

In accordance with another aspect of the present invention, there is provided a pharmaceutical composition for preventing or treating cancers, tumors, inflammatory diseases, autoimmune diseases, or immunologically mediated diseases which comprises the compound of formula (I) or a pharmaceutically acceptable salt thereof.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
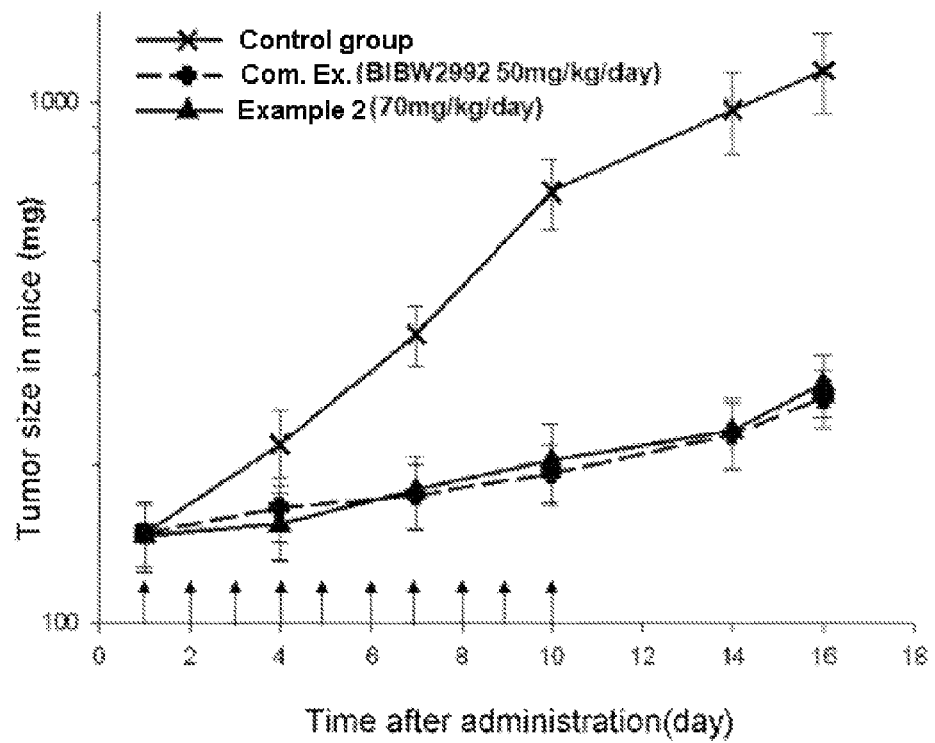
FIG. 1: size change of tumors by oral administration of the compound obtained in Example 2 in nude mice xenografted with NCI-H1975 cancer cells.

In the compound of formula (I), preferred examples of Z include substituents selected from the group consisting of formulae Z1 to Z203, but are not limited thereto:

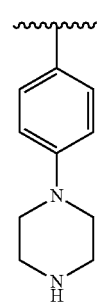

Z1

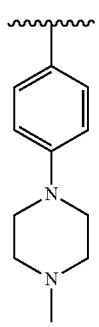
Z2
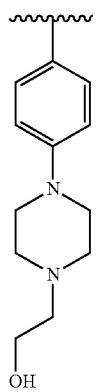
Z6
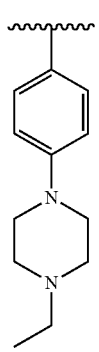
Z3
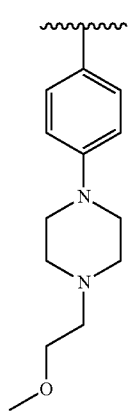
Z7
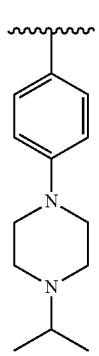
Z4
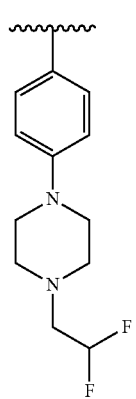
Z8
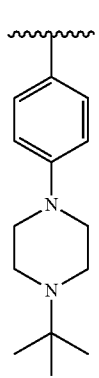
Z5
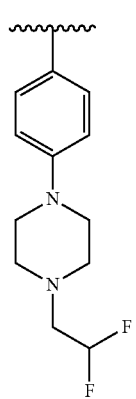
Z9

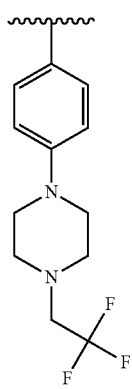 Z10
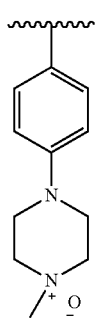 Z11
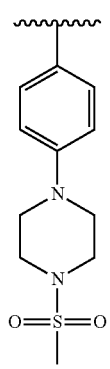 Z12
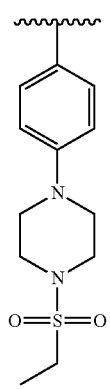 Z13
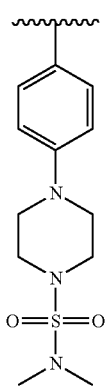 Z14
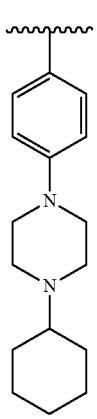 Z15
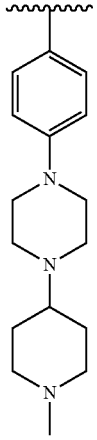 Z16
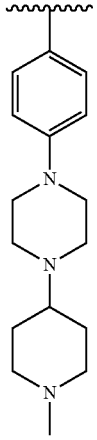 Z17

-continued
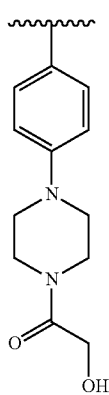
Z18
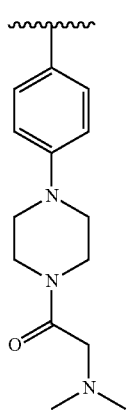
Z19
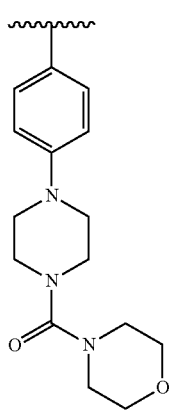
Z20
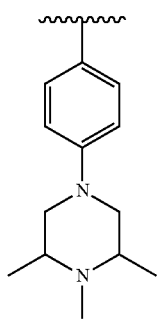
Z21
-continued
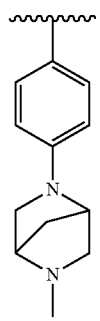
Z22
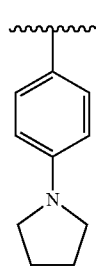
Z23
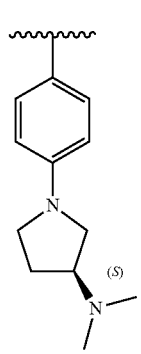
Z24
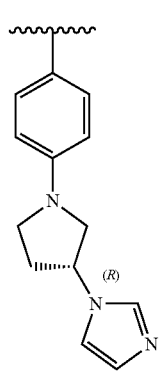
Z25
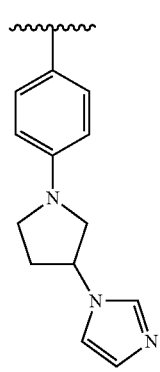
Z26

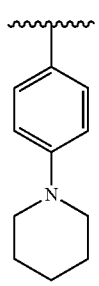 Z27
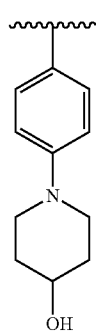 Z32
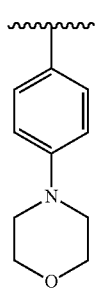 Z28
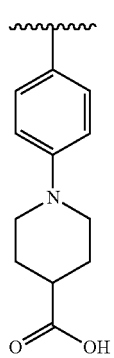 Z33
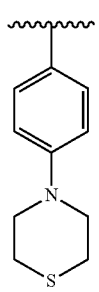 Z29
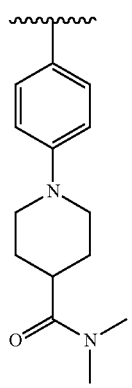 Z34
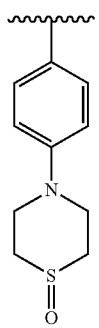 Z30
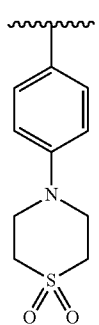 Z31
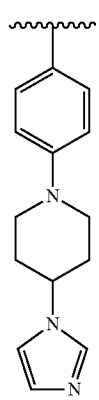 Z35

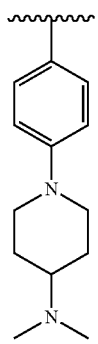 Z36
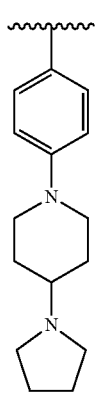 Z37
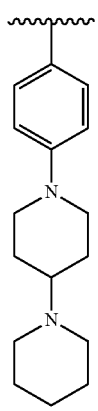 Z38
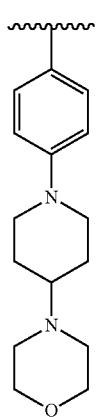 Z39
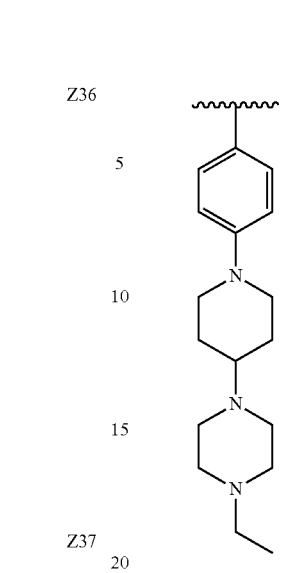 Z40
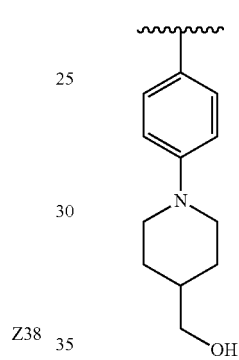 Z41
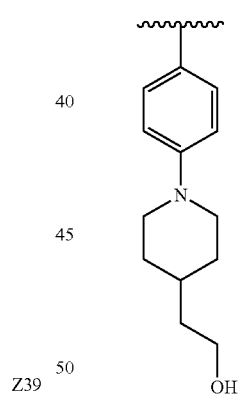 Z42
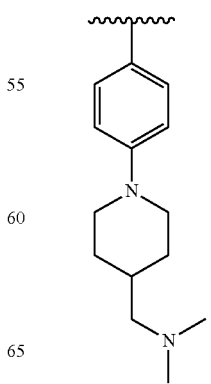 Z43

-continued
Z44 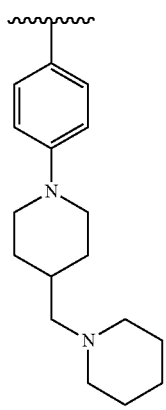
Z45 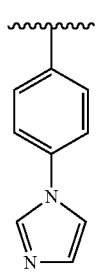
Z46 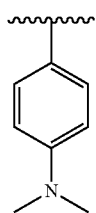
Z47 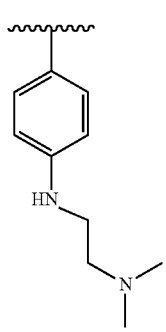
Z48 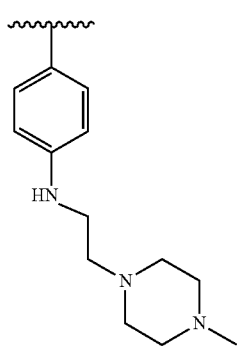
-continued
Z49 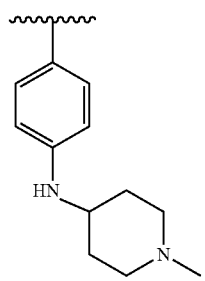
Z50 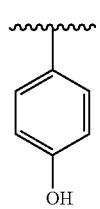
Z51 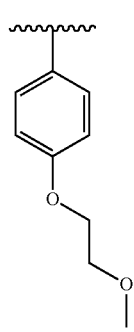
Z52 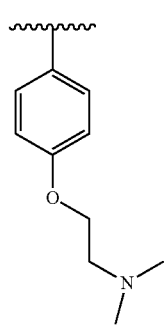
Z53 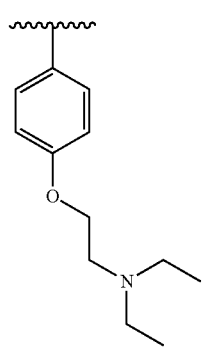

| | |
|---|---|
| 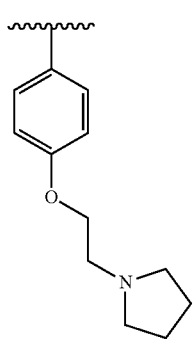 Z54 | 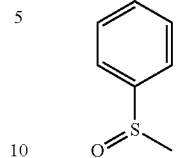 Z59 |
| 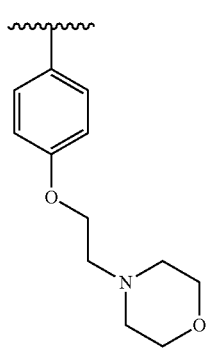 Z55 | 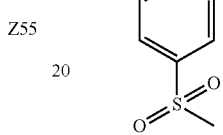 Z60 |
| 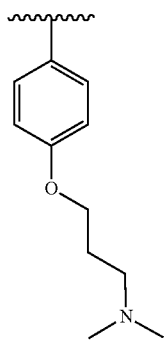 Z56 | 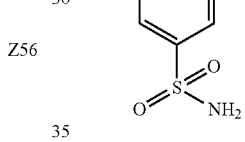 Z61 |
| 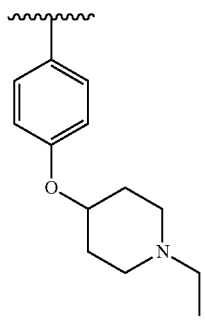 Z57 | 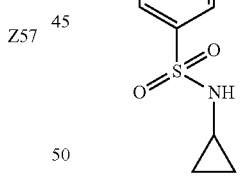 Z62 |
| 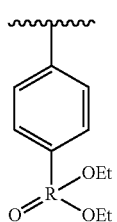 Z58 | 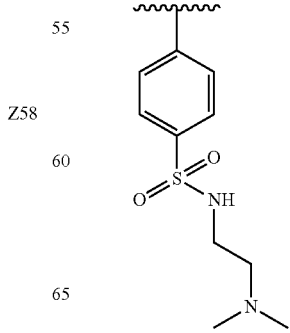 Z63 |

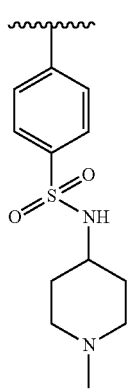 Z64
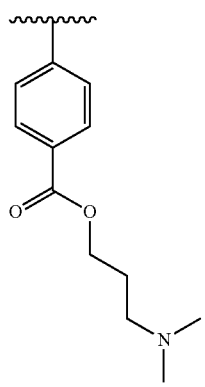 Z68
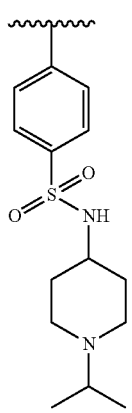 Z65
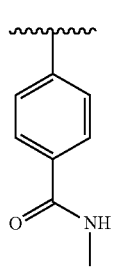 Z69
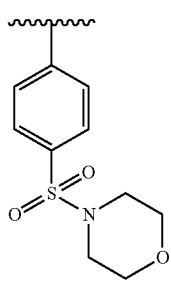 Z66
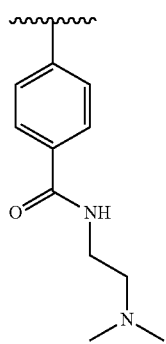 Z70
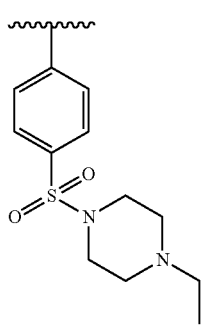 Z67
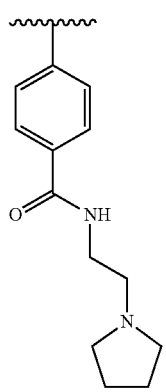 Z71

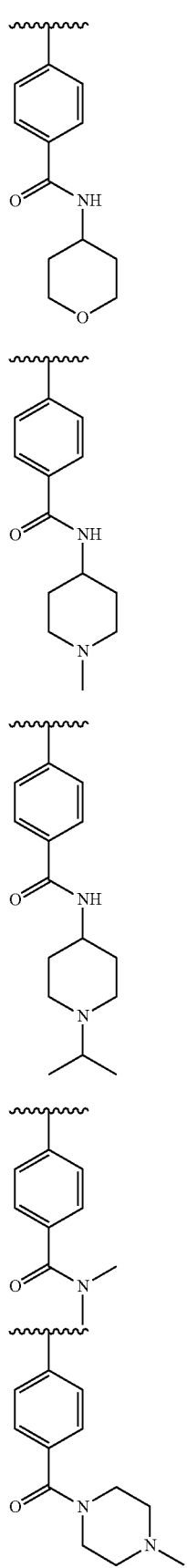
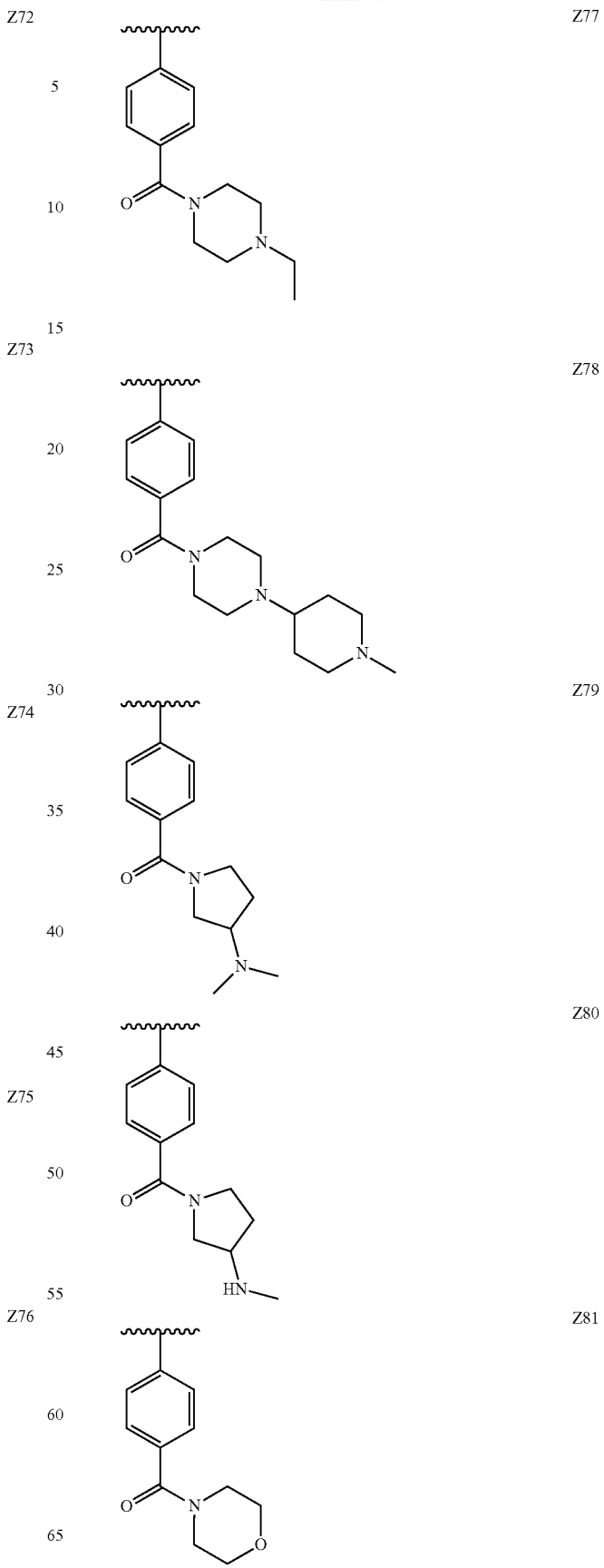

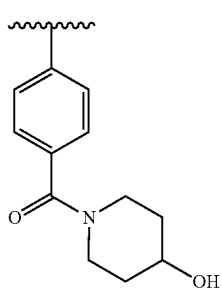 Z82
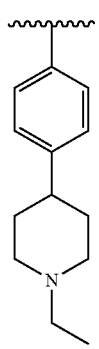 Z87
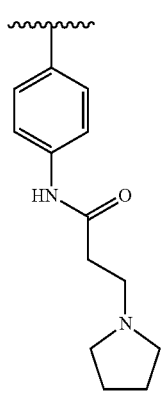 Z83
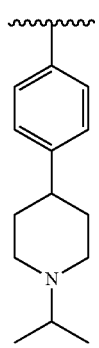 Z88
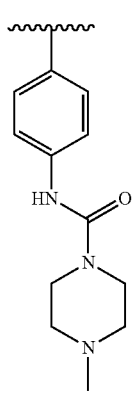 Z84
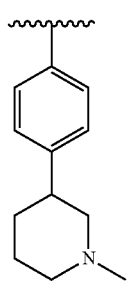 Z89
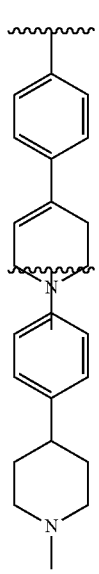 Z85
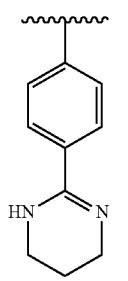 Z90
Z86
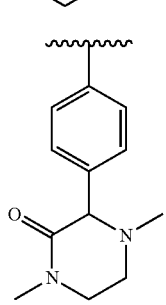 Z91

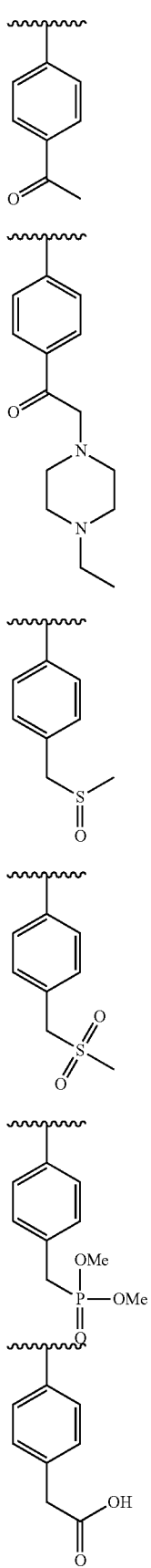
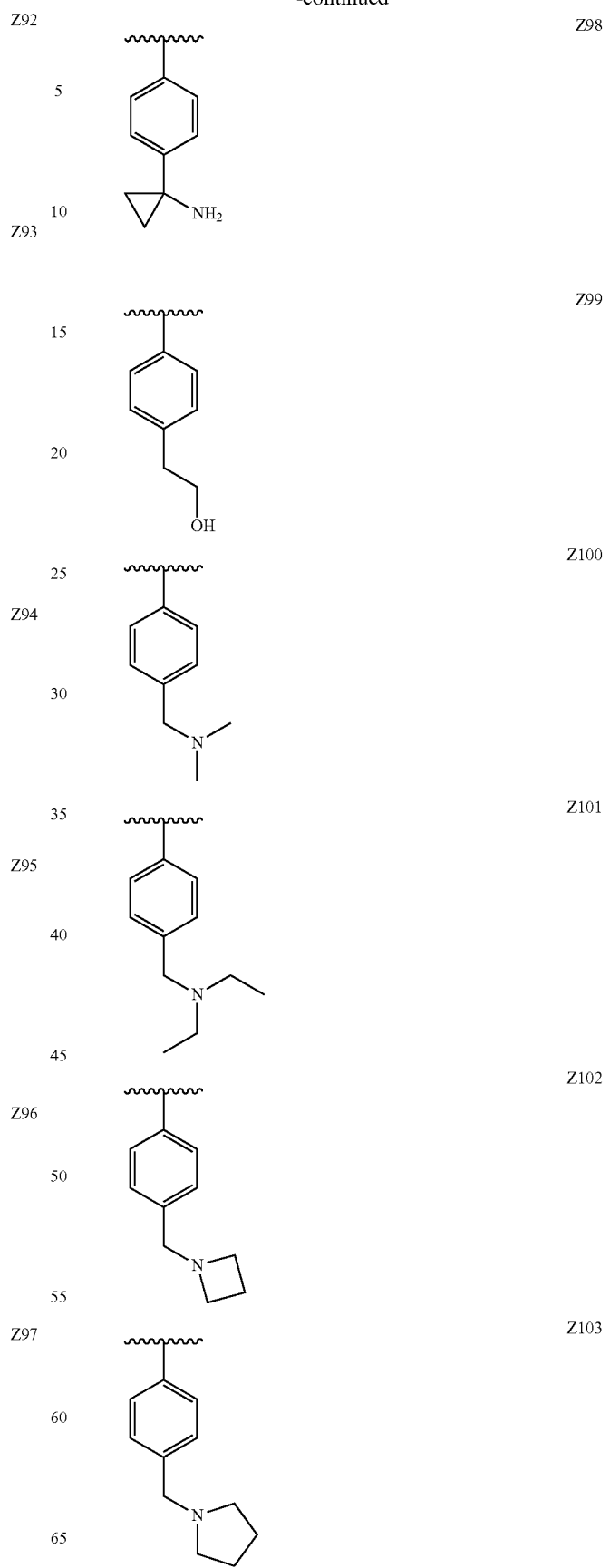

Z104 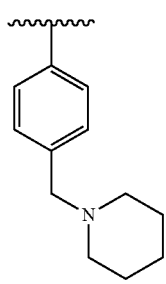
Z105 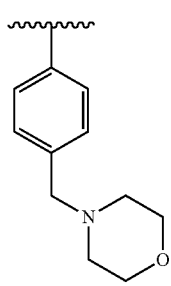
Z106 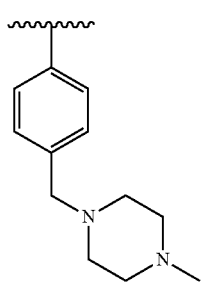
Z107 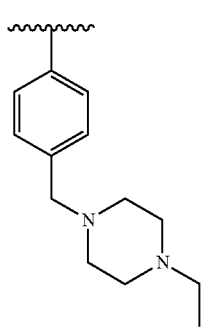
Z108 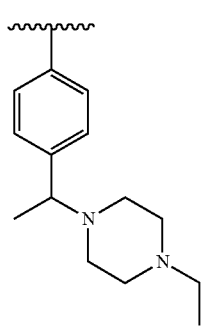
Z109 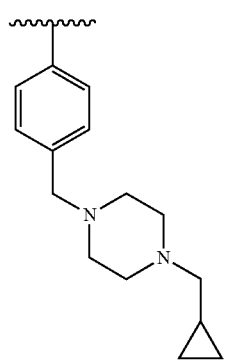
Z110 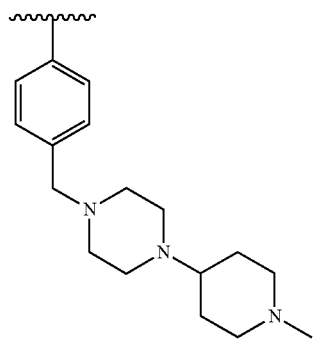
Z111 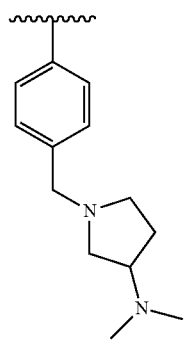
Z112 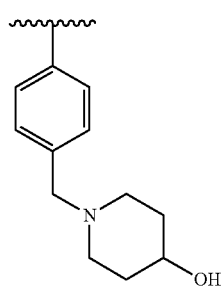
Z113 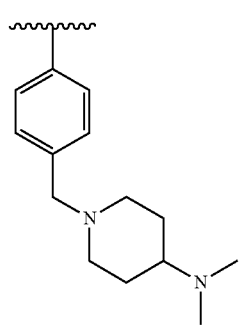

Z114 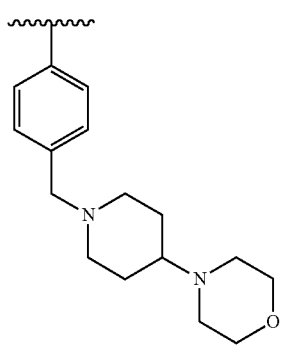
Z115 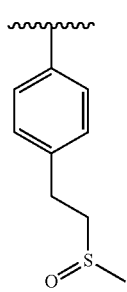
Z116 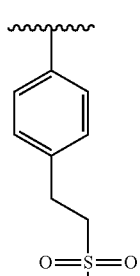
Z117 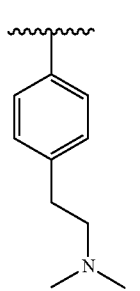
Z118 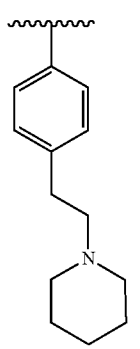
Z119 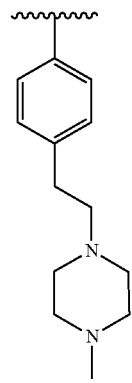
Z120 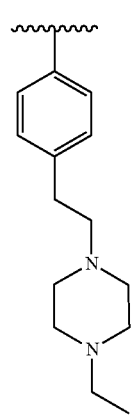
Z121 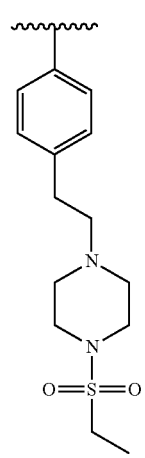
Z122 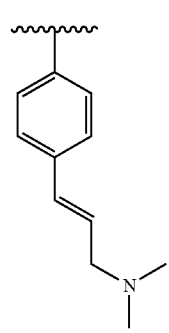

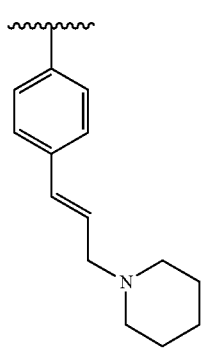 Z123
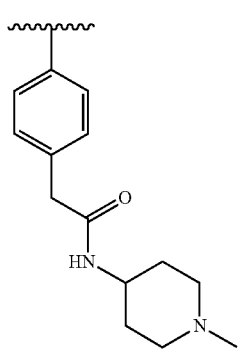 Z124
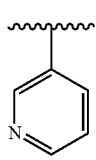 Z125
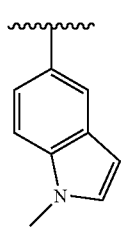 Z126
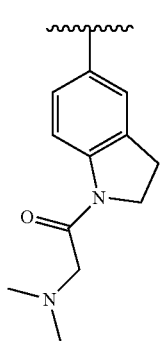 Z127
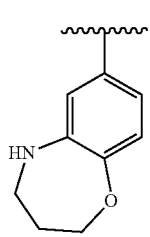 Z128
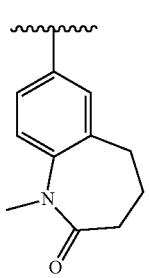 Z129
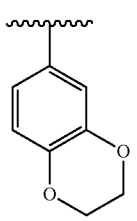 Z130
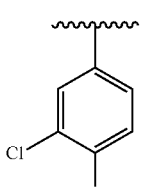 Z131
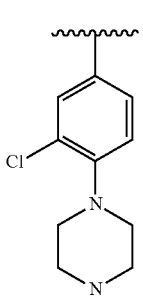 Z132
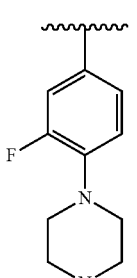 Z133
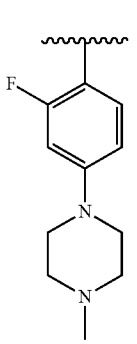 Z134

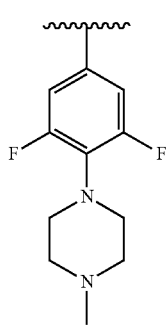 Z135
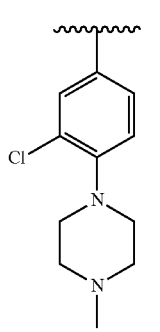 Z136
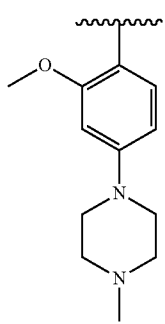 Z137
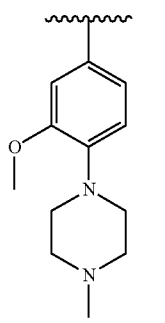 Z138
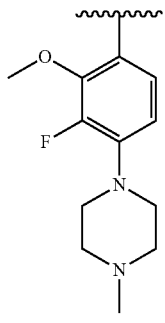 Z139
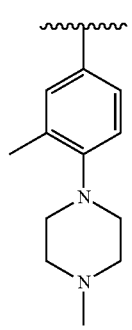 Z140
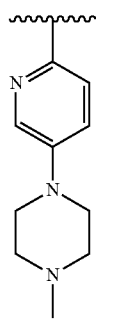 Z141
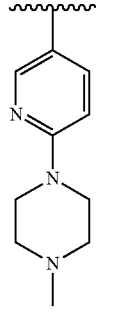 Z142
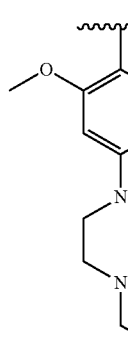 Z143
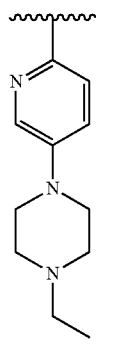 Z144

Z145 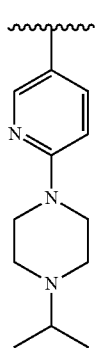
Z146 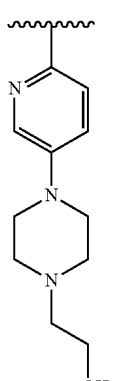
Z147 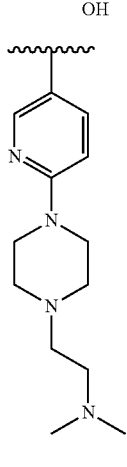
Z148 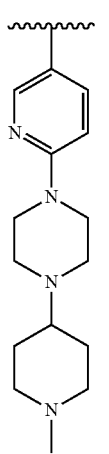
Z149 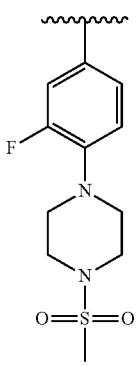
Z150 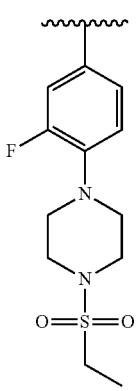
Z151 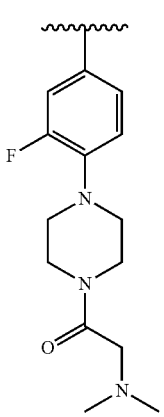
Z152 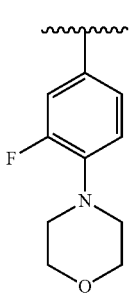

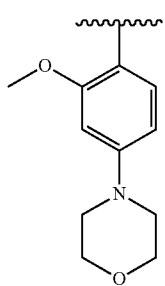 Z153
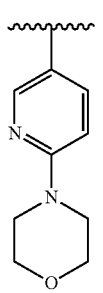 Z154
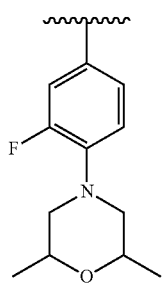 Z155
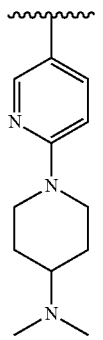 Z156
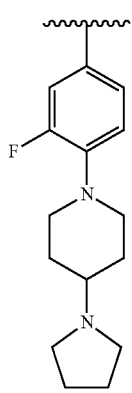 Z157
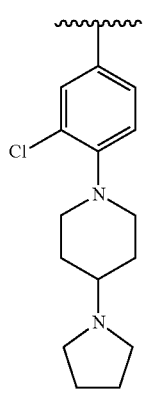 Z158
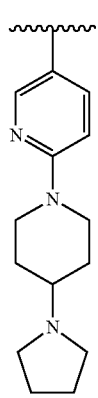 Z159
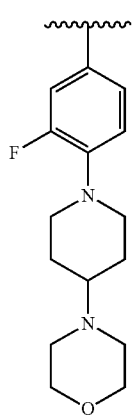 Z160
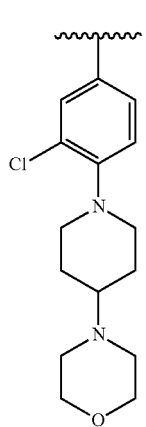 Z161

Z162
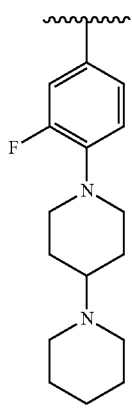
Z163
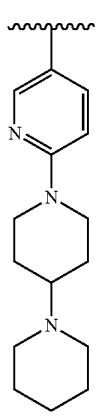
Z164
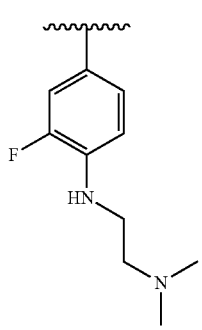
Z165
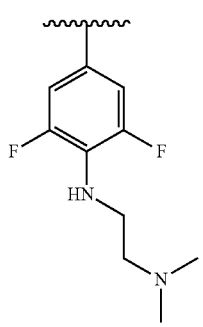
Z166
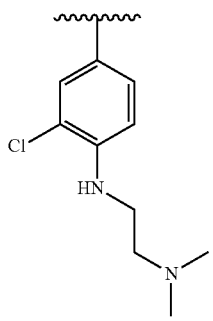
Z167
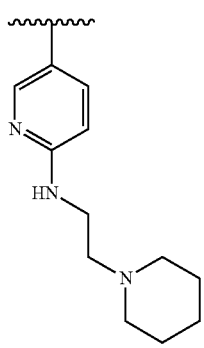
Z168
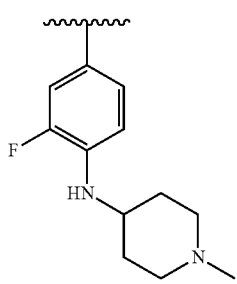
Z169
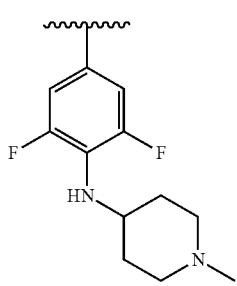
Z170

43
-continued
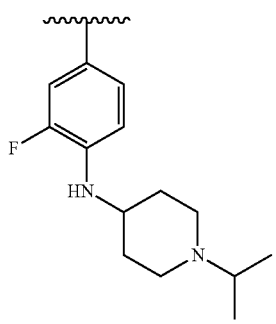
Z171
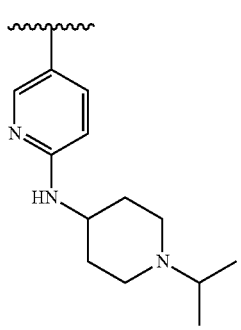
Z172
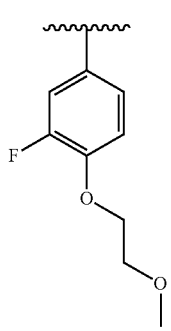
Z173
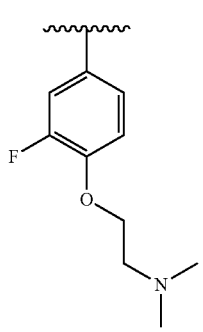
Z174
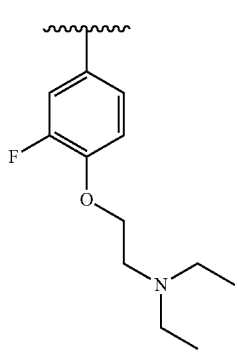
Z175
44
-continued
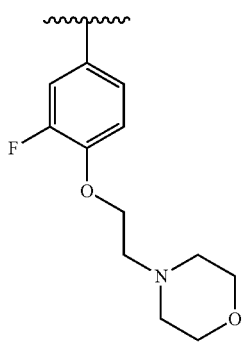
Z176
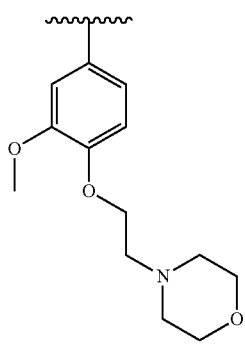
Z177
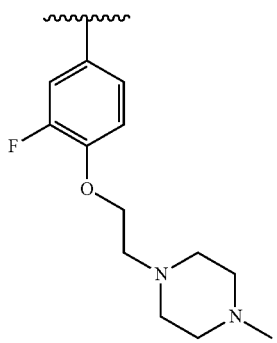
Z178
Z179
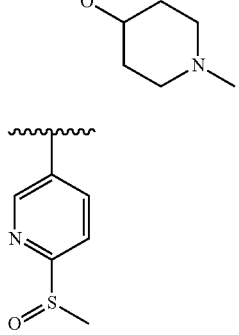
Z180

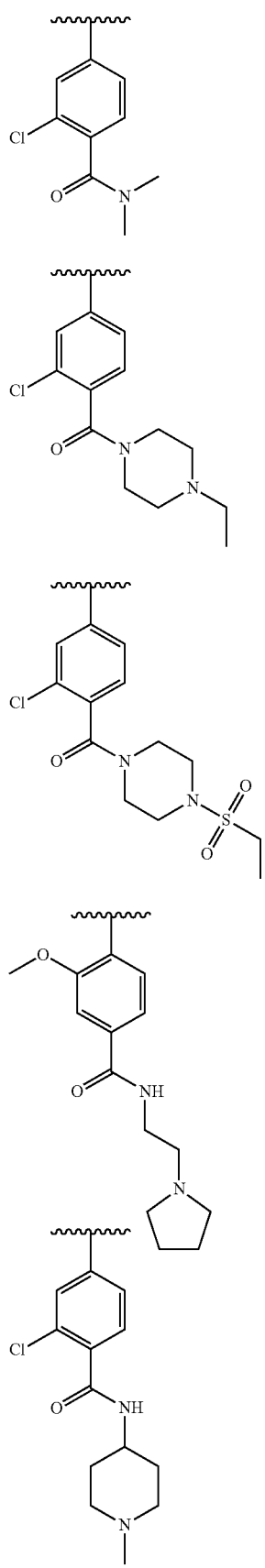
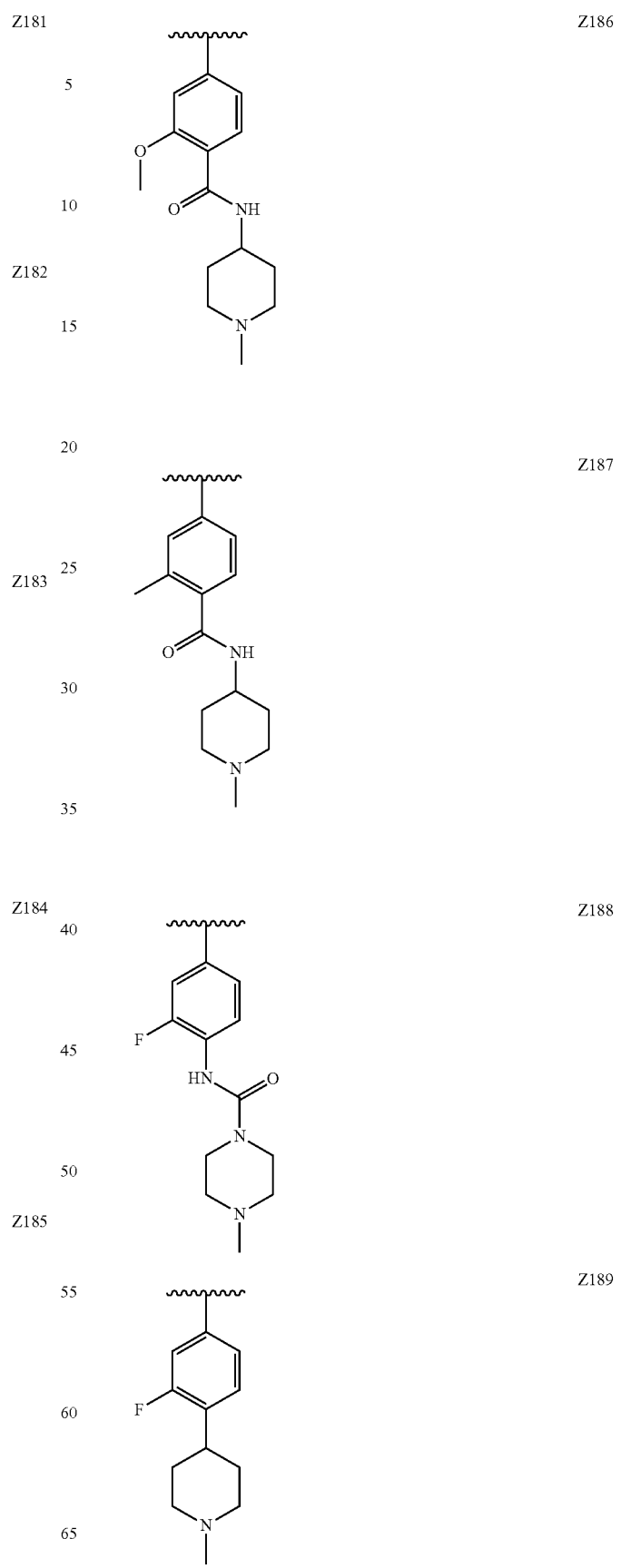

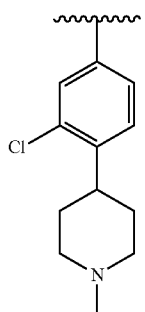
Z190
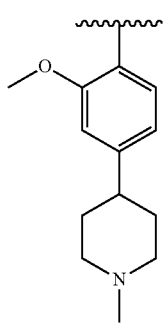
Z191
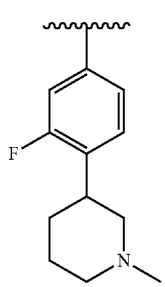
Z192
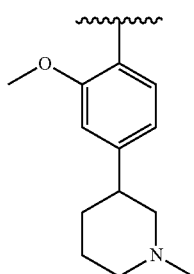
Z193
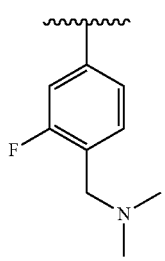
Z194
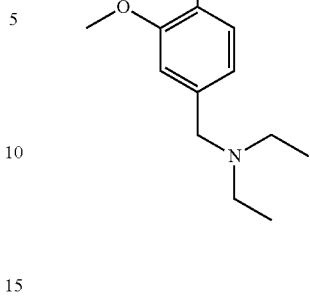
Z195
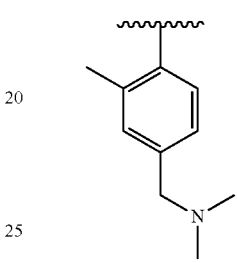
Z196
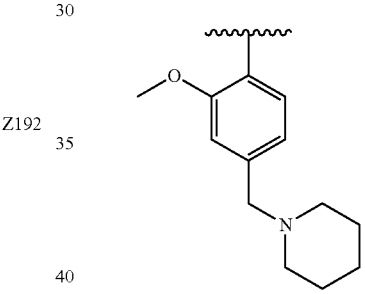
Z197
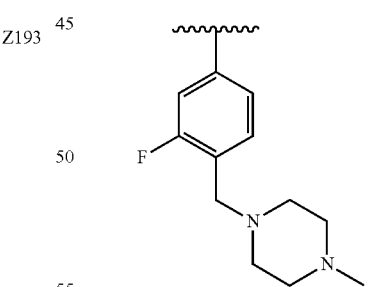
Z198
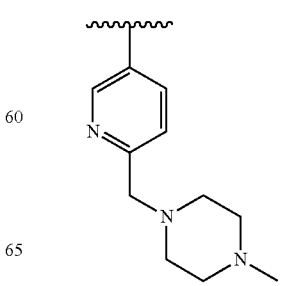
Z199

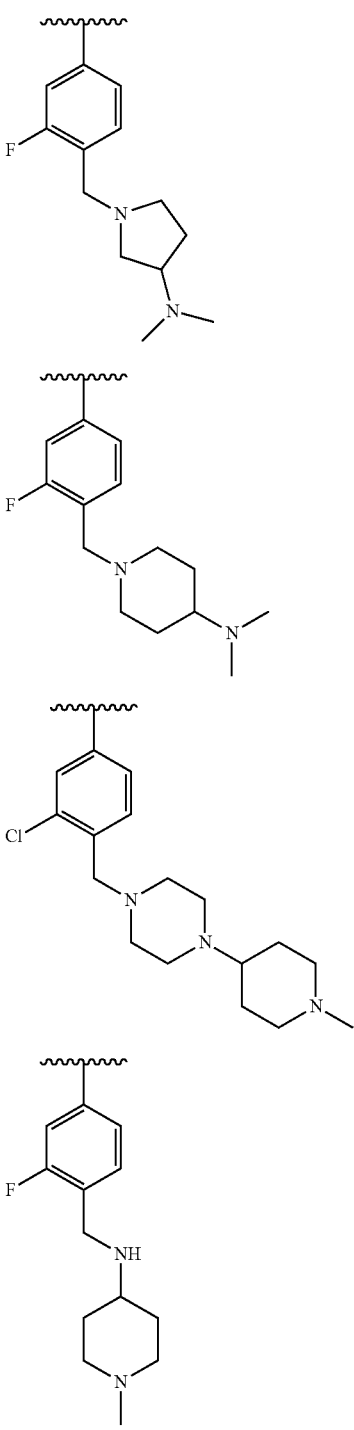

More preferred examples of the compound of formula (I) according to the present invention are as follows:

N-(3-(2-(2-methoxy-4-(4-methylpiperazin-1-yl)phenylamino)thieno[3,2-d]pyrimidin-4-yloxy)phenyl)acrylamide;

N-(3-(2-(4-(4-methylpiperazin-1-yl)phenylamino)thieno[3,2-d]pyrimidin-4-yloxy)phenyl)acrylamide;

N-(3-(2-(4-(4-tert-butyl-piperazin-1-yl)-phenylamino)-thieno[3,2-d]pyrimidin-4-yloxy)-phenyl)-acrylamide;

N-(3-(2-(4-(4-(2-fluoro-ethyl)-piperazin-1-yl)-phenylamino)-thieno[3,2-d]pyrimidin-4-yloxy)-phenyl)-acrylamide;

N-(3-(2-(4-(4-(2,2,2-trifluoro-ethyl)-piperazin-1-yl)-phenylamino)-thieno[3,2-d]pyrimidin-4-yloxy)-phenyl)-acrylamide;

N-(3-(2-(4-(4-(2-methoxy-ethyl)-piperazin-1-yl)-phenylamino)-thieno[3,2-d]pyrimidin-4-yloxy)-phenyl)-acrylamide;

N-(3-(2-(4-(4-(2-hydroxy-ethyl)-piperazin-1-yl)-phenylamino)-thieno[3,2-d]pyrimidin-4-yloxy)-phenyl)-acrylamide;

N-(3-(2-(4-(4-hydroxy-4-methyl-piperazin-1-yl)-phenylamino)-thieno[3,2-d]pyrimidin-4-yloxy)-phenyl)-acrylamide;

N-(3-(2-(4-(3,4,5-trimethyl-piperazin-1-yl)-phenylamino)-thieno[3,2-d]pyrimidin-4-yloxy)-phenyl)-acrylamide;

N-(3-(2-(4-(5-methyl-2,5-diaza-bicyclo[2.2.1]hept-2-yl)-phenylamino)-thieno[3,2-d]pyrimidin-4-yloxy)-phenyl)-acrylamide;

N-(3-(2-(1-methyl-2-oxo-2,3,4,5-tetrahydro-1H-benzo[b]azepin-7-ylamino)-thieno[3,2-d]pyrimidin-4-yloxy)-phenyl)-acrylamide;

N-(3-(2-(2-methoxy-4-(1-methyl-piperidin-4-yl)-phenylamino)-thieno[3,2-d]pyrimidin-4-yloxy)-phenyl)-acrylamide;

N-(3-(2-(2-methoxy-4-(1-methyl-piperidin-3-yl)-phenylamino)-thieno[3,2-d]pyrimidin-4-yloxy)-phenyl)-acrylamide;

N-(3-(2-(3-fluoro-4-(4-methylpiperazin-1-yl)phenylamino)thieno[3,2-d]pyrimidin-4-yloxy)phenyl)acrylamide;

Diethyl(4-((4-(3-acrylamidophenoxy)thieno[3,2-d]pyrimidin-2-yl)amino)phenyephosphonate;

N-(3-(2-(4-[1,4]bipiperidinyl-1'-yl-3-fluoro-phenylamino)-thieno[3,2-d]pyrimidin-4-yloxy)-phenyl)-acrylamide;

N-(3-((2-((3-chloro-4-(4-methylpiperazin-1-yl)phenyl)amino)thieno[3,2-d]pyrimidin-4-yl)oxy)phenyl)acrylamide;

N-(3-(2-(4-(1-methylpiperidin-4-ylamino)-3-chlorophenylamino)thieno[3,2-d]pyrimidin-4-yloxy)phenyl)acrylamide;

N-(3-(2-(2-fluoro-4-(4-methylpiperazin-1-yl)phenylamino)thieno[3,2-d]pyrimidin-4-yloxy)phenyl)acrylamide;

N-(3-(2-(3-methyl-4-(4-methylpiperazin-1-yl)phenylamino)thieno[3,2-d]pyrimidin-4-yloxy)phenyl)acrylamide;

4-((4-(3-acrylamidophenoxy)thieno[3,2-d]pyrimidin-2-yl)amino)-2-methyl-N-(1-methylpiperidin-4-yl)benzamide;

N-(4-methyl-3-(2-(4-(4-methylpiperazin-1-yl)phenylamino)thieno[3,2-d]pyrimidin-4-yloxy)phenyl)acrylamide;

N-(4-fluoro-3-(2-(4-(4-methyl-piperazin-1-yl)-phenylamino)-thieno[3,2-d]pyrimidin-4-yloxy)-phenyl)-acrylamide;

N-(4-methoxy-3-(2-(4-(4-methylpiperazin-1-yl)-phenylamino)thieno[3,2-d]pyrimidin-4-yloxy)phenyl)acrylamide;

N-(3-(2-(5-(4-methylpiperazin-1-yl)pyridin-2-ylamino)thieno[3,2-d]pyrimidin-4-yloxy)phenyl)acrylamide;

4-methyl-piperazin-1-carboxylic acid (4-(4-(3-acryloylamino-phenoxy)-thieno[3,2-d]pyrimidin-2-ylamino)-phenyl)-amide;

N-(4-((4-(3-acrylamidophenoxy)thieno[3,2-d]pyrimidin-2-yl)amino)-2-fluorophenyl)-4-methylpiperazin-1-carboxamide;

N-(3-(2-(4-(4-ethylpiperazin-1-yl)phenylamino)thieno[3,2-d]pyrimidin-4-yloxy)phenyl)acrylamide;

N-(3-(2-(4-(4-isopropyl-piperazin-1-yl)-phenylamino)-thieno[3,2-d]pyrimidin-4-yloxy)-phenyl)-acrylamide;

N-(3-(2-(4-(4-(2,2-difluoro-ethyl)-piperazin-1-yl)-phenylamino)-thieno[3,2-d]pyrimidin-4-yloxy)-phenyl)-acrylamide;

N-(3-(2-(4-imidazol-1-yl-phenylamino)-thieno[3,2-d]pyrimidin-4-yloxy)-phenyl)-acrylamide;

N-(3-(2-(4-(piperazin-1-yl)phenylamino)thieno[3,2-d]pyrimidin-4-yloxy)phenyl)acrylamide;

N-(3-(2-(4-(4-(2-dimethylamino-acetyl)-piperazin-1-yl)-3-fluoro-phenylamino)-thieno[3,2-d]pyrimidin-4-yloxy)-phenyl)-acrylamide;

N-(3-(2-(3-chloro-4-(piperazin-1-yl)phenylamino)thieno[3,2-d]pyrimidin-4-yloxy)phenyl)acrylamide;

N-(3-(2-(4-(4-(methylsulfonyl)piperazin-1-yl)phenylamino)thieno[3,2-d]pyrimidin-4-yloxy)phenyl)acrylamide;

N-(3-(2-(4-(4-acetylpiperazin-1-yl)phenylamino)thieno[3,2-d]pyrimidin-4-yloxy)phenyl)acrylamide;

N-(3-(2-(4-(4-(morpholin-4-carbonyl)-piperazin-1-yl)-phenylamino)-thieno[3,2-d]pyrimidin-4-yloxy)-phenyl)-acrylamide;

N-(3-(2-(4-(1,4-dimethyl-3-oxo-piperazin-2-yl)-phenylamino)-thieno[3,2-d]pyrimidin-4-yloxy)-phenyl)-acrylamide;

N-(3-(2-(4-morpholinophenylamino)thieno[3,2-d]pyrimidin-4-yloxy)phenyl)acrylamide;

N-(3-((2-((4-((2-(dimethylamino)ethyl)amino)phenyl)amino)thieno[3,2-d]pyrimidin-4-yl)oxy)phenyl)acrylamide;

N-(3-((2-((4-((2-(4-methylpiperazin-1-yl)ethyl)amino)phenyl)amino)thieno[3,2-d]pyrimidin-4-yl)oxy)phenyl)acrylamide;

N-(3-(2-(4-thiomorpholinophenylamino)thieno[3,2-d]pyrimidin-4-yloxy)phenyl)acrylamide;

N-(3-(2-(4-(1-oxo-1$\lambda^4$-thiomorpholin-4-yl)-phenylamino)-thieno[3,2-d]pyrimidin-4-yloxy)-phenyl)-acrylamide;

(S)—N-(3-(2-(4-(3-(dimethylamino)pyrrolidin-1-yl)phenylamino)thieno[3,2-d]pyrimidin-4-yloxy)phenyl)acrylamide;

N-(3-(2-(4-(4-pyrrolidin-1-yl-piperidin-1-yl)-phenylamino)-thieno[3,2-d]pyrimidin-4-yloxy)-phenyl)-acrylamide;

N-(3-(2-(4-[1,4']bipiperidinyl-1'-yl-phenylamino)-thieno[3,2-d]pyrimidin-4-yloxy)-phenyl)-acrylamide;

1-(4-(4-(3-acryloylamino-phenoxy)-thieno[3,2-d]pyrimidin-2-ylamino)-phenyl)-piperidin-4-carboxylic acid dimethylamide;

N-(3-(2-(4-(dimethylamino)phenylamino)thieno[3,2-d]pyrimidin-4-yloxy)phenyl)acrylamide;

N-(3-(2-(4-(2-hydroxy-ethyl)-phenylamino)-thieno[3,2-d]pyrimidin-4-yloxy)-phenyl)-acrylamide;

N-(3-(2-(4-(2-dimethylamino-ethyl)-phenylamino)-thieno[3,2-d]pyrimidin-4-yloxy)-phenyl)-acrylamide;

N-(3-(2-(3-chloro-4-fluorophenylamino)thieno[3,2-d]pyrimidin-4-yloxy)phenyl)acrylamide;

N-(3-(2-(4-hydroxyphenylamino)thieno[3,2-d]pyrimidin-4-yloxy)phenyl)acrylamide;

N-(3-((2-((4-acetylphenyl)amino)thieno[3,2-d]pyrimidin-4-yl)oxy)phenyl)acrylamide;

N-(3-((2-((4-(1,4,5,6-tetrahydropyrimidin-2-yl)phenyl)amino)thieno[3,2-d]pyrimidin-4-yl)oxo)phenyl)acrylamide;

N-(3-(2-(3-fluoro-2-methoxy-4-(4-methyl-piperazin-1-yl)-phenylamino)-thieno[3,2-d]pyrimidin-4-yloxy)-phenyl)-acrylamide;

N-(3-(2-(4-(4-(4-ethylpiperazin-1-yl)piperidin-1-yl)phenylamino)thieno[3,2-d]pyrimidin-4-yloxy)phenyl)acrylamide;

N-(3-(2-(4-(3R-imidazol-1-yl-pyrrolidin-1-yl)-phenylamino]-thieno[3,2-d]pyrimidin-4-yloxy)-phenyl)-acrylamide;

N-(3-(2-(4-(3-imidazol-1-yl-pyrrolidin-1-yl)-phenylamino)-thieno[3,2-d]pyrimidin-4-yloxy)-phenyl)-acrylamide;

N-(3-(2-(4-(4-imidazol-1-yl-piperidin-1-yl)-phenylamino)-thieno[3,2-d]pyrimidin-4-yloxy)-phenyl)-acrylamide;

N-(3-(2-(4-(4-dimethylamino-piperidin-1-yl)-phenylamino)-thieno[3,2-d]pyrimidin-4-yloxy)-phenyl)-acrylamide;

N-(3-(2-(4-(4-morpholin-4-yl-piperidin-1-yl)-phenylamino)-thieno[3,2-d]pyrimidin-4-yloxy)-phenyl)-acrylamide;

N-(3-(2-(3-fluoro-4-(4-pyrrolidin-1-yl-piperidin-1-yl)-phenylamino)-thieno[3,2-d]pyrimidin-4-yloxy)-phenyl)-acrylamide;

N-(3-(2-(3-fluoro-4-(4-morpholin-4-yl-piperidin-1-yl)-phenylamino)-thieno[3,2-d]pyrimidin-4-yloxy)-phenyl)-acrylamide;

N-(3-(2-(3-chloro-4-(4-pyrrolidin-1-yl-piperidin-1-yl)-phenylamino)-thieno[3,2-d]pyrimidin-4-yloxy)-phenyl)-acrylamide;

N-(3-(2-(3-chloro-4-(4-morpholin-4-yl-piperidin-1-yl)-phenylamino)-thieno[3,2-d]pyrimidin-4-yloxy)-phenyl)-acrylamide;

N-(3-(2-(4-(4-hydroxypiperidin-1-yl)phenylamino)thieno[3,2-d]pyrimidin-4-yloxy)phenyl)acrylamide;

N-(3-((2-((4-(4-(hydroxymethyl)piperidin-1-yl)phenyl)amino)thieno[3,2-d]pyrimidin-4-yl)oxy)phenyl)acrylamide;

N-(3-((2-((4-(4-(2-hydroxyethyl)piperidin-1-yl)phenyl)amino)thieno[3,2-d]pyrimidin-4-yl)oxy)phenyl)acrylamide;

N-(3-(2-(4-(4-(ethylsulfonyl)piperazin-1-yl)phenylamino)thieno[3,2-d]pyrimidin-4-yloxy)phenyl)acrylamide;

N-(3-(2-(4-((4-ethylpiperazin-1-yl)methyl)phenylamino)thieno[3,2-d]pyrimidin-4-yloxy)phenyl)acrylamide;

N-(3-(2-(4-(diethylaminomethyl-phenylamino)-thieno[3,2-d]pyrimidin-4-yloxy)-phenyl)-acrylamide;

N-(3-(2-(4-(4-morpholin-4-yl-piperidin-1-ylmethyl)-phenylamino)-thieno[3,2-d]pyrimidin-4-yloxy)-phenyl)-acrylamide;

(E)-N-(3-((2-((4-(3-(dimethylamino)prop-1-en-1-yl)phenyl)amino)thieno[3,2-d]pyrimidin-4-yl)oxy)phenyl)acrylamide;

N-(3-((2-((4-((1-methylpiperidin-4-yl)amino)phenyl)amino)thieno[3,2-d]pyrimidin-4-yl)oxy)phenyl)acrylamide;

N-(3-(2-(4-diethylaminomethyl-2-methoxy-phenylamino)-thieno[3,2-d]pyrimidin-4-yloxy)-phenyl)-acrylamide;

N-(3-(2-(4-((4-methylpiperazin-1-yl)methyl)phenylamino)thieno[3,2-d]pyrimidin-4-yloxy)phenyl)acrylamide;

N-(3-(2-(3-fluoro-4-(4-methyl-piperazin-1-ylmethyl)-phenylamino)-thieno[3,2-d]pyrimidin-4-yloxy)-phenyl)-acrylamide;

N-(3-(2-(4-(piperidin-1-ylmethyl)phenylamino)thieno[3,2-d]pyrimidin-4-yloxy)phenyl)acrylamide;

N-(3-(2-(4-azetidin-1-ylmethyl-phenylamino)-thieno[3,2-d]pyrimidin-4-yloxy)-phenyl)-acrylamide;

N-(3-(2-(4-pyrrolidin-1-ylmethyl-phenylamino)-thieno[3,2-d]pyrimidin-4-yloxy)-phenyl)-acrylamide;

N-(3-(2-(4-(morpholinomethyl)phenylamino)thieno[3,2-d]pyrimidin-4-yloxy)phenyl)acrylamide;

N-(3-((2-((4-((3-(dimethylamino)pyrrolidin-1-yl)methyl)phenyl)amino)thieno[3,2-d]pyrimidin-4-yl)oxy)phenyl)acrylamide;

N-(3-((2-((4-((4-hydroxypiperidin-1-yl)methyl)phenyl)amino)thieno[3,2-d]pyrimidin-4-yl)oxy)phenyl)acrylamide;

N-(3-((2-((4-((4-(dimethylamino)piperidin-1-yl)methyl)phenyl)amino)thieno[3,2-d]pyrimidin-4-yl)oxy)phenyl)acrylamide;

Dimethyl(4-((4-(3-acrylamidophenoxy)thieno[3,2-d]pyrimidin-2-yl)amino)benzylphosphonate;

N-(3-(2-(4-((dimethylamino)methyl)-3-fluorophenylamino)thieno[3,2-d]pyrimidin-4-yloxy)phenyl)acrylamide;

N-(3-(2-(4-((3-(dimethylamino)pyrrolidin-1-yl)methyl)-3-fluorophenylamino)thieno[3,2-d]pyrimidin-4-yloxy)phenyl)acrylamide;

N-(3-(2-(4-((4-(dimethylamino)piperidin-1-yl)methyl)-3-fluorophenylamino)thieno[3,2-d]pyrimidin-4-yloxy)phenyl)acrylamide;

N-(3-(2-(4-((1-methylpiperidin-4-ylamino)methyl)-3-fluorophenylamino)-thieno[3,2-d]pyrimidin-4-yloxy)-phenyl)-acrylamide;

N-(3-(2-(4-dimethylaminomethyl-2-methyl-phenylamino)-thieno[3,2-d]pyrimidin-4-yloxy)-phenyl)-acrylamide;

N-(3-(2-(4-((4-(cyclopropylmethyl)piperazin-1-yl)methyl)phenylamino)thieno[3,2-d]pyrimidin-4-yloxy)phenyl)acrylamide;

N-(3-(2-(4-((4-(1-methylpiperidin-4-yl)piperazin-1-yl)methyl)phenylamino)thieno[3,2-d]pyrimidin-4-yloxy)phenyl)acrylamide;

N-(3-(2-(4-methanesulfonylmethyl-phenylamino)-thieno[3,2-d]pyrimidin-4-yloxy)-phenyl)-acrylamide;

N-(3-(2-(4-(2-methanesulfonyl-ethyl)-phenylamino)-thieno[3,2-d]pyrimidin-4-yloxy)-phenyl)-acrylamide;

N-(3-(2-(3-chloro-4-(4-(1-methyl-piperidin-4-yl)piperazin-1-ylmethyl)phenylamino)-thieno[3,2-d]pyrimidin-4-yloxy)-phenyl)-acrylamide;

N-(3-(2-(4-(4-(1-methylpiperidin-4-yl)piperazin-1-yl)phenylamino)thieno[3,2-d]pyrimidin-4-yloxy)phenyl)acrylamide;

N-(3-(2-(4-(4-cyclohexyl-piperazin-1-yl)-phenylamino)-thieno[3,2-d]pyrimidin-4-yloxy)-phenyl)-acrylamide;

N-(3-(2-(5-(4-ethylpiperazin-1-yl)pyridin-2-ylamino)thieno[3,2-d]pyrimidin-4-yloxy)phenyl)acrylamide;

N-(3-(2-(5-(4-(2-hydroxy-ethyl)-piperazin-1-yl)-piridin-2-ylamino)-thieno[3,2-d]pyrimidin-4-yloxy)-phenyl)-acrylamide;

N-(3-(2-(4-(1-(4-ethylpiperazin-1-yl)ethyl)phenylamino)thieno[3,2-d]pyrimidin-4-yloxy)phenyl)acrylamide;

N-(3-(2-(4-(4-ethylpiperazin-1-carbonyl)phenylamino)thieno[3,2-d]pyrimidin-4-yloxy)phenyl)acrylamide;

N-(3-(2-(4-(4-(2-hydroxy-acetyl)-piperazin-1-yl)-phenylamino)-thieno[3,2-d]pyrimidin-4-yloxy)-phenyl)-acrylamide;

N-(3-(2-(4-(4-(2-dimethylamino-acetyl)-piperazin-1-yl)-phenylamino)-thieno[3,2-d]pyrimidin-4-yloxy)-phenyl)-acrylamide;

2-(4-((4-(3-acrylamidophenoxy)thieno[3,2-d]pyrimidin-2-yl)amino)phenyl)acetic acid;

N-(3-((2-((4-(methylsulfinyl)phenyl)amino)thieno[3,2-d]pyrimidin-4-yl)oxy)phenyl)acrylamide;

N-(3-((2-((4-(methylsulfonyl)phenyl)amino)thieno[3,2-d]pyrimidin-4-yl)oxy)phenyl)acrylamide;

4-((4-(3-acrylamidophenoxy)thieno[3,2-d]pyrimidin-2-yl)amino)-N-methylbenzamide;

4-((4-(3-acrylamidophenoxy)thieno[3,2-d]pyrimidin-2-yl)amino)-N,N-dimethylbenzamide;

N-(3-((2-((4-(morpholin-4-carbonyl)phenyl)amino)thieno[3,2-d]pyrimidin-4-yl)oxy)phenyl)acrylamide;

N-(3-((2-((4-(4-methylpiperazin-1-carbonyl)phenyl)amino)thieno[3,2-d]pyrimidin-4-yl)oxy)phenyl)acrylamide;

N-(3-(2-(4-(4-(1-methyl-piperidin-4-yl)-piperazin-1-carbonyl)-phenylamino)-thieno[3,2-d]pyrimidin-4-yloxy)-phenyl)-acrylamide;

N-(3-(2-(4-(4-hydroxy-piperidin-1-carbonyl)-phenylamino)-thieno[3,2-d]pyrimidin-4-yloxy)-phenyl)-acrylamide;

N-(3-(2-(4-(3-methylamino-pyrrolidin-1-carbonyl)-phenylamino)-thieno[3,2-d]pyrimidin-4-yloxy)-phenyl)-acrylamide;

N-(3-(2-(4-(3-dimethylamino-pyrrolidin-1-carbonyl)-phenylamino)-thieno[3,2-d]pyrimidin-4-yloxy)-phenyl)-acrylamide;

4-(4-(3-acryloylamino-phenoxy)-thieno[3,2-d]pyrimidin-2-ylamino)-N-(2-dimethylamino-ethyl)-benzamide;

N-(3-(2-(3-chloro-4-(4-ethylpiperazin-1-carbonyl)phenylamino)thieno[3,2-d]pyrimidin-4-yloxy)phenyl)acrylamide;

N-(3-((2-((3-chloro-4-((2-(dimethylamino)ethyl)amino)phenyl)amino)thieno[3,2-d]pyrimidin-4-yl)oxy)phenyl)acrylamide;

4-(4-(3-acryloylamino-phenoxy)-thieno[3,2-d]pyrimidin-2-ylamino)-2-chloro-N,N-dimethyl-benzamide;

N-(3-(2-(3-chloro-4-(4-ethanesulfonyl-piperazin-1-carbonyl)-phenylamino)-thieno[3,2-d]pyrimidin-4-yloxy)-phenyl)-acrylamide;

4-((4-(3-acrylamidophenoxy)thieno[3,2-d]pyrimidin-2-yl)amino-2-chloro-N-(1-methylpiperidin-4-yl)benzamide;

N-(3-(2-(4-(4-ethylpiperazin-1-ylsulfonyl)phenylamino)thieno[3,2-d]pyrimidin-4-yloxy)phenyl)acrylamide;

N-(3-((2-((4-((methylsulfinyl)methyl)phenyl)amino)thieno[3,2-d]pyrimidin-4-yl)oxy)phenyl)acrylamide;

N-(3-((2-((4-(2-(methylsulfinyl)ethyl)phenyl)amino)thieno[3,2-d]pyrimidin-4-yl)oxy)phenyl)acrylamide;

N-(3-((2-((4-sulfamoylphenyl)amino)thieno[3,2-d]pyrimidin-4-yl)oxy)phenyl)acrylamide;

N-(3-((2-((4-(morpholinosulfonyl)phenyl)amino)thieno[3,2-d]pyrimidin-4-yl)oxy)phenyl)acrylamide;

N-(3-((2-((4-(N-cyclopropylsulfamoyl)phenyl)amino)thieno[3,2-d]pyrimidin-4-yl)oxy)phenyl)acrylamide;

N-(3-((2-((4-(N-(2-(dimethylamino)ethyl)sulfamoyl)phenyl)amino)thieno[3,2-d]pyrimidin-4-yl)oxy)phenyl)acrylamide;

N-(3-((2-((4-(N-(1-methylpiperidin-4-yl)sulfamoyl)phenyl)amino)thieno[3,2-d]pyrimidin-4-yl)oxy)phenyl)acrylamide;

N-(3-((2-((4-(N-(1-isopropylpiperidin-4-yl)sulfamoyl)phenyl)amino)thieno[3,2-d]pyrimidin-4-yl)oxy)phenyl)acrylamide;

3-(dimethylamino)propyl-4-((4-(3-acrylamidophenoxy)thieno[3,2-d]pyrimidin-2-yl)amino)benzoate;

N-(3-(2-(4-(2-(4-ethylpiperazin-1-yl)ethyl)phenylamino)thieno[3,2-d]pyrimidin-4-yloxy)phenyl)acrylamide;

N-(3-(2-(4-(2-piperidin-1-yl-ethyl)-phenylamino)-thieno[3,2-d]pyrimidin-4-yloxy)-phenyl)-acrylamide;

N-(3-(2-(4-(1,1-dioxo-1$\lambda^6$-thiomorpholin-4-yl)-phenylamino)-thieno[3,2-d]pyrimidin-4-yloxy)-phenyl)-acrylamide;

N-(3-(2-(4-(2-(4-ethylpiperazin-1-yl)acetyl)phenylamino)thieno[3,2-d]pyrimidin-4-yloxy)phenyl)acrylamide;

N-(3-(2-(4-(1-ethylpiperidin-4-yloxy)phenylamino)thieno[3,2-d]pyrimidin-4-yloxy)phenyl)acrylamide;

N-(3-(2-(3-fluoro-4-(1-methyl-piperidin-4-yloxy)-phenylamino)-thieno[3,2-d]pyrimidin-4-yloxy)-phenyl)-acrylamide;

N-(3-(2-(4-(2-morpholinoethoxy)phenylamino)thieno[3,2-d]pyrimidin-4-yloxy)phenyl)acrylamide;

N-(3-(2-(4-(2-methoxy-ethoxy)-phenylamino)-thieno[3,2-d]pyrimidin-4-yloxy)-phenyl)-acrylamide;

N-(3-((2-((4-(2-(dimethylamino)ethoxy)phenyl)amino)thieno[3,2-d]pyrimidin-4-yl)oxy)phenyl)acrylamide;

N-(3-((2-((4-(2-(diethylamino)ethoxy)phenyl)amino)thieno[3,2-d]pyrimidin-4-yl)oxy)phenyl)acrylamide;

N-(3-((2-((4-(2-(pyrrolidin-1-yl)ethoxy)phenyl)amino)thieno[3,2-d]pyrimidin-4-yl)oxy)phenyl)acrylamide;

N-(3-((2-((2,3,4,5-tetrahydrobenzo[b][1,4]oxazepin-7-yl)amino)thieno[3,2-d]pyrimidin-4-yl)oxy)phenyl)acrylamide;

N-(3-(2-(2,3-dihydro-benzo[1,4]dioxin-6-ylamino)-thieno[3,2-d]pyrimidin-4-yloxy)-phenyl)-acrylamide;

N-(3-(2-(3-fluoro-4-(2-methoxy-ethoxy)-phenylamino)-thieno[3,2-d]pyrimidin-4-yloxy)-phenyl)-acrylamide;

N-(3-(2-(4-(2-dimethylamino-ethoxy)-3-fluoro-phenylamino)-thieno[3,2-d]pyrimidin-4-yloxy)-phenyl)-acrylamide;

N-(3-(2-(4-(2-diethylamino-ethoxy)-3-fluoro-phenylamino)-thieno[3,2-d]pyrimidin-4-yloxy)-phenyl)-acrylamide;

N-(3-(2-(3-fluoro-4-(2-(4-methyl-piperazin-1-yl)-ethoxy)-phenylamino)-thieno[3,2-d]pyrimidin-4-yloxy)-phenyl)-acrylamide;

N-(3-(2-(3-methoxy-4-(2-morpholin-4-yl-ethoxy)-phenylamino)-thieno[3,2-d]pyrimidin-4-yloxy)-phenyl)-acrylamide;

(E)-4-(dimethylamino)-N-(3-(2-(4-(4-methylpiperazin-1-yl)phenylamino)thieno[3,2-d]pyrimidin-4-yloxy)phenyl)but-2-enamide;

N-(3-(2-(4-(4-methylpiperazin-1-yl)phenylamino)thieno[3,2-d]pyrimidin-4-ylamino)phenyl)acrylamide;

N-(3-(2-(4-(4-ethyl-piperazin-1-yl)-phenylamino)-thieno[3,2-d]pyrimidin-4-ylamino)-phenyl)-acrylamide;

N-(3-(2-(4-(4-isopropyl-piperazin-1-yl)-phenylamino)-thieno[3,2-d]pyrimidin-4-ylamino)-phenyl)-acrylamide;

N-(3-(2-(4-(1-methyl-piperidin-4-yl)-phenylamino)-thieno[3,2-d]pyrimidin-4-ylamino)-phenyl)-acrylamide;

N-(3-(2-(4-(1-methyl-piperidin-3-yl)-phenylamino)-thieno[3,2-d]pyrimidin-4-ylamino)-phenyl)-acrylamide;

N-(3-(2-(4-dimethylaminomethyl-phenylamino)-thieno[3,2-d]pyrimidin-4-ylamino)-phenyl)-acrylamide;

N-(3-(2-(4-piperidin-1-ylmethyl-phenylamino)-thieno[3,2-d]pyrimidin-4-ylamino)-phenyl)-acrylamide;

N-(3-(2-(4-(2-dimethylamino-ethyl)-phenylamino)-thieno[3,2-d]pyrimidin-4-ylamino)-phenyl)-acrylamide;

N-(3-((2-((4-(2-(4-methylpiperazin-1-yl)ethyl)phenyl)amino)thieno[3,2-d]pyrimidin-4-yl)amino)phenyl)acrylamide;

N-(3-(2-(4-(2-dimethylamino-ethoxy)-phenylamino)-thieno[3,2-d]pyrimidin-4-ylamino)-phenyl)-acrylamide;

N-(3-(2-(4-(3-dimethylamino-propoxy)-phenylamino)-thieno[3,2-d]pyrimidin-4-ylamino)-phenyl)-acrylamide;

N-(3-(2-(3-fluoro-4-(4-methyl-piperazin-1-yl)-phenylamino)-thieno[3,2-d]pyrimidin-4-ylamino)-phenyl)-acrylamide;

N-(3-(2-(3-fluoro-4-(1-methyl-piperidin-4-yl)-phenylamino)-thieno[3,2-d]pyrimidin-4-ylamino)-phenyl)-acrylamide;

N-(3-(2-(3-fluoro-4-(1-methyl-piperidin-4-yl)-phenylamino)-thieno[3,2-d]pyrimidin-4-ylamino)-phenyl)-acrylamide;

N-(3-(2-(2-methoxy-4-piperidin-1-ylmethyl-phenylamino)-thieno[3,2-d]pyrimidin-4-ylamino)-phenyl)-acrylamide;

N-(4-fluoro-3-(2-(4-(4-methyl-piperazin-1-yl)-phenylamino)-thieno[3,2-d]pyrimidin-4-ylamino)-phenyl)-acrylamide;

N-(4-fluoro-3-(2-(3-fluoro-4-(4-methyl-piperazin-1-yl)-phenylamino)-thieno[3,2-d]pyrimidin-4-ylamino)-phenyl)-acrylamide;

N-(3-(2-(4-(4-methylpiperazin-1-yl)phenylamino)thieno[3,2-d]pyrimidin-4-ylthio)phenyl)acrylamide;

N-(3-(2-(3-fluoro-4-(1-methyl-piperidin-4-yl)-phenylamino)-thieno[3,2-d]pyrimidin-4-ylsulfanyl)-phenyl)-acrylamide;

N-(3-(2-(3-fluoro-4-morpholin-4-yl-phenylamino)-thieno[3,2-d]pyrimidin-4-ylsulfanyl)-phenyl)-acrylamide;

(E)-4-(dimethylamino)-N-(3-(2-(4-(4-methylpiperazin-1-yl)phenylamino)thieno[3,2-d]pyrimidin-4-ylthio)phenyl)but-2-enamide;

N-(3-(2-(4-(4-methylpiperazin-1-yl)phenylamino)thieno[3,2-d]pyrimidin-4-ylsulfinyl)phenyl)acrylamide;

(Z)-3-chloro-N-(3-(2-(4-(4-methylpiperazin-1-yl)phenylamino)thieno[3,2-d]pyrimidin-4-yloxy)phenyl)acrylamide;

(E)-3-chloro-N-(3-(2-(4-(4-methylpiperazin-1-yl)phenylamino)thieno[3,2-d]pyrimidin-4-yloxy)phenyl)acrylamide;

N-(3-(2-(4-(4-ethylpiperazin-1-yl)-2-methoxyphenylamino)thieno[3,2-d]pyrimidin-4-yloxy)phenyl)acrylamide;

N-(3-(2-(2-methoxy-4-morpholinophenylamino)thieno[3,2-d]pyrimidin-4-yloxy)phenyl)acrylamide;

4-((4-(3-acrylamidophenoxy)thieno[3,2-d]pyrimidin-2-yl)amino)-2-methoxy-N-(1-methylpiperidin-4-yl)benzamide;

N-(3-(2-(4-(piperidin-1-yl)phenylamino)thieno[3,2-d]pyrimidin-4-yloxy)phenyl)acrylamide;

N-(3-(2-(4-(pyrrolidin-1-yl)phenylamino)thieno[3,2-d]pyrimidin-4-yloxy)phenyl)acrylamide;

1-(4-((4-(3-acrylamidophenoxy)thieno[3,2-d]pyrimidin-2-yl)amino)phenyl)piperidin-4-carboxylic acid;

N-(3-(2-(4-(4-dimethylaminomethyl-piperidin-1-yl)-phenylamino)-thieno[3,2-d]pyrimidin-4-yloxy)-phenyl)-acrylamide;

N-(3-(2-(4-(4-piperidin-1-ylmethyl-piperidin-1-yl)-phenylamino)-thieno[3,2-d]pyrimidin-4-yloxy)-phenyl)-acrylamide;

N-(3-(2-(4-(1-methyl-1,2,3,6-tetrahydro-piridin-4-yl)-phenylamino)-thieno[3,2-d]pyrimidin-4-yloxy)-phenyl)-acrylamide;

N-(3-(2-(4-(1-methyl-piperidin-4-yl)-phenylamino)-thieno[3,2-d]pyrimidin-4-yloxy)-phenyl)-acrylamide;

N-(3-(2-(4-(1-ethyl-piperidin-4-yl)-phenylamino)-thieno[3,2-d]pyrimidin-4-yloxy)-phenyl)-acrylamide;

N-(3-(2-(4-(1-isopropyl-piperidin-4-yl)-phenylamino)-thieno[3,2-d]pyrimidin-4-yloxy)-phenyl)-acrylamide;

N-(3-(2-(4-(1-methyl-piperidin-3-yl)-phenylamino)-thieno[3,2-d]pyrimidin-4-yloxy)-phenyl)-acrylamide;

N-(3-(2-(4-dimethylaminomethyl-phenylamino)-thieno[3,2-d]pyrimidin-4-yloxy)-phenyl)-acrylamide;

N-(3-(2-(3-chloro-4-(1-methyl-piperidin-4-yl)-phenylamino)-thieno[3,2-d]pyrimidin-4-yloxy)-phenyl)-acrylamide;

4-(4-(3-acrylamidophenoxy)thieno[3,2-d]pyrimidin-2-ylamino)-N-(2-(pyrrolidin-1-yl)ethyl)benzamide;

N-(3-((2-((4-(2-((1-methylpiperidin-4-yl)amino)-2-oxoethyl)phenyl)amino)thieno[3,2-d]pyrimidin-4-yl)oxy)phenyl)acrylamide;

N-(3-(2-(4-(3-piperidin-1-yl-propenyl)-phenylamino)-thieno[3,2-d]pyrimidin-4-yloxy)-phenyl)-acrylamide;

N-(3-(2-(4-(3-pyrrolidin-1-yl-propionylamino)-phenylamino)-thieno[3,2-d]pyrimidin-4-yloxy)-phenyl)-acrylamide;
4-((4-(3-acrylamidophenoxy)thieno[3,2-d]pyrimidin-2-yl)amino-N-(tetrahydro-2H-pyran-4-yl)benzamide;
4-((4-(3-acrylamidophenoxy)thieno[3,2-d]pyrimidin-2-yl)amino-N-(1-methylpiperidin-4-yl)benzamide;
4-((4-(3-acrylamidophenoxy)thieno[3,2-d]pyrimidin-2-yl)amino)-N-(1-isopropylpiperidin-4-yl)benzamide;
4-(4-(3-acryloylamino-phenoxy)-thieno[3,2-d]pyrimidin-2-ylamino)-3-methoxy-N-(2-pyrrolidin-1-yl-ethyl)-benzamide;
N-(3-(2-(4-(4-(N,N-dimethylsulfamoyl)piperazin-1-yl)phenylamino)thieno[3,2-d]pyrimidin-4-yloxy)phenyl)acrylamide;
N-(3-(2-(4-(2-(4-(ethylsulfonyl)piperazin-1-yl)ethyl)phenylamino)thieno[3,2-d]pyrimidin-4-yloxy)phenyl)acrylamide;
N-(3-(2-(6-(4-methylpiperazin-1-yl)pyridin-3-ylamino)thieno[3,2-d]pyrimidin-4-yloxy)phenyl)acrylamide;
N-(3-((2-(piridin-3-ylamino)thieno[3,2-d]pyrimidin-4-yl)oxy)phenyl)acrylamide;
N-(3-((2-((6-morpholinopiridin-3-yl)amino)thieno[3,2-d]pyrimidin-4-yl)oxy)phenyl)acrylamide;
N-(3-((2-((6-(4-isopropylpiperazin-1-yl)pyridin-3-yl)amino)thieno[3,2-d]pyrimidin-4-yl)oxy)phenyl)acrylamide;
N-(3-((2-((6-(4-(1-methylpiperidin-4-yl)piperazin-1-yl)pyridin-3-yl)amino)thieno[3,2-d]pyrimidin-4-yl)oxy)phenyl)acrylamide;
N-(3-((2-((6-(4-(2-(dimethylamino)ethyl)piperazin-1-yl)pyridin-3-yl)amino)thieno[3,2-d]pyrimidin-4-yl)oxy)phenyl)acrylamide;
N-(3-((2-((6-(4-(dimethylamino)piperidin-1-yl)pyridin-3-yl)amino)thieno[3,2-d]pyrimidin-4-yl)oxy)phenyl)acrylamide;
N-(3-((2-((6-(4-(pyrrolidin-1-yl)piperidin-1-yl)pyridin-3-yl)amino)thieno[3,2-d]pyrimidin-4-yl)oxy)phenyl)acrylamide;
N-(3-((2-((6-([1,4'-bipiperidin]-1'-yl)pyridin-3-yl)amino)thieno[3,2-d]pyrimidin-4-yl)oxy)phenyl)acrylamide;
N-(3-((2-((6-((4-methylpiperazin-1-yl)methyl)pyridin-3-yl)amino)thieno[3,2-d]pyrimidin-4-yl)oxy)phenyl)acrylamide;
N-(3-((2-((6-((2-(piperidin-1-yl)ethyl)amino)pyridin-3-yl)amino)thieno[3,2-d]pyrimidin-4-yl)oxy)phenyl)acrylamide;
N-(3-((2-((6-((1-isopropylpiperidin-4-yl)amino)pyridin-3-yl)amino)thieno[3,2-d]pyrimidin-4-yl)oxy)phenyl)acrylamide;
N-(3-((2-((6-(methylsulfinyl)pyridin-3-yl)amino)thieno[3,2-d]pyrimidin-4-yl)oxy)phenyl)acrylamide;
N-(3-(2-(3-fluoro-4-morpholinophenylamino)thieno[3,2-d]pyrimidin-4-yloxy)phenyl)acrylamide;
N-(3-((2-((3-fluoro-4-((1-methylpiperidin-4-yl)amino)phenyl)amino)thieno[3,2-d]pyrimidin-4-yl)oxy)phenyl)acrylamide;
N-(3-((3-fluoro-4-((1-isopropylpiperidin-4-yl)amino)phenyl)amino)thieno[3,2-d]pyrimidin-4-yl)oxy)phenyl)acrylamide;
N-(3-(2-(3-fluoro-4-(4-(methylsulfonyl)piperazin-1-yl)phenylamino)thieno[3,2-d]pyrimidin-4-yloxy)phenyl)acrylamide;
N-(3-(2-(4-(4-(ethanesulfonylpiperazin-1-yl)-3-fluoro-phenylamino)thieno[3,2-d]pyrimidin-4-yloxy)-phenyl)-acrylamide;
N-(3-(2-(4-(2,6-cis-dimethylmorpholino)-3-fluorophenylamino)thieno[3,2-d]pyrimidin-4-yloxy)phenyl)acrylamide;
N-(3-(2-(3-fluoro-4-(1-methyl-piperidin-4-yl)-phenylamino)-thieno[3,2-d]pyrimidin-4-yloxy)-phenyl)-acrylamide;
N-(3-(2-(3-fluoro-4-(1-methyl-piperidin-3-yl)-phenylamino)-thieno[3,2-d]pyrimidin-4-yloxy)-phenyl)-acrylamide;
N-(3-(2-(3-fluoro-4-(2-morpholin-4-yl-ethoxy)phenylamino)-thieno[3,2-d]pyrimidin-4-yloxy)-phenyl)-acrylamide;
N-(3-((2-((4-((2-(dimethylamino)ethyl)amino)-3-fluorophenyl)amino)thieno[3,2-d]pyrimidin-4-yl)oxy)phenyl)acrylamide;
N-(3-((2-((3,5-difluoro-4-(4-methylpiperazin-1-yl)phenyl)amino)thieno[3,2-d]pyrimidin-4-yl)oxy)phenyl)acrylamide;
N-(3-((2-((4-((2-(dimethylamino)ethyl)amino)-3,5-difluorophenyl)amino)thieno[3,2-d]pyrimidin-4-yl)oxy)phenyl)acrylamide;
N-(3-((2-((3,5-difluoro-4-((1-methylpiperidin-4-yl)amino)phenyl)thieno[3,2-d]pyrimidin-4-yl)oxy)phenyl)acrylamide;
N-(3-(2-(4-(1-amino-cyclopropyl)-phenylamino)-thieno[3,2-d]pyrimidin-4-yloxy)-phenyl)-acrylamide;
N-(3-(2-[1-(2-dimethylamino-acetyl)-2,3-dihydro-1H-indol-5-ylamino]-thieno[3,2-d]pyrimidin-4-yloxy)-phenyl)-acrylamide;
N-(3-(2-(1-methyl-1H-indol-5-ylamino)-thieno[3,2-d]pyrimidin-4-yloxy)-phenyl)-acrylamide;
N-(3-((2-((4-(4-methylpiperazin-1-yl)phenyl)amino)furo[3,2-d]pyrimidin-4-yl)oxy)phenyl)acrylamide;
N-(3-((2-((4-(4-isopropylpiperazin-1-yl)phenyl)amino)furo[3,2-d]pyrimidin-4-yl)oxy)phenyl)acrylamide;
N-(3-((2-((4-morpholinophenyl)amino)furo[3,2-d]pyrimidin-4-yl)oxy)phenyl)acrylamide;
N-(3-((2-((4-((dimethylamino)methyl)phenyl)amino)furo[3,2-d]pyrimidin-4-yl)oxy)phenyl)acrylamide;
N-(3-((2-((4-((4-(dimethylamino)piperidin-1-yl)methyl)phenyl)amino)furo[3,2-d]pyrimidin-4-yl)oxy)phenyl)acrylamide;
N-(3-((2-((3-fluoro-4-(1-methylpiperazin-4-yl)phenyl)amino)furo[3,2-d]pyrimidin-4-yl)oxy)phenyl)acrylamide;
N-(3-((2-((4-(2-dimethylamino)ethyl)amino)-3-fluorophenyl)amino)furo[3,2-d]pyrimidin-4-yl)oxy)phenyl)acrylamide;
N-(3-((2-((3-fluoro-4-((1-methylpiperidin-4-yl)amino)phenyl)amino)furo[3,2-d]pyrimidin-4-yl)oxy)phenyl)acrylamide;
N-(3-(2-(3-methoxy-4-(4-methyl-piperazin-1-yl)-phenylamino)-furo[3,2-d]pyrimidin-4-yloxy)-phenyl)-acrylamide; and
N-(3-((2-((4-sulfamoylphenyl)amino)furo[3,2-d]pyrimidin-4-yl)oxy)phenyl)acrylamide.

The compound of formula (I) according to the present invention may be prepared by the procedure shown in Reaction Scheme (I):

Reaction Scheme (I)

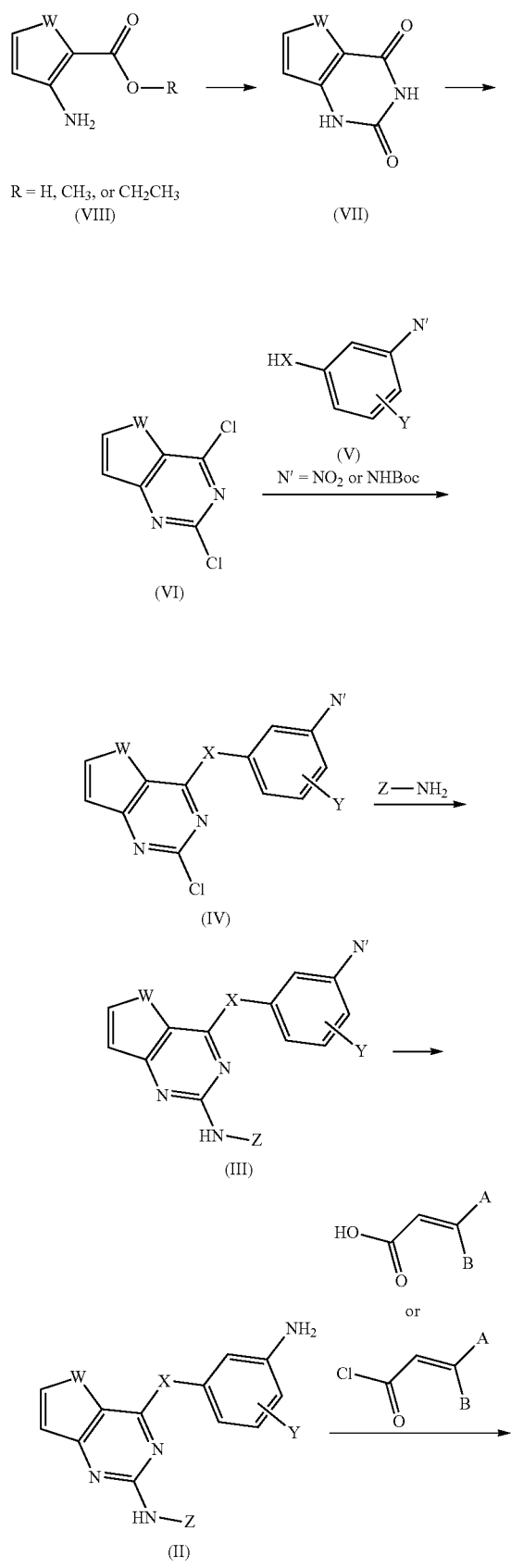

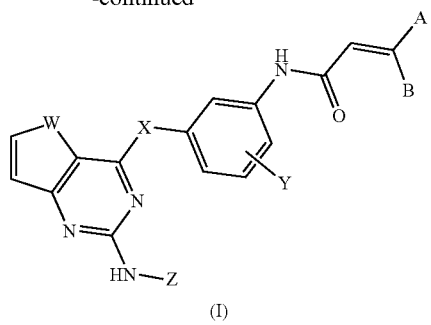

wherein,
A, B, W, X, Y and Z have the same meanings as defined above;
R is hydrogen, methyl, or ethyl; and
N' is nitro, or amine protected with tert-butyloxycarbonyl (Boc).

As shown in Reaction Scheme (I), a compound of formula (VIII) is subjected to a condensation reaction with urea in an organic solvent (e.g., N,N-dimethylformamide, N,N-dimethylacetamide or N-methylpyrrolidone) at a temperature ranging from reflux temperature to 200° C.; or with potassium cyanate under an acidic condition such as 6% to 50% of aqueous acetic acid at a temperature ranging from room temperature to 100° C., to obtain a condensed compound of formula (VII).

The compound of formula (VII) thus obtained is refluxed with stirring in the presence of a chlorinating agent (e.g., phosphorus oxychloride or thionyl chloride) to obtain a chlorinated compound of formula (VI), followed by a reaction in an organic solvent (e.g., dimethylsulfoxide, N,N-dimethylformamide, N,N-dimethylacetamide, N-methylpyrrolidone, acetonitrile, tetrahydrofuran, 1,4-dioxane, toluene or benzene) in the presence of an inorganic base (e.g., cesium carbonate, sodium carbonate or potassium carbonate) at a temperature ranging from room temperature to 100° C., inducing the substitution at the C-4 position of the compound of formula (VI) with aniline, phenol or thiophenol derivative of formula (V), to obtain a compound of formula (IV).

The compound of formula (IV) is reacted with Z—$NH_2$ in an alcohol solution (e.g., 2-propanol or 2-butanol) in the presence of an inorganic acid (e.g., hydrochloric acid) or organic acid (e.g., trifluoroacetic acid) at a temperature ranging from 70° C. to reflux temperature; or with Z—$NH_2$ in an organic solvent (e.g., 1,4-dioxane) in the presence of a palladium catalyst (e.g., palladium (II) acetate or tris(dibenzylidenacetone)dipalladium(0), and in the presence of a ligand (e.g., bis(diphenylphosphino)(Xanthene)(Xantphos) or 2,2'-bis(disphenylphosphino)-1,1'-binaphthyl (BINAP)) and an inorganic base (e.g., cesium carbonate or sodium t-butoxide) at a temperature of about 100° C., to obtain a compound of formula (III) having a Z—$NH_2$ group.

The compound of formula (III) in which N' is nitro group is subjected to a hydrogenation using a palladium/carbon catalyst, or a reduction reaction mediated with Fe, to obtain an aniline compound of formula (II) whose a nitro group is substituted with an amino group. The compound of formula (III) in which N' is amine group protected with tert-butyloxycarbonyl (Boc) is subjected to a reaction with an acid (e.g., trifluoroacetic acid or hydrochloric acid) in an organic solvent (e.g., methylene chloride), to obtain a deprotected aniline compound of formula (II).

Subsequently, the aniline compound of formula (II) is subjected to a reaction with an acryloyl chloride substituted with A and B, in an organic solvent (e.g., methylene chloride or tetrohydrofuran) or a mixed solvent such as 50% aqueous tetrohydrofuran in the presence of an inorganic base (e.g., sodium bicarbonate) or organic base (e.g., triethylamine or diisopropylethylamine) at a low temperature ranging from −10° C. to 10° C.; or with acrylic acid substituted with A and B, in pyridine using a coupling agent (e.g., 1-ethyl-3-(3-dimethylaminopropyl)carbodiimide (EDCI) or 2-(1H-7-azabenzotriazol-1-yl)-1,1,3,3-tetramethyl uronium hexafluoro phosphate methaneaminium (HATU)), to obtain the inventive compound of formula (I) having an acrylamide group.

The compound of formula (I) of the present invention may also be prepared in the form of a pharmaceutically acceptable salt formed with an inorganic or organic acid such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid and toluenesulfonic acid.

The pharmaceutically acceptable salt of the present invention may be prepared by conventional methods, for example, by dissolving the compound of formula (I) in a water-miscible organic solvent such as acetone, methanol, ethanol and acetonitrile, adding thereto an excess amount of an organic acid or an aqueous solution of inorganic acid, to induce precipitation of salts from the resulting mixture, removing the solvent and remaining free acid therefrom, and isolating the precipitated salts.

The inventive compound of formula (I) or the pharmaceutically acceptable salt thereof may include a hydrate and a solvate thereof.

Accordingly, the present invention provides a use of the inventive compound for the manufacture of a medicament for preventing or treating cancers, tumors, inflammatory diseases, autoimmune diseases, or immunologically mediated diseases.

In addition, the present invention provides a pharmaceutical composition for preventing or treating cancers, tumors, inflammatory diseases, autoimmune diseases, or immunologically mediated diseases which comprises the inventive compound as an active ingredient.

Further, the present invention provides a method for preventing or treating cancers, tumors, inflammatory diseases, autoimmune diseases, or immunologically mediated diseases, which comprises administering the inventive compound to a mammal in need thereof.

The inventive compound of formula (I) or a pharmaceutically acceptable salt thereof selectively and effectively inhibits the growth of cancer cells induced by an epidermal growth factor receptor (EGFR) tyrosine kinase or a mutant thereof as well as the resistance against drugs. Accordingly, the present invention provides a pharmaceutical composition for preventing or treating cancers or tumors induced by an EGFR tyrosine kinase or a mutant thereof which comprises the compound of formula (I) or a pharmaceutically acceptable salt thereof as an active ingredient.

Representative examples of the cancers or tumors may include, but are not limited to, liver cancer, hepatocellular carcinoma, thyroid cancer, colorectal cancer, testicular cancer, bone cancer, oral cancer, basal cell carcinoma, ovarian cancer, brain tumor, gallbladder carcinoma, biliary tract cancer, head and neck cancer, colorectal cancer, vesical carcinoma, tongue cancer, esophageal cancer, glioma, glioblastoma, renal cancer, malignant melanoma, gastric cancer, breast cancer, sarcoma, pharynx carcinoma, uterine cancer, cervical cancer, prostate cancer, rectal cancer, pancreatic cancer, lung cancer, skin cancer, and other solid cancer.

The inventive compound of formula (I) or a pharmaceutically acceptable salt thereof can provide enhanced anticancer effects when it is administered in combination with another anticancer agent for treating cancers or tumors.

Representative examples of the anticancer agent for treating cancers or tumors may include, but are not limited to, cell signal transduction inhibitors (e.g., imatinib, gefitinib, bortezomib, erlotinib, sorafenib, sunitinib, dasatinib, vorinostat, lapatinib, temsirolimus, nilotinib, everolimus, pazopanib, trastuzumab, bevacizumab, cetuximab, ranibizumab, pegaptanib, panitumumab and the like), mitosis inhibitors (e.g., paclitaxel, vincristine, vinblastine and the like), alkylating agents (e.g., cisplatin, cyclophosphamide, chromabucil, carmustine and the like), anti-metabolites (e.g., methotrexate, 5-FU and the like), intercalating anticancer agents, (e.g., actinomycin, anthracycline, bleomycin, mitomycin-C and the like), topoisomerase inhibitors (e.g., irinotecan, topotecan, teniposide and the like), immunotherapic agents (e.g., interleukin, interferon and the like) and antihormonal agents (e.g., tamoxifen, raloxifene and the like), and at least one anticancer agent selected therefrom may be included in the inventive pharmaceutical composition.

Further, the inventive compound of formula (I) or a pharmaceutically acceptable salt thereof selectively and effectively inhibits Bruton's tyrosine kinase (BTK), janus kinase 3 (JAK3), interleukin-2 inducing T-cell kinase (ITK), resting lymphocyte kinase (RLK), and bone marrow tyrosine kinase (BMX), which are mainly expressed in abnormally activated B-lymphocytes and/or T-lymphocytes. Namely, the inventive compound of formula (I) or a pharmaceutically acceptable salt thereof can treat or prevent cancers, tumors, inflammatory diseases, autoimmune diseases or immunologically mediated diseases caused by the abnormally activated B-lymphocytes, T-lymphocytes or both. Therefore, the present invention also provides a pharmaceutical composition for treating or preventing cancers, tumors, inflammatory diseases, autoimmune diseases, or immunologically mediated diseases which comprises the compound of formula (I) or a pharmaceutically acceptable salt thereof as an active ingredient.

Representative examples of the inflammatory diseases, autoimmune diseases and immunologically mediated diseases may include, but are not limited to, arthritis, rheumatoid arthritis, spondyloarthropathy, gouty arthritis, osteoarthritis, juvenile arthritis, other arthritic condition, lupus, systemic lupus erythematosus (SLE), skin-related disease, psoriasis, eczema, dermatitis, atopic dermatitis, pain, pulmonary disorder, lung inflammation, adult respiratory distress syndrome (ARDS), pulmonary sarcoidosis, chronic pulmonary inflammatory disease, chronic obstructive pulmonary disease (COPD), cardiovascular disease, artherosclerosis, myocardial infarction, congestive heart failure, cardiac reperfusion injury, inflammatory bowel disease, Crohn's disease, ulcerative colitis, irritable bowel syndrome, asthma, sjogren syndrome, autoimmunity thyroid disease, urticaria (cnidosis), multiple sclerosis, scleroderma, organ transplantation rejection, heteroplastic graft, idiopathic thrombocytopenic purpura (ITP), Parkinson's disease, Alzheimer's disease, diabetic associated disease, inflammation, pelvic inflammatory disease, allergic rhinitis, allergic bronchitis, allergic sinusitis, leukemia, lymphoma, B-cell lymphoma, T-cell lymphoma, myeloma, acute lymphoid leukemia (ALL), chronic lymphoid leukemia (CLL), acute myeloid leukemia (AML), chronic myeloid leukemia (CML), hairy cell leukemia, Hodgkin's disease, non-Hodgkin's lymphoma, multiple myeloma, myelodysplastic syndrome (MDS), myeloproliferative neoplasms (MPN), diffuse large B-cell lymphoma, and follicular lymphoma.

The inventive compound of formula (I) or a pharmaceutically acceptable salt thereof can provide enhanced therapeutic effects when it is administered in combination with another therapeutic agent for treating inflammatory diseases, autoimmune diseases, or immunologically mediated diseases.

Representative examples of the therapeutic agent for treating the inflammatory diseases, autoimmune diseases, or immunologically mediated diseases may include, but are not limited to, steroid drugs (e.g., prednisone, prednisolone, methyl prednisolone, cortisone, hydroxycortisone, betametasone, dexametasone and the like), methotrexates, leflunomides, anti-TNFα agents (e.g., etanercept, infliximab, adalimunab and the like), calcineurin inhibitors (e.g., tacrolimus, pimecrolimus and the like) and antihistaminic drugs (e.g., diphenhydramine, hydroxyzine, loratadine, ebastine, ketotifen, cetirizine, levocetirizine, fexofenadine and the like), and at least one therapeutic agent selected therefrom may be included in the inventive pharmaceutical composition.

The inventive compound of formula (I) or a pharmaceutically acceptable salt thereof may be administered orally or parenterally as an active ingredient in an effective amount ranging from about 0.1 to 2,000 mg/kg, preferably 1 to 1,000 mg/kg body weight per a day in case of mammals including human (of approximately 70 kg body weight) in a single to 4 divided doses per a day, or on/off schedules. The dosage of the active ingredient may be adjusted in light of various relevant factors such as the condition of the subject to be treated, type and seriousness of illness, administration rate, and opinion of doctor. In certain cases, an amount less than the above dosage may be suitable. An amount greater than the above dosage may be used unless it causes deleterious side effects and such amount can be administered in divided doses per day.

The inventive pharmaceutical composition may be formulated in accordance with any of the conventional methods in the form of tablet, granule, powder, capsule, syrup, emulsion or microemulsion for oral administration, or for parenteral administration including intramuscular, intravenous and subcutaneous routes.

The inventive pharmaceutical composition for oral administration may be prepared by mixing the active ingredient with a carrier such as cellulose, calcium silicate, corn starch, lactose, sucrose, dextrose, calcium phosphate, stearic acid, magnesium stearate, calcium stearate, gelatin, talc, surfactant, suspension agent, emulsifier and diluent. Examples of the carrier employed in the injectable composition of the present invention are water, a saline solution, a glucose solution, a glucose-like solution, alcohol, glycol, ether (e.g., polyethylene glycol 400), oil, fatty acid, fatty acid ester, glyceride, a surfactant, a suspension agent and an emulsifier.

The present invention is further described and illustrated in examples provided below, which are, however, not intended to limit the scope of the present invention.

Example 1

Preparation of N-(3-(2-(4-(4-methylpiperazin-1-yl)phenylamino)thieno[3,2-d]pyrimidine-4-yloxy)phenyl)acrylamide

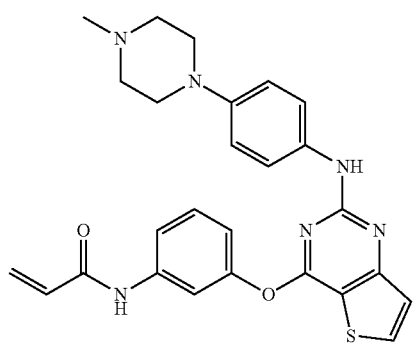 [SMILES: C=CC(=O)Nc1cccc(Oc2nc(Nc3ccc(N4CCN(C)CC4)cc3)nc3ccsc23)c1]

Step 1) Preparation of thieno[3,2-d]pyrimidine-2,4(1H,3H)-dione

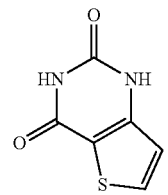 [SMILES: O=c1[nH]c(=O)c2sccc2[nH]1]

Methyl 3-aminothiophene-2-carboxylate (4.9 g, 31.3 mmol) and urea (19 g, 187 mmol) were dissolved in N,N-dimethylformamide (10 mL), the reaction temperature was raised to 190° C., followed by stirring for 12 hours. After the reaction was complete, the reaction mixture was added to 1N NaOH aqueous solution, cooled to room temperature and filtered under a reduced pressure to remove the insoluble precipitate. The filtrate was acidified (pH 2) with 2N HCl aqueous solution, and the resulting solid was filtered under a reduced pressure with washing using distilled water. The resulting solid was dried under a reduced pressure to obtain the title compound (yield: 3.2 g, 61.5%).

$^1$H-NMR (300 MHz, CDCl$_3$) δ 11.59 (s, 1H), 11.14 (s, 1H), 8.00 (d, 1H), 6.90 (d, 1H).

Step 2) Preparation of 2,4-dichlorothieno[3,2-d]pyrimidine

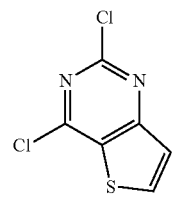 [SMILES: Clc1nc(Cl)c2sccc2n1]

The compound (3.2 g, 19.4 mmol) obtained in Step 1 was dissolved in phosphorous oxychloride (12 mL) and refluxed with stirring for 3 hours at 200° C. After the reaction was complete, the reaction mixture was cooled to room temperature and added dropwise to 4° C. distilled water with stirring vigorously. The resulting solid was filtered under a reduced pressure with washing using distilled water, and the resulting solid was dried under a reduced pressure to obtain the title compound (yield: 2.9 g, 73.3%).

$^1$H-NMR (300 MHz, DMSO-$d_6$) δ 8.74 (d, 1H), 7.78 (d, 1H).

Step 3) Preparation of 2-chloro-4-(3-nitrophenoxy)thieno[3,2-d]pyrimidine

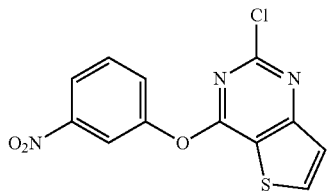

The compound (2.9 g, 14.2 mmol) obtained in Step 2 was dissolved in N,N-dimethylsulfoneamide (70 mL), and 3-nitrophenol (1.9 g, 14.2 mmol) and cesium carbonate (9.2 g, 28.4 mmol) were added thereto, followed by stirring room temperature for 1 hour. After the reaction was complete, distilled water was added to the reaction mixture, and the resulting solid was filtered under a reduced pressure with washing with distilled water. The resulting solid was dried under a reduced pressure to obtain the title compound (yield: 4.0 g, 91.8%).

$^1$H-NMR (300 MHz, CDCl$_3$) δ 8.25-8.17 (m, 2H), 8.08 (s, 1H), 7.69-7.66 (m, 2H), 7.57 (d, 1H).

Step 4) Preparation of N-(4-(4-methylpiperazin-1-yl)phenyl)-4-(3-nitrophenoxy)thieno[3,2-d]pyrimidine-2-amine

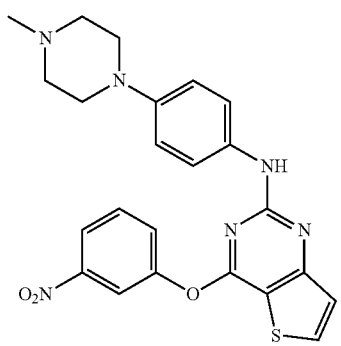

The compound (12.9 mmol) obtained in Step 3 was dissolved in 2-butanol (70 mL), and 4-(4-methylpiperazin-1-yl)benzeneamine (12.9 mmol) and trifluoroacetic acid (12.9 mmol) were added thereto. The mixture was stirred at 100° C. for 16 hours to complete the reaction, diluted with dichloromethane, and then washed with sat. NaHCO$_3$ aqueous solution. The organic layer was dried with anhydrous sodium sulfate and then filtered and distilled under a reduced pressure. The residue was separated by column chromatography (dichloromethane:methanol=20:1 (volume ratio)) to obtain the title compound (yield: 42%).

Step 5) Preparation of 4-(3-aminophenoxy)-N-(4-(4-methylpiperazin-1-yl)phenyl)thieno[3,2-d]pyrimidine-2-amine

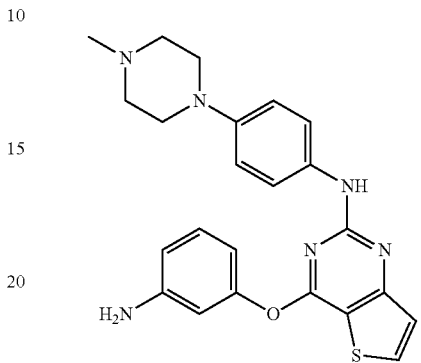

Iron (27.1 mmol) and 12 N HCl aqueous solution (2.17 mmol) were diluted with 50% ethanol aqueous solution (30 mL), followed by stirring at 100° C. for 10 min. The compound (5.42 mmol) obtained in Step 4 was dissolved in 50% ethanol aqueous solution (30 mL) and then added to the reaction flask in which iron was activated, followed by stirring at 100° C. for 1 hour. After the reaction was complete, the reaction mixture was filtered with celite to remove iron, and the filtrate was distilled under a reduced pressure. The residue was distilled with dichloromethane and washed with sat. NaHCO$_3$ aqueous solution. The organic layer was dried with anhydrous sodium sulfate and then filtered and distilled under a reduced pressure. The residue was separated by column chromatography (dichloromethane:methanol=10:1 (volume ratio)) to obtain the title compound (yield: 67.8%).

Step 6) Preparation of N-(3-(2-(4-(4-methylpiperazin-1-yl)phenylamino)thieno[3,2-d]pyrimidine-4-yloxy)phenyl)acrylamide The compound (3.69 mmol) obtained in Step 5 and NaHCO$_3$ (11.07 mmol) were distilled with tetrahydrofuran (40 mL) and distilled water (6 mL), and acryloyl chloride (3.69 mmol) was added thereto slowly at 0° C. with stirring for 15 min. After the reaction was complete, the reaction mixture was distilled with dichloromethane and then washed with sat. NaHCO$_3$ aqueous solution. The organic layer was dried with anhydrous sodium sulfate and then filtered and distilled under a reduced pressure, and the residue was separated by column chromatography (chloroform:methanol=20:1 (volume ratio)) to obtain the title compound (yield: 68.2%).

$^1$H-NMR (300 MHz, CD$_3$OD) δ 8.03 (d, 1H), 7.67 (t, 1H), 7.63 (d, 1H), 7.43 (t, 1H), 7.35 (d, 2H), 7.23 (d, 1H), 7.03 (m, 1H), 6.78 (d, 2H), 6.39 (m, 2H), 5.77 (m, 1H), 3.08 (m, 4H), 2.59 (m, 4H), 2.33 (s, 3H);

MS (ESI$^+$): m/z=487.4 [M+H]$^+$.

The procedure of Example 1 was repeated except for using various amine derivatives represented by Z—NH$_2$ (Z is the same as defined above) instead of 4-(4-methylpiperazin-1-yl)benzeneamine in Step 4 to prepare the compounds of Examples 2 to 156 which are shown in Tables 1a to 1v below.

TABLE 1a

| Example | Structure | Analysis data |
|---|---|---|
| 2 | 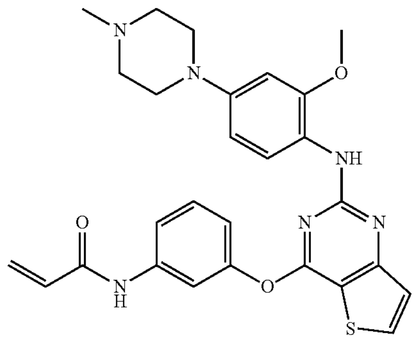 [SMILES: C=CC(=O)Nc1cccc(Oc2nc(Nc3ccc(N4CCN(C)CC4)cc3OC)nc3ccsc23)c1] | $^{1}$H-NMR (300 MHz, CDCl$_3$) δ 7.96 (m, 1H), 7.83 (d, 1H), 7.70 (d, 1H), 7.61 (s, 1H), 7.45 (m, 2H), 7.25 (m, 2H), 7.01 (m, 1H), 6.45 (d, 1H), 6.35-6.32 (m, 3H), 5.71 (dd, 1H); MS (ESI$^+$): m/z = 517.1 [M + H]$^+$. |
| 3 | 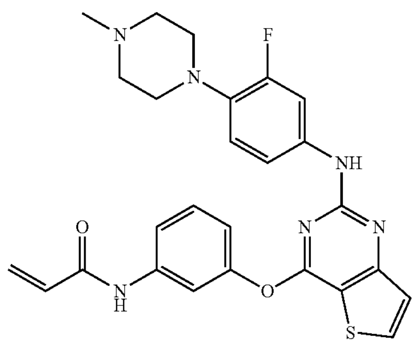 [SMILES: C=CC(=O)Nc1cccc(Oc2nc(Nc3ccc(N4CCN(C)CC4)c(F)c3)nc3ccsc23)c1] | $^{1}$H-NMR (300 MHz, CDCl$_3$) δ 7.83 (d, 1H), 7.70 (s, 1H), 7.45 (m, 1H), 7.42 (m, 1H), 7.40 (m, 1H), 7.04 (m, 2H), 6.83 (dd, 1H), 6.80 (t, 1H), 6.43 (dd, 1H), 6.27 (dd, 1H), 5.76 (dd, 1H), 3.03 (m, 4H), 2.60 (m, 4H), 2.36 (s, 3H); MS (ESI$^+$): m/z = 505.10 [M + H]$^+$. |
| 4 | 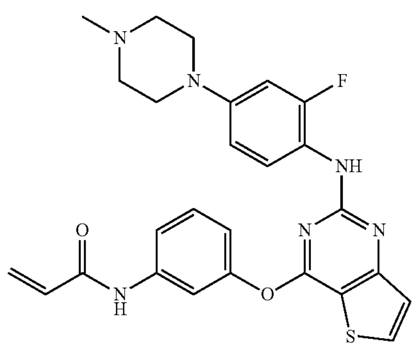 [SMILES: C=CC(=O)Nc1cccc(Oc2nc(Nc3ccc(N4CCN(C)CC4)cc3F)nc3ccsc23)c1] | $^{1}$H-NMR (300 MHz, CDCl$_3$) δ 7.99 (m, 1H), 7.87 (m, 1H), 7.73 (s, 1H), 7.46 (m, 2H), 7.29 (m, 1H), 7.00 (d, 1H), 6.79 (dd, 1H), 6.52 (t, 1H), 6.45 (dd, 1H), 6.26 (dd, 1H), 5.78 (dd, 1H), 2.86 (m, 4H), 2.57 (m, 4H), 2.35 (s, 3H); MS (ESI$^+$): m/z = 505.10 [M + H]$^+$. |
| 5 | 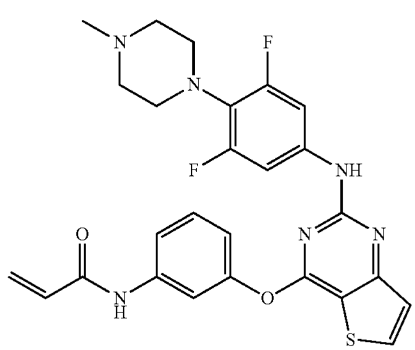 [SMILES: C=CC(=O)Nc1cccc(Oc2nc(Nc3cc(F)c(N4CCN(C)CC4)c(F)c3)nc3ccsc23)c1] | $^{1}$H-NMR (300 MHz, DMSO-d$_6$) δ 10.35 (s, 1H), 9.75 (s, 1H), 8.33 (d, 1H), 7.77 (m, 1H), 7.48 (m, 1H), 7.41 (m, 2H), 7.27 (m, 2H), 7.01 (m, H), 6.43 (m, 1H), 6.21 (dd, 1H), 5.75 (dd, 1H), 2.97 (s, 4H), 2.37 (s, 4H), 2.19 (s, 3H); MS (ESI$^+$): m/z = 523.2 [M + H]$^+$. |

TABLE 1a-continued

| Example | Structure | Analysis data |
|---|---|---|
| 6 | 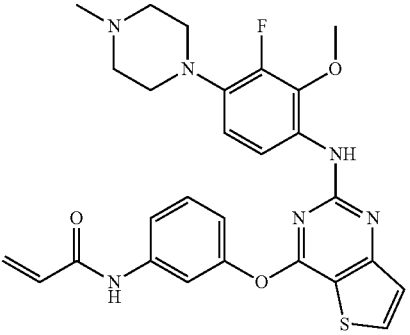 [SMILES: C=CC(=O)Nc1cccc(Oc2nc(Nc3ccc(N4CCN(C)CC4)c(F)c3OC)nc3ccsc23)c1] | ¹H-NMR (300 MHz, DMSO-d$_6$) δ 10.34 (s, NH), 8.28 (d, 1H), 8.21 (s, NH), 7.71 (s, 1H), 7.56 (d, 1H), 7.45 (t, 1H), 7.40 (d, 1H), 7.29 (d, 1H), 7.06 (d, 1H), 6.51 (t, 1H), 6.45 (m, 1H), 6.38 (d, 1H), 5.75 (d, 1H), 3.76 (s, 3H), 2.90 (br, 4H), 2.44 (br, 4H), 2.21 (s, 3H);<br>MS (ESI⁺): m/z = 535.0 [M + H]⁺. |
| 7 | 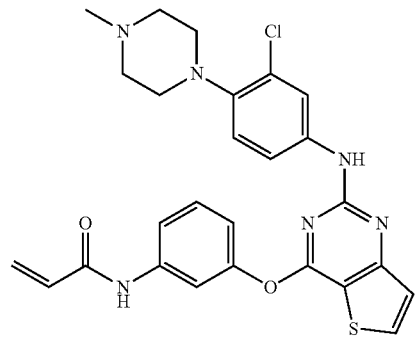 [SMILES: C=CC(=O)Nc1cccc(Oc2nc(Nc3ccc(N4CCN(C)CC4)c(Cl)c3)nc3ccsc23)c1] | ¹H-NMR (300 MHz, DMSO-d$_6$) δ 10.33 (brs, 1H), 9.51 (brs, 1H), 8.30-8.28 (m, 1H), 7.72-7.69 (m, 2H), 7.56 (m, 1H), 7.46-7.41 (m, 2H), 7.36-7.34 (m, 1H), 7.07-7.03 (m, 1H), 6.92-6.89 (m, 1H), 6.40-6.37 (m, 1H), 6.26 (m, 1H), 5.77-5.76 (m, 1H), 2.77 (m, 4H), 2.42 (m, 4H), 2.20 (s, 3H);<br>MS (ESI⁺): m/z = 521.1 [M + H]⁺. |
| 8 | 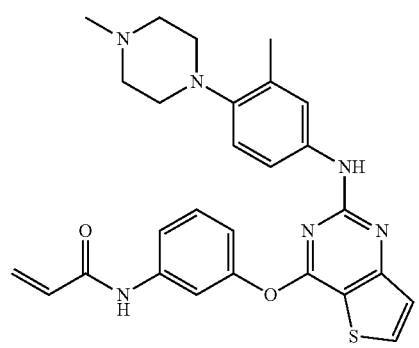 [SMILES: C=CC(=O)Nc1cccc(Oc2nc(Nc3ccc(N4CCN(C)CC4)c(C)c3)nc3ccsc23)c1] | ¹H-NMR (300 MHz, CDCl$_3$) δ 7.82 (d, 1H), 7.58 (d, 1H), 7.43 (t, 1H), 7.36 (d, 1H), 7.05 (dd, 1H), 6.80 (s, 1H), 6.77 (d, 2H), 6.45 (dd, 1H), 6.26 (d, 1H), 5.65 (dd, 1H), 3.40 (m, 4H), 2.76 (m, 4H);<br>MS (ESI⁺): m/z = 501.13 [M + H]⁺. |

TABLE 1b

| Example | Structure | Analysis data |
|---|---|---|
| 9 | 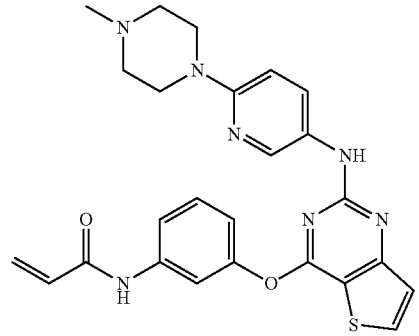 [SMILES: C=CC(=O)Nc1cccc(Oc2nc(Nc3ccc(N4CCN(C)CC4)nc3)nc3ccsc23)c1] | ¹H-NMR (300 MHz, CDCl$_3$) δ 7.83 (d, 1H), 7.70 (s, 1H), 7.45 (m, 1H), 7.42 (m, 1H), 7.40 (m, 1H), 7.04 (m, 2H), 6.83 (dd, 1H), 6.80 (t, 1H), 6.43 (dd, 1H), 6.27 (dd, 1H), 5.76 (dd, 1H), 3.03 (m, 4H), 2.60 (m, 4H), 2.36 (s, 3H);<br>MS (ESI⁺): m/z = 505.10 [M + H]⁺. |

TABLE 1b-continued

| Example | Structure | Analysis data |
|---|---|---|
| 10 | 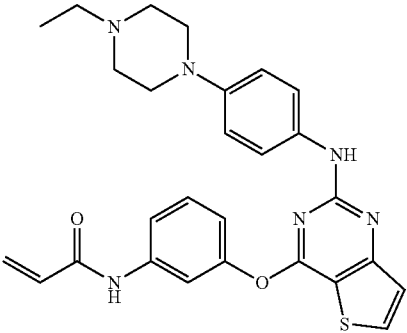 | $^1$H-NMR (300 MHz, CDCl$_3$) δ 7.81-7.79 (m, 1H), 7.59-7.49 (m, 2H), 7.42-7.37 (t, 1H), 7.29-7.26 (m, 2H), 7.05-7.02 (m, 1H), 6.90 (m, 1H), 6.81-6.78 (m, 2H), 6.46-6.40 (m, 1H), 6.28-6.24 (m, 1H), 5.78-5.75 (m, 1H), 3.14-3.11 (m, 4H), 2.63-2.60 (m, 4H), 2.52-2.45 (q, 2H), 1.16-1.11 (t, 3H); MS (ESI$^+$): m/z = 501.2 [M + H]$^+$. |
| 11 | 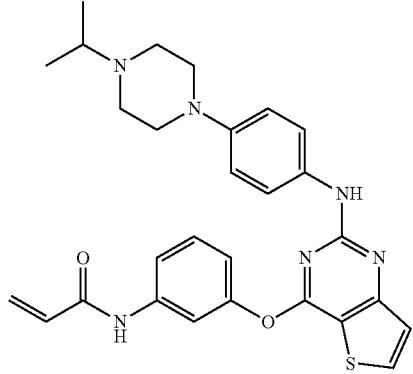 | $^1$H-NMR (300 MHz, CD$_3$OD) δ 8.04 (d, 1H), 7.66 (m, 2H), 7.43 (t, 1H), 7.33 (d, 2H), 7.23 (d, 1H), 7.03 (m, 1H), 6.78 (d, 2H), 6.40 (m, 2H), 5.78 (m, 1H), 3.08 (m, 4H), 2.65 (m, 5H). 1.14 (d, 6H); MS (ESI$^+$): m/z = 515.04 [M + H]$^+$. |
| 12 | 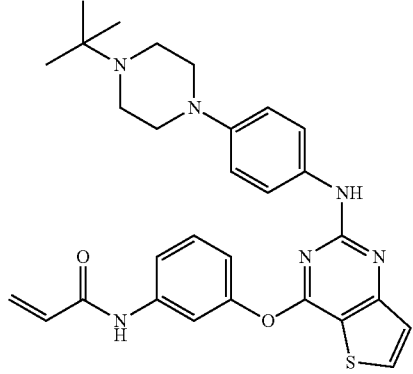 | $^1$H-NMR (300 MHz, CDCl$_3$) δ 7.81-7.80 (d, 1H), 7.60-7.57 (m, 2H), 7.44-7.32 (m, 4H), 7.06-7.03 (m, 1H), 6.83-6.78 (m, 3H), 6.47-6.41 (m, 1H), 6.29-6.20 (m, 1H), 5.80-5.76 (m, 1H), 3.13-3.10 (m, 4H), 2.76-2.73 (m, 4H), 1.12 (s, 9H); (ESI$^+$): m/z = 529 [M + H]$^+$. |
| 13 | 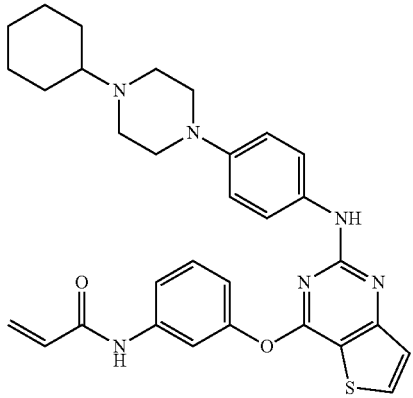 [SMILES: C=CC(=O)Nc1cccc(Oc2nc(Nc3ccc(N4CCN(C5CCCCC5)CC4)cc3)nc3ccsc23)c1] | $^1$H-NMR (300 MHz, DMSO-d$_6$) δ; 10.35 (s, 1H), 9.21 (s, 2H), 8.24 (d, 1H), 7.68 (m, 1H), 7.61 (d, 1H), 7.44 (d, 1H), 7.38 (m, 2H), 7.29 (d, 1H), 7.03 (dd, 1H), 6.68 (d, 1H), 6.37 (dd, 1H), 6.27 (dd, 1H), 5.76 (dd, 1H), 2.93 (m, 4H), 2.58 (m, 4H), 2.25 (m, 1H), 1.74 (m, 5H), 1.19 (m, 5H); MS (ESI$^+$): m/z = 555 [M + H]$^+$. |

TABLE 1b-continued
| Example | Structure | Analysis data |
|---|---|---|
| 14 | 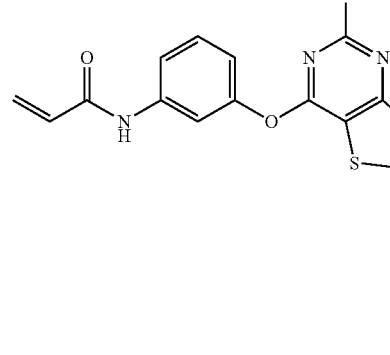 | $^1$H-NMR (300 MHz, CD$_3$OD) δ 8.08-8.06 (d, 1H), 7.69-7.68 (m, 2H), 7.49-7.43 (t, 1H), 7.39-7.36 (d, 2H), 7.27-7.25 (d, 1H), 7.07 (m, 1H), 6.83-6.80 (d, 2H), 6.45-6.40 (m, 2H), 5.82-5.78 (m, 1H), 4.73-4.70 (t, 1H), 4.57-4.54 (t, 1H), 3.14-3.11 (m, 4H), 2.85-2.82 (t, 1H), 2.75-2.72 (m, 5H). |
| 15 | 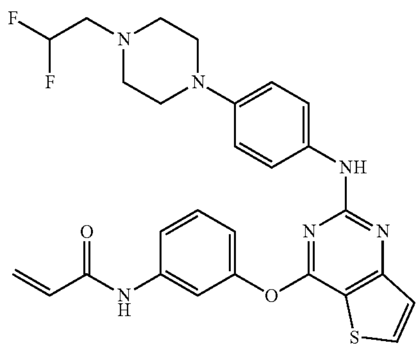 [SMILES: C=CC(=O)Nc1cccc(Oc2nc(Nc3ccc(N4CCN(CC(F)F)CC4)cc3)nc3ccsc23)c1] | $^1$H-NMR (300 MHz, DMSO-d$_6$) δ 10.3 (s, 1H), 9.21 (s, 1H), 8.24 (d, 1H), 7.68 (m, 1H), 7.60 (d, 2H), 7.46 (s, 1H), 7.43 (m, 2H), 7.29 (d, 1H), 7.04 (dd, 1H), 6.69 (d, 2H), 6.41 (dd, 1H), 6.27 (dd, 1H), 6.16 (t, 1H), 5.75 (dd, 1H), 2.98 (m, 4H), 2.75 (t, 2H), 2.63 (m, 4H);<br>MS (ESI$^+$): m/z = 537.2 [M + H]$^+$. |
TABLE 1c
| Example | Structure | Analysis data |
|---|---|---|
| 16 | 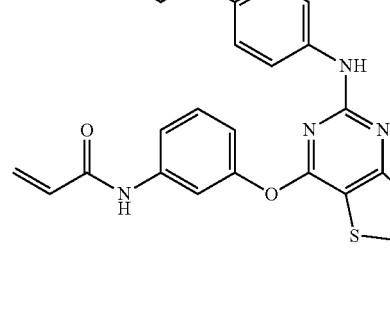 | $^1$H-NMR (300 MHz, DMSO-d$_6$) δ 10.34 (brs, 1H), 9.22 (brs, 1H), 8.26-8.24 (d, 1H), 7.67 (s, 1H), 7.62-7.60 (m, 1H), 7.46-7.39 (m, 3H), 7.31-7.29 (d, 1H), 7.05-7.02 (m, 1H), 6.70-6.68 (m, 2H), 6.46-6.37 (m, 1H), 6.27-6.21 (m, 1H), 5.77-5.74 (m, 1H), 3.25-3.15 (q, 2H), 2.98 (m, 4H), 2.71 (m, 4H);<br>MS (ESI$^+$): m/z = 554.97 [M + H]$^+$. |

TABLE 1c-continued
| Example | Structure | Analysis data |
| --- | --- | --- |
| 17 | 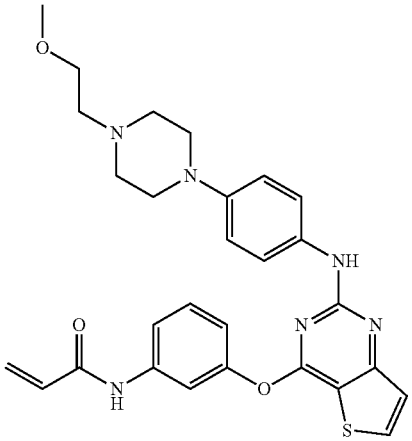 [SMILES: C=CC(=O)Nc1cccc(Oc2nc(Nc3ccc(N4CCN(CCOC)CC4)cc3)nc3ccsc23)c1] | ¹H-NMR (300 MHz, CDCl₃) δ 7.81-7.79 (m, 1H), 7.55 (m, 2H), 7.42-7.32 (m, 3H), 7.23 (m, 1H), 7.05-7.02 (m, 1H), 6.90 (brs, 1H), 6.80-6.77 (m, 2H), 6.46-6.40 (m, 1H), 6.27-6.24 (m, 1H), 5.78-5.74 (m, 1H), 3.57-3.53 (t, 2H), 3.37 (s, 3H), 3.14-3.10 (m, 4H), 2.67-2.61 (m, 4H);<br>MS (ESI⁺): m/z = 531.3 [M + H]⁺. |
| 18 | 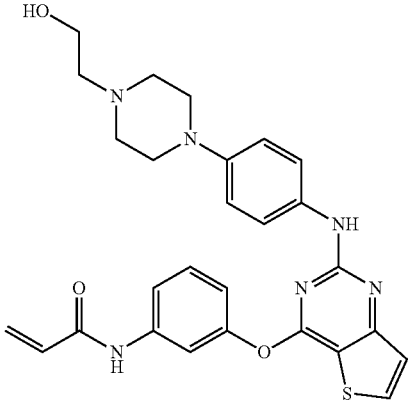 [SMILES: C=CC(=O)Nc1cccc(Oc2nc(Nc3ccc(N4CCN(CCO)CC4)cc3)nc3ccsc23)c1] | ¹H-NMR (300 MHz, DMSO-d₆) δ 10.35 (brs, 1H), 9.22 (brs, 1H), 8.27-8.25 (d, 1H), 7.70-7.69 (m, 1H), 7.64-7.61 (m, 1H), 7.48-7.40 (m, 2H), 7.32-7.30 (m, 1H), 7.07-7.04 (m, 1H), 6.72-6.69 (m, 2H), 6.43-6.39 (m, 1H), 6.29-6.24 (m, 1H), 5.80-5.76 (m, 1H), 4.43-4.39 (t, 1H), 3.56-3.50 (q, 2H), 2.98 (m, 4H), 2.51 (m, 4H), 2.44-2.40 (t, 2H);<br>MS (ESI⁺): m/z = 517.2 [M + H]⁺. |
| 19 | 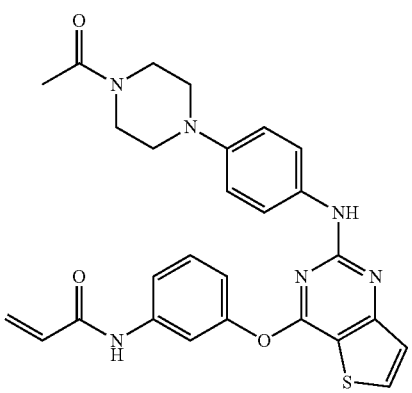 [SMILES: C=CC(=O)Nc1cccc(Oc2nc(Nc3ccc(N4CCN(C(C)=O)CC4)cc3)nc3ccsc23)c1] | ¹H-NMR (300 MHz, DMSO-d₆) δ 10.33 (brs, 1H), 9.41 (brs, 1H), 8.26-8.24 (m, 1H), 7.68-7.67 (m, 1H), 7.63-7.60 (m, 1H), 7.46-7.41 (m, 3H), 7.31-7.29 (m, 1H), 7.06-7.03 (m, 1H), 6.74-6.71 (m, 2H), 6.41-6.38 (m, 1H), 6.28-6.27 (m, 1H), 5.78-5.74 (m, 1H), 3.54-3.52 (m, 4H), 2.99-2.96 (m, 2H), 2.93-2.89 (m, 2H), 2.01 (s, 3H);<br>MS (ESI⁺): m/z = 515.3 [M + H]⁺. |

TABLE 1c-continued

| Example | Structure | Analysis data |
|---|---|---|
| 20 | 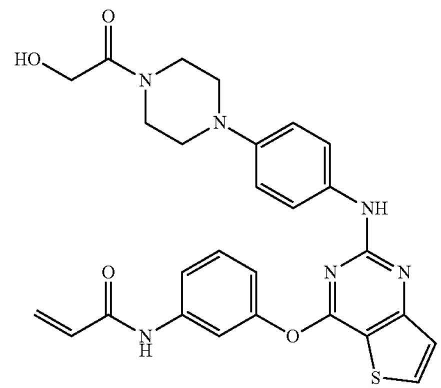 [SMILES: C=CC(=O)Nc1cccc(Oc2nc(Nc3ccc(N4CCN(C(=O)CO)CC4)cc3)nc3ccsc23)c1] | $^1$H-NMR (300 MHz, DMSO-d$_6$) δ 10.45 (brs, 1H), 9.59 (brs, 1H), 8.31-8.30 (m, 1H), 7.88 (s, 1H), 7.80-7.43 (m, 4H), 7.37 (d, 1H), 7.19-7.09 (m, 3H), 6.51-6.43 (m, 1H), 6.29-6.23 (m, 1H), 5.79-5.76 (m, 1H), 4.10 (s, 2H), 3.51-3.49 (m, 4H), 3.21-3.18 (m, 4H); MS (ESI$^+$): m/z = 531.1 [M + H]$^+$. |
| 21 | 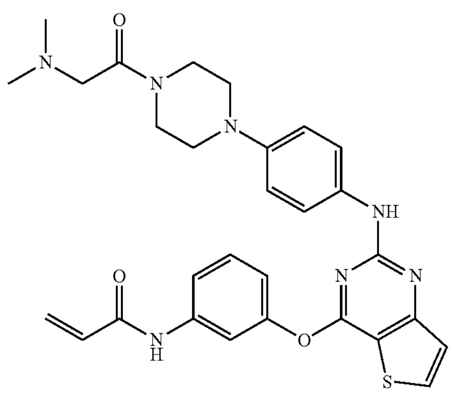 [SMILES: C=CC(=O)Nc1cccc(Oc2nc(Nc3ccc(N4CCN(C(=O)CN(C)C)CC4)cc3)nc3ccsc23)c1] | $^1$H-NMR (300 MHz, CDCl$_3$) δ 7.85 (d, 1H), 7.65-7.60 (m, 2H), 7.42-7.35 (m, 4H), 7.26 (d, 1H), 7.03-7.01 (m, 1H), 6.80.-6.87 (m, 2H), 6.41-6.41 (m, 1H), 6.35-6.32 (m, 1H), 5.77-5.74 (m, 1H), 3.83-3.74 (m, 4H), 3.19 (s, 2H), 3.15-3.06 (m, 4H), 2.32 (s, 6H); MS (ESI$^+$): m/z = 558.2 [M + H]$^+$. |
| 22 | 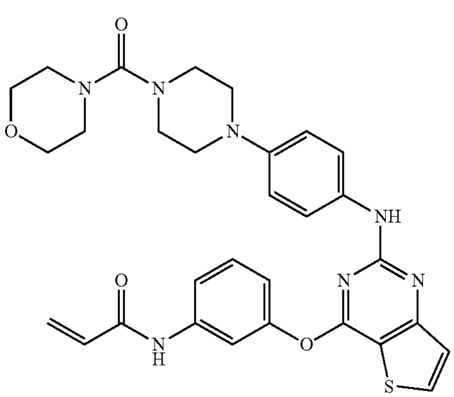 [SMILES: C=CC(=O)Nc1cccc(Oc2nc(Nc3ccc(N4CCN(C(=O)N5CCOCC5)CC4)cc3)nc3ccsc23)c1] | $^1$H-NMR (300 MHz, DMSO-d$_6$) δ 10.38 (brs, 1H), 9.28 (brs, 1H), 8.31-8.26 (m, 2H), 7.68-7.62 (m, 2H), 7.48-7.43 (m, 2H), 7.31 (d, 1H), 7.08 (d, 1H), 6.74-6.71 (m, 2H), 6.49-6.40 (m, 1H), 6.29-6.23 (m, 1H), 5.79-5.76 (m, 1H), 3.59-3.57 (m, 4H), 3.34-3.28 (m, 4H), 3.18-3.17 (m, 4H), 3.05-2.97 (m, 4H); MS (ESI$^+$): m/z = 586.2 [M + H]$^+$. |

TABLE 1d

| Example | Structure | Analysis data |
| --- | --- | --- |
| 23 | 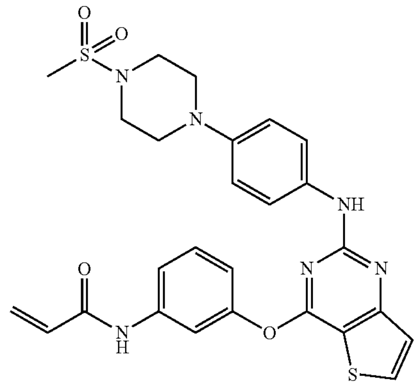 [SMILES: C=CC(=O)Nc1cccc(Oc2nc(Nc3ccc(N4CCN(S(C)(=O)=O)CC4)cc3)nc3ccsc23)c1] | ¹H-NMR (300 MHz, DMSO-d₆) δ 10.34 (brs, 1H), 9.26 (brs, 1H), 8.27-8.25 (m, 1H), 7.68 (s, 1H), 7.63-7.60 (m, 1H), 7.47-7.42 (m, 3H), 7.32-7.30 (m, 1H), 7.07-7.03 (m, 1H), 6.77-6.74 (m, 2H), 6.42-6.38 (m, 1H), 6.28-6.22 (m, 2H), 5.79-5.75 (m, 1H), 3.22-3.20 (m, 4H), 3.10-3.08 (m, 4H), 2.91 (s, 3H); MS (ESI⁺): m/z = 551.2 [M + H]⁺. |
| 24 | 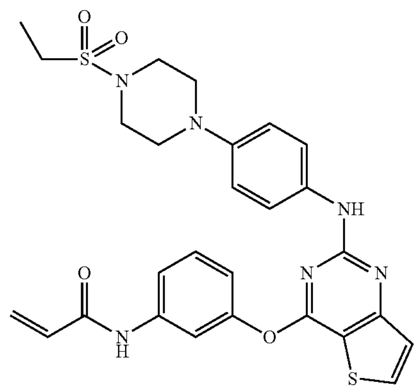 [SMILES: C=CC(=O)Nc1cccc(Oc2nc(Nc3ccc(N4CCN(S(=O)(=O)CC)CC4)cc3)nc3ccsc23)c1] | ¹H-NMR (300 MHz, DMSO-d₆) δ 10.33 (brs, 1H), 9.25 (brs, 1H), 8.26-8.24 (d, 1H), 7.68-7.67 (m, 1H), 7.62-7.59 (m, 1H), 7.47-7.41 (m, 3H), 7.31-7.29 (d, 1H), 7.06-7.03 (m, 1H), 6.75-6.72 (m, 2H), 6.43-6.38 (m, 1H), 6.28-6.27 (m, 1H), 5.78-5.74 (m, 1H), 3.27-3.26 (m, 4H), 3.12-3.06 (q, 2H), 3.06-3.03 (m, 4H), 1.24-1.29 (t, 3H); MS (ESI⁺): m/z = 565.09 [M + H]⁺. |
| 25 | 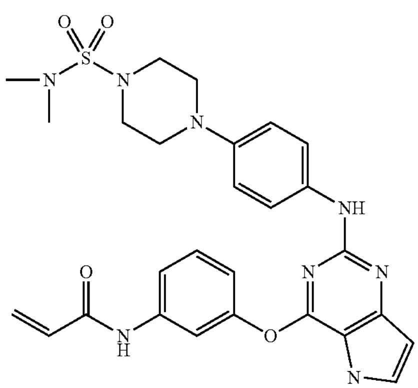 [SMILES: C=CC(=O)Nc1cccc(Oc2nc(Nc3ccc(N4CCN(S(=O)(=O)N(C)C)CC4)cc3)nc3cc[nH]c23)c1] | ¹H-NMR (300 MHz, DMSO-d₆) δ 10.33 (brs, 1H), 9.26 (brs, 1H), 8.26-8.24 (d, 1H), 7.68-7.67 (m, 1H), 7.63-7.60 (m, 1H), 7.46-7.41 (m, 3H), 7.31-7.30 (d, 1H), 7.06-7.03 (m, 1H), 6.74-6.71 (m, 2H), 6.41-6.38 (m, 1H), 6.28-6.27 (m, 1H), 5.78-5.74 (m, 1H), 3.27-3.24 (m, 4H), 3.04-3.01 (m, 4H), 2.78 (s, 6H); MS (ESI⁺): m/z = 580.08 [M + H]⁺. |
| 26 | 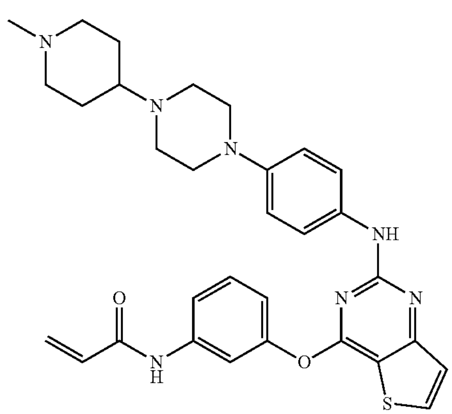 [SMILES: C=CC(=O)Nc1cccc(Oc2nc(Nc3ccc(N4CCN(C5CCN(C)CC5)CC4)cc3)nc3ccsc23)c1] | ¹H-NMR (300 MHz, CD₃OD) δ; 8.07 (d, 1H), 7.69 (m, 2H), 7.48 (t, 1H), 7.38 (d, 2H), 7.27 (d, 1H), 7.06 (dd, 1H), 6.82 (d, 2H), 6.44-6.40 (m, 2H), 5.82-5.78 (dd, 1H), 3.12 (m, 4H), 3.08 (m, 2H), 2.77 (m, 4H), 2.29 (s, 1H), 2.09 (m, 3H), 1.98 (m, 2H), 1.64 (m, 2H) MS (ESI⁺): m/z = 570.3 [M + H]⁺. |

TABLE 1d-continued

| Example | Structure | Analysis data |
|---|---|---|
| 27 | 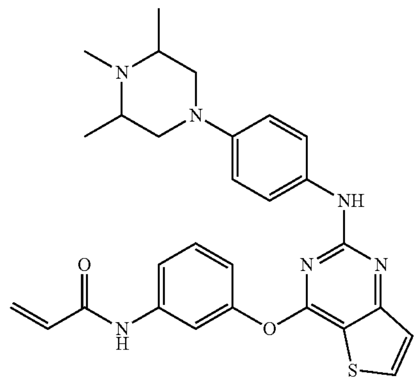 [SMILES: C=CC(=O)Nc1cccc(Oc2nc(Nc3ccc(N4CC(C)N(C)C(C)C4)cc3)nc3ccsc23)c1] | ¹H-NMR (300 MHz, CDCl₃) δ 10.35 (s, NH), 9.35 (s, NH), 8.25 (d, 1H), 7.68 (m, 2H), 7.41 (m, 3H), 7.30 (d, 1H), 7.04 (d, 1H), 6.71 (d, 2H), 6.45 (dd, 1H), 6.24 (d, 1H), 5.76 (d, 1H), 3.38 (m, 2H), 2.30 (m, 4H), 2.17 (s, 3H), 1.05 (s, 6H); MS (ESI⁺): m/z = 515.2 [M + H]⁺. |
| 28 | 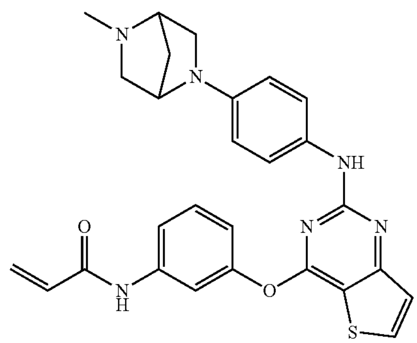 [SMILES: C=CC(=O)Nc1cccc(Oc2nc(Nc3ccc(N4CC5CC4CN5C)cc3)nc3ccsc23)c1] | ¹H-NMR (300 MHz, CDCl₃) δ 7.80-7.78 (d, 1H), 7.59 (m, 1H), 7.52 (m, 1H), 7.44-7.22 (m, 3H), 7.06-7.03 (m, 1H), 6.74 (s, 1H), 6.55-6.41 (m, 3H), 6.28-6.15 (m, 1H), 5.80-5.76 (m, 1H), 4.14 (s, 1H), 3.51-3.25 (m, 4H), 2.94-2.91 (m, 1H), 2.63-2.60 (m, 1H), 2.35 (s, 3H), 1.98-1.80 (m, 3H), 1.25-1.12 (m, 2H); MS (ESI⁺): m/z = 499 [M + H]⁺. |
| 29 | 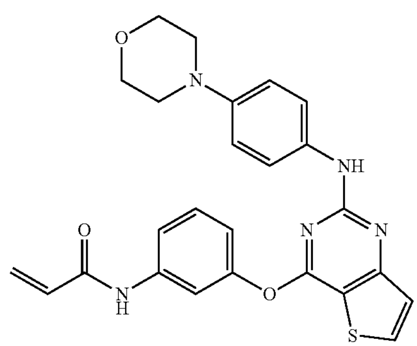 | ¹H-NMR (300 MHz, DMSO-d₆) δ 10.37 (s, 1H), 9.27 (s, 1H), 8.29 (d, 1H), 7.71 (d, 1H), 7.64 (d, 1H), 7.48 (m, 2H), 7.34 (d, 1H), 7.08 (d, 1H), 6.74 (m, 2H), 6.45 (m, 1H), 6.27 (d, 1H), 5.80 (d, 1H), 3.72 (m, 4H), 2.98 (m, 4H); MS (ESI⁺): m/z = 474.4 [M + H]⁺. |

TABLE 1e

| Example | Structure | Analysis data |
|---|---|---|
| 30 | 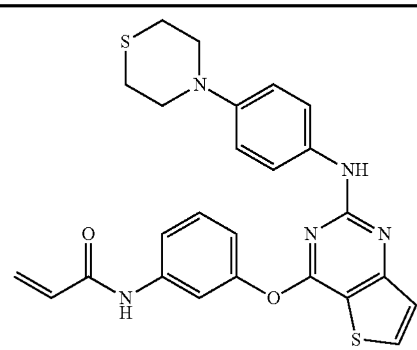 | ¹H-NMR (300 MHz, CDCl₃) δ 7.82 (d, 1H), 7.58 (d, 1H), 7.43 (m, 1H), 7.36 (d, 1H), 7.05 (dd, 1H), 6.80 (s, 2H), 6.77 (d, 2H), 6.45 (dd, 1H), 6.26 (d, 1H), 5.65 (dd, 1H), 3.40 (m, 4H), 2.76 (m, 4H); MS (ESI⁺): m/z = 490.05 [M + H]⁺. |

TABLE 1e-continued

| Example | Structure | Analysis data |
| --- | --- | --- |
| 31 | 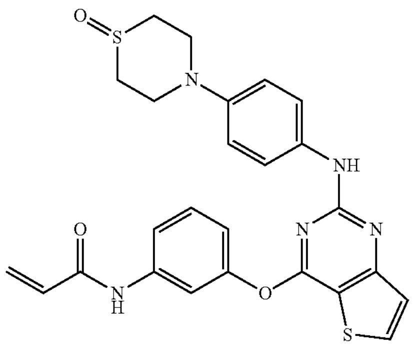 [SMILES: C=CC(=O)Nc1cccc(Oc2nc(Nc3ccc(N4CCS(=O)CC4)cc3)nc3ccsc23)c1] | $^1$H-NMR (300 MHz, DMSO-d$_6$) δ 8.04 (brs, 1H), 7.84-7.82 (d, 1H), 7.61-7.57 (m, 2H), 7.43-7.37 (t, 1H), 7.36-7.33 (m, 2H), 7.25 (s, 1H), 7.05-7.02 (m, 2H), 6.79-6.76 (m, 2H), 6.41 (m, 1H), 6.32-6.29 (m, 1H), 5.77-5.74 (m, 1H), 3.88-3.79 (m, 2H), 3.42-3.34 (m, 2H), 2.91-2.81 (m, 4H); MS (ESI$^+$): m/z = 506.00 [M + H]$^+$. |
| 32 | 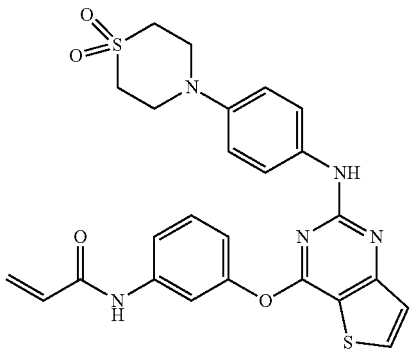 [SMILES: C=CC(=O)Nc1cccc(Oc2nc(Nc3ccc(N4CCS(=O)(=O)CC4)cc3)nc3ccsc23)c1] | $^1$H-NMR (300 MHz, CDCl$_3$) δ 7.86-7.84 (s, 1H), 7.60-7.53 (m, 3H), 7.46-7.43 (m, 1H), 7.40-7.36 (m, 2H), 7.07-7.04 (m, 1H), 6.99 (s, 1H), 6.79-6.76 (m, 2H), 6.48-6.43 (m, 1H), 6.30-6.21 (m, 1H), 5.82-5.78 (m, 1H), 3.74 (m, 4H), 3.11-3.10 (m, 4H); MS (ESI$^+$): m/z = 522.02 [M + H]$^+$. |
| 33 | 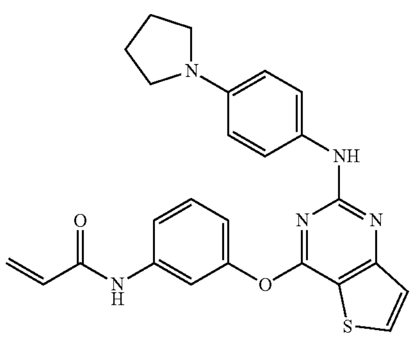 [SMILES: C=CC(=O)Nc1cccc(Oc2nc(Nc3ccc(N4CCCC4)cc3)nc3ccsc23)c1] | $^1$H-NMR (300 MHz, DMSO-d$_6$) δ 10.34 (brs, 1H), 9.04 (s, 1H), 8.22 (d, 1H), 7.69 (s, 1H), 7.61-7.55 (m, 1H), 7.45-7.26 (m, 4H), 7.08-7.03 (m, 1H), 6.47-6.23 (m, 6H), 5.76 (d, 1H), 3.16-3.12 (m, 4H), 1.91 (m, 4H); MS (ESI$^+$): m/z = 458.16 [M + H]$^+$. |
| 34 | 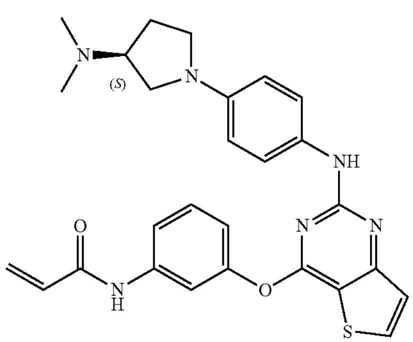 | $^1$H-NMR (300 MHz, CDCl$_3$) δ 7.79 (d, 1H), 7.54 (m, 1H), 7.35 (m, 2H), 7.32 (m, 2H), 7.25 (m, 1H), 7.23 (d, 1H), 6.75 (s, 1H), 6.46 (m, 1H), 6.25 (m, 1H), 5.77 (d, 1H), 3.35 (m, 1H), 3.11 (t, 1H), 2.83 (m, 2H), 2.32 (s, 6H), 2.18 (m, 1H), 1.72 (m, 1H); MS (ESI$^+$): m/z = 501.4 [M + H]$^+$. |

TABLE 1e-continued

| Example | Structure | Analysis data |
|---|---|---|
| 35 | 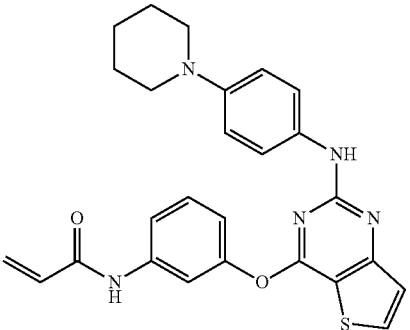 | ¹H-NMR (300 MHz, DMSO-$d_6$) δ 10.33 (s, NH), 9.17 (s, NH), 8.25 (d, 1H), 7.73 (d, 2H), 7.59 (d, 1H), 7.47 (m, 3H), 7.30 (d, 1H), 7.23 (s, 1H), 7.07 (d, 1H), 6.92 (s, 1H), 6.47 (m, 2H), 6.27 (d, 1H), 5.77 (d, 1H), 5.00 (m, 1H), 3.62 (m, 1H), 3.44 (m, 3H), 2.51 (m, 2H); MS (ESI⁺): m/z = 524.2 [M + H]⁺. |
| 36 | 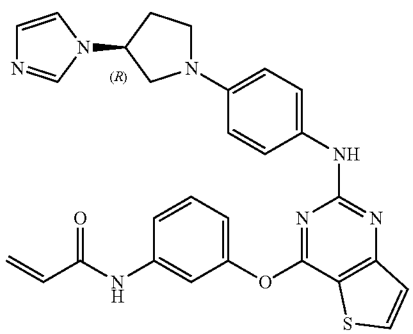 | ¹H-NMR (300 MHz, DMSO-$d_6$) δ 10.33 (s, NH), 9.13 (s, NH), 8.24 (d, 1H), 7.96 (s, 1H), 7.72 (t, 1H), 7.68 (d, 1H), 7.45 (t, 1H), 7.43 (m, 2H), 7.29 (d, 1H), 7.22 (s, 1H), 7.05 (dd, 1H), 6.91 (s, 1H), 6.42 (m, 3H), 6.26 (dd, 1H), 5.75 (dd, 1H), 4.99 (m, 1H), 3.61 (m, 1H), 3.41 (m, 3H), 2.49 (m, 2H); MS (ESI⁺): m/z = 524.2 [M + H]⁺ |

TABLE 1f

| Example | Structure | Analysis data |
|---|---|---|
| 37 | 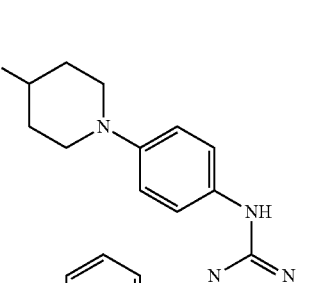 | ¹H-NMR (300 MHz, DMSO-$d_6$) δ 10.36 (s, 1H), 9.22 (s, 1H), 8.26 (d, 1H), 7.70 (s, 1H), 7.64 (m, 1H), 7.47 (d, 1H), 7.41 (m, 2H), 7.31 (d, 1H), 7.05 (d, 1H), 6.71 (m, 2H), 6.44 (m, 1H), 6.26 (m, 1H), 5.78 (m, 1H), 2.96 (t, 4H), 1.59 (m, 4H), 1.50 (m, 2H); MS (ESI⁺): m/z = 472.10 [M + H]⁺. |
| 38 | 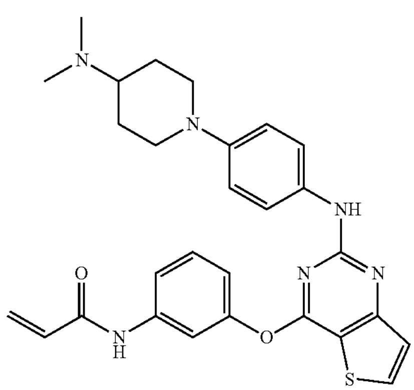 | ¹H-NMR (300 MHz, DMSO-$d_6$) δ 10.37 (s, 1H), 9.27 (s, 1H), 8.29 (d, 1H), 7.71 (d, 1H), 7.64 (d, 1H), 7.48 (m, 2H), 7.34 (d, 1H), 7.08 (d, 1H), 6.74 (m, 2H), 6.45 (m, 1H), 6.27 (d, 1H), 5.80 (d, 1H), 3.72 (m, 4H), 2.98 (m, 4H); MS (ESI⁺): m/z = 515 [M + H]⁺. |

TABLE 1f-continued

| Example | Structure | Analysis data |
|---|---|---|
| 39 | 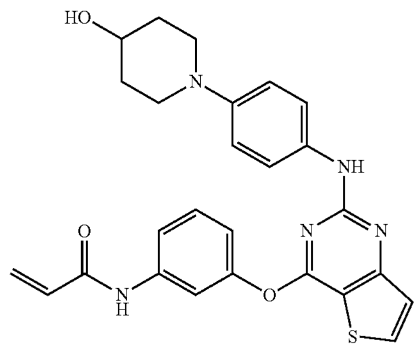 [SMILES: C=CC(=O)Nc1cccc(Oc2nc(Nc3ccc(N4CCC(O)CC4)cc3)nc3ccsc23)c1] | $^1$H-NMR (300 MHz, DMSO-d$_6$) δ 10.39 (s, 1H), 9.25 (s, 1H), 8.29 (d, 1H), 7.73 (m, 1H), 7.66 (m, 1H), 7.49 (d, 1H), 7.44 (m, 2H), 7.34 (d, 1H), 7.09 (m, 1H), 6.73 (m, 2H), 6.47 (m, 1H), 6.30 (m, 1H), 5.81 (m, 1H), 4.67 (d, 1H), 3.59 (m, 1H), 3.40 (m, 2H), 2.71 (m, 2H), 1.82 (m, 2H), 1.50 (m, 2H); MS (ESI$^+$): m/z = 488.4 [M + H]$^+$. |
| 40 | 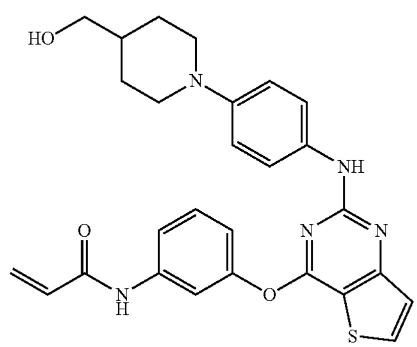 [SMILES: C=CC(=O)Nc1cccc(Oc2nc(Nc3ccc(N4CCC(CO)CC4)cc3)nc3ccsc23)c1] | $^1$H-NMR (300 MHz, CD$_3$OD) δ 8.05 (S, 1H), 7.63 (d, 1H), 7.34 (m, 3H), 6.97 (d, 2H), 6.70 (S, 2H), 6.28 (m, 2H), 5.69 (d, 1H), 3.49 (s, 2H), 3.01 (m, 4H) 1.58 (m, 1H), 134 (m, 4H); MS (ESI$^+$): m/z = 501.1 [M + H]$^+$. |
| 41 | 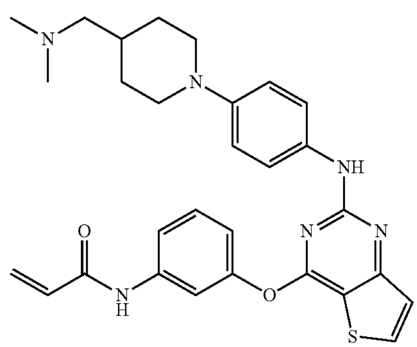 [SMILES: C=CC(=O)Nc1cccc(Oc2nc(Nc3ccc(N4CCC(CN(C)C)CC4)cc3)nc3ccsc23)c1] | $^1$H-NMR (300 MHz, CDCl$_3$) δ 7.80 (d, 1H), 7.61 (s, 1H), 7.56 (s, 1H), 7.48 (s, 1H), 7.44 (t, 1H), 7.40 (d, 2H), 7.25 (m, 1H), 7.05 (m, 1H), 6.82 (m, 3H), 6.45 (d, 1H), 6.30 (m, 1H), 5.77 (m, 1H), 3.55 (d, 2H), 2.62 (t, 2H), 2.27 (s, 6H), 2.20 (d, 2H), 1.82 (m, 3H), 1.37 (m, 2H); MS (ESI$^+$): m/z = 529 [M + H]$^+$. |
| 42 | 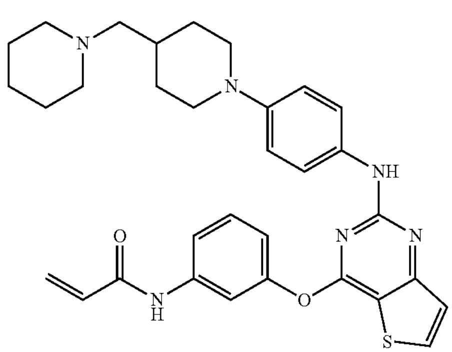 [SMILES: C=CC(=O)Nc1cccc(Oc2nc(Nc3ccc(N4CCC(CN5CCCCC5)CC4)cc3)nc3ccsc23)c1] | $^1$H-NMR (300 MHz, DMSO-d$_6$) δ 10.35 (s, 1H), 9.20 (s, 1H), 8.25 (d, 1H), 7.68 (m, 1H), 7.61 (m, 1H), 7.44 (t, 1H), 7.37 (m, 2H), 7.30 (d, 1H), 7.05 (m, 1H), 6.68 (m, 2H), 6.43 (m, 1H), 6.25 (m, 1H), 5.77 (m, 1H), 3.48 (d, 2H), 2.55 (m, 2H), 2.34 (m, 4H), 2.17 (d, 2H), 1.85 (m, 2H), 1.57 (m, 5H), 1.42 (m, 4H); MS (ESI$^+$): m/z = 569 [M + H]$^+$. |

TABLE 1f-continued

| Example | Structure | Analysis data |
|---|---|---|
| 43 | (structure) | $^1$H-NMR (300 MHz, CD$_3$OD) δ 8.04 (s, 1H), 7.66 (s, 1H), 7.35 (m, 3H), 7.03 (d, 2H), 6.81 (d, 2H), 6.38 (m, 2H), 5.78 (d, 1H), 3.50 (t, 2H), 3.01 (m, 4H) 1.49 (m, 1H), 1.43 (m, 2H), 1.34 (m, 4H); MS (ESI$^+$): m/z = 515.2 [M + H]$^+$. |

TABLE 1g

| Example | Structure | Analysis data |
|---|---|---|
| 44 | (structure) | $^1$H-NMR (300 MHz, DMSO-d$_6$) δ 12.17 (brs, 1H), 10.31 (brs, 1H), 9.23 (brs, 1H), 8.25 (d, 1H), 7.69 (s, 1H), 7.62 (d, 1H), 7.47-7.38 (m, 3H), 7.30 (d, 1H), 7.04 (d, 1H), 6.70 (d, 2H), 6.44-6.38 (m, 1H), 6.25 (dd, 1H), 5.78 (d, 1H), 3.42 (d, 2H), 2.48-2.35 (m, 3H), 1.89-1.85 (m, 2H), 1.63-1.56 (m, 2H); MS (ESI$^+$): m/z = 516.16 [M + H]$^+$. |
| 45 | (structure) | $^1$H-NMR (300 MHz, DMSO) δ 10.35 (s, NH), 9.22 (s, NH), 8.31 (d, 1H), 7.69 (s, 1H), 7.48 (d, 2H), 7.39-7.31 (m, 3H), 7.28 (d, 1H), 7.07 (m, 1H), 6.73 (d, 2H), 6.48 (m, 1H), 6.29 (m, 1H), 5.79 (m, 1H), 3.55 (d, 2H), 3.04 (s, 3H), 2.72 (s, 3H), 2.67-2.57 (m, 3H), 1.67 (m, 4H); MS (ESI$^+$): m/z = 543.0 [M + H]$^+$. |

TABLE 1g-continued

| Example | Structure | Analysis data |
|---|---|---|
| 46 | 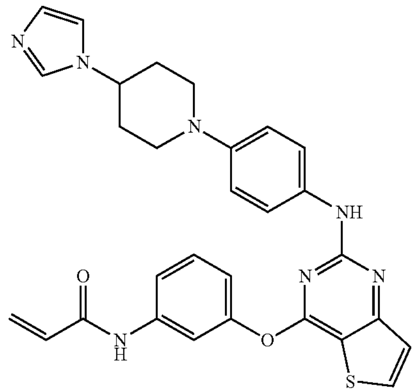 [SMILES: C=CC(=O)Nc1cccc(Oc2nc(Nc3ccc(N4CCC(n5ccnc5)CC4)cc3)nc3ccsc23)c1] | ¹H-NMR (300 MHz, CD3OD) δ 8.08 (d, 1H), 7.80 (s, 1H), 7.68 (m, 2H), 7.43 (t, 1H), 7.39 (m, 2H), 7.27 (m, 2H), 7.06 (d, 1H), 7.03 (s, 1H), 6.87 (d, 2H), 6.44 (m, 2H), 5.81 (m, 1H), 4.23 (m, 1H), 3.68 (d, 2H), 2.84 (t, 2H), 2.24 (m, 4H); MS (ESI⁺): m/z = 538.2 [M + H]⁺. |
| 47 | 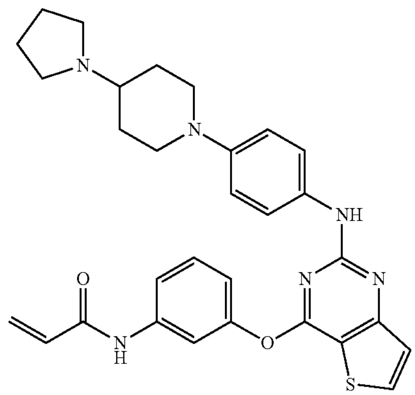 [SMILES: C=CC(=O)Nc1cccc(Oc2nc(Nc3ccc(N4CCC(N5CCCC5)CC4)cc3)nc3ccsc23)c1] | ¹H-NMR (300 MHz, CDCl3) δ 8.40 (s, NH), 7.77 (d, 1H), 7.68 (s, 1H), 7.63 (d, 1H), 7.33 (t, 1H), 7.32 (d, 2H), 7.21 (d, 1H), 7.11 (s, NH), 7.01 (d, 1H), 6.98 (d, 2H), 6.43 (m, 2H), 5.68 (m, 1H), 3.49 (m, 2H), 2.73 (m, 4H), 2.56 (t, 2H), 2.27 (m, 1H), 2.04 (m, 2H), 1.92 (m, 4H), 1.74 (m, 2H); MS (ESI⁺): m/z = 541.0 [M + H]⁺. |
| 48 | 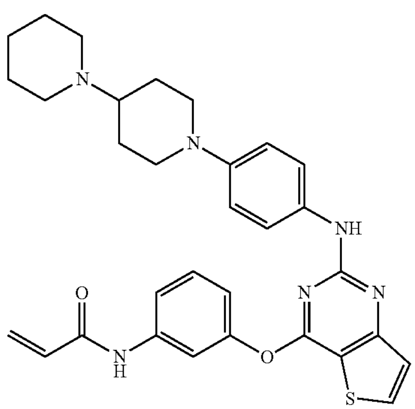 [SMILES: C=CC(=O)Nc1cccc(Oc2nc(Nc3ccc(N4CCC(N5CCCCC5)CC4)cc3)nc3ccsc23)c1] | ¹H-NMR (300 MHz, CD₃OD) δ 8.05 (d, 1H), 7.64 (d, 2H), 7.47 (t, 1H), 7.35 (d, 2H), 7.23 (d, 1H), 7.04 (d, 1H), 6.81 (d, 2H), 6.40 (m, 2H), 5.77 (dd, 1H), 4.78 (m, 2H), 3.61 (m, 2H), 3.25 (m, 2H), 2.67 (m, 2H), 2.56 (m, 2H), 2.46 (m, 1H), 2.01 (m, 2H), 1.71 (m, 2H), 1.51 (m, 2H); MS (ESI⁺): m/z = 555.0 [M + H]⁺. |
| 49 | 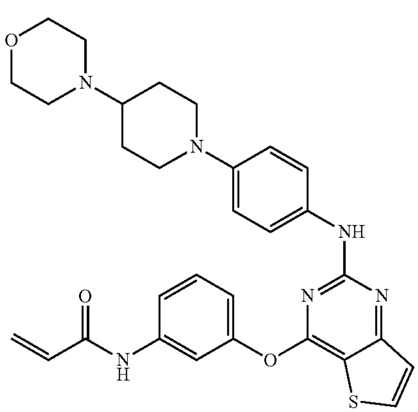 [SMILES: C=CC(=O)Nc1cccc(Oc2nc(Nc3ccc(N4CCC(N5CCOCC5)CC4)cc3)nc3ccsc23)c1] | ¹H-NMR (300 MHz, DMSO-d₆) δ 10.3 (s, 1H), 9.13 (s, 1H), 8.17 (d, 1H), 7.65 (s, 1H), 7.53 (d, 1H), 7.34 (d, 1H), 7.32 (m, 2H), 7.29 (d, 1H), 6.98 (d, 1H), 6.63 (d, 2H), 6.34 (dd, 1H), 6.21 (d, 1H), 3.50 (m, 4H), 3.43 (m, 1H), 3.20 (brs, 1H); MS (ESI⁺): m/z = 556.68 [M + H]⁺. |

TABLE 1g-continued

| Example | Structure | Analysis data |
|---|---|---|
| 50 | 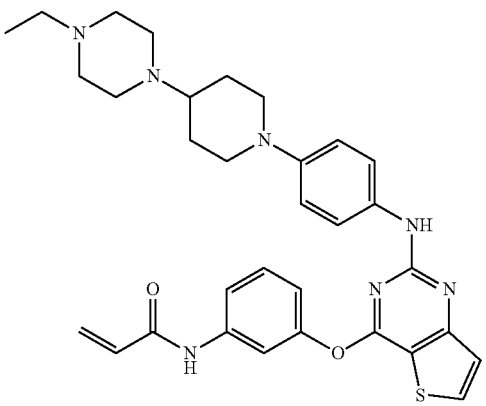 [SMILES: C=CC(=O)Nc1cccc(Oc2nc(Nc3ccc(N4CCC(N5CCN(CC)CC5)CC4)cc3)nc3ccsc23)c1] | $^1$H-NMR (300 MHz, DMSO-d$_6$) δ 10.34 (s, 1H), 9.23 (s, 1H), 8.25 (d, 1H), 7.68 (s, 1H), 7.62 (d, 1H), 7.45 (d, 1H), 7.40 (m, 2H), 7.30 (d, 1H), 7.04 (m, 1H), 6.70 (m, 2H), 6.43 (m, 1H), 6.26 (m, 1H), 5.77 (m, 1H), 3.46 (m, 2H), 2.56 (m, 1H), 2.50 (m, 6H), 2.33 (m, 4H), 2.29 (m, 2H), 1.80 (m, 2H), 1.48 (m, 2H), 0.97 (t, 3H); MS (ESI$^+$): m/z = 584.3 [M + H]$^+$. |

TABLE 1h

| Example | Structure | Analysis data |
|---|---|---|
| 51 | 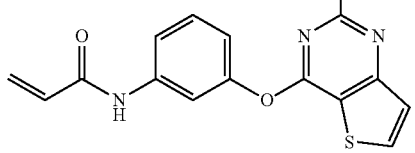 | $^1$H-NMR (300 MHz, CDCl$_3$) δ 7.85 (d, 1H), 7.67 (s, 1H), 7.56 (m, 1H), 7.43 (m, 3H), 7.31 (s, 1H), 7.21 (m, 2H), 7.06 (d, 1H), 6.46 (m, 1H), 6.27 (m, 1H), 5.98 (m, 1H), 5.78 (d, 1H), 3.12 (m, 2H), 2.69 (t, 2H), 2.57 (m, 2H), 2.42 (s, 3H); MS (ESI$^+$): m/z = 484.1 [M + H]$^+$. |
| 52 | 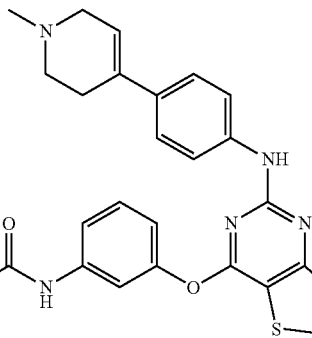 | $^1$H-NMR (300 MHz, CDCl$_3$) δ 8.13 (s, 1H), 7.83 (d, 1H), 7.76 (s, 1H), 7.52 (m, 1H), 7.39 (t, 1H), 7.34 (d, 2H), 7.25 (d, 1H), 7.11 (s, 1H), 7.02 (d, 3H), 6.36 (m, 2H), 5.74 (d, 1H), 3.01 (m, 2H), 2.41 (m, 1H), 2.37 (s, 3H), 2.31 (m, 2H), 2.09 (m, 2H), 1.85 (m, 2H); MS (ESI$^+$): m/z = 486.2 [M + H]$^+$. |
| 53 | 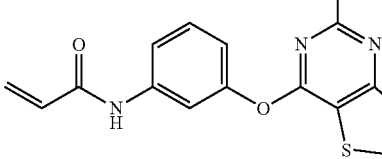 | $^1$H-NMR (3(00 MHz, CDCl$_3$) δ 8.27 (s, 1H), 7.81 (d, 1H), 7.75 (s, 1H), 7.51 (d, 1H), 7.33 (m, 3H), 7.25 (d, 1H), 7.14 (s, 1H), 7.02 (s, 2H), 6.99 (s, 1H), 6.38 (m, 2H). 5.71 (m, 1H), 3.11 (m. 2H), 2.51 (q, 2H), 2.44 (m, 1H), 2.07 On. 2H), 1.80 (m, 4H), 1.16 (t, 3H); MS (ESI$^+$): m/z = 500.2 [M + H]$^+$. |

TABLE 1h-continued
| Example | Structure | Analysis data |
|---|---|---|
| 54 | 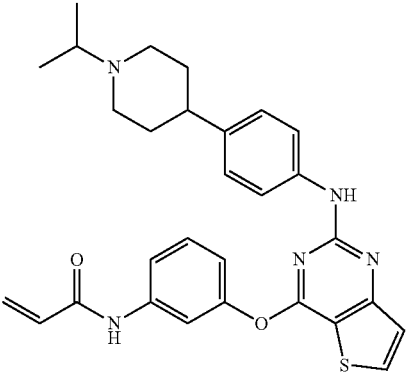 [SMILES: C=CC(=O)Nc1cccc(Oc2nc(Nc3ccc(C4CCN(C(C)C)CC4)cc3)nc3ccsc23)c1] | ¹H-NMR (300 MHz, CDCl₃) δ 9.63 (s, 1H), 8.21 (s, 1H), 7.84 (d, 1H), 7.48 (d, 1H), 7.35 (t, 1H), 7.20 (m, 4H), 6.94 (m, 3H), 6.67 (m, 1H), 6.39 (m, 1H), 5.65 (m, 1H), 3.35 (m, 2H), 3.28 (m, 1H), 2.67 (m, 2H), 2.50 (m, 1H), 2.40 (m, 2H), 1.84 (m, 2H), 1.35 (d, 6H); MS (ESI⁺): m/z = 514.2 [M + H]⁺. |
| 55 | 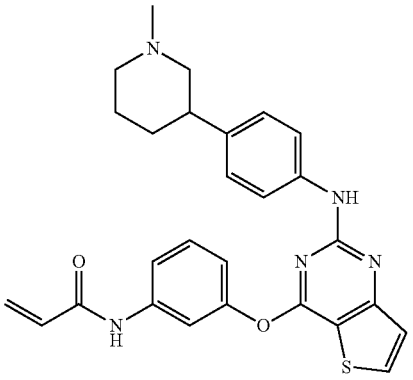 [SMILES: C=CC(=O)Nc1cccc(Oc2nc(Nc3ccc(C4CCCN(C)C4)cc3)nc3ccsc23)c1] | ¹H-NMR (300MHz, CDCl₃) δ 7.83 (d, 1H), 7.78 (s, 1H), 7.65 (s, 1H), 7.56 (d, 1H), 7.43 (m, 3H), 7.27 (d, 1H), 7.11 (s, 1H), 7.04 (m, 3H), 6.45 (m, 1H), 6.27 (m, 1H), 5.76 (m, 1H), 2.94 (m, 2H), 2.79 (m, 1H), 2.32 (s, 3H), 2.02 (m, 3H), 1.85 (m, 2H), 1.36 (m, 1H); MS (ESI⁺): m/z = 486.2 [M + H]⁺. |
| 56 | 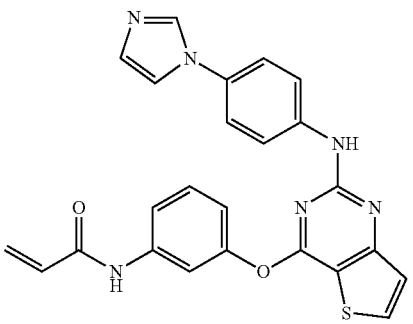 [SMILES: C=CC(=O)Nc1cccc(Oc2nc(Nc3ccc(-n4ccnc4)cc3)nc3ccsc23)c1] | ¹H-NMR (300 MHz, DMSO-d₆) δ 10.39 (s, NH), 9.67 (s, NH), 8.33 (d, 1H), 8.08 (s, 1H), 7.73 (m, 3H), 7.58 (m, 2H), 7.47 (t, 1H), 7.34 (m, 3H), 7.08 (m, 2H), 6.43 (m, 1H), 6.27 (m, 1H), 5.74 (m, 1H); MS (ESI⁺): m/z = 455.0 [M + H]⁺. |
| 57 | 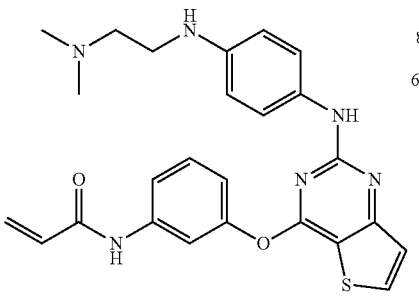 | ¹H-NMR (300 MHz, DMSO-d₆) δ 10.34 (s, 1H), 9.08 (s, 1H), 8.35 (d, 1H), 8.23 (m, 1H), 7.65 (d, 1H), 7.57 (m, 1H), 7.42 (m, 2H), 7.28 (d, 1H), 7.04 (m, 1H), 6.42 (m, 2H), 6.28 (m, 2H), 6.02 (d, 1H), 5.74 (dd, 1H), 2.67 (m, 4H), 2.16 (m, 2H), 1.84 (m, 2H), 1.33 (m, 2H), 0.97 (m, 6H) MS (ESI⁺): m/z = 475.2 [M + H]⁺. |

TABLE 1i

| Example | Structure | Analysis data |
|---|---|---|
| 58 | 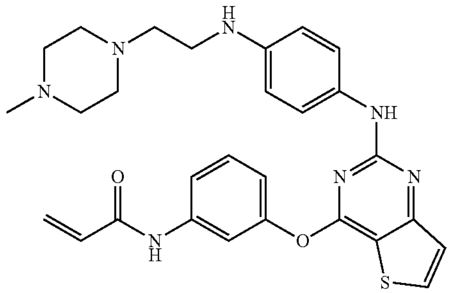 [SMILES: C=CC(=O)Nc1cccc(Oc2nc(Nc3ccc(NCCN4CCN(C)CC4)cc3)nc3ccsc23)c1] | ¹H-NMR (300 MHz, DMSO-d₆) δ 10.34 (s, 1H), 9.02 (s, 1H), 8.22 (d, 1H), 7.68 (d, 1H), 7.62 (m, 1H), 7.44 (m, 1H), 7.27 (m, 2H), 7.04 (m, H), 6.42 (m, 3H), 6.24 (dd, 1H), 5.76 (dd, 1H), 3.03 (m, 2H), 2.49~2.32 (m, 10H), 2.15 (s, 3H); MS (ESI⁺): m/z = 530.2 [M + H]⁺. |
| 59 | 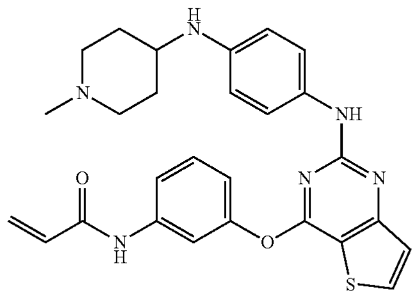 [SMILES: C=CC(=O)Nc1cccc(Oc2nc(Nc3ccc(NC4CCN(C)CC4)cc3)nc3ccsc23)c1] | ¹H-NMR (300 MHz, DMSO-d₆) δ 10.36 (s, 1H), 9.00 (s, 1H), 8.23 (d, 1H), 7.63 (m, 2H), 7.40 (m, 2H), 7.27 (m, 2H), 7.08 (m, 1H), 6.87 (m, 1H), 6.44 (m, 2H), 6.29 (d, 1H), 5.77 (d, 1H), 5.00 (d, 1H), 3.05 (m, 1H), 2.70 (m, 2H), 2.16 (s, 3H), 1.95 (m, 2H), 1.82 (m, 2H), 1.31 (m, 2H); MS (ESI⁺): m/z = 501.2 [M + H]⁺. |
| 60 | 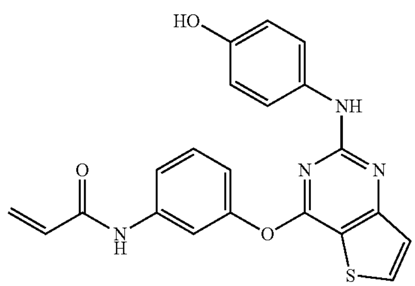 [SMILES: C=CC(=O)Nc1cccc(Oc2nc(Nc3ccc(O)cc3)nc3ccsc23)c1] | ¹H-NMR (300 MHz, DMSO-d₆) δ 10.39 (brs, 1H), 9.12 (brs, 1H), 8.97 (brs, 1H), 8.26 (d, 1H), 7.73 (s, 1H), 7.61 (d, 1H), 7.49-7.31 (m, 4H), 7.10-7.06 (m, 1H). 6.57-6.41 (m, 3H), 6.30-6.25 (m, 1H), 5.81-5.77 (m, 1H); MS (ESI⁺): m/z = 405.09 [M + H]⁺. |
| 61 | 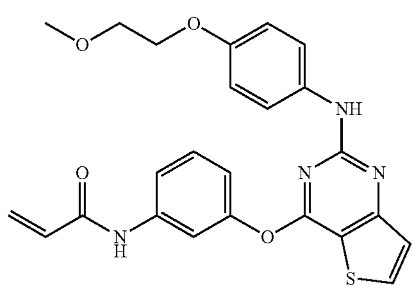 [SMILES: C=CC(=O)Nc1cccc(Oc2nc(Nc3ccc(OCCOC)cc3)nc3ccsc23)c1] | ¹H-NMR (300 MHz, DMSO-d₆) δ 10.34 (s, NH), 9.30 (s, NH), 8.28 (d, 1H), 7.72 (s, 1H), 7.60 (dd, 1H), 7.48-7.43 (m, 3H), 7.32 (d, 1H), 7.08 (dd, 1H), 6.72 (d, 2H), 6.44 (m, 1H), 6.29 (m, 1H), 5.79 (m, 1H), 4.00 (m, 2H), 3.63 (m, 2H), 3.27 (s, 3H); MS (ESI⁺): m/z = 463.2 [M + H]⁺. |
| 62 | 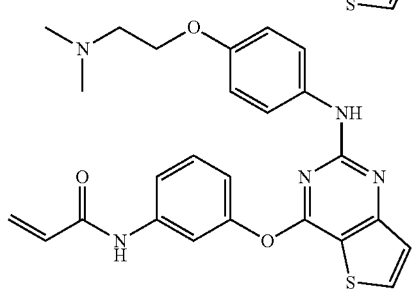 | ¹H-NMR (300 MHz, DMSO-d₆) δ 10.37 (s, 1H), 9.31 (s, 1H), 8.28 (d, 1H), 7.72 (s, 1H), 7.59 (d, 1H), 7.44 (m, 3H), 7.33 (d, 1H), 7.07 (d, 1H), 6.69 (d, 2H), 6.39 (dd, 1H), 6.29 (d, 1H), 5.79 (d, 1H), 3.95 (t, 2H), 2.60 (t, 2H), 2.22 (s, 6H); MS (ESI⁺): m/z = 476.2 [M + H]⁺. |

TABLE 1i-continued

| Example | Structure | Analysis data |
|---|---|---|
| 63 | 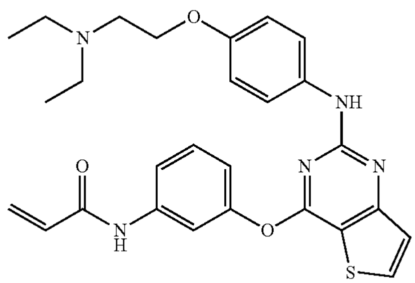 [SMILES: C=CC(=O)Nc1cccc(Oc2nc(Nc3ccc(OCCN(CC)CC)cc3)nc3ccsc23)c1] | ¹H-NMR (300 MHz, DMSO-d6) δ 10.36 (s, 1H), 9.30 (s, 1H), 8.27 (d, 1H), 7.72 (s, 1H), 7.60 (d, 1H), 7.45 (m, 3H), 7.32 (d, 1H), 7.07 (d, 1H), 6.69 (d, 2H), 6.41 (dd, 1H), 6.25 (d, 1H), 5.76 (d, 1H), 3.90 (t, 2H), 3.34 (m, 4H), 2.70 (t, 2H), 2.50 (m, 4H), 1.03 (s, 6H);<br>MS (ESI⁺): m/z = 504.2 [M + H]⁺. |
| 64 | 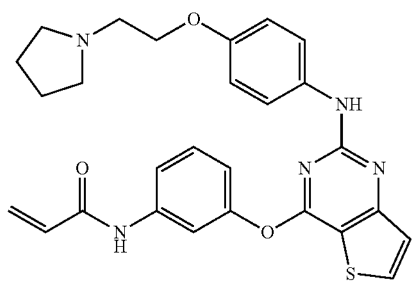 [SMILES: C=CC(=O)Nc1cccc(Oc2nc(Nc3ccc(OCCN4CCCC4)cc3)nc3ccsc23)c1] | ¹H-NMR (300 MHz, DMSO-d₆) δ 10.38 (s, 1H), 9.33 (s, 1H), 8.27 (d, 1H), 7.72 (s, 1H), 7.60 (d, 1H), 7.47 (m, 3H), 7.33 (d, 1H), 7.05 (d, 1H), 6.70 (m, 2H), 6.44 (dd, 1H), 6.25 (d, 1H), 5.77 (d, 1H), 3.95 (t, 2H), 2.72 (t, 2H), 2.50 (m, 4H), 1.67 (m, 4H);<br>MS (ESI⁺): m/z = 502.2 [M + H]⁺. |

TABLE 1j

| Example | Structure | Analysis data |
|---|---|---|
| 65 | 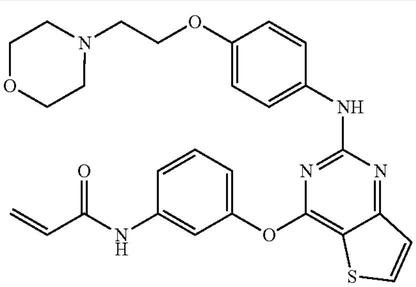 [SMILES: C=CC(=O)Nc1cccc(Oc2nc(Nc3ccc(OCCN4CCOCC4)cc3)nc3ccsc23)c1] | ¹H-NMR (300 MHz, CDCl₃) δ 8.14 (s, 1H), 7.80 (d, 1H), 7.61 (s, 1H), 7.48 (d, 1H), 7.34 (m, 3H), 7.24 (m, 2H), 6.99 (d, 1H), 6.72 (d, 2H), 6.39 (d, 1H), 6.25 (dd, 2H), 5.72 (d, 1H), 4.03 (t, 2H), 3.71 (m, 4H), 2.75 (t, 2H), 2.56 (m, 4H);<br>MS (ESI⁺): m/z = 518.4 [M + H]⁺. |
| 66 | 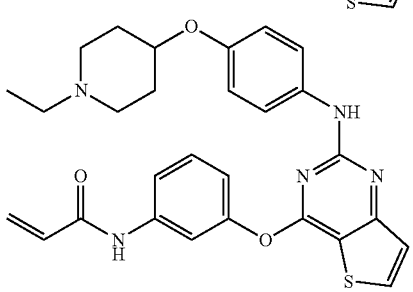 | ¹H-NMR (300 MHz, CDCl₃) δ 7.82 (d, 1H), 7.63 (s, 1H), 7.43 (m, 6H), 7.04 (d, 1H), 6.89 (s, 1H), 6.76 (m, 2H), 6.45 (d, 1H), 6.26 (m, 1H), 5.74 (d, 1H), 4.23 (m, 2H), 2.77 (m, 2H), 2.47 (q, 2H), 2.33 (m, 2H), 2.04 (m, 2H), 1.80 (m, 2H), 1.12 (t, 3H);<br>MS (ESI⁺): m/z = 516.3 [M + H]⁺. |
| 67 | 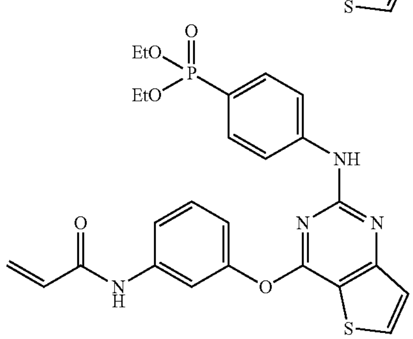 | ¹H-NMR (300 MHz, DMSO-d₆) δ 10.38 (brs, 1H), 9.92 (brs, 1H), 8.34 (d, 1H), 7.87-7.31 (m, 8H), 7.09 (d, 1H), 6.46-6.37 (m, 1H), 6.23 (d, 1H), 5.75 (d, 1H), 3.91 (t, 4H), 1.20-1.12 (m, 6H);<br>MS (ESI⁺): m/z = 525.13 [M + H]⁺. |

TABLE 1j-continued

| Example | Structure | Analysis data |
| --- | --- | --- |
| 68 | 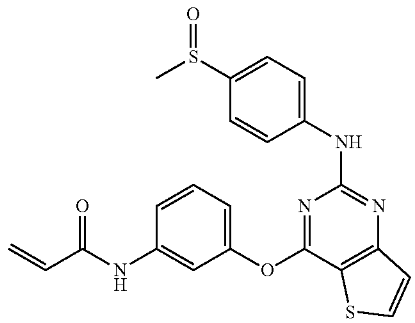 [SMILES: C=CC(=O)Nc1cccc(Oc2nc(Nc3ccc(S(C)=O)cc3)nc3ccsc23)c1] | $^1$H-NMR (300 MHz, DMSO-D$_6$) δ 10.39 (s, 1H), 9.86 (s, 1H), 8.35 (d, 1H), 7.77 (m, 2H), 7.58 (m, 1H), 7.40 (m, 4H), 7.11 (d, 1H), 6.43 (dd, 1H), 6.25 (d, 1H), 5.77 (d, 1H), 2.65 (s, 3H); MS (ESI$^+$): m/z = 451.1 [M + H]$^+$. |
| 69 | 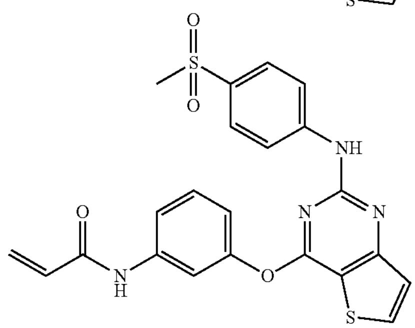 | $^1$H-NMR (300 MHz, DMSO-D$_6$) δ 10.40 (s, 1H), 10.09 (s, 1H), 8.55 (m, 1H), 7.80 (m, 3H), 7.62 (m, 3H), 7.50 (m, 2H), 7.10 (m, 1H), 6.54 (dd, 1H), 6.28 (d, 1H), 5.79 (d, 1H), 3.10 (s, 3H); MS (ESI$^+$): m/z = 467.5 [M + H]$^+$. |
| 70 | 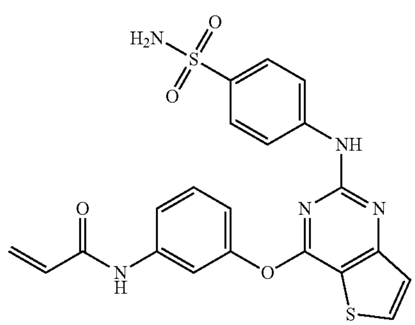 [SMILES: C=CC(=O)Nc1cccc(Oc2nc(Nc3ccc(S(N)(=O)=O)cc3)nc3ccsc23)c1] | $^1$H-NMR (300 MHz, DMSO-d$_6$) δ 10.32 (s, 1H), 9.86 (s, 1H), 8.35 (d, 1H), 7.70 (m, 3H), 7.54 (m, 3H), 7.45 (m, 2H), 7.12 (s, 2H), 6.42 (m, 1H), 6.23 (dd, 1H), 5.75 (dd, 1H); MS (ESI$^+$): m/z = 468.1 [M + H]$^+$. |
| 71 | 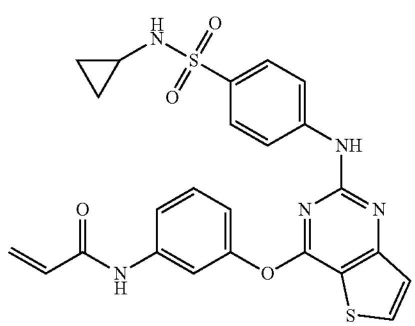 [SMILES: C=CC(=O)Nc1cccc(Oc2nc(Nc3ccc(S(=O)(=O)NC4CC4)cc3)nc3ccsc23)c1] | $^1$H-NMR (300MHz, DMSO-d$_6$) δ 10.38 (s, 1H), 10.02 (s, 1H), 8.36 (d, 1H), 7.78 (m, 3H), 7.68 (m, 2H), 7.57 (m, 2H), 7.36 (m, 1H), 7.10 (m, 1H), 6.48 (m, 1H), 6.21 (dd, 1H), 5.75 (dd, 1H), 1.99 (m, 1H), 0.41 (m, 2H), 0.34 (m, 2H); MS (ESI$^+$): m/z = 508.1 [M+H]$^+$. |

TABLE 1k

| Example | Structure | Analysis data |
|---|---|---|
| 72 | 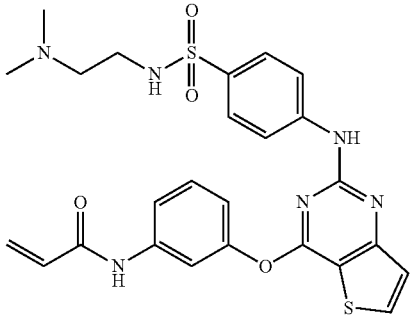 [SMILES: C=CC(=O)Nc1cccc(Oc2nc(Nc3ccc(S(=O)(=O)NCCN(C)C)cc3)nc3ccsc23)c1] | $^1$H-NMR (300 MHz, DMSO-$d_6$) δ 10.37 (s, 1H), 9.97 (s, 1H), 8.30 (d, 1H), 7.76 (m, 2H), 7.73-7.21 (m, 6H), 7.09 (m, 1H), 6.40 (m, 1H), 6.21 (dd, 1H), 5.74 (dd, 1H), 2.75 (m, 2H), 2.22 (m, 2H), 2.04 (s, 6H); MS (ESI$^+$): m/z = 539.2 [M + H]$^+$. |
| 73 | 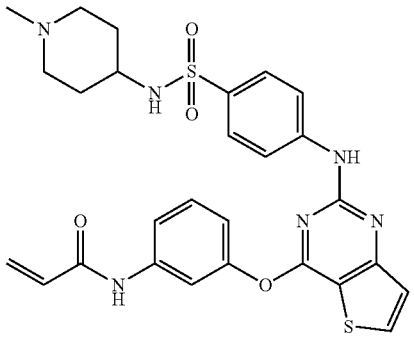 [SMILES: C=CC(=O)Nc1cccc(Oc2nc(Nc3ccc(S(=O)(=O)NC4CCN(C)CC4)cc3)nc3ccsc23)c1] | $^1$H-NMR (300 MHz, DMSO-$d_6$) δ 10.40 (s, 1H), 10.00 (s, 1H), 8.37 (d, 1H), 7.74 (m, 3H), 7.46 (m, 6H), 7.12 (d, 1H), 6.44 (dd, 1H), 6.25 (d, 1H), 5.77 (d, 1H), 2.78 (m, 1H), 2.50 (m, 2H), 1.63 (m, 2H), 1.46 (m, 2H), 1.33 (m, 2H); MS (ESI$^+$): m/z = 565.2 [M + H]$^+$. |
| 74 | 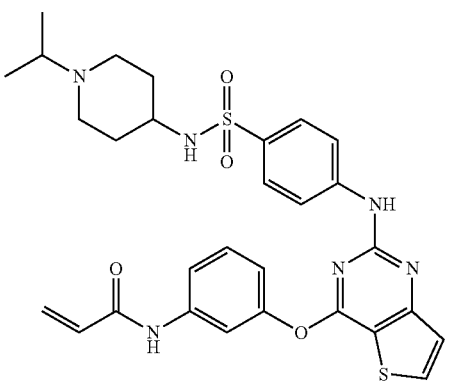 [SMILES: C=CC(=O)Nc1cccc(Oc2nc(Nc3ccc(S(=O)(=O)NC4CCN(C(C)C)CC4)cc3)nc3ccsc23)c1] | $^1$H-NMR (300 MHz, DMSO-$d_6$) δ 10.39 (s, 1H), 10.01 (s, 1H), 8.37 (d, 1H), 7.75 (m, 2H), 7.61-7.43 (m, 6H), 7.12 (m, 1H), 6.40 (m, 1H), 6.24 (dd, 1H), 5.76 (dd, 1H), 2.77 (m, 2H), 2.60 (m, 2H), 1.49 (m, 2H), 1.25 (m, 2H), 1.18 (m, 2H), 0.87 (m, 6H); MS (ESI$^+$): m/z = 593.2 [M + H]$^+$. |
| 75 | 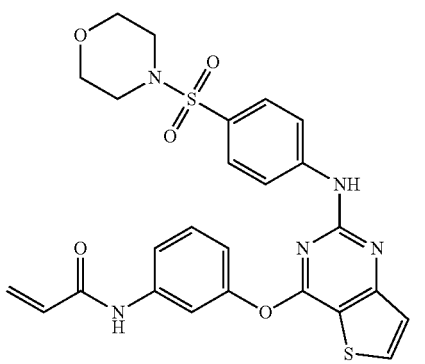 [SMILES: C=CC(=O)Nc1cccc(Oc2nc(Nc3ccc(S(=O)(=O)N4CCOCC4)cc3)nc3ccsc23)c1] | $^1$H-NMR (300 MHz, DMSO-$d_6$) δ 10.40 (s, 1H), 10.14 (s, 1H), 8.38 (d, 1H), 7.78 (m, 3H), 7.59 (m, 1H), 7.50 (m, 1H), 7.44 (m, 4H), 7.10 (m, 1H), 6.38 (m, 1H), 6.22 (dd, 1H), 5.76 (dd, 1H), 3.59 (s, 4H), 2.92 (s, 4H); MS (ESI$^+$): m/z = 538.1 [M + H]$^+$. |

TABLE 1k-continued

| Example | Structure | Analysis data |
|---|---|---|
| 76 | 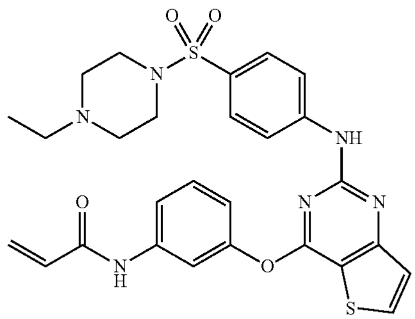 [SMILES: C=CC(=O)Nc1cccc(Oc2nc(Nc3ccc(S(=O)(=O)N4CCN(CC)CC4)cc3)nc3ccsc23)c1] | $^1$H-NMR (300 MHz, DMSO-d$_6$) δ 10.41 (s, 1H), 10.13 (s, 1H), 8.39 (d, 1H), 7.60 (m, 8H), 7.10 (m, 1H), 6.41 (m, 1H), 6.25 (m, 1H), 5.75 (m, 1H), 2.76 (m, 4H), 2.38 (m, 4H), 2.29 (q, 2H), 0.91 (t, 3H). MS (ESI$^+$): m/z = 565.4 [M + H]$^+$. |
| 77 | 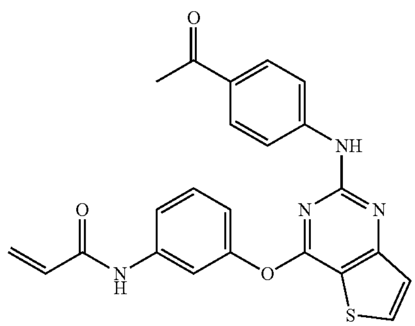 [SMILES: C=CC(=O)Nc1cccc(Oc2nc(Nc3ccc(C(C)=O)cc3)nc3ccsc23)c1] | $^1$H-NMR (300 MHz, DMSO-d$_6$) δ 10.39 (brs, 1H), 9.81 (brs, 1H), 8.37 (d, 1H), 7.78-7.71 (m, 4H), 7.62-7.58 (m, 1H), 7.52-7.49 (m, 2H), 7.17-7.09 (m, 1H), 6.48-6.39 (m, 1H), 6.25 (d, 1H), 5.77 (d, 1H), 2.46 (s, 3H); MS (ESI$^+$): m/z = 431.11 [M + H]$^+$. |
| 78 | 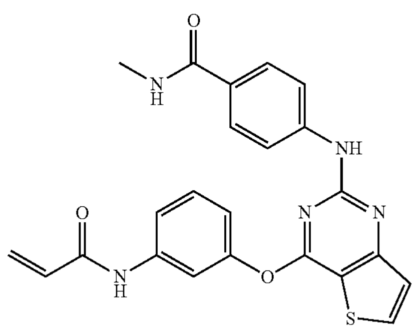 [SMILES: C=CC(=O)Nc1cccc(Oc2nc(Nc3ccc(C(=O)NC)cc3)nc3ccsc23)c1] | $^1$H-NMR (300 MHz, DMSO-d6) δ 10.39 (s, 1H), 9.79 (s, 1H), 8.34 (d, 1H), 8.16 (d, 1H), 7.67 (s, 1H), 7.57 (m, 4H), 7.46 (m, 1H), 7.42 (m, 1H), 7.11 (m, 1H), 6.48 (m, 1H), 6.28 (dd, 1H), 5.75 (dd, 1H), 2.74 (s, 3H); MS (ESI$^+$): m/z = 446.1 [M + H]$^+$. |

TABLE 1l

| Example | Structure | Analysis data |
|---|---|---|
| 79 | 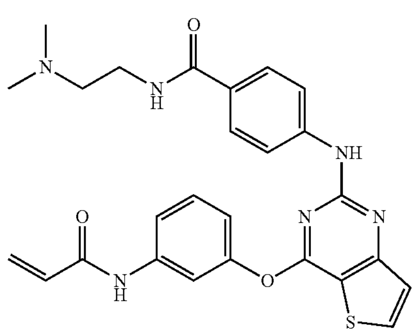 [SMILES: C=CC(=O)Nc1cccc(Oc2nc(Nc3ccc(C(=O)NCCN(C)C)cc3)nc3ccsc23)c1] | H-NMR (300 MHz, DMSO-d6) δ 10.4 (brs, 1H), 9.80 (brs, 1H), 8.36-8.34 (m, 1H), 7.87 (s, 1H), 7.64-7.43 (m, 5H), 7.41 (d, 2H), 7.13-7.10 (m, 1H), 6.46-6.41 (m, 1H), 6.28-6.23 (m, 1H), 5.79-5.75 (m, 1H), 3.31-3.17 (m, 2H), 2.63-2.50 (m, 2H), 2.31 (s, 6H); MS (ESI$^+$): m/z = 503.1 [M + H]$^+$. |

TABLE 11-continued

| Example | Structure | Analysis data |
|---|---|---|
| 80 | 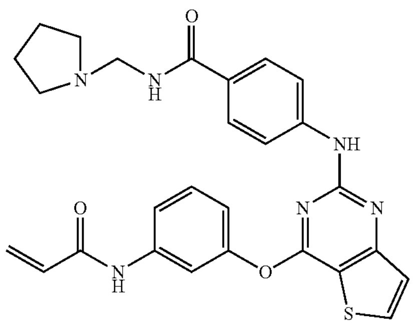 | ¹H-NMR (300 MHz, CDCl₃) δ 9.02 (s, 1H), 7.85 (d, 2H), 7.83 (d, 3H), 7.46 (d, 1H), 7.26 (t, 2H), 6.96 (d, 1H), 6.39 (d, 1H), 5.68 (dd, 1H), 3.70 (bs, 1H), 3.61 (d, 1H), 2.87 (s, 2H), 2.79 (bs, 4H), 1.89 (bs, 4H); MS (ESI⁺): m/z = 529.4 [M + H]⁺. |
| 81 | 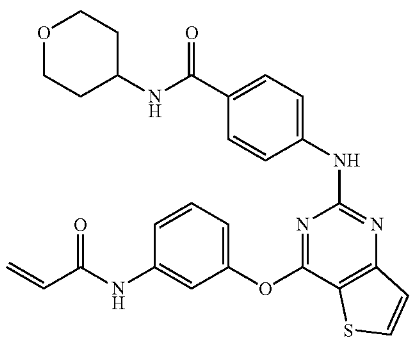 [SMILES: C=CC(=O)Nc1cccc(Oc2nc(Nc3ccc(C(=O)NC4CCOCC4)cc3)nc3ccsc23)c1] | ¹H-NMR (300 MHz, DMSO-d₆) δ 10.38 (s, 1H), 9.79 (s, 1H), 8.35 (d, 1H), 8.02 (d, 2H), 7.77 (s, 1H), 7.51 (m, 4H), 7.45 (m, 1H), 7.42 (m, 1H), 6.43 (dd, 1H), 6.28 (d, 1H), 5.78 (d, 1H), 3.96 (m, 1H), 3.86 (m, 2H), 3.38 (m, 2H), 1.74 (m, 2H), 1.58 (m, 2H); MS (ESI⁺): m/z = 516.2 [M + H]⁺. |
| 82 | 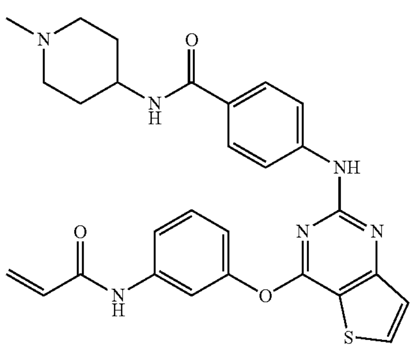 | ¹H-NMR (300 MHz, DMSO-d₆) δ 10.40 (s, 1H), 9.79 (s, 1H), 8.34 (d, 1H), 8.96 (d, 1H), 7.78 (s, 1H), 7.64 (m, 4H), 7.47 (m, 2H), 7.12 (d, 1H), 6.42 (dd, 1H), 6.28 (d, 1H), 5.77 (d, 1H), 3.69 (m, 1H), 2.75 (m, 2H), 2.16 (s, 3H), 1.92 (m, 2H), 1.73 (m, 2H), 1.55 (m, 2H); MS (ESI⁺): m/z = 529.2 [M + H]⁺. |
| 83 | 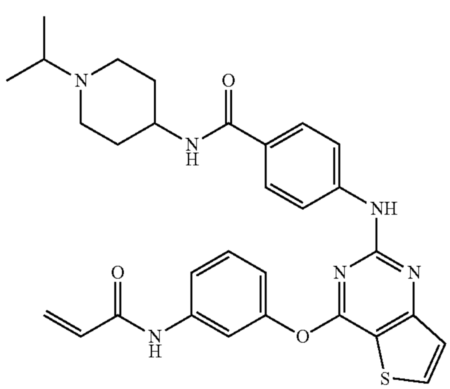 [SMILES: C=CC(=O)Nc1cccc(Oc2nc(Nc3ccc(C(=O)NC4CCN(C(C)C)CC4)cc3)nc3ccsc23)c1] | ¹H-NMR (300 MHz, DMSO-d₆) δ 10.38 (s, 1H), 9.76 (s, 1H), 8.34 (d, 1H), 7.92 (d, 1H), 7.77 (s, 1H), 7.60 (m, 5H), 7.41 (m, 2H), 6.41 (dd, 1H), 6.25 (d, 1H), 5.76 (d, 1H), 3.68 (m, 1H), 2.77 (m, 2H), 2.64 (m, 1H), 2.14 (m, 2H), 1.75 (m, 2H), 1.48 (m, 2H), 0.94 (d, 6H); MS (ESI⁺): m/z = 557.2 [M + H]⁺. |

TABLE 1l-continued

| Example | Structure | Analysis data |
| --- | --- | --- |
| 84 | 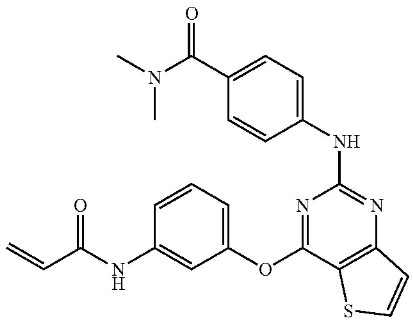 [SMILES: C=CC(=O)Nc1cccc(Oc2nc(Nc3ccc(C(=O)N(C)C)cc3)nc3ccsc23)c1] | ¹H-NMR (300 MHz, DMSO-d$_6$) δ 10.34 (s, 1H), 9.74 (s, 1H), 8.31 (d, 1H), 7.60 (s, 1H), 7.58 (m, 3H), 7.48 (m, 1H), 7.41 (m, 1H), 7.18 (m, 2H), 7.08 (m, 1H), 6.47 (m, 1H), 6.27 (dd, 1H), 5.75(dd, 1H), 2.92 (s, 6H);<br>MS (ESI⁺): m/z = 460.1 [M + H]⁺. |
| 85 | 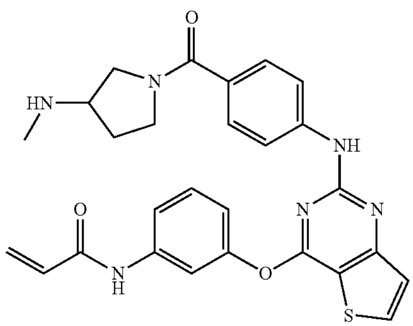 [SMILES: C=CC(=O)Nc1cccc(Oc2nc(Nc3ccc(C(=O)N4CCC(NC)C4)cc3)nc3ccsc23)c1] | ¹H-NMR (300 MHz, DMSO-d$_6$) δ 10.42 (brs, 1H), 9.78 (brs, 1H), 8.36-8.34 (m, 1H), 7.78 (s, 1H), 7.62-7.40 (m, 5H), 7.26 (d, 2H), 7.12-7.09 (m, 1H), 6.48-6.43 (m, 1H), 6.28-6.22 (m, 1H), 5.79-5.75 (m, 1H), 3.52-3.48 (m, 2H), 3.17-2.90 (m, 3H), 2.30-2.17 (m, 3H), 1.93-1.73 (m, 2H);<br>MS (ESI⁺): m/z = 515.2 [M + H]⁺. |

TABLE 1m

| Example | Structure | Analysis data |
| --- | --- | --- |
| 86 | 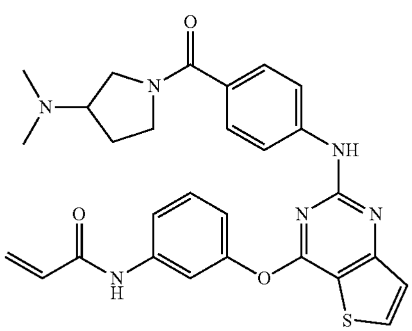 [SMILES: C=CC(=O)Nc1cccc(Oc2nc(Nc3ccc(C(=O)N4CCC(N(C)C)C4)cc3)nc3ccsc23)c1] | ¹H-NMR (300 MHz, DMSO-d$_6$) δ 10.5 (brs, 1H), 9.80 (brs, 1H), 8.30-8.20 (m, 1H), 7.78 (s, 1H), 7.60-7.40 (m, 5H), 7.35(d, 2H), 7.20 (m, 1H), 6.50-6.40 (m, 1H), 6.30-6.20 (m, 1H), 5.80-5.70 (m, 1H), 3.60-3.50 (m, 4H), 2.80-2.60 (m, 1H), 2.30-2.00 (m, 7H), 1.80-1.60 (m, 1H);<br>MS (ESI⁺): m/z = 529.1 [M + H]⁺. |
| 87 | 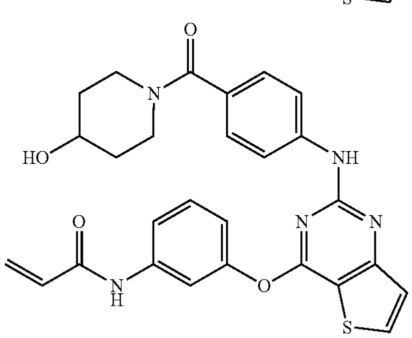 | ¹H-NMR (300 MHz, DMSO-d$_6$) δ 10.50 (brs, 1H), 9.80 (brs, 1H), 8.40-8.35 (m, 1H), 7.80 (s, 1H), 7.60-7.30 (m, 4H), 7.25 (d, 1H), 7.10-7.00 (m, 3H), 6.40-6.35 (m, 1H), 6.20-6.15 (m, 1H), 5.75-5.80 (m, 1H), 4.70 (s, 1H), 4.10-4.05 (m, 1H), 3.90-3.70 (m, 2H), 3.30 (s, 1H), 3.20-3.10 (m, 4H);<br>MS (ESI⁺): m/z = 516.2 [M + H]⁺. |

TABLE 1m-continued

| Example | Structure | Analysis data |
|---|---|---|
| 88 | 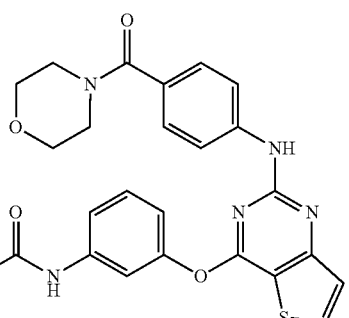 | ¹H-NMR (300 MHz, DMSO-d₆) δ 10.36-(s, 1H), 9.76 (s, 1H), 8.35 (d, 1H), 7.76 (d, 1H), 7.58 (m, 3H), 7.45 (m, 1H), 7.39 (m, 1H), 7.15 (m, 2H), 7.08 (m, 1H), 6.47 (m, 1H), 6.22 (dd, 1H), 5.75 (dd, 1H), 3.58 (m, 4H), 3.46 (m, 4H); MS (ESI⁺): m/z = 502.2 [M + H]⁺. |
| 89 | 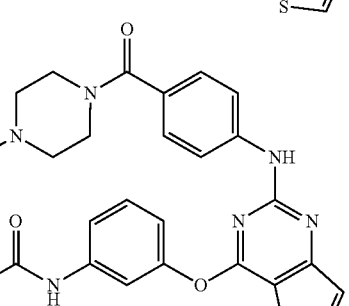 | ¹H-NMR (300 MHz, DMSO-d₆) δ 10.34 (s, 1H), 9.75 (s, 1H), 8.35 (d, 1H), 7.88 (d, 1H). 7.76 (d, 1H), 7.57 (m, 4H), 7.46 (m, 1H), 7.42 (m, 1H), 7.10 (m, 1H), 6.48 (m, 1H), 6.28 (dd, 1H), 5.78 (dd, 1H), 3.45 (m, 4H), 2.28 (m, 4H), 2.10 (s, 3H); MS (ESI⁺): m/z = 515.2 [M + H]⁺. |
| 90 | 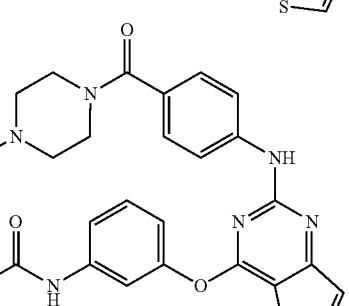 | ¹H-NMR (300 MHz, CDCl₃) δ 8.90 (s, 1H), 7.76 (d, 1H), 7.74 (s, 1H), 7.51 (s, 1H), 7.40 (s, 1H), 7.29-7.22 (m, 2H), 7.14 (d, 2H), 6.85 (d, 1H), 6.29 (d, 1H), 6.24 (s, 1H), 5.60 (d, 1H), 3.66-2.31 (m, 4H), 2.35 (t, 2H), 2.33-2.31 (m, 4H), 1.00 (t, 3H); MS (ESI⁺): m/z = 528.63 [M + H]⁺. |
| 91 | 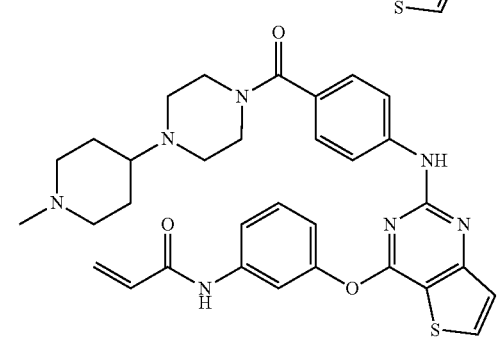 | ¹H-NMR (300 MHz, CDCl₃) δ 8.27 (d, 1H), 7.79-7.77 (d, 1H), 7.57 (m, 1H), 7.34-7.09 (m, 5H), 6.99 (m, 1H), 6.37.-6.31 (m, 1H), 6.20-6.15 (m, 1H), 5.68-5.67 (m, 1H), 5.77-5.74 (m, 1H), 4.16-4.07 (m, 4H) 2.86-2.82 (m, 2H), 2.47 (m, 4H), 2.19 (m, 3H), 1.95 (m, 4H), 1.88-1.39 (m, 5H); MS (ESI⁺): m/z = 598.2 [M + H]⁺. |
| 92 | 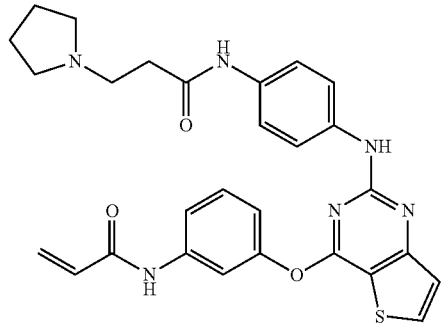 [SMILES: C=CC(=O)Nc1cccc(Oc2nc(Nc3ccc(NC(=O)CCN4CCCC4)cc3)nc3ccsc23)c1] | ¹H-NMR (300 MHz, CDCl₃) δ 9.02 (s, 1H), 7.85 (d, 2H), 7.83 (d, 3H), 7.46 (d, 1H), 7.26 (t, 2H), 6.96 (d, 1H), 6.39 (d, 1H), 5.68 (dd, 1H), 3.70 (bs, 1H), 3.61 (d, 1H), 2.87 (s, 2H), 2.79 (bs, 4H), 1.89 (bs, 4H); MS (ESI⁺): m/z = 529.4 [M + H]⁺. |

TABLE 1n

| Example | Structure | Analysis data |
|---|---|---|
| 93 | 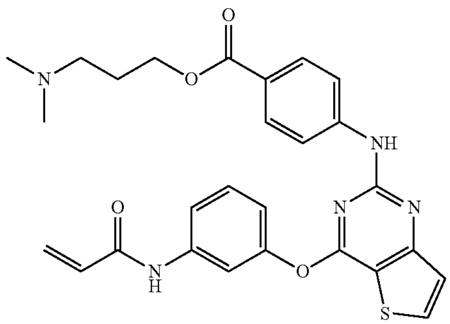 [SMILES: C=CC(=O)Nc1cccc(Oc2nc(Nc3ccc(C(=O)OCCCN(C)C)cc3)nc3ccsc23)c1] | ¹H-NMR (300 MHz, DMSO-d6) δ 10.35 (s, 1H), 9.96 (s, 1H), 8.33 (d, 1H), 7.76 (m, 2H), 7.68 (m, 3H), 7.49 (m, 1H), 7.42 (m, 1H), 7.40 (m, 1H), 7.08 (m, 1H), 6.40 (m, 1H), 6.20 (dd, 1H), 5.73 (dd, 1H), 4.20 (t, 2H), 2.30 (t, 2H), 2,12 (s, 6H), 1.76 (m, 2H);<br>MS (ESI⁺): m/z = 518.2 [M + H]⁺. |
| 94 | 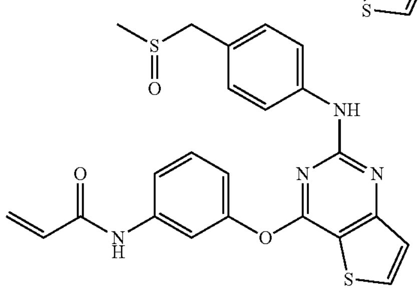 | ¹H-NMR (300 MHz, DMSO-d₆) δ 10.36 (s, 1H), 9.58 (s, 1H), 8.32 (d, 1H), 7.73 (s, 1H), 7.60 (m, 3H), 7.45 (t, 1H), 7.40 (d, 1H), 6.43 (dd, 1H), 6.22 (d, 1H), 5.78 (d, 1H), 3.85 (dd, 2H), 2.27 (s, 3H);<br>MS (ESI⁺): m/z = 465.1 [M + H]⁺. |
| 95 | 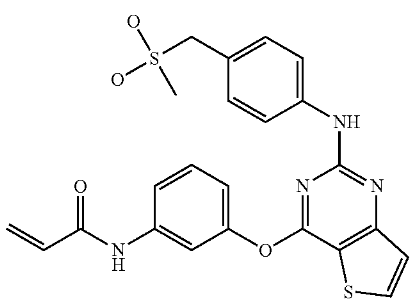 [SMILES: C=CC(=O)Nc1cccc(Oc2nc(Nc3ccc(CS(C)(O)O)cc3)nc3ccsc23)c1] | ¹H-NMR (300 MHz, DMSO-d₆) δ 10.38 (s, 1H), 9.62 (s, 1H), 8.32 (d, 1H), 7.73 (t, 1H), 7.62 (m, 3H), 7.47 (t, 1H), 7.40 (d, 1H), 7.16 (d, 2H), 7.10 (m, 1H), 6.40 (m, 1H), 6.25 (m, 1H), 5.77 (m, 1H), 4.33 (s, 2H), 2.84 (s, 3H);<br>MS (ESI⁺): m/z = 481.1 [M + H]⁺. |
| 96 | 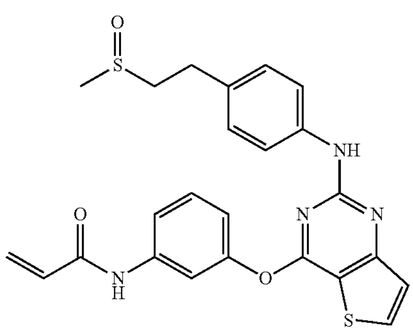 [SMILES: C=CC(=O)Nc1cccc(Oc2nc(Nc3ccc(CCS(C)=O)cc3)nc3ccsc23)c1] | ¹H-NMR (300 MHz, CDCl₃) δ 10.36 (s, 1H), 9.45 (s, 1H), 8.30 (d, 1H), 7.74 (s, 1H), 7.48 (m, 4H), 7.36 (d, 1H), 7.07 (m, 3H), 6.40 (dd, 1H), 6.25 (d, 1H), 5.77 (d, 1H), 3.30 (m, 2H), 2.95 (m, 2H), 2.54 (s, 3H);<br>MS (ESI⁺): m/z = 479.1 [M + H]⁺. |
| 97 | 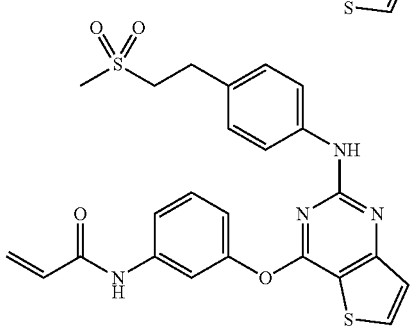 | ¹H-NMR (300 MHz, DMSO-d₆) δ 10.39 (s, 1H), 9.48 (s, 1H), 8.29 (d, 1H), 7.73 (s, 1H), 7.48 (m, 4H), 7.35 (d, 1H), 7.05 (m, 3H), 6.42 (m, 1H), 6.25 (m, 1H), 5.76 (m, 1H), 3.31 (m, 2H), 2.94 (s, 3H), 2.87 (m, 2H);<br>MS (ESI⁺): m/z = 495.1 [M + H]⁺. |

TABLE 1n-continued

| Example | Structure | Analysis data |
|---|---|---|
| 98 | 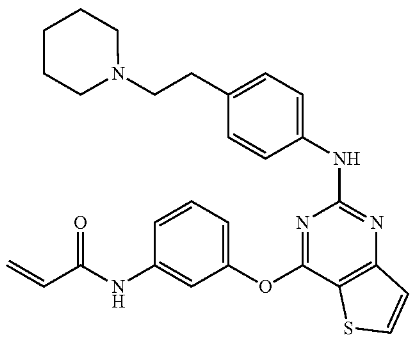 [SMILES: C=CC(=O)Nc1cccc(Oc2nc(Nc3ccc(CCN4CCCCC4)cc3)nc3ccsc23)c1] | ¹H-NMR (300 MHz, DMSO-d₆): δ 10.36 (brs, 1H), 9.40 (brs, 1H), 8.31-8.30 (d, 1H), 7.72-7.71 (m, 1H), 7.64-7.61 (m, 1H), 7.48-7.43 (m, 3H), 7.36-7.34 (d, 1H), 7.09-7.06 (m, 1H), 6.96-6.93 (m, 2H), 6.43-6.39 (m, 1H), 6.29-6.21 (m, 1H), 5.79-5.75 (m, 1H), 2.61 (m, 2H), 2.41 (m, 6H), 1.51 (m, 4H), 1.40 (m, 2H);<br>MS (ESI⁺): m/z = 500.2 [M + H]⁺. |
| 99 | 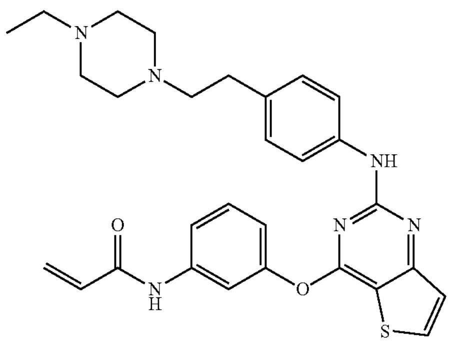 [SMILES: C=CC(=O)Nc1cccc(Oc2nc(Nc3ccc(CCN4CCN(CC)CC4)cc3)nc3ccsc23)c1] | ¹H-NMR (300 MHz, CDCl₃) δ; 7.84 (m, 1H), 7.69 (m, 1H), 7.52 (m, 1H), 7.42-7.33 (m, 3H), 7.06-7.00 (m, 4H), 6.47 (dd, 1H), 6.33 (dd, 1H), 5.75 (dd, 1H), 2.79-2.45 (m, 14H), 1.12 (t, 3H);<br>MS (ESI⁺): m/z = 529.4 [M + H]⁺. |

TABLE 1o

| Example | Structure | Analysis data |
|---|---|---|
| 100 | 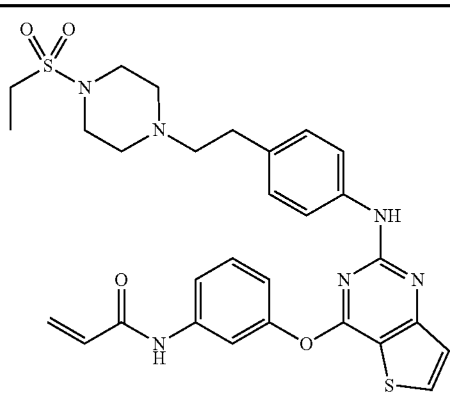 | ¹H-NMR (300 MHz, CDCl₃) δ 7.82 (t, 1H), 7.65 (s, 1H), 7.57 (m, 1H), 7.39 (m, 3H), 7.28 (m, 2H), 7.03 (m, 4H), 6.67 (m, 1H), 6.41 (m, 1H), 5.75 (m, 1H), 3.33 (s, 4H), 2.97 (m, 2H), 2.71 (m, 2H), 2.59 (brs, 6H), 1.38 (t, 3H); |
| 101 | 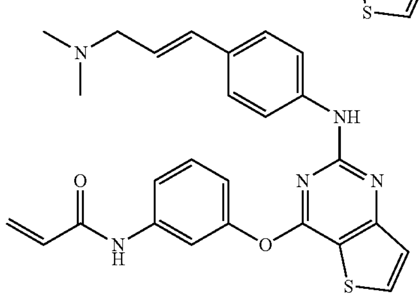 | ¹H-NMR (300 MHz, DMSO-d₆) δ 10.39 (s, 1H), 9.58 (s, 1H), 8.31 (d, 1H), 7.75 (s, 1H), 7.52 (m, 4H), 7.38 (d, 1H), 7.12 (m, 3H), 6.37 (m, 3H), 6.11 (m, 1H), 5.75 (d, 1H), 2.98 (d, 2H), 2.15 (s, 6H);<br>MS (ESI⁺): m/z = 472.2 [M + H]⁺. |

TABLE 1o-continued

| Example | Structure | Analysis data |
|---|---|---|
| 102 | 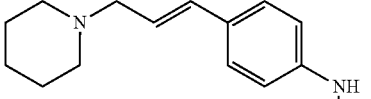 | ¹H-NMR (300 MHz, CDCl₃) δ 8.40 (m, 1H), 7.94 (s, 1H), 7.86 (m, 1H), 7.44 (m, 2H), 7.33 (m, 3H), 7.17 (m, 2H), 7.04 (m, 2H), 6.42 (m, 3H), 6.34 (m, 1H), 5.71 (m, 1H), 3.24 (d, 2H), 2.47 (m, 4H), 1.75 (m, 4H), 1.54 (m, 2H); MS (ESI⁺): m/z = 512.2 [M + H]⁺. |
| 103 | 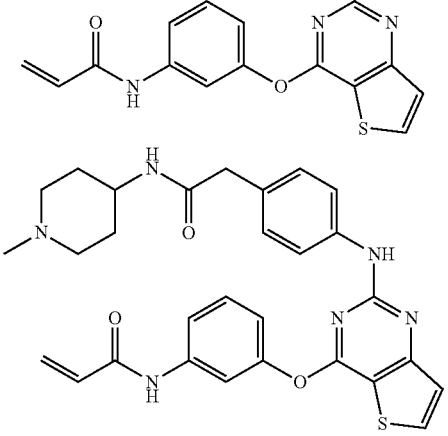 | ¹H-NMR (300 MHz, DMSO-d₆) δ 10.35 (s, 1H), 9.43 (s, 1H), 8.30 (d, 1H), 7.89 (d, 1H), 7.71 (s, 1H), 7.45 (m, 3H), 7.36 (d, 1H), 7.05 (m, 3H), 6.44 (dd, 1H), 6.25 (d, 1H), 5.76 (d, 1H), 3.43 (m, 1H), 2.70 (m, 2H), 2.14 (s, 3H), 1.94 (m, 2H), 1.66 (m, 2H), 1.40 (m, 2H); MS (ESI⁺): m/z = 543.3 [M + H]⁺. |
| 104 | 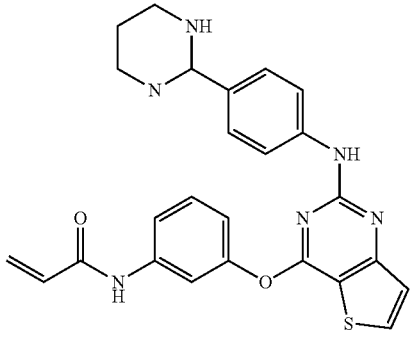 [SMILES: C=CC(=O)Nc1cccc(Oc2nc(Nc3ccc(C4NCCCN4)cc3)nc3ccsc23)c1] | ¹H-NMR (300 MHz, DMSO-d₆) δ 10.36 (s, 1H), 9.22 (s, 1H), 8.26 (d, 2H), 7.70 (s, 1H), 7.64 (m, 1H), 7.47 (d, 1H), 7.41 (m, 1H), 7.31 (d, 1H), 7.05 (d, 2H), 6.71 (m, 1H), 6.44 (m, 1H), 6.26 (m, 2H), 5.78 (m, 1H), 2.96 (m, 2H), 1.59 (m, 2H), 1.50 (m, 1H); MS (ESI⁺): m/z = 471.2 [M + H]⁺. |
| 105 | 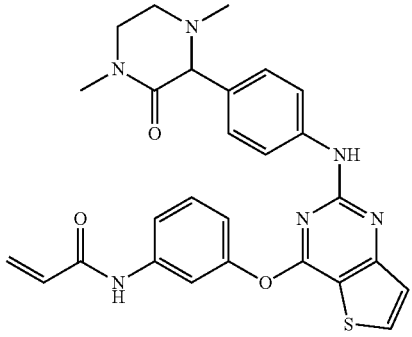 [SMILES: C=CC(=O)Nc1cccc(Oc2nc(Nc3ccc(C4C(=O)N(C)CCN4C)cc3)nc3ccsc23)c1] | ¹H-NMR (300 MHz, DMSO-d₆) δ 10.27 (brs, 1H), 9.35 (brs, 1H), 8.18 d, 1H), 7.61. (s, 1H), 7.55 (d, 1H), 7.42-7.38 (m, 3H), 7.26-7.24 (d, 1H), 6.99 (d, 1H), 6.96-6.92 (m, 2H), 6.34-6.29 (m, 1H), 6.18-6.13 (m, 1H), 5.68-5.67 (m, 1H), 3.45-3.44 (m, 2H), 3.13-3.09 (m, 1H), 2.84-2.80 (m, 1H), 2.72 (s, 3H), 1.90 (s, 3H); MS (ESI⁺): m/z = 515.2 [M + H]⁺. |
| 106 | 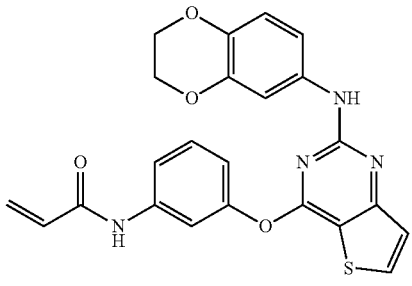 [SMILES: C=CC(=O)Nc1cccc(Oc2nc(Nc3ccc4c(c3)OCCO4)nc3ccsc23)c1] | ¹H-NMR (300 MHz, DMSO-d₆) δ 9.47 (s, NH), 8.35 (m, 2H), 8.23 (dd, 1H), 7.82-7.75 (m, 2H), 7.38 (d, 1H), 7.09 (m, 1H), 6.92 (m, 1H), 6.58 (m, 1H), 4.12 (s, 4H); MS (ESI⁺): m/z = 447.4 [M + H]⁺. |

TABLE 1p

| Example | Structure | Analysis data |
|---------|-----------|---------------|
| 107 | 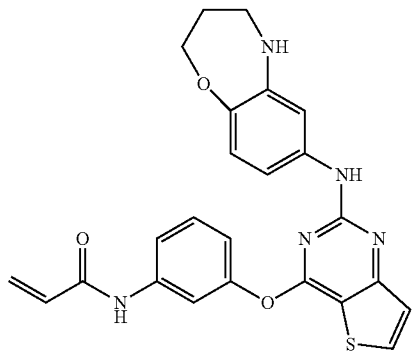 [SMILES: C=CC(=O)Nc1cccc(Oc2nc(Nc3ccc4c(c3)NCCCO4)nc3ccsc23)c1] | $^1$H-NMR (300 MHz, DMSO-d$_6$) δ 10.37 (s, 1H), 9.24 (s, 1H), 8.28 (d, 1H), 7.73 (m, 1H), 7.60 (m, 1H), 7.47 (dd, 1H), 7.32 (d, 1H), 7.08 (m, 2H), 6.82 (m, 1H), 6.57 (m, 1H), 6.42 (dd, 1H), 5.77 (dd, 1H), 4.77 (s, 1H), 3.85 (m, 2H), 3.02 (m, 2H), 1.81 (m, 2H); MS (ESI$^+$): m/z = 460.1 [M + H]$^+$. |
| 108 | 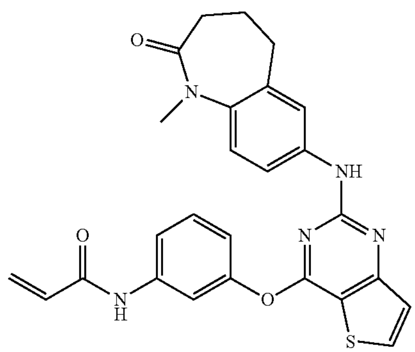 [SMILES: C=CC(=O)Nc1cccc(Oc2nc(Nc3ccc4c(c3)CCCC(=O)N4C)nc3ccsc23)c1] | $^1$H-NMR (300 MHz, DMSO-d$_6$) δ 10.50 (brs, 1H), 9.60 (brs, 1H), 8.32-8.30 (m, 1H), 7.78-7.77 (m, 1H), 7.62-7.59 (m, 1H), 7.48-7.39 (m, 3H), 7.36-7.34 (m, 1H), 7.07-7.01 (m, 2H), 6.46-6.41 (m, 1H), 6.25-6.20 (m, 1H), 5.76-5.72 (m, 1H), 3.12 (s, 3H), 2.36 (m, 2H), 2.04-2.02 (m, 2H), 1.93-1.89 (m, 2H); MS (ESI$^+$): m/z = 486.1 [M + H]$^+$. |
| 109 | 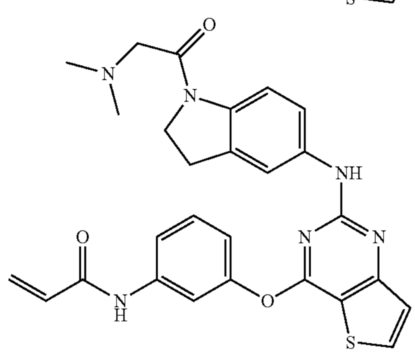 | $^1$H-NMR (300 MHz, DMSO-d$_6$) δ 9.47 (s, 1H), 8.28 (d, 1H), 7.80 (d, 1H), 7.73 (s, 1H), 7.57 (d, 1H), 7.45 (m, 2H), 7.33 (d, 1H), 7.20 (m, 1H), 7.07 (m, 1H), 6.41 (m, 1H), 6.23 (m, 1H), 5.75 (m, 1H), 4.07 (t, 2H), 3.12 (s, 2H), 2.91 (m, 2H), 2.23 (s, 6H); MS (ESI$^+$): m/z = 515.1 [M + H]$^+$. |
| 110 | 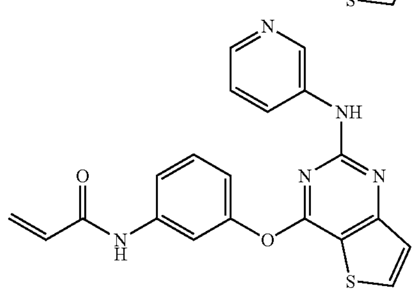 | $^1$H-NMR (300 MHz, DMSO-d$_6$) δ 10.35 (s, 1H), 9.68 (s, 1H), 8.76 (s, 1H), 8.50 (d, 1H), 8.06 (d, 2H), 7.75 (s, 1H), 7.56 (m, 1H), 7.38 (m, 2H), 7.05 (m, 2H), 6.42 (m, 1H), 6.23 (dd, 1H), 5.70 (dd, 1H); MS (ESI$^+$): m/z = 390.10 [M + H]$^+$. |
| 111 | 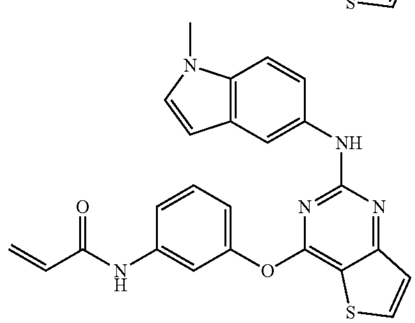 | $^1$H-NMR (300 MHz, DMSO-d$_6$) δ 10.40 (s, 1H), 9.43 (bm, 1H), 8.29 (d, 1H), 7.78 (m, 2H), 7.64 (d, 1H), 7.48 (t, 1H), 7.33 (d, 1H), 7.21 (m, 3H), 7.10 (m, 1H), 6.42 (m, 1H), 6.28 (d, 1H), 6.20 (m, 1H), 5.76 (m, 1H); MS (ESI$^+$): m/z = 441.7 [M + H]$^+$. |

TABLE 1p-continued

| Example | Structure | Analysis data |
|---|---|---|
| 112 | 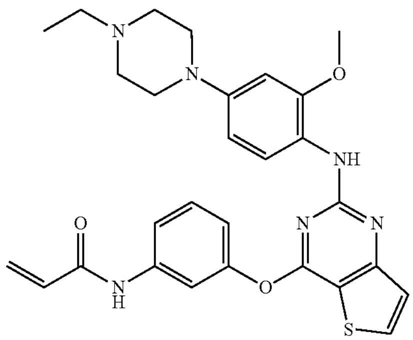 [SMILES: C=CC(=O)Nc1cccc(Oc2nc(Nc3ccc(N4CCN(CC)CC4)cc3OC)nc3ccsc23)c1] | ¹H-NMR (300 MHz, CDCl₃) δ 8.44 (bs, 1H), 7.96 (d, 1H), 7.94 (d, 1H), 7.66 (s, 1H), 7.45 (d, 2H), 7.31 (m, 1H), 7.20 (d, 1H), 6.98 (d, 1H), 6.43 (s, 1H), 6.35 (s, 1H), 6.27-6.24 (m, 2H), 5.65 (d, 1H), 3.72 (s, 3H), 3.10 (bs, 4H), 2.47 (bs, 4H), 2.45 (dd, 2H), 1.12 (t, 3H); MS (ESI⁺): m/z = 531.2 [M + H]⁺. |
| 113 | 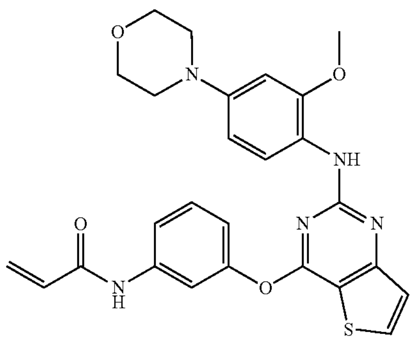 | ¹H-NMR (300 MHz, DMSO-d₆) δ 10.35 (s, 1H), 8.26 (d, 1H), 7.71 (m, 2H), 7.64 (m, 2H), 7.44 (dd, 1H), 7.31 (d, 1H), 7.07 (m, 1H), 6.59 (m, 1H), 6.40 (dd, 1H), 6.29 (m, 2H), 5.77 (dd, 1H), 3.77 (s, 3H), 3.73 (m, 4H), 3.03 (m, 4H) MS (ESI⁺): m/z = 504.08 [M + H]⁺. |

TABLE 1q

| Example | Structure | Analysis data |
|---|---|---|
| 114 | 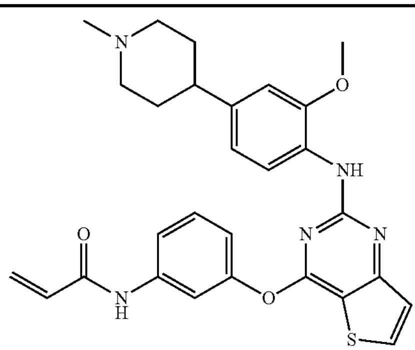 | ¹H-NMR (300 MHz, DMSO-d₆) δ 10.38 (brs, 1H), 8.31-8.30 (d, 1H), 7.84-7.72 (m, 3H), 7.63-7.60 (m, 1H), 7.48-7.43 (t, 1H), 7.36-7.34 (m, 1H), 7.09-7.06 (m, 1H), 6.84 (s, 1H), 6.61-6.58 (m, 1H), 6.49-6.40 (m, 1H), 6.29-6.24 (m, 1H), 5.80-5.76 (m, 1H), 3.81 (s, 3H), 3.18 (m, 2H), 2.54 (s, 3H), 1.91-1.71 (m, 6H); MS (ESI⁺): m/z = 516.2 [M + H]⁺. |
| 115 | 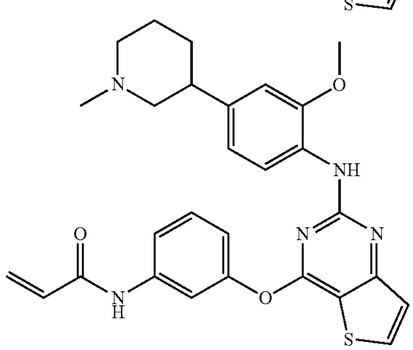 | ¹H-NMR (300 MHz, DMSO-d₆) δ 10.64 (brs, 1H), 8.31-8.29 (m, 1H), 7.82-7.76 (m, 3H0, 7.70 (m, 1H), 7.44 (m, 1H), 7.35-7.33 (m, 1H), 7.05 (m, 1H), 6.85 (m, 1H), 6.55 (m, 1H), 6.45 (m, 1H), 6.27 (m, 1H), 5.80 (m, 1H), 3.81 (s, 3H), 3.32 (m, 2H), 3.20-2.95 (m, 3H), 2.72 (s, 3H), 1.95-1.80 (m, 3H), 1.60 (m, 1H); MS (ESI⁺): m/z = 516.1 [M + H]⁺. |

TABLE 1q-continued

| Example | Structure | Analysis data |
|---|---|---|
| 116 | 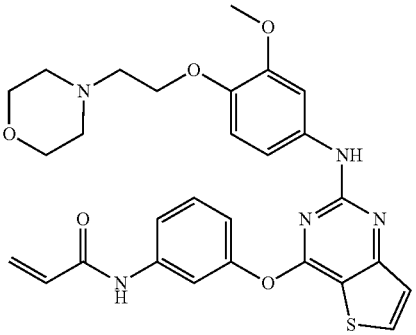 [SMILES: C=CC(=O)Nc1cccc(Oc2nc(Nc3ccc(OCCN4CCOCC4)c(OC)c3)nc3ccsc23)c1] | $^1$H-NMR (300 MHz, DMSO-d$_6$) δ 10.30 (s, 1H), 9.27 (s, 1H), 8.28 (d, 1H), 7.70 (m, 1H), 7.68 (m, 1H), 7.45 (dd, 1H), 7.35 (m, 2H), 7.18 (m, 1H), 7.07 (m, 1H), 6.74 (m, 1H), 6.44 (dd, 1H), 6.27 (dd, 1H), 5.78 (dd, 1H), 3.97 (t, 2H), 3.60 (s, 3H), 3.56 (m, 4H), 2.63 (t, 2H), 2.46 (m, 4H); MS (ESI$^+$): m/z = 548.1 [M + H]$^+$. |
| 117 | 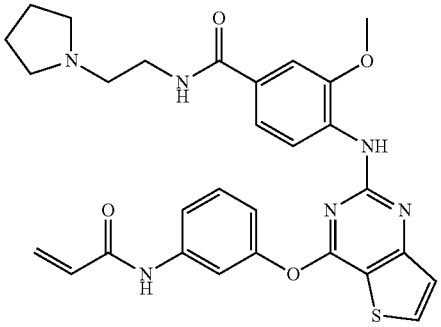 [SMILES: C=CC(=O)Nc1cccc(Oc2nc(Nc3ccc(C(=O)NCCN4CCCC4)cc3OC)nc3ccsc23)c1] | $^1$H-NMR (300 MHz, CDCl$_3$) δ 7.93 (m, 1H), 7.87 (d, 2H), 7.84 (s, 1H), 7.49 (m, 2H), 7.41 (s, 1H), 7.29 (d, 1H), 7.14 (d, 1H), 7.02 (d, 1H), 6.37 (m, 2H), 5.70 (m, 1H), 3.89 (s, 3H), 3.63 (t, 2H), 2.85 (t, 2H), 2.75 (m, 4H), 1.90 (m, 4H); MS (ESI$^+$): m/z = 558.9 [M + H]$^+$. |
| 118 | 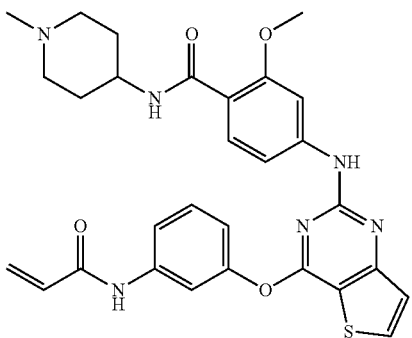 [SMILES: C=CC(=O)Nc1cccc(Oc2nc(Nc3ccc(C(=O)NC4CCN(C)CC4)c(OC)c3)nc3ccsc23)c1] | $^1$H-NMR (300 MHz, DMSO-d$_6$) δ 10.37 (s, 1H), 9.79 (s, 1H), 8.35 (d, 1H), 7.78 (m, 2H), 7.58 (m, 3H), 7.32 (m, 2H), 7.30 (d, 1H), 7.10 (d, 1H), 6.44 (dd, 1H), 6.25 (d, 1H), 5.78 (d, 1H), 3.73 (s, 3H), 2.62 (m, 2H), 2.16 (s, 3H), 2.03 (m, 2H), 1.78 (m, 2H), 1.50 (m, 2H); MS (ESI$^+$): m/z = 559.2 [M + H]$^+$. |
| 119 | 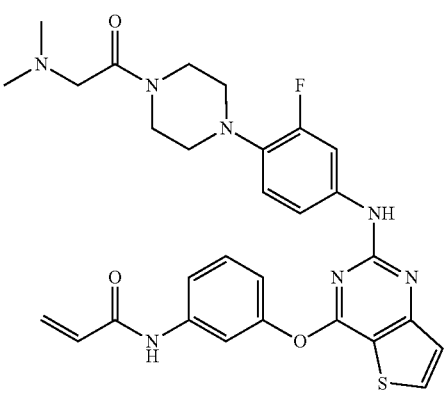 [SMILES: C=CC(=O)Nc1cccc(Oc2nc(Nc3ccc(N4CCN(C(=O)CN(C)C)CC4)c(F)c3)nc3ccsc23)c1] | $^1$H-NMR (300 MHz, CDCl$_3$) δ 7.86 (d, 1H), 7.76 (s, 1H), 7.43 (m, 3H), 7.28 (m, 1H), 6.99 (t, 2H), 6.76 (t, 1H), 6.40 (m, 2H), 5.73 (m, 1H), 3.71 (m, 4H), 3.17 (s, 2H), 2.95 (m, 4H), 2.31 (s, 6H); MS (ESI$^+$): m/z = 575.9 [M + H]$^+$. |

TABLE 1q-continued

| Example | Structure | Analysis data |
|---|---|---|
| 120 | 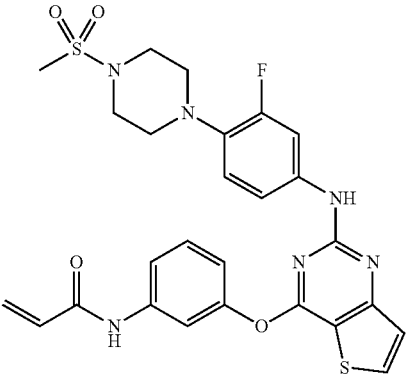 [SMILES: C=CC(=O)Nc1cccc(Oc2nc(Nc3ccc(N4CCN(S(C)(=O)=O)CC4)c(F)c3)nc3ccsc23)c1] | ¹H-NMR (300 MHz, DMSO-d$_6$) δ 10.36 (brs, 1H), 9.56 (brs, 1H), 8.33-8.31 (d, 1H), 7.74 (m, 1H), 7.61-7.43 (m, 3H), 7.39-7.38 (m, 1H), 7.27 (m, 1H), 7.10-7.07 (m, 1H), 6.87 (m, 1H), 6.43-6.39 (m, 1H), 6.28-6.22 (m, 1H), 5.79-5.75 (m, 1H), 3.24 (m, 4H), 2.98 (m, 4H), 2.93 (s, 3H); MS (ESI⁺): m/z = 591.06 [M + Na]⁺. |

TABLE 1r

| Example | Structure | Analysis data |
|---|---|---|
| 121 | 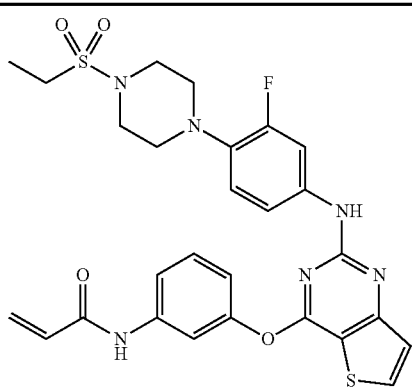 | ¹H-NMR (300 MHz, DMSO-d$_6$) δ 10.35 (brs, 1H), 9.55 (brs, 1H), 8.32-8.30 (d, 1H), 7.79 (s, 1H), 7.60-7.43 (m, 3H), 7.39-7.37 (d, 1H), 7.28-7.25 (m, 1H), 7.09-7.06 (m, 1H), 6.89-6.82 (t, 1H), 6.47-6.38 (m, 1H), 6.28-6.22 (m, 1H), 5.78-5.75 (m, 1H), 3.20-3.07 (m, 6H), 2.94 (m, 4H), 1.26-1.21 (t, 3H). |
| 122 | 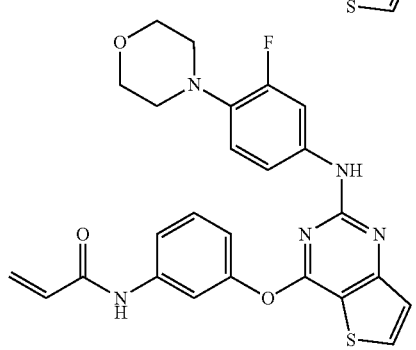 | ¹H-NMR (300 MHz, DMSO-d$_6$) δ 9.53 (s, 1H), 8.30 (m, 1H), 7.73 (s, 1H), 7.46 (m, 3H), 7.38 (d, 1H), 7.25 (m, 1H), 7.07 (d, 1H), 6.84 (d, 1H), 6.41 (m, 1H), 6.26 (d, 1H), 3.63 (m, 4H), 2.86 (m, 4H); MS (ESI⁺): m/z = 492.54 [M + H]⁺. |
| 123 | 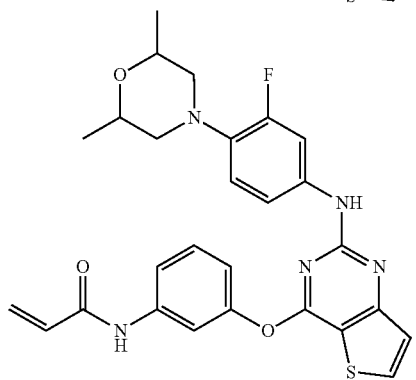 | ¹H-NMR (300 MHz, CDCl$_3$) δ 7.86 (d, 1H), 7.71 (s, 1H), 7.53 (m, 2H), 7.46 (m, 2H), 7.29 (d, 1H), 7.14 (s, 1H), 7.05 (m, 1H), 6.93 (m, 1H), 6.78 (t, 1H), 6.45 (dd, 1H), 6.25 (m, 1H), 5.79 (dd, 1H), 3.87 (m, 2H), 3.15 (d, 2H), 2.39 (t, 2H), 1.23 (d, 6H); MS (ESI⁺): m/z = 520.2 [M + H]⁺ |

TABLE 1r-continued
| Example | Structure | Analysis data |
|---|---|---|
| 124 | 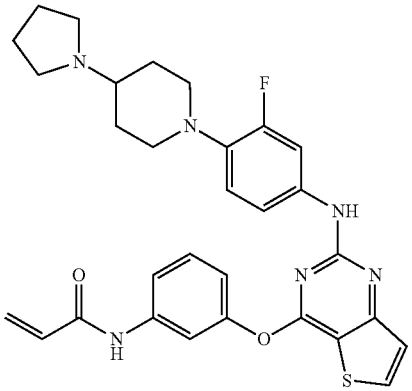 [SMILES: C=CC(=O)Nc1cccc(Oc2nc(Nc3ccc(N4CCC(N5CCCC5)CC4)c(F)c3)nc3ccsc23)c1] | ¹H-NMR (300 MHz, CDCl₃) δ 7.86 (d, 1H), 7.79 (s, 1H), 7.67 (s, 1H), 7.42 (m, 2H), 6.97 (m, 1H), 6.90 (s, 1H), 6.77 (d, 1H), 6.46 (t, 1H), 6.40 (d, 1H), 6.29 (dd, 1H), 5.76 (d, 1H), 3.42 (d, 2H), 3.09 (m, 2H), 2.95 (m, 2H), 2.06 (m, 6H); MS (ESI⁺): m/z = 559.2 [M + H]⁺. |
| 125 | 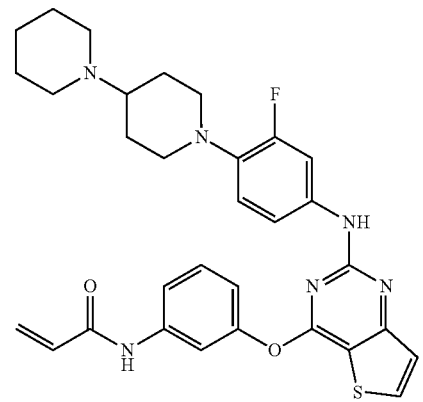 [SMILES: C=CC(=O)Nc1cccc(Oc2nc(Nc3ccc(N4CCC(N5CCCCC5)CC4)c(F)c3)nc3ccsc23)c1] | ¹H-NMR (300 MHz, CDCl₃) δ 7.87 (d, 1H), 7.78 (s, 1H), 7.48 (d, 1H), 7.25 (d, 1H), 7.01 (d, 1H), 7.00 (d, 1H), 6.82 (t, 1H), 6.47 (m, 2H), 5.70 (m, 1H), 4.42 (t, 1H), 4.37 (m, 1H), 3.33 (m, 4H), 2.58 (m, 4H), 2.35 (m, 1H), 1.95 (m, 2H), 1.78 (m, 2H), 1.63 (m, 4H), 1.46 (m, 2H); MS (ESI⁺): m/z = 573.0 [M + H]⁺. |
| 126 | 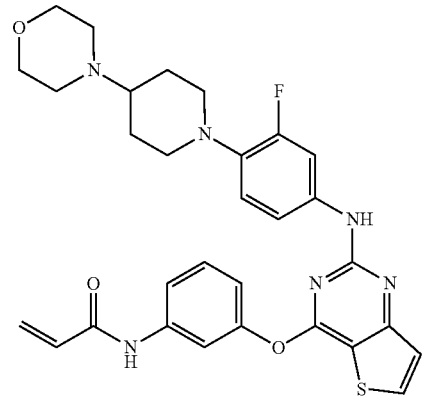 | ¹H-NMR (300 MHz, DMSO-d₆) δ 10.33 (s, 1H), 9.49 (s, 1H), 8.30 (d, 1H), 7.71 (s, 1H), 7.59 (d, 1H), 7.46 (m, 2H), 7.20 (d, 1H), 7.05 (d, 1H), 6.40 (dd, 1H), 6.26 (d, 1H), 5.77 (d, 1H), 3.68 (m, 4H), 3.19 (d, 2H), 2.71 (m, 1H), 2.67 (m, 4H), 2.20 (m, 2H), 1.81 (m, 2H), 1.47 (m, 2H); MS (ESI⁺): m/z = 575.1 [M + H]⁺. |
| 127 | 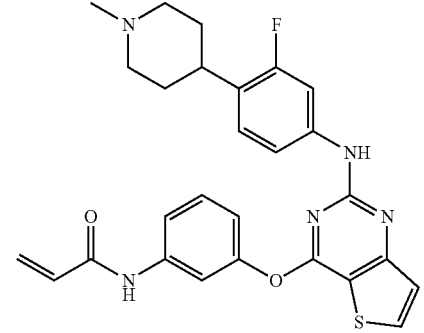 [SMILES: C=CC(=O)Nc1cccc(Oc2nc(Nc3ccc(C4CCN(C)CC4)c(F)c3)nc3ccsc23)c1] | ¹H-NMR (300 MHz, CDCl₃) δ 7.98 (s, 1H), 7.91 (d, 1H), 7.45 (m, 2H), 7.32 (m, 2H), 7.04 (m, 3H), 6.43 (m, 2H), 5.78 (m, 1H), 3.04 (m, 2H), 2.78 (m, 1H), 2.40 (s, 3H), 2.17 (m, 2H), 1.85 (m, 4H); MS (ESI⁺): m/z = 504.2 [M + H]⁺. |

TABLE 1s

| Example | Structure | Analysis data |
|---|---|---|
| 128 | 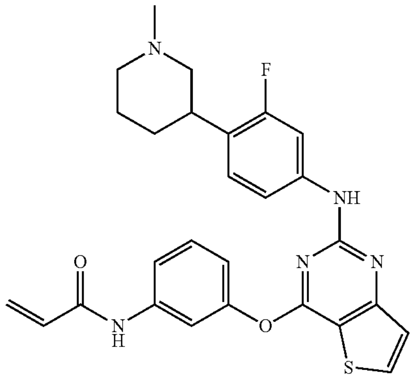 [SMILES: C=CC(=O)Nc1cccc(Oc2nc(Nc3ccc(C4CCCN(C)C4)c(F)c3)nc3ccsc23)c1] | ¹H-NMR (300 MHz, CDCl₃) δ 7.86 (d, 1H), 7.79 (s, 1H), 7.69 (s, 1H), 7.46 (m, 3H), 7.30 (d, 1H), 7.19 (s, 1H), 7.02 (m, 2H), 6.91 (m, 1H), 6.45 (m, 1H), 6.29 (m, 1H), 5.78 (m, 1H), 3.09 (m, 1H), 2.92 (m, 2H), 2.32 (s, 3H), 1.95 (m, 2H), 1.77 (m, 3H), 1.44 (m, 1H); MS (ESI⁺): m/z = 504.2 [M + H]⁺ |
| 129 | 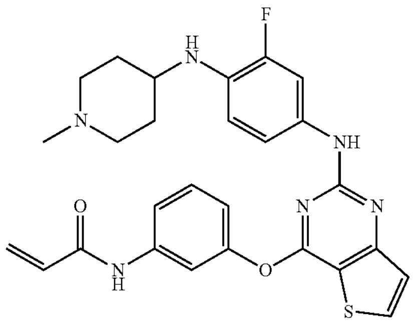 [SMILES: C=CC(=O)Nc1cccc(Oc2nc(Nc3ccc(NC4CCN(C)CC4)c(F)c3)nc3ccsc23)c1] | 1H-NMR (300 MHz, DMSO-d₆) δ 10.36 (s, 1H), 9.27 (s, 1H), 8.27 (d, 1H), 7.71 (s, 1H), 7.61 (d, 1H), 7.40 (m, 3H), 7.10 (m, 2H), 6.58 (m, 1H), 6.50 (dd, 1H), 6.40 (d, 1H), 5.78 (d, 1H), 4.58 (d, 1H), 3.10 (m, 1H), 2.72 (m, 2H), 2.17 (s, 3H), 2.00 (m, 2H), 1.80 (m, 2H), 1.44 (m, 2H); MS (ESI+): m/z = 519.2 [M + H]+. |
| 130 | 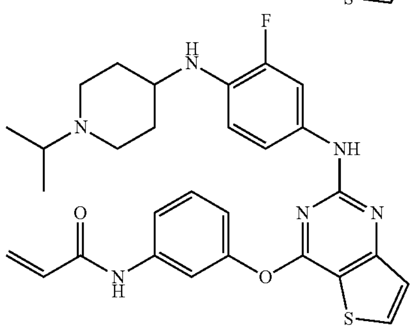 | ¹H-NMR (300 MHz, DMSO-d₆) δ 10.34 (s, 1H), 9.25 (s, 1H), 8.27 (d, 1H), 7.69 (s, 1H), 7.60 (d, 1H), 7.36 (m, 3H), 7.10 (m, 2H), 6.55 (m, 1H), 6.40 (dd, 1H), 6.25 (d, 1H), 5.77 (d, 1H), 4.52 (d, 1H), 3.10 (m, 1H), 2.66 (m, 2H), 2.15 (m, 2H), 1.83 (m, 2H), 1.35 (m, 2H), 0.96 (d, 6H); MS (ESI⁺): m/z = 547.2 [M + H]⁺. |
| 131 | 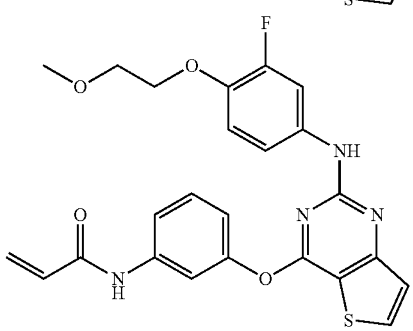 | ¹H-NMR (300 MHz, CDCl₃) δ 7.84 (d, 1H), 7.63 (s, 1H), 7.46 (dd, 1H), 7.37 (m, 2H), 7.24 (t, 1H), 7.02 (m, 1H), 6.83 (m, 2H), 6.43 (m, 1H), 6.24 (m, 1H), 5.72 (dd, 1H), 4.11 (t, 2H), 3.73 (t, 2H), 3.43 (s, 3H); MS (ESI⁺): m/z = 481.0 [M + H]⁺. |
| 132 | 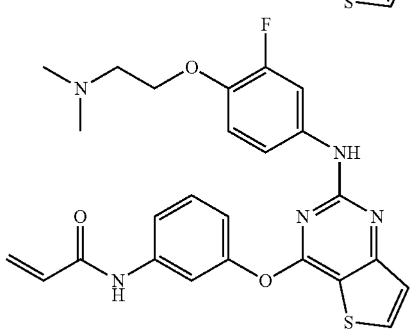 | ¹H-NMR (300 MHz, DMSO-d₆) δ 10.36 (s, 1H), 9.51 (s, 1H), 8.31 (d, 1H), 7.75 (s, 1H), 7.54 (m, 2H), 7.45 (m, 1H), 7.28 (m, 1H), 7.15 (m, 1H), 6.90 (m, 1H), 6.40 (m, 1H), 6.21 (m, 1H), 5.70 (m, 1H), 4.00 (t, 2H), 2.59 (t, 2H), 2.20 (s, 6H); MS (ESI⁺): m/z = 494.2 [M + H]⁺. |

TABLE 1s-continued

| Example | Structure | Analysis data |
|---|---|---|
| 133 | 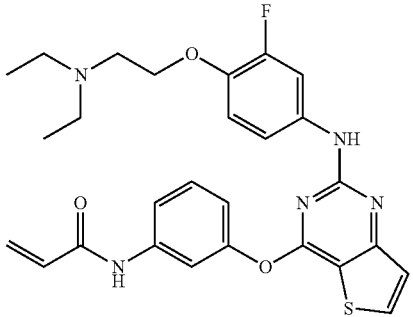 [SMILES: C=CC(=O)Nc1cccc(Oc2nc(Nc3ccc(OCCN(CC)CC)c(F)c3)nc3ccsc23)c1] | $^{1}$H-NMR (300 MHz, DMSO-d$_6$) δ 10.37 (s, 1H), 9.50 (s, 1H), 8.30 (d, 1H), 7.74 (m, 1H), 7.56 (m, 2H), 7.44 (dd, 1H), 7.37 (d, 1H), 7.35 (d, 1H), 7.15 (m, 1H), 6.95 (m, 1H), 6.43 (dd, 1H), 6.25 (dd, 1H), 5.65 (dd, 1H), 4.02 (m, 2H), 2.80 (m, 2H), 2.56 (m, 4H), 0.97 (m, 6H); MS (ESI$^+$): m/z = 522.1 [M + H]$^+$. |
| 134 | 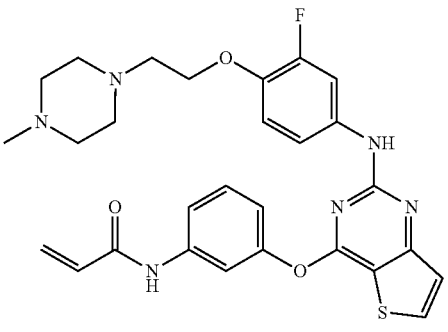 [SMILES: C=CC(=O)Nc1cccc(Oc2nc(Nc3ccc(OCCN4CCN(C)CC4)c(F)c3)nc3ccsc23)c1] | $^{1}$H-NMR (300 MHz, DMSO-d$_6$) δ 10.36 (s, 1H), 9.51 (s, 1H), 8..31 (m, 1H), 7.74 (m, 1H), 7.57 (m, 2H), 7.45 (dd, 1H), 7.38 (d, 1H), 7.22 (m, 1H), 7.08 (m, 1H), 6.94 (m, 1H), 6.43 (dd, 1H), 6.24 (dd, 1H), 5.76 (dd, 1H), 4.02 (t, 2H), 2.64 (t, 2H), 2.49 (m, 4H), 2.30 (m, 4H), 2.14 (s, 3H); MS (ESI$^+$): m/z = 549.2 [M + H]$^+$. |

TABLE 1t

| Example | Structure | Analysis data |
|---|---|---|
| 135 | 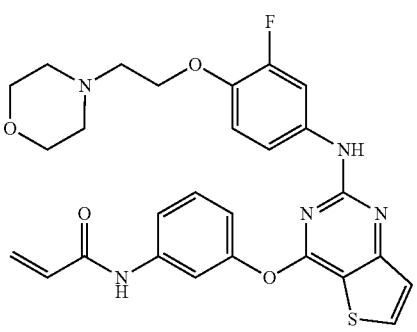 [SMILES: C=CC(=O)Nc1cccc(Oc2nc(Nc3ccc(OCCN4CCOCC4)c(F)c3)nc3ccsc23)c1] | $^{1}$H-NMR (300 MHz, CDCl$_3$) δ 7.86 (d, 1H), 7.78 (s, 1H), 7.51 (d, 1H), 7.41 (m, 2H), 7.24 (m, 1H), 7.02 (m, 1H), 6.90 (d, 1H), 6.81 (t, 1H), 6.44 (m, 1H), 6.27 (m, 1H), 5.77 (d, 1H), 4.11 (t, 2H), 3.75 (t, 4H), 2.80 (t, 2H), 2.59 (t, 4H); MS (ESI$^+$): m/z = 536.3 [M + H]$^+$. |
| 136 | 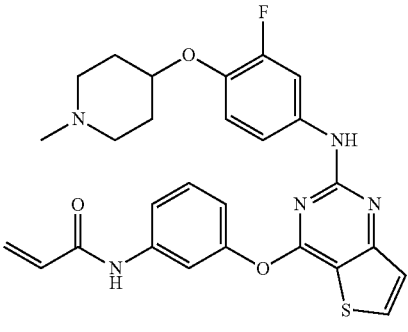 [SMILES: C=CC(=O)Nc1cccc(Oc2nc(Nc3ccc(OC4CCN(C)CC4)c(F)c3)nc3ccsc23)c1] | $^{1}$H-NMR (300 MHz, DMSO-d$_6$): δ 10.36 (brs, 1H), 9.54 (brs, 1H), 8.30-8.29 (d, 1H), 7.73 (s, 1H), 7.58-7.55 (m, 2H), 7.46-7.41 (t, 1H), 7.37-7.35 (d, 1H), 7.22-7.20 (m, 1H), 7.08-7.05 (m, 1H), 6.97-6.91 (m, 1H), 6.46-6.38 (m, 1H), 6.26-6.21 (m, 1H), 5.77-5.74 (m, 1H), 4.14 (m, 1H), 2.66 (m, 2H), 2.22 (m, 5H), 1.84 (m, 2H), 1.62-1.59 (m, 2H); MS (ESI$^+$): m/z = 520.2 [M + H]$^+$. |

TABLE 1t-continued

| Example | Structure | Analysis data |
|---|---|---|
| 137 | 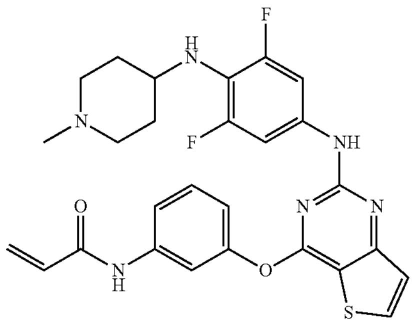 [SMILES: C=CC(=O)Nc1cccc(Oc2nc(Nc3cc(F)c(NC4CCN(C)CC4)c(F)c3)nc3ccsc23)c1] | $^1$H-NMR (300 MHz, DMSO-d$_6$) δ 10.32 (s, 1H), 9.55 (s, 1H), 8.30 (d, 1H), 7.73 (m, 1H), 7.54 (m, 1H), 7.43 (m, 1H), 7.39 (m, 1H), 7.23(m, 2H), 7.06 (m, H), 6.43(m, 1H), 6.21 (dd, 1H), 5.75 (dd, 1H), 3.58 (d, 1H), 3.02 (m, 1H), 2.49 (m, 2H), 2.11 (s, 3H), 1.84 (t, 2H), 1.67 (d, 2H), 1.35 (m, 2H); MS (ESI$^+$): m/z = 537.2 [M + H]$^+$. |
| 138 | 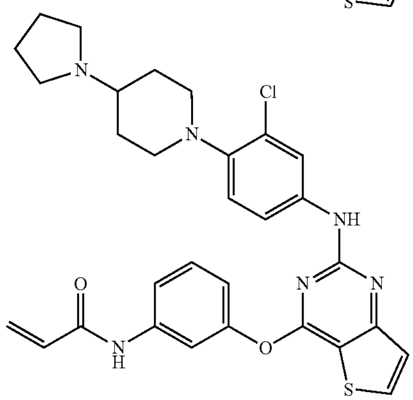 | $^1$H-NMR (300 MHz, CDCl$_3$) δ 7.85 (d, 1H), 768 (dd, 2H), 7.47 (m 1H), 7.39 (m, 1H), 7.20 (dd, 1H), 7.06 (d, 1H), 6.88 (s, 2H), 6.42 (d, 1H), 6.29 (dd, 1H), 5.78 (d, 1H), 3.28 (m, 2H), 2.80 (m, 2H), 2.01 (m, 2H), 1.98 (m, 5H), 1.25 (m, 3H); MS (ESI$^+$): m/z = 575 [M + H]$^+$. |
| 139 | 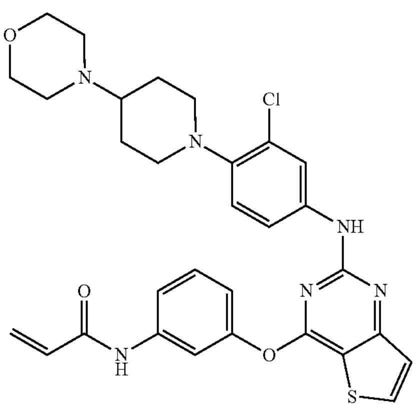 [SMILES: C=CC(=O)Nc1cccc(Oc2nc(Nc3ccc(N4CCC(N5CCOCC5)CC4)c(Cl)c3)nc3ccsc23)c1] | $^1$H-NMR (300 MHz, DMSO-d$_6$) δ 10.6 (brs, 1H), 10.4 (s, 1H), 9.57 (s, 1H), 8.33 (d, 1H), 7.74 (s, 1H), 7.65 (d, 1H), 7.38 (m, 1H), 7.09 (d, 1H), 6.95 (d, 1H), 6.42 (dd, 1H), 6.23 (d, 1H), 5.79 (d, 1H), 3.99 (d, 2H), 3.78 (m, 2H), 3.48 (d, 2H), 3.25 (d, 2H), 2.63 (m, 2H), 2.16 (m, 2H), 1.82 (m, 2H); MS (ESI$^+$): m/z = 591 [M + H]$^+$. |
| 140 | 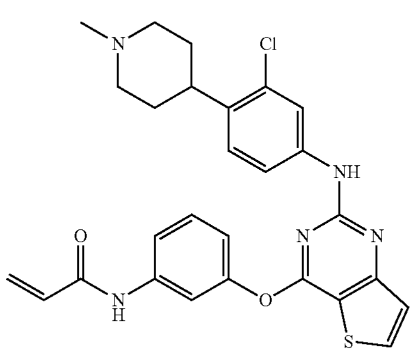 [SMILES: C=CC(=O)Nc1cccc(Oc2nc(Nc3ccc(C4CCN(C)CC4)c(Cl)c3)nc3ccsc23)c1] | $^1$H-NMR (300 MHz, CDCl$_3$) δ 7.85 (m, 2H), 7.42 (m, 2H), 7.37 (m, 2H), 7.33 (m, 2H), 7.03 (m, 4H), 6.41 (m, 1H), 6.33 (m, 1H), 5.73 (m, 1H), 3.73 (m, 1H), 3.08 (m, 2H), 2.23 (m, 2H), 1.82 (m, 4H); MS (ESI$^+$): m/z = 519.1 [M + H]$^+$. |

TABLE 1t-continued

| Example | Structure | Analysis data |
|---|---|---|
| 141 | 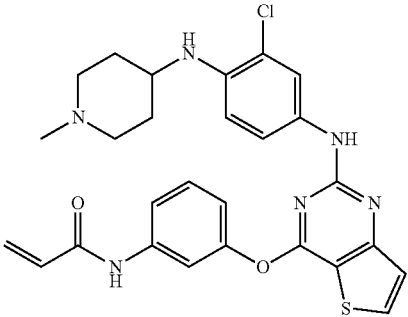 [SMILES: C=CC(=O)Nc1cccc(Oc2nc(Nc3ccc(NC4CCN(C)CC4)c(Cl)c3)nc3ccsc23)c1] | $^1$H-NMR (300 MHz, CD$_3$OD) δ 8.04 (d, 1H), 7.68 (d, 1H), 7.57 (m, 1H), 7.49 (d, 1H), 7.42 (t, 3H), 7.24-7.16 (m, 2H), 7.03-7.01 (m, 1H), 6.59 (d, 1H), 6.42-6.38 (m, 2H), 5.79-5.75 (m, 1H), 3.32-3.30 (m, 1H), 2.86-2.82 (m, 2H), 2.31-2.22 (m, 5H), 2.09-1.99 (m, 2H), 1.56-1.45 (m, 2H); MS (ESI$^+$): m/z = 535.16 [M + H]$^+$. |

TABLE 1u

| Example | Structure | Analysis data |
|---|---|---|
| 142 | 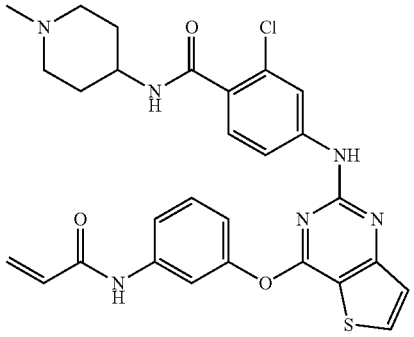 [SMILES: C=CC(=O)Nc1cccc(Oc2nc(Nc3ccc(C(=O)NC4CCN(C)CC4)c(Cl)c3)nc3ccsc23)c1] | $^1$H-NMR (300 MHz, DMSO-D$_6$) δ 10.24 (s, 1H), 8.40 (m, 2H), 7.61 (s, 1H), 7.45 (m, 1H), 7.26 (m, 4H), 6.87 (m, 1H), 6.39 (dd, 1H), 6.23 (d, 1H), 5.75 (d, 1H), 3.56 (m, 1H), 2.73 (m, 2H), 2.15 (s, 3H), 1.95 (m, 2H), 1.77 (m, 2H), 1.55 (m, 2H); MS (ESI$^+$): m/z = 563.2 [M + H]$^+$. |
| 143 | 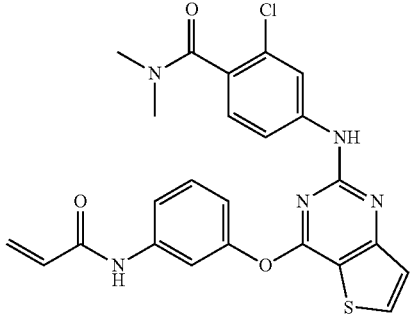 | $^1$H-NMR (300 MHz, CDCl$_3$) δ 8.04 (m, 1H), 7.89 (d, 1H), 7.45 (m, 2H), 7.36 (m, 1H), 7.27 (d, 1H), 7.15 (m, 1H), 7.03 (dd, 1H), 6.98 (dd, 1H), 6.43 (d, 1H), 6.27 (d, 1H), 5.75 (d, 1H), 3.12 (s, 3H), 2.85 (s, 3H); MS (ESI$^+$): m/z = 494 [M + H]$^+$. |
| 144 | 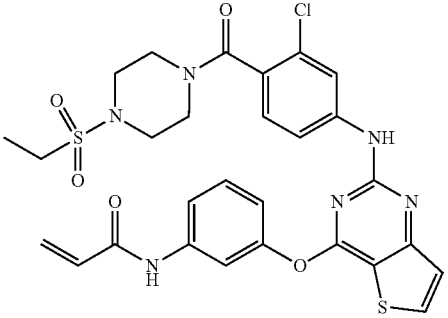 [SMILES: C=CC(=O)Nc1cccc(Oc2nc(Nc3ccc(C(=O)N4CCN(S(=O)(=O)CC)CC4)c(Cl)c3)nc3ccsc23)c1] | $^1$H-NMR (300 MHz, CDCl$_3$) δ 8.32 (d, 1H), 8.08 (s, 1H), 7.84 (s, 1H), 7.60 (s, 1H), 7.40 (m, 1H), 7.30 (m, 1H), 7.22 (d, 1H), 6.98 (m, 2H), 6.45 (d, 1H), 6.30 (dd, 1H), 5.79 (d, 1H), 4.11 (m, 2H), 3.95 (m, 2H), 3.41 (m, 2H), 3.21 (m, 2H), 1.24 (t, 2H), 1.25 (s, 3H); MS (ESI$^+$): m/z = 627.7 [M + H]$^+$. |

TABLE 1u-continued

| Example | Structure | Analysis data |
|---|---|---|
| 145 | 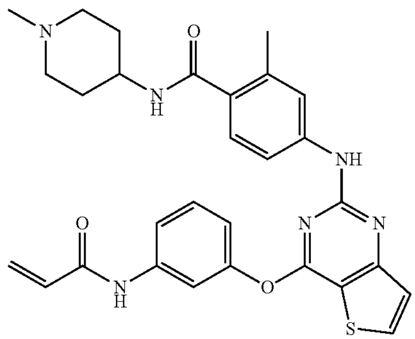 [SMILES: C=CC(=O)Nc1cccc(Oc2nc(Nc3ccc(C(=O)NC4CCN(C)CC4)c(C)c3)nc3ccsc23)c1] | $^1$H-NMR (300 MHz, DMSO-d$_6$) δ 10.40 (s. lH). 9.61 (s, 1H), 8.33 (d, 1H), 7.90 (d, 1H), 7.78 (s, 1H), 7.57 (m, 1H), 7.45 (m, 4H), 7.07 (m, 2H), 6.41 (dd, 1H), 6.25 (d, 1H), 5.76 (d, 1H), 3.64 (m, 1H), 2.74 (m, 2H), 2.15 (s, 6H), 1.94 (m, 2H), 1.73 (m, 2H), 1.49 (m, 2H);<br>MS (ESI$^+$): m/z = 543.2 [M + H]$^+$. |
| 146 | 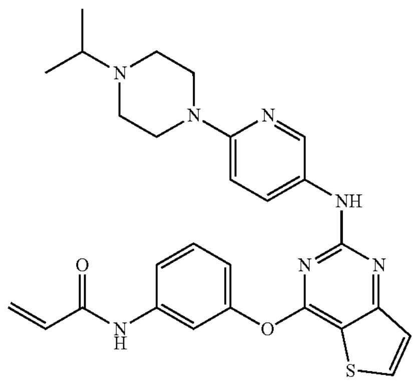 [SMILES: C=CC(=O)Nc1cccc(Oc2nc(Nc3ccc(N4CCN(C(C)C)CC4)nc3)nc3ccsc23)c1] | $^1$H-NMR (300 MHz, DMSO-d$_6$) δ 10.33 (s, 1H), 9.24 (s, 1H), 8.28 (d, 1H), 8.26 (m, 1H), 7.69 (m, 1H), 7.59 (m, 1H), 7.45 (m, 1H), 7.34 (m, 1H), 7.32 (m, 1H), 7.08 (m, 1H), 6.63 (m, 1H), 6.33 (m, 1H), 6.28 (dd, 1H), 5.77 (dd, 1H), 3.62 (m, 4H), 2.69 (m, 1H), 2.48 (m, 4H), 1.07 (d, 6H);<br>MS (ESI$^+$): m/z = 516.20 [M + H]$^+$. |
| 147 | 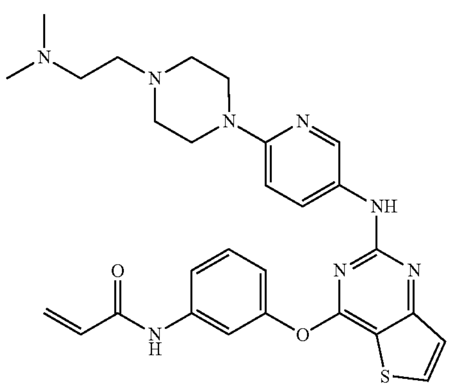 | $^1$H-NMR (300 MHz, DMSO-d$_6$) δ 10.36 (s, 1H), 9.22 (s, 1H), 8.32 (m, 1H), 8.26 (m, 1H), 7.78 (m, 1H), 7.68 (m, 1H), 7.58 (m, 1H), 7.41 (m, 2H), 7.31 (m, H), 7.05 (m, 1H), 6.64 (m, 1H), 6.42 (m, 3H), 6.24 (dd, 1H), 5.76 (dd, 1H), 3.33 (m, 2H), 2.49~2.37 (m, 10H), 2.13 (s, 6H);<br>MS (ESI$^+$): m/z = 515.2 [M + H]$^+$. |
| 148 | 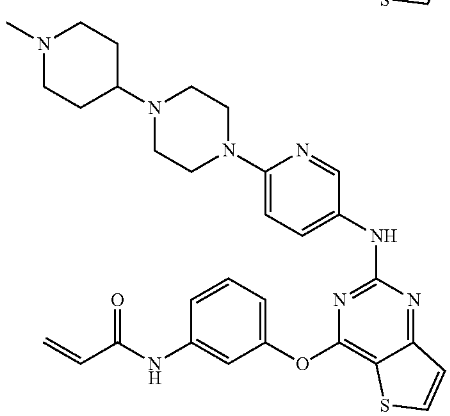 | $^1$H-NMR (300 MHz, DMSO-d$_6$) δ 10.33 (s, 1H), 9.30 (s, 1H), 8.27 (m, 1H), 8.25 (m, 1H), 7.75 (m, 1H), 7.68 (m, 1H), 7.58 (m, 1H), 7.43 (m, 1H), 7.31 (m, 1H), 7.04 (m, 1H), 6.60 (m, 1H), 6.43 (m, 1H), 6.28 (dd, 1H), 5.76 (dd, 1H), 3.31 (m, 5H), 2.76 (m, 2H), 2.50 (m, 4H), 2.12 (s, 3H), 1.74 (m, 4H), 1.38 (m, 2H);<br>MS (ESI$^+$): m/z = 571.30 [M + H]$^+$. |

TABLE 1v

| Example | Structure | Analysis data |
|---|---|---|
| 149 | 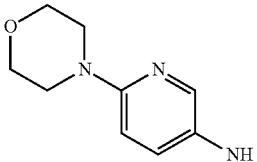 | $^1$H-NMR (300 MHz, DMSO-d$_6$) δ 10.33 (s, 1H), 9.24 (s, 1H), 8.28 (d, 1H), 8.26 (m, 1H), 7.69 (m, 1H), 7.59 (m, 1H), 7.45 (m, 1H), 7.34 (m, 1H), 7.32 (m, 1H), 7.08 (m, 1H), 6.63 (m, 1H), 6.33 (m, 1H), 6.28 (dd, 1H), 5.77 (dd, 1H), 3.65 (m, 4H), 3.57 (m, 4H); MS (ESI$^+$): m/z = 474.2 [M + H]$^+$. |
| 150 | 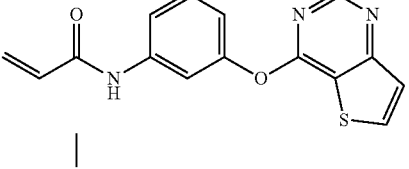 | $^1$H-NMR (300 MHz, DMSO-d$_6$) δ 10.35 (s, 1H), 9.18 (s, 1H), 8.28 (m, 1H), 8.25 (m, 1H), 7.73 (m, 1H), 7.59 (m, 1H), 7.45 (m, 1H), 7.40 (m, 1H), 7.30 (m, 1H), 7.03 (m, 1H), 6.64 (m, 1H), 6.43 (m, 1H), 6.28 (dd, 1H), 5.76 (dd, 1H), 3.32 (m, 2H), 2.63 (m, 2H), 2.23 (m, 1H), 2.15 (s, 6H), 1.74 (m, 2H), 1.29 (m, 2H); MS (ESI$^+$): m/z = 516.2 [M + H]$^+$. |
| 151 | 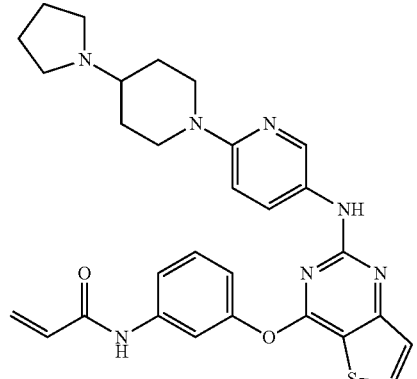 | $^1$H-NMR (300 MHz, DMSO-d$_6$) δ 10.36 (s, 1H), 9.24 (s, 1H), 8.31 (d, 1H), 8.25 (m, 1H), 7.82 (m, 1H), 7.79 (m, 1H), 7.55 (m, 1H), 7.40 (m, 1H), 7.33 (m, 1H), 7.05 (m, 1H), 6.63 (m, 1H), 6.33 (m, 1H), 6.28 (dd, 1H), 5.77 (dd, 1H), 4.01 (m, 2H), 3.16 (m, 2H), 2.78 (m, 2H), 2.51 (m, 2H), 2.12 (m, 1H), 1.88 (m, 2H), 1.67 (m, 4H), 1.44 (m, 2H); MS (ESI$^+$): m/z = 542.2 [M + H]$^+$. |
| 152 | 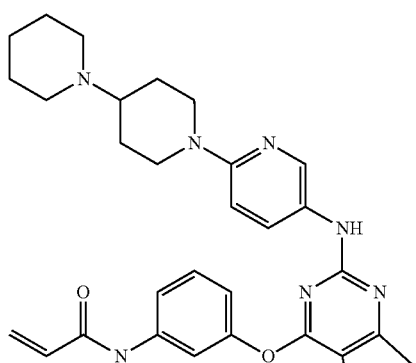 | $^1$H-NMR (300 MHz, DMSO-d$_6$) δ 10.33 (s, 1H), 9.18 (s, 1H), 8.36 (m, 1H), 8.25 (m, 1H), 7.73 (m, 1H), 7.69 (m, 1H), 7.47 (m, 1H), 7.41 (m, 1H), 7.31 (m, 1H), 7.04 (m, 1H), 6.61 (m, 1H), 6.45 (m, 1H), 6.29 (dd, 1H), 5.76 (dd, 1H), 4.08 (m, 2H), 3.43 (m, 1H), 2.65 (m, 2H), 2.49 (m, 4H), 1.72 (m, 2H), 1.39 (m, 4H), 1.36 (m, 4H); MS (ESI$^+$): m/z = 556.2 [M + H]$^+$. |

| Example | Structure | Analysis data |
|---|---|---|
| 153 | 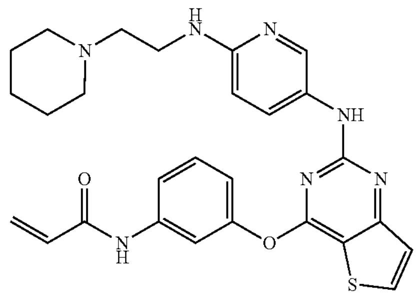 [SMILES: C=CC(=O)Nc1cccc(Oc2nc(Nc3ccc(NCCN4CCCCC4)nc3)nc3ccsc23)c1] | ¹H-NMR (300 MHz, DMSO-d₆) δ 10.33(s, 1H), 9.24(s, 1H), 8.31 (d, 1H), 8.26 (m, 1H), 7.82 (m, 1H), 7.79 (m, 1H), 7.58 (m, 1H), 7.42 (m, 1H), 7.32 (m, 1H), 7.05 (m, 1H), 6.63 (m, 1H), 6.33 (m, 1H), 6.28 (dd, 1H), 5.76 (dd, 1H), 3.67 (m, 4H), 3.28 (m, 4H); MS (ESI⁺): m/z = 516.2 [M + H]⁺. |
| 154 | 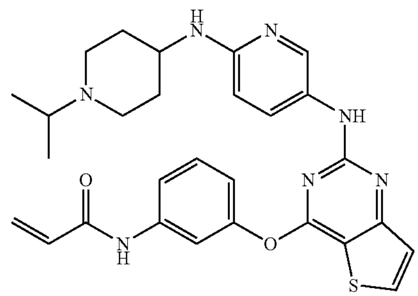 [SMILES: C=CC(=O)Nc1cccc(Oc2nc(Nc3ccc(NC4CCN(C(C)C)CC4)nc3)nc3ccsc23)c1] | ¹H-NMR (300 MHz, DMSO-d₆) δ 10.34 (s, 1H), 9.08 (s, 1H), 8.35 (d, 1H), 8.23 (m, 1H), 7.65 (d, 1H), 7.57 (m, 1H), 7.42 (m, 2H), 7.28 (d, 1H), 7.04 (m, 1H), 6.42 (m, 2H), 6.28 (m, 2H), 6.02 (d, 1H), 5.74 (dd, 1H), 2.67 (m, 4H), 2.16 (m, 2H), 1.84 (m, 2H), 1.33 (m, 2H), 0.97 (m, 6H); MS (ESI⁺): m/z = 530.2 [M + H]⁺. |
| 155 | 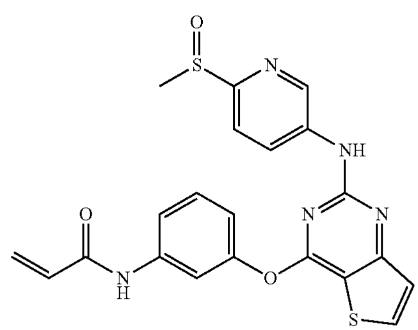 [SMILES: C=CC(=O)Nc1cccc(Oc2nc(Nc3ccc(S(C)=O)nc3)nc3ccsc23)c1] | ¹H-NMR (300 MHz, DMSO-d₆) δ 10.39 (s, 1H), 10.05 (s, 1H), 8.86 (s, 1H), 8.37 (d, 1H), 8.31 (d, 1H), 7.80 (s, 1H), 7.45~7.63 (m, 4H), 7.10 (d, 1H), 6.39 (m, 1H), 6.22 (dd, 1H), 5.75 (dd, 1H); MS (ESI⁺): m/z = 452.1 [M + H]⁺. |
| 156 | 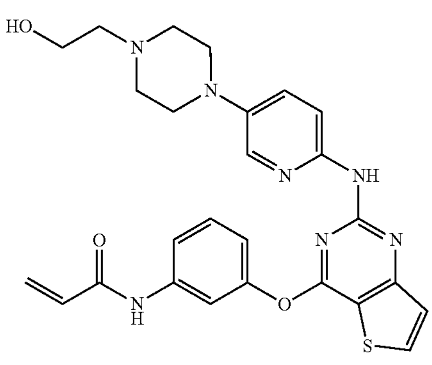 [SMILES: C=CC(=O)Nc1cccc(Oc2nc(Nc3ccc(N4CCN(CCO)CC4)cn3)nc3ccsc23)c1] | ¹H-NMR (300 MHz, DMSO-d₆): δ 10.38 (brs, 1H), 9.33 (s, 1H), 8.31-8.29 (d, 1H), 7.88 (s, 1H), 7.71 (s, 1H), 7.65-7.61 (m, 2H), 7.48-7.43 (t, 1H), 7.36-7.34 (d, 1H), 7.09-7.02 (m, 2H), 6.48-6.41 (m, 1H), 6.27-6.21 (m, 1H), 5.78-5.75 (m, 1H), 4.52-4.41 (m, 1H), 3.53-3.44 (m, 2H), 3.03 (m, 4H), 2.66-2.48 (m, 6H); MS (ESI⁺): m/z = 518 [M + H]⁺. |

Example 157

Preparation of N-(3-(2-(4-(4-methyl-4-oxy-piperazin-1-yl)-phenylamino)-thieno[3,2-d]pyrimidine-4-yloxy)-phenyl)-acrylamide

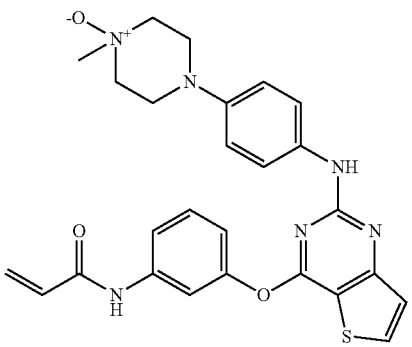

The compound (100 mg, 0.21 mmol) obtained in Example 1 was dissolved in dichloromethane (2 mL), and m-chloroperbenzoic acid (71 mg, 0.42 mmol) was added thereto, followed by stirring at 45° C. for 12 hours. After the reaction was complete, the reaction mixture was diluted with dichloromethane and washed with sat. NaHCO$_3$ aqueous solution. The organic layer was dried with anhydrous sodium sulfate and then filtered and distilled under a reduced pressure, and the residue was separated by column chromatography (chloroform saturated with ammonia:methanol=4:1 (volume ratio)) to obtain the title compound (yield: 25 mg, 40%).

$^1$H-NMR (300 MHz, DMSO-d$_6$) δ 10.38 (s, NH), 9.27 (s, NH), 8.28 (d, 1H), 7.74 (s, 1H), 7.60 (d, 1H), 7.46 (m, 3H), 7.33 (d, 1H), 7.05 (d, 1H), 6.78 (d, 2H), 6.43 (m, 1H), 6.28 (m, 1H), 5.76 (m, 1H), 3.57 (m, 4H), 2.98 (s, 3H), 2.95 (m, 2H), 2.50 (m, 2H);

MS (ESI$^+$): m/z=503.1 [M+H]$^+$.

Example 158

Preparation of N-(3-(2-(4-(piperazin-1-yl)phenylamino)-thieno[3,2-d]pyrimidine-4-yloxy)-phenyl)-acrylamide

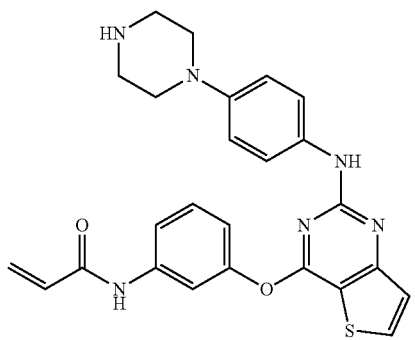

Step 1) Preparation of 4-(4-(4-(3-acryloylaminophenoxy)-thieno[3,2-d]pyrimidine-2-ylamino)-phenyl)-piperazin-1-carboxylic acid tert-butyl ester

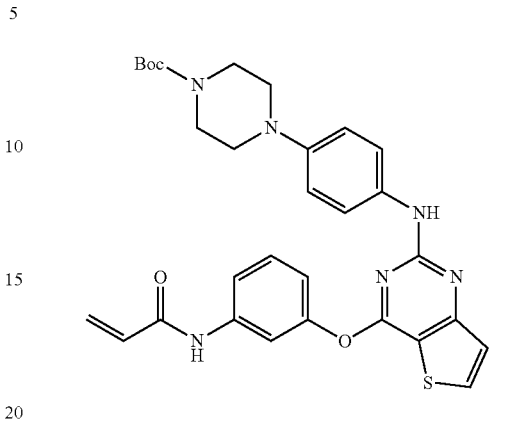

The procedure of Step 4 of Example 1 was repeated except for using tert-butyl 4-(4-aminophenyl)piperazin-1-carboxylate instead of 4-(4-methylpiperazin-1-yl)benzeneamine to obtain the title compound (yield: 610 mg, 91%).

$^1$H-NMR (300 MHz, CDCl$_3$) δ 7.82-7.80 (m, 1H), 7.59-7.52 (m, 3H), 7.43-7.34 (m, 3H), 7.06-7.03 (m, 1H), 6.92 (s, 1H), 6.80-6.77 (m, 2H), 6.47-6.41 (m, 1H), 6.27-6.24 (m, 1H), 5.79-5.75 (m, 1H), 3.57 (m, 4H), 3.02-2.99 (m, 4H), 1.48 (s, 9H).

Step 2) Preparation of N-(3-(2-(4-(piperazin-1-yl)-phenylamino)-thieno[3,2-d]pyrimidine-4-yloxy)-phenyl)-acrylamide The compound (600 mg, 1.05 mmol) obtained in Step 1 was dissolved in dichloromethane (10 mL), and trifluoroacetic acid (1.62 mL, 21.0 mmol) was added thereto, followed by stirring at room temperature for 1 hour. After the reaction was complete, the reaction mixture was distilled under a reduced pressure to remove solvent, alkalify (pH 8) with sat. NaHCO$_3$ aqueous solution, and extracted with chloroform 2 times. The organic layer was separated, washed with water and sat. brine, dried with anhydrous sodium sulfate, and then filtered and distilled under a reduced pressure. The residue was separated by column chromatography (chloroform:methanol=10:1 (volume ratio)) to obtain the title compound (yield: 316 mg, 72%).

$^1$H-NMR (300 MHz, CDCl$_3$) δ 10.28 (brs, 1H), 9.15 (brs, 1H), 8.26-8.24 (m, 1H), 7.68 (s, 1H), 7.62-7.59 (m, 1H), 7.50-7.41 (m, 1H), 7.31-7.29 (m, 1H), 7.06-7.00 (m, 1H), 6.74-6.71 (m, 2H), 6.44-6.38 (m, 1H), 6.27-6.21 (m, 1H), 5.78-5.74 (m, 1H), 3.31 (m, 4H), 3.04-2.96 (m, 4H);

MS (ESI$^+$): m/z=473.4 [M+H]$^+$.

The procedure of Example 158 was repeated except for using tert-butyl 4-(4-amino-2-chlorophenyl)piperazin-1-carboxylate or [1-(4-aminophenyl)cyclopropyl]carbamic acid tert-butyl ester instead of tert-butyl 4-(4-aminophenyl)piperazin-1-carboxylate in Step 4, to prepare the compounds of Examples 159 and 160 which are shown in Table 2 below.

TABLE 2

| Example | Structure | Analysis data |
|---|---|---|
| 159 | 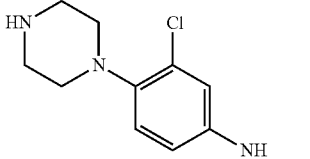 | $^1$H-NMR (300 MHz, DMSO-d$_6$) δ 9.54 (brs, 1H), 8.30 (d, 1H), 7.86-7.71 (m, 2H), 7.59 (d, 1H), 7.47-7.41 (m, 2H), 7.35 (d, 1H), 7.05 (m, 1H), 6.92 (m, 1H), 6.39-6.50 (m, 1H), 6.27-6.16 (m, 1H), 5.77-5.74 (m, 1H), 2.99-2.89 (m, 8H); MS (ESI$^+$): m/z = 507.13 [M + H]$^+$. |
| 160 | 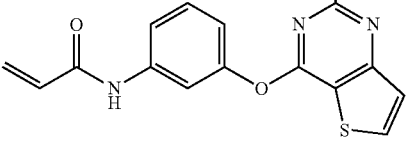 | $^1$H-NMR (300 MHz, CDCl$_3$) δ 7.85 (d, 1H), 7.66 (m, 2H), 7.55 (m, 1H), 7.42 (m, 2H), 7.15 (d, 2H), 7.11 (d, 1H), 7.01 (s, 1H), 6.42 (d, 1H), 6.25 (dd, 1H), 5.79 (d, 1H), 0.96 (m, 2H), 0.89 (m, 2H); MS (ESI$^+$): m/z = 444 [M + H]$^+$. |

Example 161

Preparation of (Z)-3-chloro-N-(3-(2-(4-(4-methylpiperazin-1-yl)phenylamino)thieno[3,2-d]pyrimidine-4-yloxy)phenyl)acrylamide

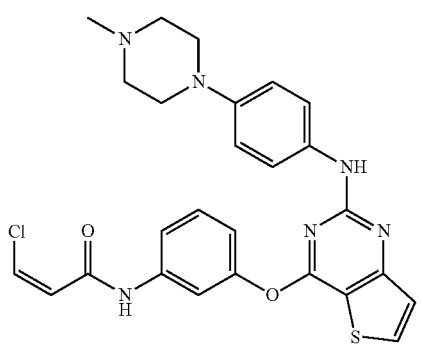 [SMILES: CN1CCN(c2ccc(Nc3nc(Oc4cccc(NC(=O)/C=C\Cl)c4)c4sccc4n3)cc2)CC1]

The compound (50 mg, 0.12 mmol) obtained in Step 5 of Example 1 was dissolved in pyridine (1.5 mL), and cis-3-chloroacrylic acid (18 mg, 0.17 mmol) and N-(3-dimethylaminopropyl)-N'-ethylcarbodiimide hydrochloric acid salt (44 mg, 0.23 mmol) were added thereto, followed by stirring at room temperature for 1 hour. After the reaction was complete, the reaction mixture was diluted with a mixed solvent (chloroform:2-propanol=3:1 (volume ratio)) and washed with sat. brine. The organic layer was dried with anhydrous sodium sulfate and then filtered and distilled under a reduced pressure. The residue was separated by column chromatography (dichloromethane:methanol=6:1 (volume ratio)) to obtain the title compound (yield: 15 mg, 24%).

$^1$H-NMR (300 MHz, CDCl$_3$) δ 8.24 (s, 1H), 7.82 (d, 1H), 7.62 (s, 1H), 7.57 (d, 1H), 7.44 (d, 1H), 7.39 (d, 1H), 7.35 (s, 1H), 7.26 (d, 1H), 7.08 (m, 1H), 6.98 (s, 1H), 6.81 (d, 2H), 6.62 (d, 1H), 6.34 (d, 1H), 3.13 (t, 4H), 2.59 (t, 4H), 2.36 (s, 3H);

MS (ESI$^+$): m/z=521.4 [M+H]$^+$.

The procedure of Example 161 was repeated except for using trans-3-chloroacrylic acid and (E)-4-(dimethylamino)-2-butenoic acid to prepare the compounds of Examples 162 and 163 which are shown in Table 3 below.

TABLE 3

| Example | Structure | Analysis data |
|---|---|---|
| 162 | 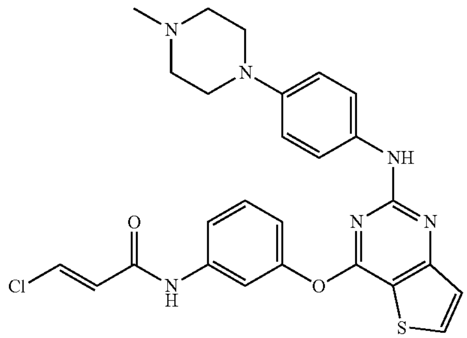 [SMILES: CN1CCN(c2ccc(Nc3nc(Oc4cccc(NC(=O)/C=C/Cl)c4)c4sccc4n3)cc2)CC1] | $^1$H-NMR (300 MHz, CDCl$_3$) δ 7.82 (d, 1H), 7.62 (m, 2H), 7.55 (d, 1H), 7.42 (s, 1H), 7.41 (d, 1H), 7.35 (d, 2H), 7.25 (d, 1H), 7.08 (d, 1H), 6.92 (s, 1H), 6.81 (d, 2H), 6.40 (d, 1H), 3.14 (t, 4H), 2.61 (t, 4H), 2.38 (s, 3H); MS (ESI$^+$): m/z = 521.3 [M + H]$^+$. |
| 163 | 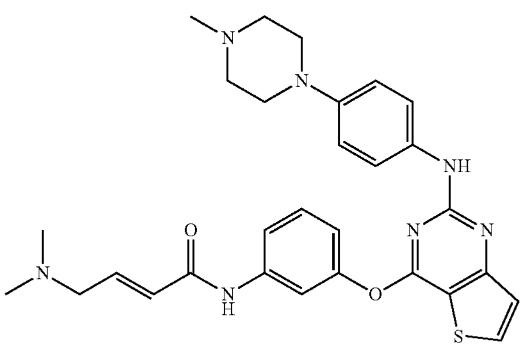 [SMILES: CN(C)C/C=C/C(=O)Nc1cccc(Oc2nc(Nc3ccc(N4CCN(C)CC4)cc3)nc3ccsc23)c1] | $^1$H-NMR (300 MHz, CDCl$_3$) δ 7.80 (d, 1H), 7.56 (m, 2H), 7.41 (d, 2H), 7.36 (d, 2H), 7.25 (d, 1H), 6.99 (d, 1H), 6.95 (m, 1H), 6.90 (s, 1H), 6.80 (d, 2H), 6.07 (m, 1H), 3.12 (t, 4H), 3.10 (d, 2H), 2.59 (t, 4H), 2.36 (s, 3H) 2.27 (s, 6H); MS (ESI$^+$): m/z = 544.2 [M + H]$^+$. |

Example 164

Preparation of N-(4-methyl-3-(2-(4-(4-methylpiperazin-1-yl)phenylamino)thieno[3,2-d]pyrimidin-4-yloxy)phenyl)acrylamide

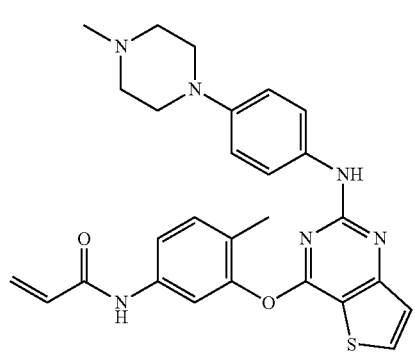 [SMILES: C=CC(=O)Nc1ccc(C)c(Oc2nc(Nc3ccc(N4CCN(C)CC4)cc3)nc3ccsc23)c1]

A similar procedure as the procedure of Example 1 was carried out except for using 2-methyl-5-nitrophenol (25 mmol), instead of 3-nitrophenol in step 3), to obtain the title compound (30 mg, final yield: 34%).

$^1$H-NMR (300 MHz, DMSO-d$_6$) δ 10.27 (s, 1H), 9.21 (s, 1H), 8.25 (d, 1H), 7.62 (s, 1H), 7.55 (d, 1H), 7.33 (m, 4H), 6.69 (m, 2H), 6.39 (m, 1H), 6.25 (m, 1H), 5.75 (d, 1H), 2.96 (m, 4H), 2.42 (m, 4H), 2.20 (s, 3H), 2.07 (s, 3H);

MS (ESI$^+$): m/z=501.2 [M+H]$^+$.

A similar procedure as the procedure of Example 164 was carried out except for using 2-fluoro-5-nitrophenol and 2-methoxy-5-nitrophenol, to obtain compounds of Example 165 and Example 166, respectively.

TABLE 4

| Example | Structure | Analysis data |
|---|---|---|
| 165 | 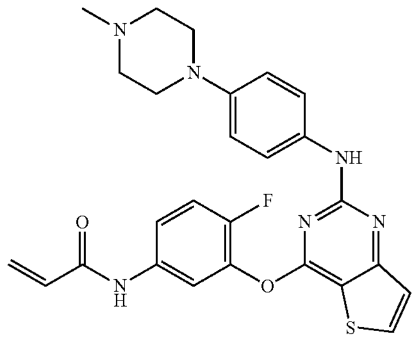 [SMILES: C=CC(=O)Nc1ccc(F)c(Oc2nc(Nc3ccc(N4CCN(C)CC4)cc3)nc3ccsc23)c1] | ¹H-NMR (300 MHz, DMSO-d$_6$) δ 10.40 (s, 1H), 9.30 (s, 1H), 8.31 (d, 1H), 7.83 (m, 1H), 7.64 (m, 1H), 7.46 (dd, 1H), 7.38 (m, 2H), 7.34 (d, 1H), 6.71 (m, 1H), 6.41 (dd, 1H), 6.27 (dd, 1H), 5.79 (dd, 1H), 3.00 (m, 4H), 2.44 (m, 4H), 2.22 (s, 3H);<br>MS (ESI⁺): m/z = 505.2 [M + H]⁺. |
| 166 | 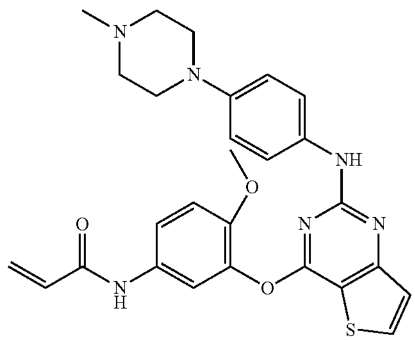 [SMILES: C=CC(=O)Nc1ccc(OC)c(Oc2nc(Nc3ccc(N4CCN(C)CC4)cc3)nc3ccsc23)c1] | ¹H-NMR (300 MHz, DMSO-d$_6$) δ 10.18 (s, 1H), 9.20 (s, 1H), 8.24 (d, 1H), 7.63 (m, 2H), 7.35 (d, 2H), 7.29 (d, 1H), 7.20 (d, 1H), 6.69 (d, 2H), 6.36 (dd, 1H), 6.22 (dd, 1H), 5.75 (dd, 1H), 3.68 (s, 3H), 2.98 (m, 4H), 2.44 (m, 4H), 2.20 (s, 3H);<br>MS (ESI⁺): m/z = 517.2 [M + H]⁺. |

Example 167

Preparation of N-(3-(2-(5-(4-methylpiperazin-1-yl)piridin-2-ylamino)thieno[3,2-d]pyrimidin-4-yloxy)phenyl)acrylamide

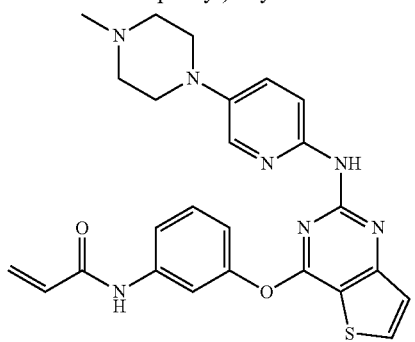

Step 1) Preparation of N-(5-(4-methylpiperazin-1-yl)piridin-2-yl)-4-(3-nitrophenoxy)thieno[3,2-d]pyrimidin-2-amine

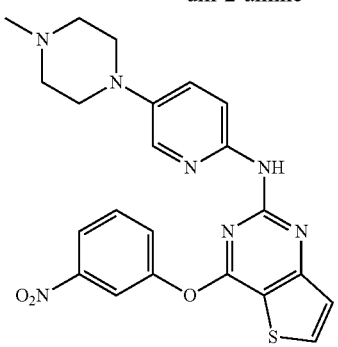

0.6 g (1.94 mmol) of the compound obtained in Step 3 of Example 1 and 0.75 g (3.88 mmol) of 5-(4-methylpiperazin-1-yl)piridin-2-amine were dissolved in 8 ml of 1,4-dioxane, and 178 mg (0.2 mmol) of tris(dibenzylideneacetone)dipalladium(O) and 122 mg (0.2 mmol) of 2,2'-bis(diphenylphosphino)-1,1'-binaphthy were added thereto, and stirred for 5 minutes at room temperature. 1.27 g (3.88 mmol) of cesium carbonate was added thereto, and stirred for 3 hours at 100° C. Upon the completion of the reaction, the resulting mixture was cooled to room temperature and filtered over a short bed of Celite filter, and diluted with dichloromethane and washed with water. The organic layer was separated, dried over anhydrous Na$_2$SO$_4$, and filtered and distilled under a reduced pressure. The resulting residue was separated by column chromatography (dichloromethane:methanol (20:1, v/v)) to obtain 630 mg of the title compound (yield: 70%).

¹H-NMR (300 MHz, DMSO-d$_6$) δ 9.42 (s, 1H), 8.33 (m, 2H), 8.20 (m, 1H), 7.91 (m, 2H), 7.80 (m, 1H), 7.59 (m, 1H), 7.39 (m, 1H), 7.05 (m, 1H), 3.05 (m, 4H), 2.49 (m, 4H), 2.22 (s, 3H).

Step 2) Preparation of N-(3-(2-(5-(4-methylpiperazin-1-yl)piridin-2-ylamino)thieno[3,2-d]pyrimidin-4-yloxy)phenyl)acrylamide The procedure of step 5) and 6) of Example 1 were repeated sequentially except for using the compound obtained in the step 1) (1.35 mmol), instead of N-(4-(4-methylpiperazin-1-yl)phenyl)-4-(3-nitrophenoxy)thieno[3,2-d]pyrimidin-2-amine, to obtain 50 mg of the title compound (final yield: 34%).

¹H-NMR (300 MHz, DMSO-d₆) δ 10.50 (s, 1H), 9.37 (s, 1H), 8.10 (d, 1H), 7.90 (d, 1H), 7.72 (m, 1H), 7.64 (m, 2H), 7.47 (dd, 1H), 7.37 (d, 1H), 7.09 (m, 2H), 6.42 (dd, 1H), 6.25 (dd, 1H), 5.77 (dd, 1H), 3.01 (m, 4H), 2.42 (m, 4H), 2.22 (s, 3H);

MS (ESI⁺): m/z=488.3[M+H]⁺.

The procedure of Example 167 or a similar procedure was repeated except for using various amine derivatives of Z—NH₂ (Z has the same meaning as defined in the present invention), instead of 5-(4-methylpiperazin-1-yl)piridin-2-amine in step 1) of Example 167, to obtain the title compounds of Examples 168 to 205 as shown in Tables 5a to 5f.

TABLE 5a

| Example | Structure | Analysis data |
|---|---|---|
| 168 | 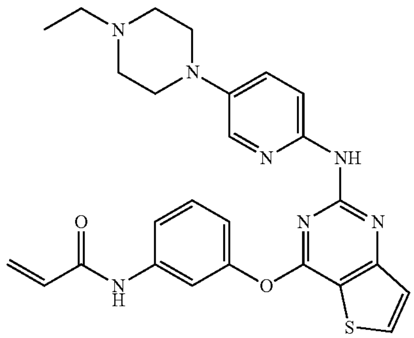 [SMILES: C=CC(=O)Nc1cccc(Oc2nc(Nc3ccc(N4CCN(CC)CC4)cn3)nc3ccsc23)c1] | ¹H-NMR (300 MHz, CDCl₃) δ 7.94 (d, 1H), 7.91 (d, 1H), 7.85 (d, 1H), 7.63 (s, 1H), 7.60 (m, 1H), 7.55 (s, 1H), 7.43 (d, 1H), 7.41 (d, 1H), 7.31 (d, 1H), 7.10 (dd, 1H), 7.02 (dd, 1H), 6.45 (dd, 1H), 6.23 (m, 1H), 5.79 (dd, 1H), 3.14 (t, 4H), 2.62 (t, 4H), 2.48 (q, 2H), 1.14 (t, 3H); MS (ESI⁺): m/z = 502.4 [M + H]⁺. |
| 169 | 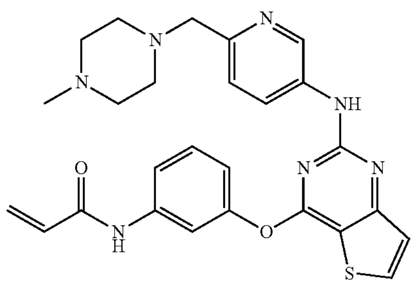 [SMILES: C=CC(=O)Nc1cccc(Oc2nc(Nc3ccc(CN4CCN(C)CC4)nc3)nc3ccsc23)c1] | ¹H-NMR (300 MHz, DMSO-d₆) δ 10.35 (s, 1H), 9.62 (s, 1H), 8.77 (s, 1H), 8.30 (d, 1H), 7.99 (m, 1H), 7.71 (m, 1H), 7.54 (m, 1H), 7.37 (m, 2H), 7.06 (m, 2H), 6.41 (m, 1H), 6.21 (dd, 1H), 5.74 (dd, 1H), 3.45 (m, 2H), 2.32 (m, 8H), 2.12 (s, 3H); MS (ESI⁺): m/z = 502.2 [M + H]⁺. |
| 170 | 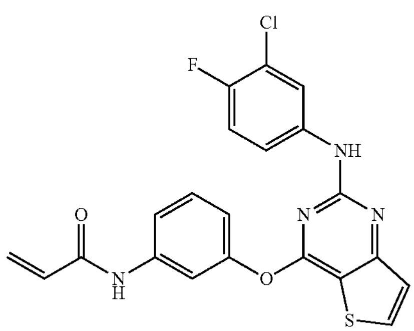 [SMILES: C=CC(=O)Nc1cccc(Oc2nc(Nc3ccc(F)c(Cl)c3)nc3ccsc23)c1] | ¹H-NMR (300 MHz, DMSO-d₆) δ 10.35 (brs, 1H), 9.71 (brs, 1H), 8.33-8.31 (m, 1H), 7.85-7.84 (m, 1H), 7.74 (s, 1H), 7.56-7.37 (m, 3H), 7.17-7.11 (t, 1H), 7.08-7.05 (m, 1H), 6.45-6.36 (m, 1H), 6.25-6.20 (m, 1H), 5.77-5.73 (m, 1H); MS (ESI⁺): m/z = 441.3 [M + H]⁺. |
| 171 | 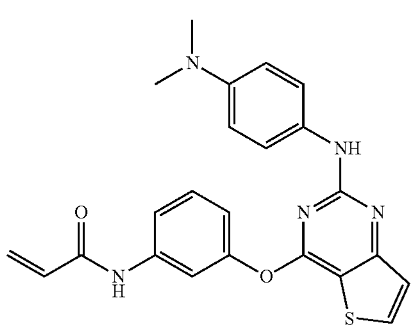 [SMILES: C=CC(=O)Nc1cccc(Oc2nc(Nc3ccc(N(C)C)cc3)nc3ccsc23)c1] | ¹H-NMR (300 MHz, DMSO-d₆) δ 10.35 (s, 1H), 9.12 (s, 1H), 8.25 (d, 1H), 7.63 (m, 2H), 7.42 (m, 4H), 7.06 (m, 1H), 6.50 (m, 3H), 6.24 (m, 1H), 5.77 (m, 1H), 2.78 (s, 3H); MS (ESI⁺): m/z = 432.3 [M + H]⁺. |

TABLE 5a-continued

| Example | Structure | Analysis data |
|---|---|---|
| 172 | 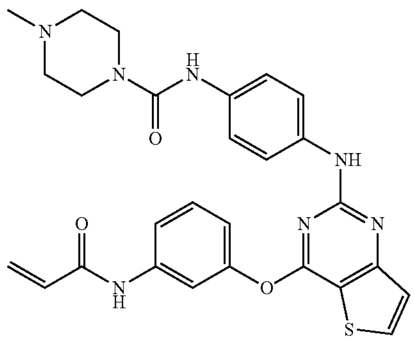 [SMILES: C=CC(=O)Nc1cccc(Oc2nc(Nc3ccc(NC(=O)N4CCN(C)CC4)cc3)nc3ccsc23)c1] | ¹H-NMR (300 MHz, DMSO-d₆) δ 10.60 (s, 1H), 9.45 (s, 1H), 8.29 (s, 2H), 7.70 (m, 1H), 7.58 (m, 1H), 7.46 (m, 3H), 7.34 (m, 1H), 7.17 (m, 2H), 7.09 (m, 1H), 6.40 (dd, 1H), 6.26 (dd, 1H), 5.77 (dd, 1H), 3.42 (m, 4H), 2.29 (m, 4H), 2.17 (s, 3H); MS (ESI⁺): m/z = 530.2 [M + H]⁺. |
| 173 | 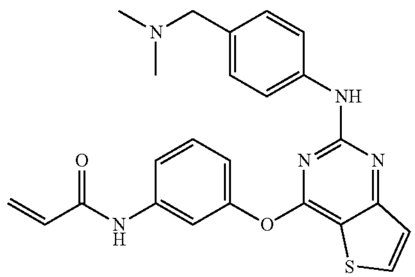 [SMILES: C=CC(=O)Nc1cccc(Oc2nc(Nc3ccc(CN(C)C)cc3)nc3ccsc23)c1] | ¹H-NMR (300 MHz, DMSO-d₆) δ 10.34 (s, 1H), 9.46 (s, 1H), 8.29 (d, 1H), 7.72 (s, 1H), 7.60 (m, 1H), 7.48 (m, 3H), 7.35 (d, 1H), 7.07 (d, 1H), 6.99 (d, 2H), 6.40 (m, 1H), 6.23 (m, 1H), 5.75 (m, 1H), 3.22 (s, 2H), 2.06 (s, 6H); MS (ESI⁺): m/z = 446.4 [M + H]⁺. |
| 174 | 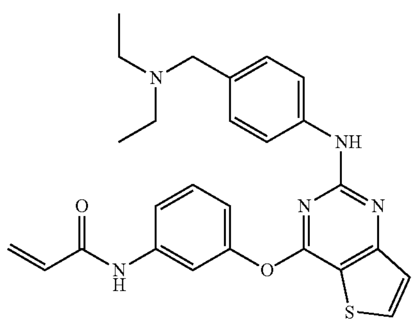 [SMILES: C=CC(=O)Nc1cccc(Oc2nc(Nc3ccc(CN(CC)CC)cc3)nc3ccsc23)c1] | ¹H-NMR (300 MHz, CDCl₃) δ 7.87-7.83 (m, 2H), 7.48 (m, 1H), 7.42-7.37 (t, 1H), 7.33-7.30 (m, 2H), 7.20-7.17 (m, 2H), 7.10 (brs, 1H), 7.02-6.99 (m, 1H), 6.43-6.37 (m, 2H), 5.73-5.69 (m, 1H), 3.48 (s, 2H), 2.71-2.64 (m, 4H), 1.08-1.03 (t, 6H); MS (ESI⁺): m/z = 473.96 [M + H]⁺. |

TABLE 5b

| Example | Structure | Analysis data |
|---|---|---|
| 175 | 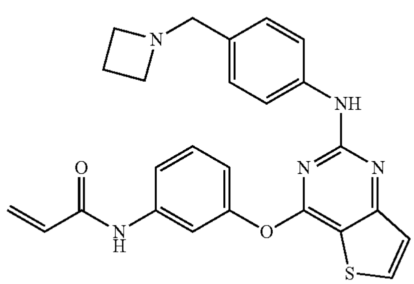 [SMILES: C=CC(=O)Nc1cccc(Oc2nc(Nc3ccc(CN4CCC4)cc3)nc3ccsc23)c1] | ¹H-NMR (300 MHz, CDCl₃) δ 8.06 (s, 1H), 7.87 (d, 1H), 7.44 (s, 1H), 7.36 (m, 1H), 7.33 (m, 3H), 7.04 (m, 3H), 7.02 (s, 1H), 6.39 (d, 1H), 6.27 (dd, 1H), 5.72 (d, 1H), 3.48 (s, 2H), 3.18 (m, 4H), 2.03 (m, 2H); MS (ESI⁺): m/z = 458.17 [M + H]⁺. |

TABLE 5b-continued

| Example | Structure | Analysis data |
|---|---|---|
| 176 | 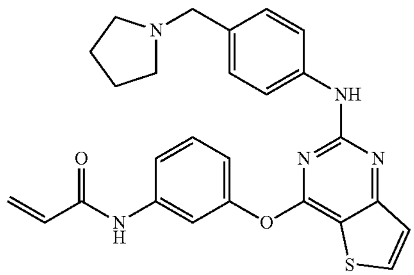 [SMILES: C=CC(=O)Nc1cccc(Oc2nc(Nc3ccc(CN4CCCC4)cc3)nc3ccsc23)c1] | ¹H-NMR (300 MHz, CDCl₃) δ 9.75 (brs, 1H), 8.37 (s, 1H), 7.87 (d, 2H), 7.46 (m, 2H), 7.37 (d, 1H), 7.21 (m, 3H), 6.96 (d, 1H), 6.63 (dd, 1H), 6.36 (dd, 1H), 5.67 (d, 1H), 3.85 (s, 2H), 3.02 (m, 4H), 2.17 (m, 4H);<br>MS (ESI⁺): m/z = 472.2 [M + H]⁺. |
| 177 | 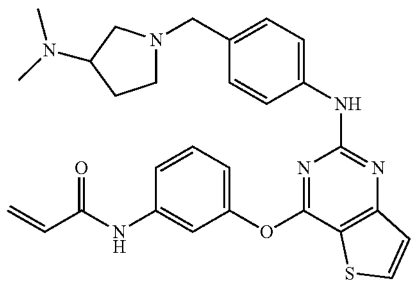 [SMILES: C=CC(=O)Nc1cccc(Oc2nc(Nc3ccc(CN4CCC(N(C)C)C4)cc3)nc3ccsc23)c1] | ¹H-NMR (300 MHz, CD₃OD) δ 8.07 (d, 1H), 7.72 (S, 1H), 7.60 (d, 1H), 7.48-7.42 (m, 3H), 7.28 (d, 1H), 7.10-7.03 (m, 3H), 6.43-6.38 (m, 2H), 5.80-5.76 (m, 1H), 3.59-3.47 (m, 2H), 2.91-2.74 (m, 3H), 2.50-2.47 (m, 6H), 2.30-2.22 (m, 7H), 2.01-1.99 (m, 1H), 1.72-1.71 (m, 1H);<br>MS (ESI⁺): m/z = 515.22 [M + H]⁺. |
| 178 | 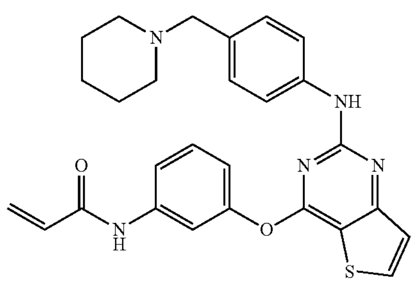 [SMILES: C=CC(=O)Nc1cccc(Oc2nc(Nc3ccc(CN4CCCCC4)cc3)nc3ccsc23)c1] | ¹H-NMR (300 MHz, CDCl₃) δ 8.03 (s, 1H), 7.80 (d, 1H), 7.78-7.28 (m, 4H), 7.19 (s, 2H), 6.88 (d, 1H), 6.57 (dd, 1H), 6.27 (d, 1H), 5.59 (d, 1H), 3.78 (s, 2H), 2.75 (t, 4H), 1.82 (t, 4H), 1.53-1.51 (m, 2H);<br>MS (ESI⁺): m/z = 486.3 [M + H]⁺. |
| 179 | 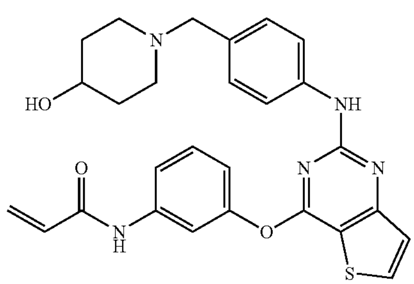 [SMILES: C=CC(=O)Nc1cccc(Oc2nc(Nc3ccc(CN4CCC(O)CC4)cc3)nc3ccsc23)c1] | ¹H-NMR (300 MHz, DMSO-d₆) δ 10.42 (brs, 1H), 9.61 (brs, 1H), 8.32 (d, 1H), 7.74-7.08 (m, 9H), 6.45-6.40 (d, 1H), 6.26 (dd, 1H), 5.77 (dd, 1H), 3.74-3.62 (m, 2H), 2.75-2.71 (m, 2H), 2.13-2.06 (m, 2H), 1.88-1.85 (m, 2H), 1.62-1.52 (m, 3H);<br>MS (ESI⁺): m/z = 502.18 [M + H]⁺. |
| 180 | 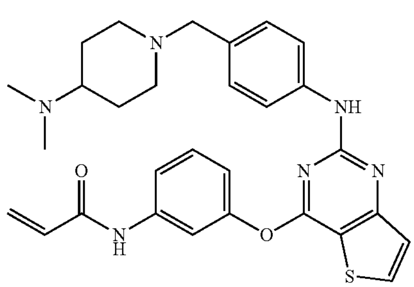 [SMILES: C=CC(=O)Nc1cccc(Oc2nc(Nc3ccc(CN4CCC(N(C)C)CC4)cc3)nc3ccsc23)c1] | ¹H-NMR (300 MHz, DMSO-d₆) δ 10.33 (brs, 1H), 9.45 (brs, 1H), 8.28 (d, 1H), 7.71 (S, 1H), 7.60 (d, 1H), 7.50-7.42 (m, 3H), 7.34 (d, 1H), 7.08-7.05 (m, 1H), 6.98 (d, 2H), 6.46-6.37 (m, 1H), 6.27-6.21 (m, 1H), 5.75 (dd, 1H), 3.33-3.21 (m, 2H), 2.76-2.72 (m, 2H), 2.11 (s, 6H), 1.99-1.96 (m, 1H), 1.84-1.77 (m, 2H), 1.66-1.62 (m, 2H), 1.28-1.04 (m, 2H);<br>MS (ESI⁺): m/z = 529.23 [M + H]⁺. |

TABLE 5b-continued

| Example | Structure | Analysis data |
|---|---|---|
| 181 | 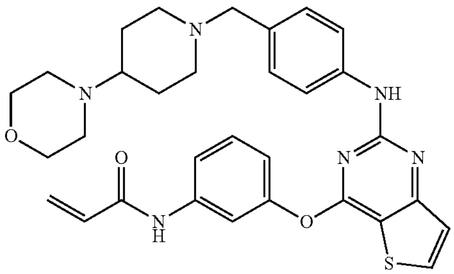 [SMILES: C=CC(=O)Nc1cccc(Oc2nc(Nc3ccc(CN4CCC(N5CCOCC5)CC4)cc3)nc3ccsc23)c1] | $^1$H-NMR (300 MHz, DMSO-d$_6$) δ 10.36 (s, NH), 9.47 (s, NH), 8.32 (d, !H), 7.73 (s, 1H), 7.64 (d, 1H), 7.52 (m, 3H), 7.38 (d, !H), 7.11 (d, 1H), 7.02 (d, 1H), 6.43 (dd, 1H), 6.24 (d, 1H), 5.76 (d, 1H), 3.59 (s, 1H), 3.47 (m, 1H), 3.31 (m, 4H), 2.76 (m, 2H), 2.43 (m, 4H), 1.86 (m, 2H), 1.79 (m, 2H), 1.36 (m, 2H); MS (ESI$^+$): m/z = 571.2 [M + H]$^+$. |

TABLE 5c

| Example | Structure | Analysis data |
|---|---|---|
| 182 | 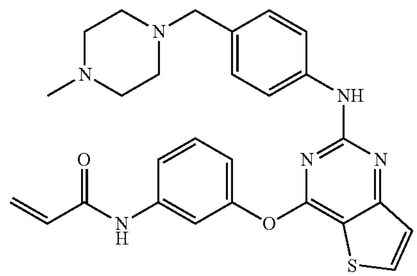 [SMILES: C=CC(=O)Nc1cccc(Oc2nc(Nc3ccc(CN4CCN(C)CC4)cc3)nc3ccsc23)c1] | $^1$H-NMR (300 MHz, DMSO-d$_6$) δ 7.97 (d, 1H), 7.55 (m, 1H), 7.45 (m, 1H), 7.30 (m, 3H), 7.25 (d, 1H), 6.95 (m, 3H), 6.29 (m, 2H), 6.02 (m, 1H), 3.41 (s, 2H), 2.55 (m, 8H), 2.36 (s, 3H); MS (ESI$^+$): m/z = 501.11 [M + H]$^+$. |
| 183 | 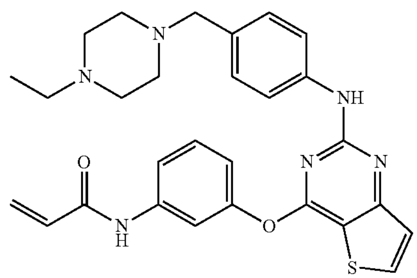 [SMILES: C=CC(=O)Nc1cccc(Oc2nc(Nc3ccc(CN4CCN(CC)CC4)cc3)nc3ccsc23)c1] | $^1$H-NMR (300 MHz, CD$_3$OD) δ 8.08 (d, 1H), 8.02 (m, 1H), 7.61 (m, 1H), 7.46 (m, 3H), 7.27 (d, 1H), 7.08 (m, 3H), 6.46 (d, 1H), 6.39 (d, 1H), 5.78 (m, 1H), 3.47 (s, 2H), 2.56 (br, 8H), 2.46 (q, 2H), 1.13 (t, 3H); MS (ESI$^+$): m/z = 515.4 [M + H]$^+$. |
| 184 | 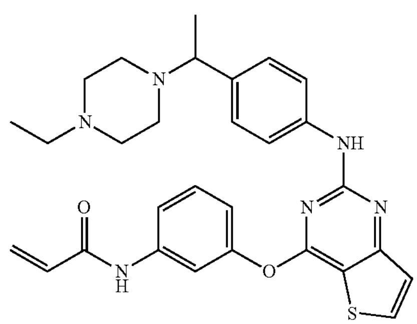 [SMILES: C=CC(=O)Nc1cccc(Oc2nc(Nc3ccc(C(C)N4CCN(CC)CC4)cc3)nc3ccsc23)c1] | $^1$H-NMR (300 MHz, CDCl$_3$) δ 8.10 (s, 1H), 7.82 (d, 1H), 7.69 (s, 1H), 7.47 (m, 1H), 7.40 (s, 1H), 7.37 (d, 1H), 7.34 (d, 1H), 7.26 (d, 1H), 7.10 (m, 3H), 7.02 (d, 1H), 6.42 (m, 1H), 6.25 (m, 1H), 5.73 (m, 1H), 3.29 (q, 1H), 2.46 (m, 8H), 2.39 (q, 2H), 1.34 (d, 3H), 1.06 (t, 3H); MS (ESI$^+$): m/z = 529.3 [M + H]$^+$. |
| 185 | 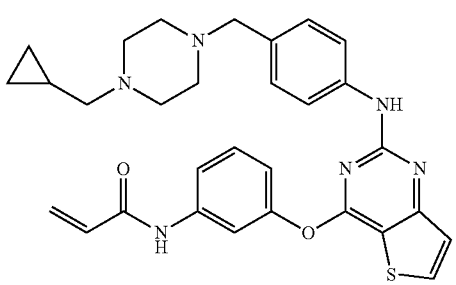 [SMILES: C=CC(=O)Nc1cccc(Oc2nc(Nc3ccc(CN4CCN(CC5CC5)CC4)cc3)nc3ccsc23)c1] | $^1$H-NMR (300 MHz, CDCl$_3$) δ 7.85-7.83 (d, 1H), 7.50-7.22 (m, 6H), 7.14-7.11 (m, 2H), 7.06-7.01 (m, 2H), 6.46-6.41 (m, 2H), 6.30-6.21 (m, 1H), 5.78-5.75 (m, 1H), 3.46 (s, 2H), 2.51 (m, 6H), 2.28 (d, 2H), 1.76 (m, 2H), 0.88-0.83 (m, 1H), 0.53-0.47 (m, 2H), 0.12-0.07 (m, 2H); MS (ESI$^+$): m/z = 541.4 [M + H]$^+$. |

TABLE 5c-continued

| Example | Structure | Analysis data |
|---|---|---|
| 186 | 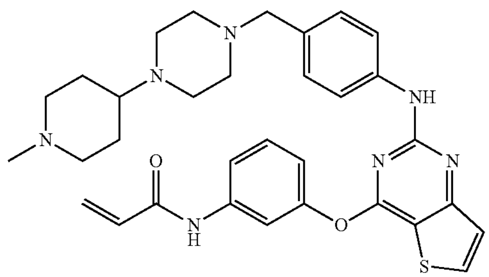 [SMILES: C=CC(=O)Nc1cccc(Oc2nc(Nc3ccc(CN4CCN(C5CCN(C)CC5)CC4)cc3)nc3ccsc23)c1] | $^1$H-NMR (300 MHz, CDCl$_3$) δ 7.84 (d, 1H), 7.61 (m, 2H), 7.49 (m, 1H), 7.43 (d, 3H), 7.19 (d, 2H), 6.97 (s, 1H), 6.45 (d, 1H), 6.26 (d, 1H), 5.78 (d, 1H), 3.48 (d, 2H), 3.43 (s, 1H), 2.89 (d, 2H), 2.57 (m, 4H), 2.46 (m, 3H), 2.25 (s, 3H), 1.91 (t, 2H), 1.70 (m, 3H), 1.60 (s, 2H). |
| 187 | 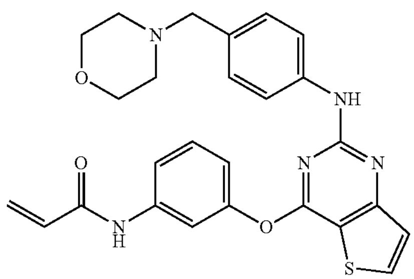 [SMILES: C=CC(=O)Nc1cccc(Oc2nc(Nc3ccc(CN4CCOCC4)cc3)nc3ccsc23)c1] | $^1$H-NMR (300 MHz, CDCl$_3$) δ 7.82 (m, 2H), 7.62 (s, 1H), 7.48 (d, 1H), 7.38 (m, 2H), 7.13 (m, 3H), 7.04 (d, 1H), 6.42 (dd, 1H), 6.24 (m, 1H), 5.76 (dd, 1H), 3.68 (m, 4H), 3.47 (s, 2H), 2.40 (m, 4H); MS (ESI$^+$): m/z = 488.17 [M + H]$^+$. |
| 188 | 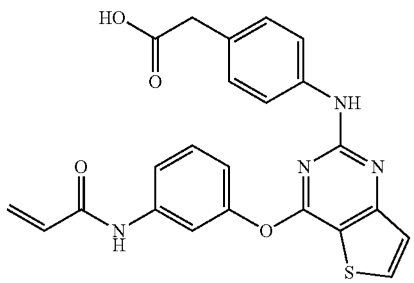 [SMILES: C=CC(=O)Nc1cccc(Oc2nc(Nc3ccc(CC(=O)O)cc3)nc3ccsc23)c1] | $^1$H-NMR (300 MHz, DMSO-d$_6$) δ 10.40 (s, 1H), 9.42 (s, 1H), 8.29 (d, 1H), 7.74 (s, 1H), 7.58 (d, 1H), 7.47 (m, 4H), 7.04 (m, 2H), 6.44 (dd, 1H), 6.25 (d, 1H), 5.71 (d, 1H), 3.70 (s, 3H); MS (ESI$^+$): m/z = 447.64 [M + H]$^+$. |

TABLE 5d

| Example | Structure | Analysis data |
|---|---|---|
| 189 | 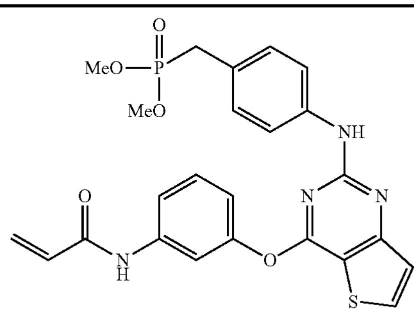 | $^1$H-NMR (300 MHz, DMSO-d$_6$) δ 10.37 (brs, 1H), 9.49 (brs, 1H), 8.30 (d, 1H) 7.73 (s, 1H), 7.59-7.47 (m, 4H), 7.37 (d, 1H), 7.03-7.00 (m, 3H), 6.48-6.41 (m, 1H), 6.31-6.29 (m, 1H), 5.79-5.92 (m, 1H), 3.59 (s, 3H), 3.55 (s, 3H), 3.16 (s, 2H); MS (ESI$^+$): m/z = 511.11 [M + H]$^+$. |
| 190 | 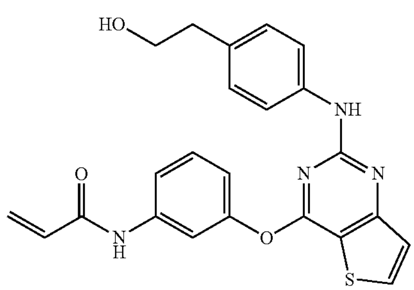 [SMILES: C=CC(=O)Nc1cccc(Oc2nc(Nc3ccc(CCO)cc3)nc3ccsc23)c1] | $^1$H-NMR (300 MHz, DMSO-d$_6$) δ 10.4 (s, 1H), 9.39 (s, 1H), 8.29 (d, 1H), 7.49 (d, 2H), 7.44 (m, 3H), 7.35 (d, 1H), 7.08 (dd, 1H), 6.95 (d, 2H), 6.42 (q, 1H), 6.24 (dd, 1H), 5.77 (dd, 1H), 3.51 (m, 2H), 2.60 (m, 2H); MS (ESI$^+$): m/z = 433 [M + H]$^+$. |

TABLE 5d-continued
| Example | Structure | Analysis data |
|---|---|---|
| 191 | 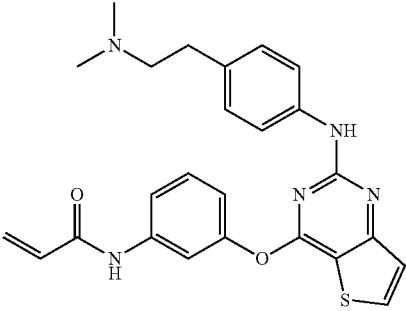 [SMILES: C=CC(=O)Nc1cccc(Oc2nc(Nc3ccc(CCN(C)C)cc3)nc3ccsc23)c1] | ¹H-NMR (300 MHz, CDCl₃) δ 7.83 (d, 1H), 7.54 (s, 1H), 7.45 (s, 1H), 7.41 (d, 1H), 7.38 (m, 1H), 7.35 (m, 2H), 7.03 (m, 2H), 7.00 (s, 1H), 6.43 (d, 1H), 6.31 (t, 3H), 5.74 (dd, 1H), 2.53 (m, 2H), 2.48 (m, 2H), 2.30 (s, 6H); MS (ESI⁺): m/z = 460 [M + H]⁺. |
| 192 | 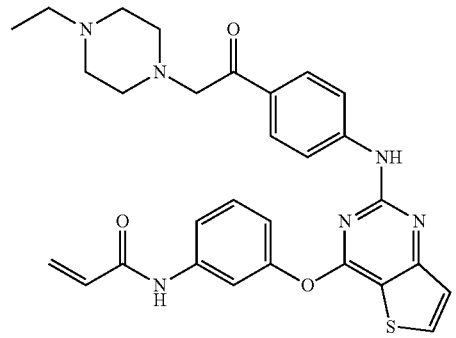 [SMILES: C=CC(=O)Nc1cccc(Oc2nc(Nc3ccc(C(=O)CN4CCN(CC)CC4)cc3)nc3ccsc23)c1] | ¹H-NMR (300 MHz, CDCl₃) δ 7.81 (d, 1H), 7.69 (s, 1H), 7.38-7.29 (m, 4H), 7.25-7.19 (m, 3H), 7.00 (d, 1H), 6.40 (d, 1H), 6.34 (dd, 1H), 5.72 (d, 1H), 3.66 (s, 2H), 3.42-3.40 (m, 2H), 2.40-2.38 (m, 4H), 1.58-1.55 (m, 4H), 1.01 (t, 3H); |
| 193 | 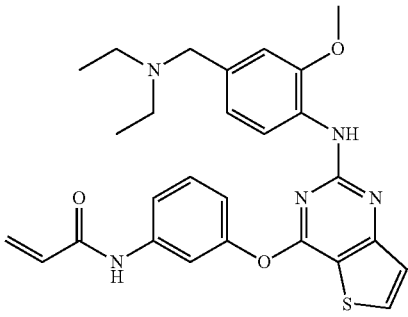 [SMILES: C=CC(=O)Nc1cccc(Oc2nc(Nc3ccc(CN(CC)CC)cc3OC)nc3ccsc23)c1] | ¹H-NMR (300 MHz, CDCl₃) δ 9.01 (s, 1H), 7.97 (s, 1H), 7.86 (d, 2H), 7.71 (s, 1H), 7.46 (m, 2H), 7.28 (m, 1H), 7.00 (m, 1H), 6.95 (d, 1H), 6.78 (s, 1H), 6.43 (m, 2H), 5.69 (m, 1H), 3.90 (s, 2H), 3.84 (s, 3H), 2.94 (m, 4H), 1.15 (m, 6H); MS (ESI⁺): m/z = 504.2 [M + H]⁺. |
| 194 | 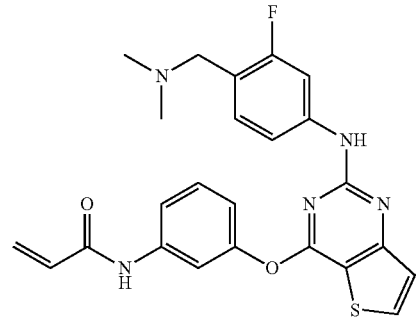 [SMILES: C=CC(=O)Nc1cccc(Oc2nc(Nc3ccc(CN(C)C)c(F)c3)nc3ccsc23)c1] | ¹H-NMR (300 MHz, CD₃OD) δ 8.10 (d, 1H), 7.78 (s, 1H), 7.61-7.56 (m, 2H), 7.47-7.42 (m, 1H), 7.32 (d, 1H), 7.20-7.05 (m, 3H), 6.50-6.33 (m, 2H), 5.78 (d, 1H), 3.58 (s, 2H), 2.32 (s, 6H); MS (ESI⁺): m/z = 464.15 [M + H]⁺. |

TABLE 5d-continued

| Example | Structure | Analysis data |
| --- | --- | --- |
| 195 | 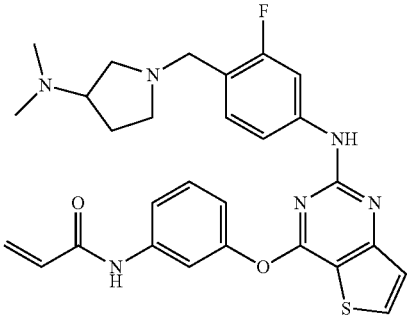 [SMILES: C=CC(=O)Nc1cccc(Oc2nc(Nc3ccc(CN4CCC(N(C)C)C4)c(F)c3)nc3ccsc23)c1] | $^1$H-NMR (300 MHz, CD$_3$OD) δ 8.10 (d, 1H), 7.78-7.77 (m, 1H), 7.59-7.42 (m, 3H), 7.32 (d, 1H), 7.15-7.04 (m, 3H), 6.43-6.38 (m, 2H), 5.78 (dd, 1H), 3.59-3.57 (m, 2H), 2.91-2.88 (m, 1H), 2.88-2.75 (m, 2H), 2.52-2.48 (m, 1H), 2.32-2.20 (m, 6H), 2.09-1.92 (m, 1H), 1.78-1.63 (m, 1H); MS (ESI$^+$): m/z = 533.21 [M + H]$^+$. |

TABLE 5e

| Example | Structure | Analysis data |
| --- | --- | --- |
| 196 | 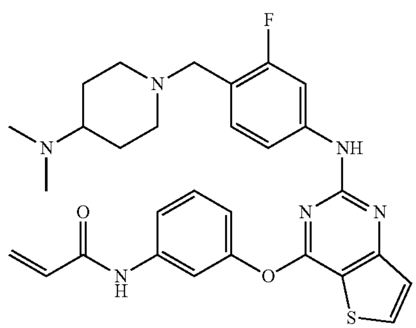 [SMILES: C=CC(=O)Nc1cccc(Oc2nc(Nc3ccc(CN4CCC(N(C)C)CC4)c(F)c3)nc3ccsc23)c1] | $^1$H-NMR (300 MHz, CD$_3$OD) δ 8.16 (d, 1H), 7.82 (s, 1H), 7.50-7.44 (m, 3H), 7.33 (d, 1H), 7.19-7.05 (m, 3H), 6.51-6.34 (m, 2H), 5.80 (dd, 1H), 3.49-3.45 (m, 2H), 2.98-2.94 (m, 2H), 2.41-2.01 (m, 9H), 1.90-1.81 (m, 2H), 1.69-1.42 (m, 2H); MS (ESI$^+$): m/z = 547.22 [M + H]$^+$. |
| 197 | 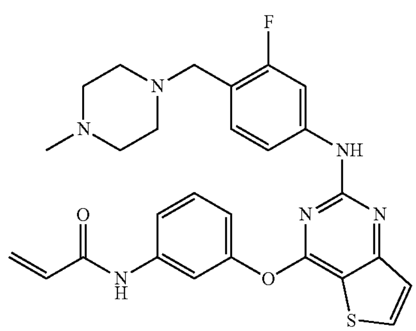 [SMILES: C=CC(=O)Nc1cccc(Oc2nc(Nc3ccc(CN4CCN(C)CC4)c(F)c3)nc3ccsc23)c1] | $^1$H-NMR (300 MHz, DMSO-d$_6$) δ 10.36 (s, 1H), 9.71 (s, 1H), 8.33 (d, 1H), 7.76 (s, 1H), 7.50 (m, 4H), 7.29 (m, 1H), 7.07 (m, 2H), 6.43 (dd, 1H), 6.24 (dd, 1H), 5.76 (dd, 1H), 3.36 (s, 2H), 2.33 (m, 8H), 2.08 (s, 3H); MS (ESI$^+$): m/z = 519.2 [M + H]$^+$. |
| 198 | 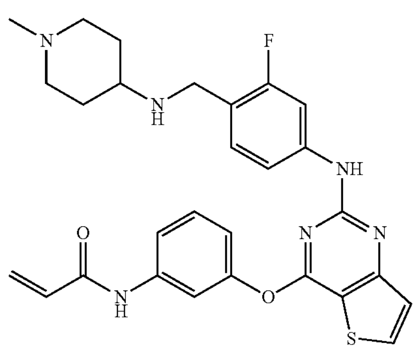 [SMILES: C=CC(=O)Nc1cccc(Oc2nc(Nc3ccc(CNC4CCN(C)CC4)c(F)c3)nc3ccsc23)c1] | $^1$H-NMR (300 MHz, CD$_3$OD) δ 8.11 (d, 1H), 7.74-7.73 (m, 1H), 7.60-7.58 (m, 2H), 7.45 (t, 1H), 7.32 (d, 1H), 7.17-7.12 (m, 2H), 7.07-7.04 (m, 1H), 6.48-6.33 (m, 2H), 5.79-5.76 (m, 1H), 3.78-3.77 (m, 2H), 2.94-2.90 (m, 2H), 2.55-2.52 (m, 1H), 2.30 (s, 3H), 2.15-1.89 (m, 4H), 1.53-1.49 (m, 2H); MS (ESI$^+$): m/z = 533.21 [M + H]$^+$. |

TABLE 5e-continued

| Example | Structure | Analysis data |
|---|---|---|
| 199 | 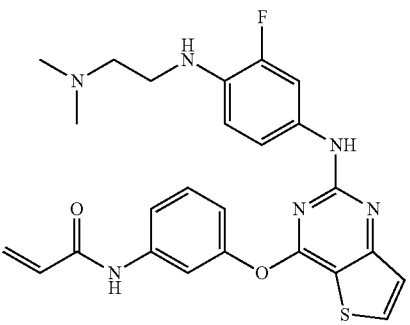 [SMILES: C=CC(=O)Nc1cccc(Oc2nc(Nc3ccc(NCCN(C)C)c(F)c3)nc3ccsc23)c1] | $^1$H-NMR (300 MHz, DMSO-d$_6$) δ 10.35 (s, 1H), 9.27 (s, 1H), 8.27 (m, 1H), 7.72 (m, 1H), 7.57 (m, 1H), 7.46 (m, 1H), 7.35 (m, 2H), 7.15 (m, H), 7.06 (m, 1H), 6.52 (m, 2H), 6.43 (m, 3H), 6.23 (dd, 1H), 5.76 (dd, 1H), 3.05 (m, 2H), 2.44 (m, 2H), 2.17 (s, 3H);<br>MS (ESI$^+$): m/z = 493.2 [M + H]$^+$. |
| 200 | 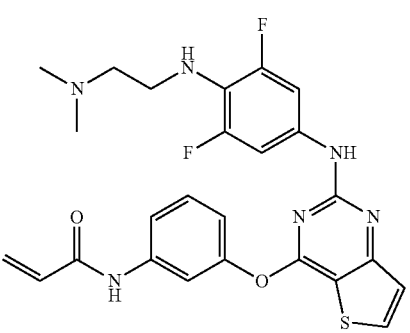 [SMILES: C=CC(=O)Nc1cccc(Oc2nc(Nc3cc(F)c(NCCN(C)C)c(F)c3)nc3ccsc23)c1] | $^1$H-NMR (300 MHz, DMSO-d$_6$) δ 10.33 (s, 1H), 9.51 (s, 1H), 8.29 (d, 1H), 7.74 (m, 1H), 7.46 (m, 1H), 7.41 (m, 1H), 7.37 (m, 1H), 7.23 (m, 2H), 7.05 (m, H), 6.43 (m, 1H), 6.21 (dd, 1H), 5.75 (dd, 1H), 4.30 (m, 1H), 3.11 (m, 2H), 2.33 (t, 2H), 2.12 (s, 6H);<br>MS (ESI$^+$): m/z = 511.2 [M + H]$^+$. |
| 201 | 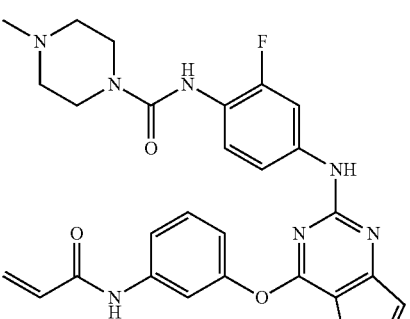 | $^1$H-NMR (300 MHz, DMSO-d$_6$) δ 10.39 (s, 1H), 9.70 (s, 1H), 8..37 (d, 1H), 8.08 (s, 1H), 7.80 (d, 1H), 7.60 (m, 2H), 7.50 (m, 2H), 7.27 (m, 1H), 7.12 (m, 2H), 6.43 (m, 1H), 6.31 (m, 1H), 5.82 (m, 1H), 3.41 (m, 4H), 2.33 (m, 4H), 2.24 (s, 3H);<br>MS (ESI$^+$): m/z = 548.2 [M + H]$^+$. |
| 202 | 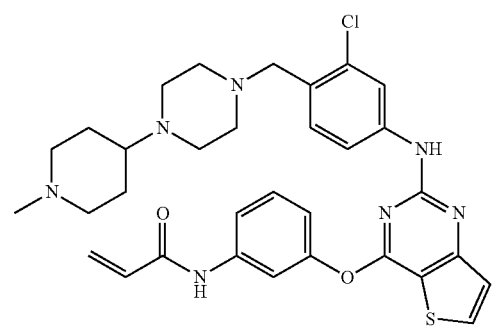 [SMILES: C=CC(=O)Nc1cccc(Oc2nc(Nc3ccc(CN4CCN(C5CCN(C)CC5)CC4)c(Cl)c3)nc3ccsc23)c1] | $^1$H-NMR (300 MHz, CDCl$_3$) δ 7.86 (d, 1H), 7.66 (m, 3H), 7.38 (m, 2H), 7.28 (d, 1H), 7.21 (m, 2H), 7.13 (s, 1H), 7.03 (m, 1H), 6.45 (m, 1H), 6.27 (m, 1H), 5.77 (m, 1H), 3.54 (s, 2H), 2.65 (m, 8H), 2.26 (s, 3H), 1.90 (m, 4H), 1.45 (m, 4H);<br>MS (ESI$^+$): m/z = 618.2 [M + H]$^+$. |

TABLE 5f

| Example | Structure | Analysis data |
|---|---|---|
| 203 | 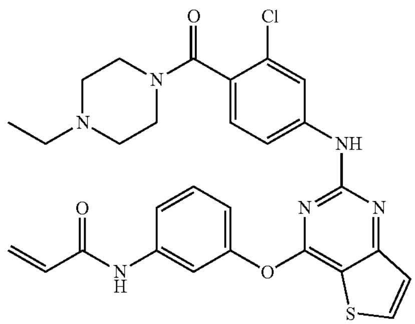 [SMILES: C=CC(=O)Nc1cccc(Oc2nc(Nc3ccc(C(=O)N4CCN(CC)CC4)c(Cl)c3)nc3ccsc23)c1] | ¹H-NMR (300 MHz, CD₃OD) δ 8.07 (d, 1H), 7.83 (s, 1H), 7.77 (s, 1H), 7.53 (d, 1H), 7.42 (d, 2H), 7.29 (d, 1H), 7.03 (d, 1H), 6.41 (s, 1H), 6.38 (d, 1H), 5.77 (dd, 1H), 3.76-3.74 (m, 2H), 3.26-3.24 (m, 2H), 2.48 (dd, 2H), 2.44 (d, 2H), 2.37 (m, 1H), 1.09 (t, 3H); MS (ESI⁺): m/z = 563.4 [M + H]⁺. |
| 204 | 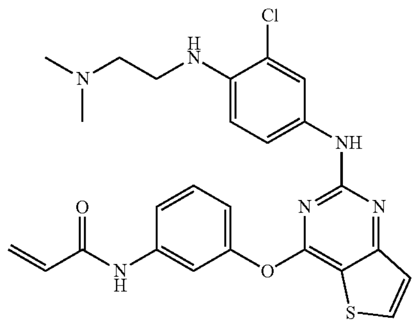 [SMILES: C=CC(=O)Nc1cccc(Oc2nc(Nc3ccc(NCCN(C)C)c(Cl)c3)nc3ccsc23)c1] | ¹H-NMR (300 MHz, DMSO-d₆) δ 10.33 (s, 1H), 9.22 (s, 1H), 8.24 (m, 1H), 7.75 (m, 1H), 7.57 (m, 1H), 7.42 (m, 1H), 7.30 (m, 2H), 7.14 (m, H), 7.06 (m, 1H), 6.52 (m, 2H), 6.43 (m, 3H), 6.23 (dd, 1H), 5.76 (dd, 1H), 3.05 (m, 2H), 2.44 (m, 2H), 2.17 (s, 3H); MS (ESI⁺): m/z = 509.1 [M + H]⁺. |
| 205 | 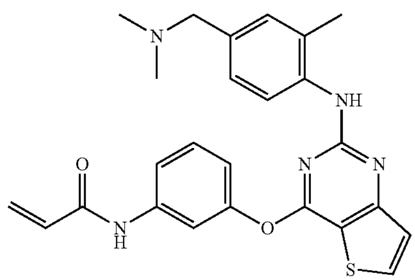 [SMILES: C=CC(=O)Nc1cccc(Oc2nc(Nc3ccc(CN(C)C)cc3C)nc3ccsc23)c1] | ¹H-NMR (300 MHz, CDCl₃) δ 7.97 (s, 1H), 7.86 (d, 1H), 7.83 (d, 1H), 7.73 (s, 1H), 7.48 (d, 1H), 7.41 (t, 1H), 7.28 (d, 1H), 7.06 (m, 2H), 6.99 (d, 1H), 6.81 (s, 1H), 6.46 (dd, 1H), 6.30 (dd, 1H), 5.79 (dd, 1H), 3.38 (s, 2H), 2.28 (s, 3H), 2.26 (s, 6H); MS (ESI⁺): m/z = 459.94 [M + H]⁺. |

Example 206

Preparation of N-(3-(2-(4-(4-methylpiperazin-1-yl)phenylamino)thieno[3,2-d]pyrimidin-4-ylamino)phenyl)acrylamide The procedure of Example 1 was repeated except for using 3-nitrobenzeneamine (0.05 mmol), instead of 3-nitrophenol in step 3) of Example 1, to obtain 5 mg of the title compound (final yield: 55%).

¹H-NMR (300 MHz, CDCl₃) δ 8.10 (m, 1H), 7.90 (d, 1H), 7.51 (m, 3H), 7.42 (m, 1H), 7.28 (t, 1H), 7.10 (d, 1H), 6.89 (d, 2H), 6.39 (m, 2H), 5.79 (d, 1H), 3.29 (m, 4H), 2.68 (m, 4H), 2.38 (s, 3H);

MS (ESI⁺): m/z=486.2 [M+H]⁺.

The procedure of Example 206 or a similar procedure was repeated except for using various amine derivatives of Z—NH₂ (Z has the same meaning as defined in the present invention), instead of 5-(4-methylpiperazin-1-yl)piridin-2-amine in Example 1, to obtain the title compounds of Examples 207 to 217 as shown in Tables 6a and 6b.

TABLE 6a

| Example | Structure | Analysis data |
|---|---|---|
| 207 | 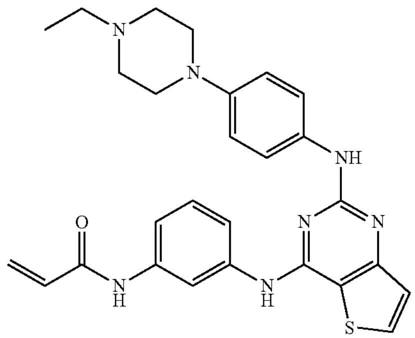 [SMILES: C=CC(=O)Nc1cccc(Nc2nc(Nc3ccc(N4CCN(CC)CC4)cc3)nc3ccsc23)c1] | $^1$H-NMR (300 MHz, DMSO-d$_6$) δ 8.14 (s, NH), 7.80 (d, 1H), 7.68 (d, 1H), 7.59 (s, NH), 7.42 (m, 2H), 7.32 (m, 2H), 7.00 (m, 2H), 6.49 (d, 1H), 6.31 (m, 1H), 5.77 (d, 1H), 3.00 (d, 2H), 2.75 (m, 1H), 2.34 (s, 3H), 2.08 (m, 2H), 1.75 (m, 4H);<br>MS (ESI$^+$): m/z = 500.2 [M + H]$^+$. |
| 208 | 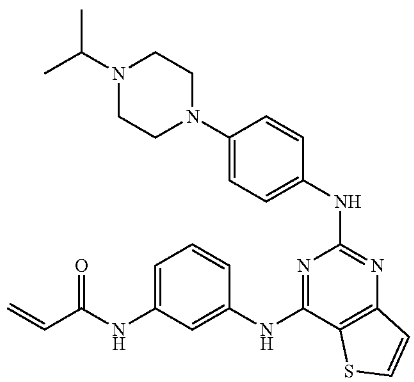 [SMILES: C=CC(=O)Nc1cccc(Nc2nc(Nc3ccc(N4CCN(C(C)C)CC4)cc3)nc3ccsc23)c1] | $^1$H-NMR (300 MHz, DMSO-d$_6$) δ 10.12 (s, NH), 9.59 (s, NH), 8.80 (s, NH), 8.01 (m, 2H), 7.59 (m 3H), 7.41 (d, 1H), 7.31 (t, 1H), 7.19 (d, 1H) 6.80 (d, 2H), 6.48 (m, 1H), 6.25 (d, 1H), 5.78 (d, 1H), 3.01 (br, 4H), 2.71 (m, 1H), 2.61 (br, 4H), 1.01 (d, 6H);<br>MS (ESI$^+$): m/z = 514.2 [M + H]$^+$. |
| 209 | 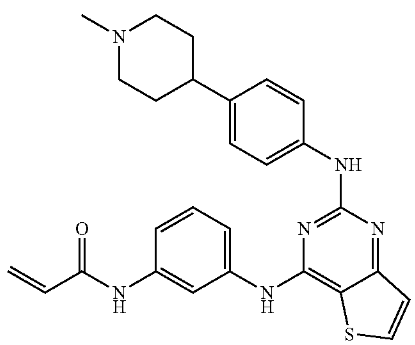 [SMILES: C=CC(=O)Nc1cccc(Nc2nc(Nc3ccc(C4CCN(C)CC4)cc3)nc3ccsc23)c1] | $^1$H-NMR (300 MHz, DMSO-d$_6$) δ 10.20 (s, 1H), 9.53 (s, 1H), 9.00 (s, 1H), 8.07 (m, 2H), 7.67 (d, 2H), 7.50 (m, 2H), 7.29 (dd, 1H), 7.18 (d, 1H), 7.02 (d, 2H), 6.46 (dd, 1H), 6.25 (dd, 1H), 5.74 (dd, 1H), 2.88 (m, 2H), 2.35 (m, 1H), 2.22 (s, 3H), 2.01 (m, 2H), 1.62 (m, 4H);<br>MS (ESI$^+$) m/z = 485.2 [M + H]$^+$. |
| 210 | 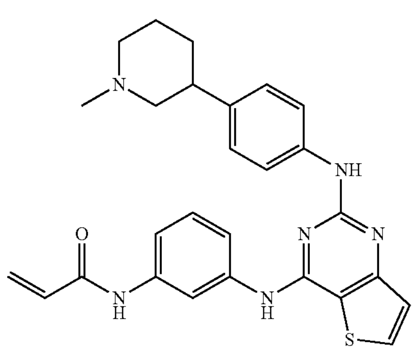 [SMILES: C=CC(=O)Nc1cccc(Nc2nc(Nc3ccc(C4CCCN(C)C4)cc3)nc3ccsc23)c1] | $^1$H-NMR (300 MHz, CDCl$_3$) δ 8.09 (s, 1H), 7.66-7.65 (d, 1H), 7.59-7.56 (m, 2H), 7.51 (brs, 1H), 7.40-7.31 (m, 3H), 7.23-7.21 (d, 1H), 7.17-7.14 (m, 2H), 7.09 (s, 1H), 6.75 (s, 1H), 6.50-6.44 (m, 1H), 5.81-5.77 (m, 1H), 6.30 (m, 1H), 2.97-2.80 (m, 1H), 2.32 (s, 3H), 1.97-1.75 (m, 6H);<br>MS (ESI$^+$): m/z = 485.2 [M + H]$^+$. |

TABLE 6a-continued

| Example | Structure | Analysis data |
|---|---|---|
| 211 | 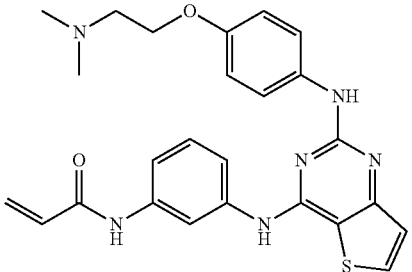 [SMILES: C=CC(=O)Nc1cccc(Nc2nc(Nc3ccc(OCCN(C)C)cc3)nc3ccsc23)c1] | ¹H-NMR (300 MHz, DMSO-d₆) δ 10.13 (s, 1H), 9.49 (s, 1H), 8.84 (s, 1H), 8.04 (m, 2H), 7.62 (m, 2H), 7.53 (m, 1H), 7.40 (m, 1H), 7.28 (m, 1H), 7.16 (m, 1H), 6.75 (m 2H), 6.44 (m, 1H), 6.24 (m, 1H), 5.74 (m, 1H), 3.95 (t, 2H), 2.57 (t, 2H), 2.19 (s, 6H); MS (ESI⁺): m/z = 475.2 [M + H]⁺. |
| 212 | 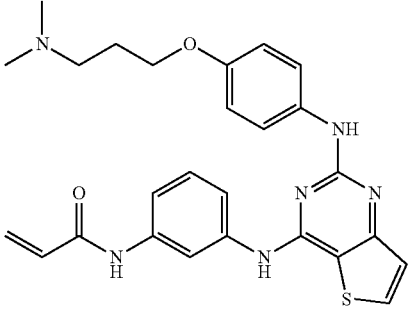 [SMILES: C=CC(=O)Nc1cccc(Nc2nc(Nc3ccc(OCCCN(C)C)cc3)nc3ccsc23)c1] | ¹H-NMR (300 MHz, DMSO-d₆) δ 10.20 (s, 1H), 9.50 (s, 1H), 8.87 (s, 1H), 8.05 (m, 2H), 7.63 (m, 2H), 7.55 (m, 1H), 7.42 (m, 1H), 7.31 (m, 1H), 7.17 (m, 1H), 6.76 (m 2H), 6.47 (m, 1H), 6.25 (m, 1H), 5.75 (m, 1H), 3.91 (t, 2H), 2.34 (t, 2H), 2.14 (s, 6H), 1.80 (m, 2H); MS (ESI⁺): m/z = 489.2 [M + H]⁺. |
| 213 | 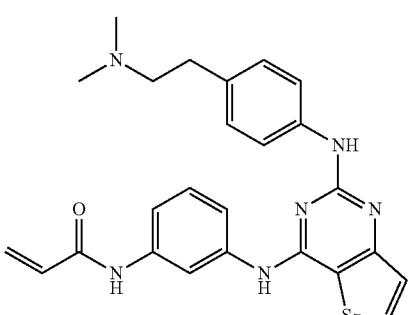 | ¹H-NMR (300 MHz, DMSO-d₆) δ 10.14 (s, 1H), 9.54 (s, 1H), 8.99 (s, 1H), 8.06-8.03 (m, 2H), 7.69-7.67 (m, 2H), 7.56-7.54 (m, 1H), 7.45-7.42 (m, 1H), 7.32-7.27 (m, 1H), 7.19-7.18 (d, 1H), 7.05-7.02 (m, 2H), 6.47-6.41 (m, 1H), 6.29-6.22 (m, 1H), 5.77-5.73 (m, 1H), 2.67 (m, 4H), 2.38 (s, 6H); MS (ESI⁺): m/z = 459.1 [M + H]⁺. |

TABLE 6b

| Example | Structure | Analysis data |
|---|---|---|
| 214 | 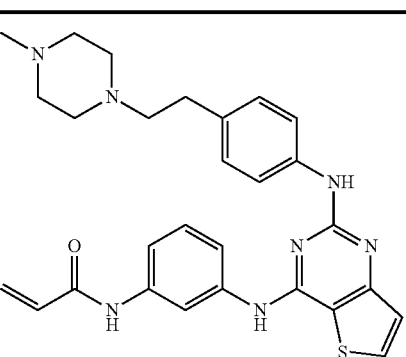 | ¹H-NMR (300 MHz, CDCl₃) δ 8.13 (s, 1H), 7.68-7.66 (d, 1H), 7.59-7.56 (m, 2H), 7.42-7.32 (4H), 7.24-7.22 (d, 1H), 7.16-7.13 (m, 2H), 7.05 (s, 1H), 6.96 (s, 1H), 6.50-6.44 (m, 1H), 6.22 (m, 1H), 5.82-5.78 (m, 1H), 2.81-2.52 (m, 12H), 2.32 (s, 3H); MS (ESI⁺): m/z = 514.2 [M + H]⁺. |

TABLE 6b-continued

| Example | Structure | Analysis data |
|---|---|---|
| 215 | 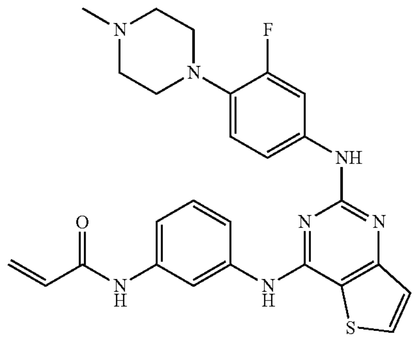 [SMILES: C=CC(=O)Nc1cccc(Nc2nc(Nc3ccc(N4CCN(C)CC4)c(F)c3)nc3ccsc23)c1] | $^1$H-NMR (300 MHz, DMSO-$d_6$) δ 10.06 (s, NH), 9.50 (s, NH), 9.02 (s, NH), 8.00 (d, 1H), 7.96 (s, 1H), 7.63 (d, 1H), 7.46 (d, 1H), 7.37 (m, 2H), 7.25 (t, 1H), 7.12 (d, 1H), 6.81 (t, 1H), 6.41 (m, 1H), 6.19 (d, 1H), 5.64 (d, 1H), 2.91 (m, 4H), 2.41 (m, 4H), 2.13 (s, 3H); MS (ESI$^+$): m/z = 504.2 [M + H]$^+$. |
| 216 | 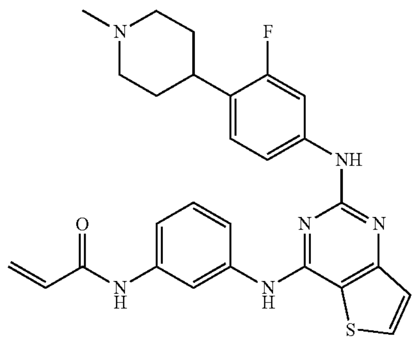 [SMILES: C=CC(=O)Nc1cccc(Nc2nc(Nc3ccc(C4CCN(C)CC4)c(F)c3)nc3ccsc23)c1] | $^1$H-NMR (300 MHz, DMSO-$d_6$) δ 10.12 (s. NH), 9.60 (s, NH), 9.21 (s, NH), 8.08 (d, 1H), 8.01 (s, 1H), 7.77 (d, 1H), 7.53 (d, 1H), 7.41 (m, 2H), 7.34 (t, 1H), 7.21 (d, 1H), 7.07 (t, 1H), 6.45 (m, 1H), 6.26 (d, 1H), 5.72 (d, 1H), 2.85 (m, 2H), 2.60 (m, 1H), 1.90 (m, 2H), 1.64 (m, 4H); MS (ESI$^+$): m/z = 503.2 [M + H]$^+$. |
| 217 | 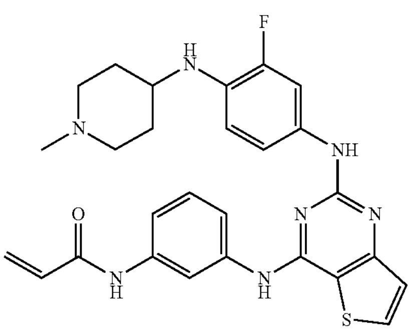 | $^1$H-NMR (300 MHz, DMSO-$d_6$) δ 10.23 (s, NH), 9.49 (s, NH), 8.84 (s, NH), 8.02 (d, 1H), 7.57 (m, 2H), 7.41 (d, 1H), 7.29 (m, 2H), 7.18 (d, 1H), 6.65 (t, 1H), 6.48 (m, 1H), 6.43 (m, 1H), 5.75 (d, 1H), 4.50 (d, 1H), 3.11 (m, 1H), 2.70 (m, 2H), 2.16 (s, 3H), 2.01 (m, 2H), 1.80 (m, 2H), 1.40 (m, 2H); MS (ESI$^+$): m/z = 518.2 [M + H]$^+$. |

Example 218

Preparation of N-(4-fluoro-3-(2-(4-(4-methyl-piperazin-1-yl)-phenylamino)-thieno[3,2-d]pyrimidin-4-ylamino)-phenyl)-acrylamide

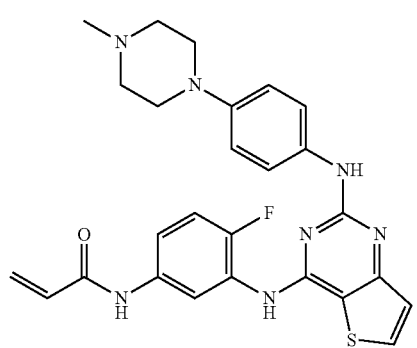 [SMILES: C=CC(=O)Nc1ccc(F)c(Nc2nc(Nc3ccc(N4CCN(C)CC4)cc3)nc3ccsc23)c1]

Step 1) Preparation of N-(4-fluoro-3-nitro-phenyl)-acrylamide

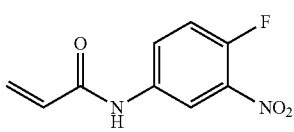

2 g (12.81 mmol) of 4-fluoro-3-nitroaniline and 3.2 g (38.43 mmol) of sodium bicarbonate were diluted in 20 mL of tetrahydrofuran and 5 mL of distilled water, and 1.14 mL (14.09 mmol) of acryloyl chloride was slowly added thereto at 0° C., and stirred for 1 hour. Upon the completion of the reaction, the resulting mixture was diluted with ethylacetate and washed with a saturated aqueous solution of sodium bicarbonate. The organic layer was separated, dried over anhydrous Na$_2$SO$_4$, and filtered and distilled under a reduced pressure to obtain 2 g of the title compound (yield: 74%).

¹H-NMR (300 MHz, DMSO-d₆) δ 10.58 (s, 1H), 8.58 (m, 1H), 7.91 (m, 1H), 7.54 (t, 1H), 6.35 (m, 2H), 5.81 (m, 1H);

Step 2) Preparation of
N-(3-amino-4-fluoro-phenyl)-acrylamide

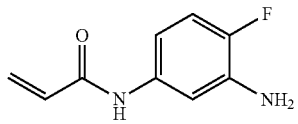

2.65 g (47.59 mmol) of Iron and 0.31 mL (3.80 mmol) of 12 N aqueous hydrochloric acid were diluted in 40 mL of 50% aqueous ethanol and stirred for 1 hour at 100° C. 2.00 g (9.51 mmol) of the compound obtained in the Step 1 was added thereto, and stirred for 1 hour at 100° C. Upon the completion of the reaction, the resulting mixture was filtered over a short bed of Celite filter to remove Iron, and distilled under a reduced pressure. The resulting residue was diluted with dichloromethane and washed with a saturated aqueous solution of sodium bicarbonate. The organic layer was separated, dried over anhydrous Na₂SO₄, and filtered and distilled under a reduced pressure. The resulting residue was separated by column chromatography (n-hexane:ethylacetate (1:1, v/v)) to obtain 1.5 g of the title compound (yield: 75%).

¹H-NMR (300 MHz, DMSO-d₆) δ 9.87 (s, 1H), 7.17 (m, 1H), 6.89 (t, 1H), 6.75 (m, 1H), 6.39 (m, 1H), 6.20 (m, 1H), 5.70 (m, 1H), 5.16 (s, 2H);

Step 3) Preparation of N-(3-(2-chloro-thieno[3,2-d]pyrimidin-4-ylamino)-4-fluoro-phenyl)-acrylamide

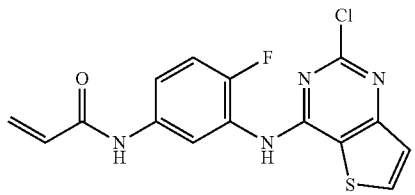 [SMILES: C=CC(=O)Nc1ccc(F)c(Nc2nc(Cl)nc3ccsc23)c1]

The compound obtained in Step 2) of Example 1 and 461 mg (2.22 mmol) of the compound obtained in the Step 2) were dissolved in 5 ml of 1-propanol, and 0.6 mL (3.33 mmol) of diisopropylethylamine was added thereto, and stirred for 24 hours at 110° C. Upon the completion of the reaction, the resulting mixture was cooled to 0° C. to form solid, and filtered under a reduced pressure while washing with propanol. The resulting solid was dried over under a reduce pressure to obtain 270 mg of the title compound (yield: 36%).

¹H-NMR (300 MHz, DMSO-d₆) δ 10.31 (s, 1H), 10.22 (s, 1H), 8.25 (d, 1H), 7.86 (m, 1H), 7.59 (m, 1H), 7.40 (d, 1H), 7.32 (t, 1H), 6.42 (m, 1H), 6.29 (m, 1H), 5.76 (m, 1H);

Step 4) Preparation of N-(4-fluoro-3-(2-(4-(4-methyl-piperazin-1-yl)-phenylamino)-thieno[3,2-d]pyrimidin-4-ylamino)-phenyl)-acrylamide 100 mg (0.30 mmol) of the compound obtained in the Step 3) was dissolved in 3 ml of 2-butanol, and 55 mg (0.28 mmol) of 4-(4-methylpiperazin-1-yl)benzeneamine and 42 μl (0.57 mmol) of trifluoroacetic acid were added thereto, and stirred for 5 hours at 100° C. Upon the completion of the reaction, the resulting mixture was diluted with ethylacetate and washed with a saturated aqueous solution of sodium bicarbonate. The organic layer was separated, dried over anhydrous Na₂SO₄, and filtered and distilled under a reduced pressure. The resulting residue was separated by column chromatography (dichloromethane:methanol (10:1, v/v)) to obtain 77 mg of the title compound (yield: 50%).

¹H-NMR (300 MHz, DMSO-d₆) δ 10.26 (s, 1H), 9.38 (s, 1H), 8.77 (s, 1H), 8.02 (d, 1H), 7.82 (d, 1H), 7.62 (m, 1H), 7.44 (d, 2H), 7.30 (t, 1H), 7.15 (d, 1H), 6.68 (m, 2H), 6.40 (m, 1H), 6.22 (m, 1H), 5.73 (m, 1H), 2.96 (m, 4H), 2.42 (m, 4H), 2.20 (s, 3H);

MS (ESI⁺): m/z=504.1 [M+H]⁺.

Example 219

Preparation of N-(4-fluoro-3-(2-(3-fluoro-4-(4-methyl-piperazin-1-yl)-phenylamino)-thieno[3,2-d]pyrimidin-4-ylamino)-phenyl)-acrylamide

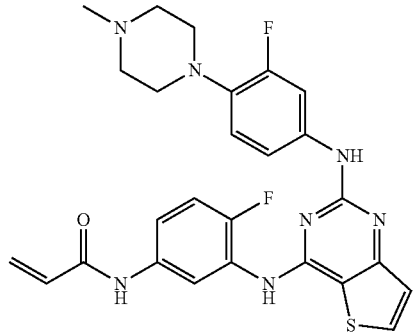 [SMILES: C=CC(=O)Nc1ccc(F)c(Nc2nc(Nc3ccc(N4CCN(C)CC4)c(F)c3)nc3ccsc23)c1]

A similar procedure as the procedure of Step 4) of Example 218 was carried out except for using 3-fluoro-4-(4-methylpiperazin-1-yl)anilline (0.03 mmol), instead of 4-(4-methylpiperazin-1-yl)benzeneamine in the Step 4) of Example 218, to obtain 8 mg of the title compound (final yield: 50%).

¹H-NMR (300 MHz, DMSO-d₆) δ 10.25 (s, 1H), 9.50 (s, 1H), 9.08 (s, 1H), 8.07 (d, 1H), 7.85 (d, 1H), 7.59 (m, 2H), 7.26 (m, 2H), 7.19 (d, 1H), 6.78 (t, 1H), 6.38 (m, 1H), 6.27 (m, 1H), 5.75 (m, 1H), 2.87 (m, 4H), 2.25 (m, 4H), 2.21 (s, 3H);

MS (ESI⁺): m/z=522.2 [M+H]⁺.

Example 220

Preparation of N-(3-(2-(4-dimethylaminomethyl-phenylamino)-thieno[3,2-d]pyrimidin-4-ylamino)-phenyl)-acrylamide

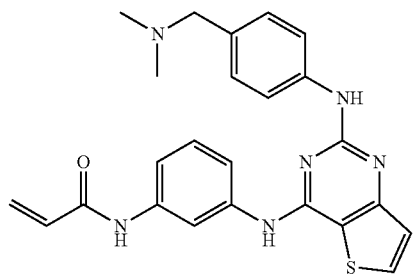 [SMILES: C=CC(=O)Nc1cccc(Nc2nc(Nc3ccc(CN(C)C)cc3)nc3ccsc23)c1]

A procedure similar to the procedure of the Step 4) of Example 218 was carried out except for using 0.67 g (1.94 mmol) of N-(3-(2-chloro-thieno[3,2-d]pyrimidin-4-ylamino)phenyl)acrylamide obtained in Step 1) to 3) of Example 218 and 0.29 g (1.94 mmol) of 4-((dimethylamino)methyl)anilline to obtain 0.69 g of the title compounds (yield: 80%).

¹H-NMR (300 MHz, CDCl₃) δ 8.11 (d, 2H), 7.63 (dd, 3H), 7.55 (m, 4H), 7.18 (m, 2H), 7.05 (s, 1H), 6.45 (d, 1H), 6.30 (q, 1H), 5.74 (d, 1H), 3.38 (s, 2H), 2.01 (s, 6H);

MS (ESI⁺): m/z=467.1 [M+H]⁺.

A procedure similar to the procedure of Example 220 was carried out except for using 4-(piperidin-1-yl)methylphenylamine and 2-methoxy-4-(piperidin-1-yl)methylphenylamine to obtain the title compounds of Examples 221 and 222 as shown in Table 7.

TABLE 7

| Example | Structure | Analysis data |
| --- | --- | --- |
| 221 | 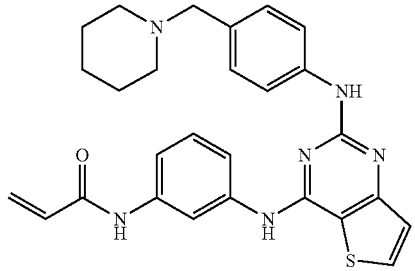 [SMILES: C=CC(=O)Nc1cccc(Nc2nc(Nc3ccc(CN4CCCCC4)cc3)nc3ccsc23)c1] | 1H-NMR (300 MHz, DMSO-$d_6$) δ 10.36 (s, NH), 8.32 (d, 1H), 8.30 (m, 2H), 7.61 (d, 1H), 7.36 (d, 1H), 7.09 (d, 1H), 6.88 (s, NH), 6.61 (d, 1H), 6.42 (dd, 1H), 6.23 (d, 1H), 5.75 (d, 1H), 3.79 (s, 3H), 3.33 (s, 2H), 2.28 (br, 4H), 1.48 (br, 4H), 1.24 (br, 2H);<br>MS (ESI$^+$): m/z = 485.2 [M + H]$^+$. |
| 222 | 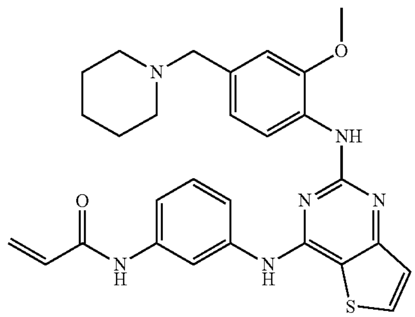 [SMILES: C=CC(=O)Nc1cccc(Nc2nc(Nc3ccc(CN4CCCCC4)cc3OC)nc3ccsc23)c1] | $^1$H-NMR (300 MHz, DMSO-$d_6$) δ 10.36 (s, NH), 8.32 (d, 1H), 8.30 (m, 2H), 7.61 (d, 1H), 7.48 (t, 1H), 7.36 (d, 1H), 7.09 (d, 1H), 6.88 (s, NH), 6.61 (d, 1H), 6.42 (dd, 1H), 6.23 (d, 1H), 5.75 (d, 1H), 3.79 (s, 3H), 3.33 (s, 2H), 2.28 (br, 4H), 1.48 (br, 4H), 1.24 (br, 2H);<br>MS (ESI$^+$): m/z = 516.1 [M + H]$^+$. |

Example 223

Preparation of N-(3-(2-(4-(4-methylpiperazin-1-yl) phenylamino)thieno[3,2-d]pyrimidin-4-ylthio)phenyl)acrylamide

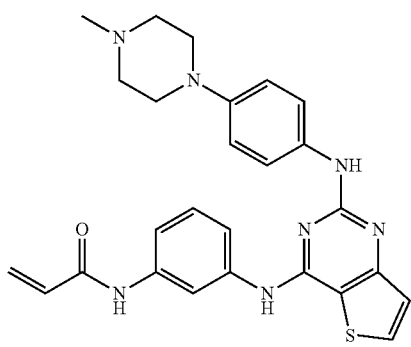 [SMILES: C=CC(=O)Nc1cccc(Nc2nc(Nc3ccc(N4CCN(C)CC4)cc3)nc3ccsc23)c1]

Step 1) Preparation of tert-butyl 3-(2-chlorothieno[3,2-d]pyrimidin-4-ylthio)phenylcarbamate

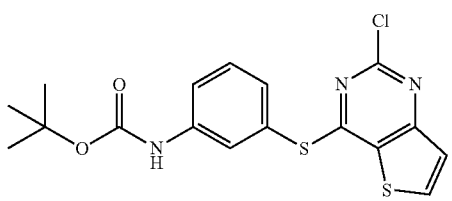 [SMILES: CC(C)(C)OC(=O)Nc1cccc(Sc2nc(Cl)nc3ccsc23)c1]

1.1 g (5.32 mmol) of the compound obtained in Step 2) of Example 1 was dissolved in 30 ml of N,N-dimethylsulfonamide, and 1.2 g (5.32 mmol) of tert-butyl-3-mercaptophenylcarbamate and 3.4 g (10.6 mmol) of cesium carbonate were added thereto, and stirred for 1 hour at room temperature. Upon the completion of the reaction, the distilled water was added to the resulting mixture to form a solid, and the resulting mixture was filtered under a reduced pressure while washing with distilled water. The resulting solid was dried over under a reduce pressure to obtain 1.5 g of the title compound (yield: 70%).

$^1$H-NMR (300 MHz, CDCl$_3$) δ 7.92 (d, 1H), 7.77 (s, 1H), 7.56 (d, 1H), 7.45-7.36 (m, 3H), 1.54 (s, 9H).

Step 2) Preparation of tert-butyl 3-(2-(4-(4-methylpiperazin-1-yl)phenylamino)thieno[3,2-d]pyrimidin-4-ylthio)phenylcarbamate

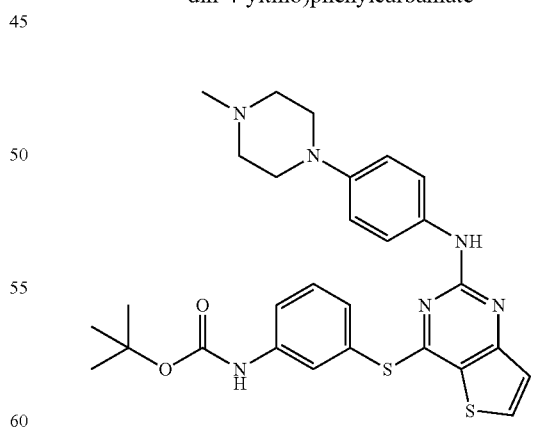

1.5 g (3.72 mmol) of the compound obtained in the Step 1) was dissolved in 30 ml of 2-butanol, and 0.8 g (3.72 mmol) of 4-(4-methylpiperazin-1-yl)benzeneamine and 0.4 mL (3.72 mmol) of trifluoroacetic acid were added thereto. The mixture was stirred for 10 hours at 100° C., upon the completion of the reaction, diluted with dichloromethane and washed with a saturated aqueous solution of sodium bicarbonate. The organic layer was dried over anhydrous Na₂SO₄, and filtered and distilled under a reduced pressure. The residue was separated by column chromatography (dichloromethane:methanol (20:1, v/v)) to obtain 1.0 g of the title compound (yield: 46%).

¹H-NMR (300 MHz, CDCl₃) δ 7.73 (d, 1H), 7.63 (m, 1H), 7.60 (m, 1H), 7.39-7.30 (m, 2H), 7.28-7.21 (m, 2H), 7.15 (d, 1H), 6.76 (d, 2H), 3.25 (m, 4H), 2.58 (m, 4H), 2.33 (s, 3H), 1.54 (s, 9H).

Step 3) Preparation of 4-(3-aminophenylthio)-N-(4-(4-methylpiperazin-1-yl)phenyl)thieno[3,2-d]pyrimidin-2-amine

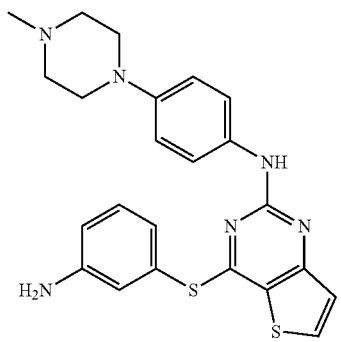

1.0 g (1.82 mmol) of the compound obtained in the Step 2) was dissolved in 20 ml of dichloromethane, and 10 mL of trifluoroacetic acid was added thereto, and stirred for 2 hours at room temperature. Upon the completion of the reaction, the resulting mixture was distilled under a reduced pressure to remove solvent, and the resulting residue was basified (pH=8) with a saturated aqueous solution of sodium bicarbonate, and extracted with chloroform. The organic layer was separated, dried over anhydrous Na₂SO₄, and filtered and distilled under a reduced pressure and dried over to obtain 603 mg of the title compound (yield: 75%).

¹H-NMR (300 MHz, CD₃OD) δ 7.96 (d, 1H), 7.33 (d, 2H), 7.21 (t, 1H), 7.17 (d, 1H), 7.02 (m, 1H), 6.94 (m, 2H) 6.80 (d, 2H), 3.14 (m, 4H), 2.65 (m, 4H).

Step 4) Preparation of N-(3-(2-(4-(4-methylpiperazin-1-yl)phenylamino)thieno[3.2-d]pyrimidin-4-ylthio)phenyl)acrylamide A similar procedure as the procedure of Step 6) of Example 1 was carried out except for using the compound obtained in the Step 3), instead of the compound obtained step 5), to obtain 452 mg of the title compound (yield: 67%).

¹H-NMR (300 MHz, CDCl₃) δ 7.78 (m, 1H), 7.75 (d, 1H), 7.46-7.41 (m, 3H), 7.20 (d, 2H), 7.18 (d, 1H), 6.77 (d, 2H), 6.41 (d, 1H), 6.21 (dd, 1H), 5.78 (d, 1H), 3.12 (m, 4H), 2.60 (m, 4H), 2.36 (s, 3H);

MS (ESI⁺): m/z=503.7 [M+H]⁺.

The procedure of Example 223 or a similar procedure was repeated except for using 3-fluoro-4-morpholin-4-ylphenylamine and 3-fluoro-4-(1-methyl-piperidin-4-yl)phenylamine, instead of 54-(4-methylpiperazin-1-yl)phenylamine in step 2) of Example 223, to obtain the title compounds of Examples 224 and 225 as shown in Table 8.

TABLE 8

| Example | Structure | Analysis data |
|---|---|---|
| 224 | 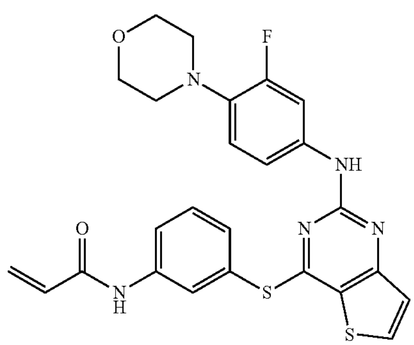 [SMILES: C=CC(=O)Nc1cccc(Sc2nc(Nc3ccc(N4CCOCC4)c(F)c3)nc3ccsc23)c1] | ¹H-NMR (300 MHz, DMSO-d₆) δ 10.37 (s, 1H), 9.57 (s, 1H), 8.24 (d, 1H), 8.01 (s, 1H), 7.98 (m, 1H), 7.50 (t, 1H), 7.41 (m, 1H), 7.31 (m, 2H), 7.15 (m, 1H), 6.73 (m, 1H), 6.42 (m, 1H), 6.27 (m, 1H), 5.74 (m, 1H), 3.70 (m, 4H), 2.85 (m, 4); MS (ESI⁺): m/z = 508.1 [M + H]⁺. |
| 225 | 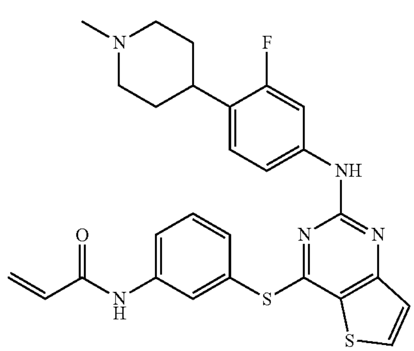 [SMILES: C=CC(=O)Nc1cccc(Sc2nc(Nc3ccc(C4CCN(C)CC4)c(F)c3)nc3ccsc23)c1] | ¹H-NMR (300 MHz, DMSO-d₆) δ 8.60 (s, 1H), 8.53 (d, 1H), 8.36 (d, 1H), 8.00 (d, 1H), 7.62 (t, 1H), 7.46 (d, 2H), 7.32 (d, 1H), 6.93 (d, 2H), 3.83 (d, 2H), 3.48 (d, 2H), 3.12 (m, 4H), 2.83 (s, 3H); MS (ESI⁺): m/z = 520.2 [M + H]⁺. |

Example 226

Preparation of (E)-4-(dimethylamino)-N-(3-(2-(4-(4-methylpiperazin-1-yl)phenylamino)thieno[3,2-d]pyrimidin-4-ylthio)phenyl)but-2-enamide

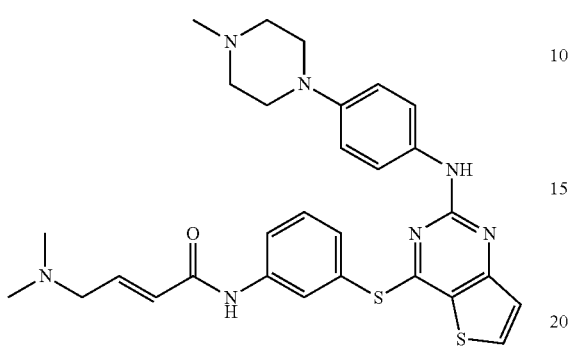

40 mg (0.09 mmol) of the compound obtained in Step 2 of Example 223 was dissolved in 1.5 mL of pyridine, and 22 mg (0.14 mmol) of (E)-4-(dimethylamino)-2-butenoic acid hydrochloride and 35 mg (0.18 mmol) of N-(3-dimethylaminopropyl)-N'-ethylcarbodiimide hydrochloride were added thereto, and stirred for 30 minutes at 80° C. Upon the completion of the reaction, the resulting mixture was diluted with mixed solvent of chloroform:2-propanol (3:1(v/v)) and washed with saturated saline. The organic layer was separated, dried over anhydrous $Na_2SO_4$, and filtered and distilled under a reduced pressure. The resulting residue was separated by column chromatography (dichloromethane:methanol=6:1 (v/v)) to obtain 2 mg of the title compound (yield: 4%).

$^1$H-NMR (300 MHz, $CDCl_3$) δ 8.10 (m, 1H), 8.02 (d, 1H), 7.93 (s, 1H), 7.50 (t, 1H), 7.42 (m, 1H), 7.21 (m, 3H), 6.90 (m, 1H), 6.74 (d, 2H), 6.28 (d, 1H), 3.20 (d, 2H), 3.10 (t, 4H), 2.66 (t, 4H), 2.39 (s, 3H), 2.17 (s, 6H);

MS (ESI$^+$): m/z=560.2 [M+H]$^+$.

Example 227

Preparation of N-(3-(2-(4-(4-methylpiperazin-1-yl)phenylamino)thieno[3,2-d]pyrimidin-4-ylsulfinyl)phenyl)acrylamide

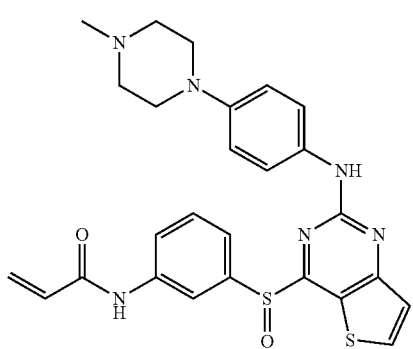 [SMILES: C=CC(=O)Nc1cccc(S(=O)c2nc(Nc3ccc(N4CCN(C)CC4)cc3)nc3ccsc23)c1]

11 mg (0.02 mmol) of the compound obtained in Example 223 was dissolved in 1.0 mL of dichloromethane, and 20 mg (0.04 mmol) of m-chloroperoxybenzoic acid was added thereto, and stirred for 60 minutes at room temperature. Upon the completion of the reaction, the resulting mixture was diluted with chloroform and washed with a saturated aqueous solution of sodium bicarbonate. The organic layer was separated, dried over anhydrous $Na_2SO_4$, and filtered and distilled under a reduced pressure. The resulting residue was separated by column chromatography (dichloromethane:methanol=6:1 (v/v)) to obtain 3.0 mg of the title compound (yield: 25%).

$^1$H-NMR (300 MHz, $CD_3OD$) δ 8.08 (m, 1H), 8.01 (d, 1H), 7.92 (m, 1H), 7.51 (t, 1H), 7.46 (m, 1H), 7.22 (m, 3H), 6.73 (d, 1H), 6.38 (m, 2H), 5.76 (dd, 1H), 3.63-3.56 (m, 4H), 3.42-3.34 (m, 4H), 3.23 (s, 3H);

MS (ESI$^+$): m/z=519.3 [M+H]$^+$.

Example 228

Preparation of N-(3-((2-((4-(4-methylpiperazin-1-yl)phenyl)amino)furo[3,2-d]pyrimidin-4-yl)oxy)phenyl)acrylamide

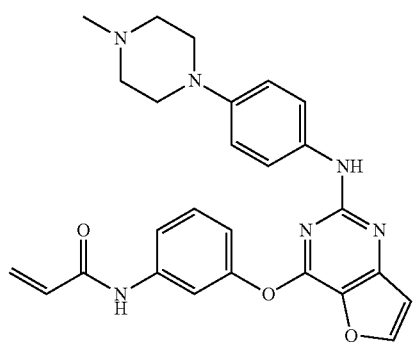 [SMILES: C=CC(=O)Nc1cccc(Oc2nc(Nc3ccc(N4CCN(C)CC4)cc3)nc3ccoc23)c1]

Step 1) Preparation of 2-chloro-4-(3-nitrophenoxy)-furo[3,2-d]pyrimidine

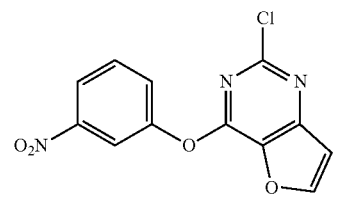 [SMILES: O=[N+]([O-])c1cccc(Oc2nc(Cl)nc3ccoc23)c1]

6.4 g (33.9 mmol) of 2,4-dichlorofuro[3,2-d]pyrimidine (see: International Publication Number WO 2008073785 and WO 2008152394) was dissolved in 32 mL of methanol, and 5.7 g (40.6 mmol) of 3-nitrophenol and 12 mL (67.7 mmol) of diisopropylethylamine were added thereto, and stirred for 24 hours at room temperature. Upon the completion of the reaction, the resulting solid was filtered and dried over under a reduced pressure to obtain 6.3 g of the title compound (yield: 64%).

$^1$H-NMR (300 MHz, DMSO-d$_6$) δ 8.61 (s, 1H), 8.33 (s, 1H), 8.21 (d, 1H), 7.90 (d, 1H), 7.79 (m, 1H), 7.27 (s, 1H);

Step 2) Preparation of N-[4-(4-methyl-piperazin-1-yl)-phenyl]-4-(3-nitrophenoxy)-furo[3,2-d]pyrimidin-2-amine

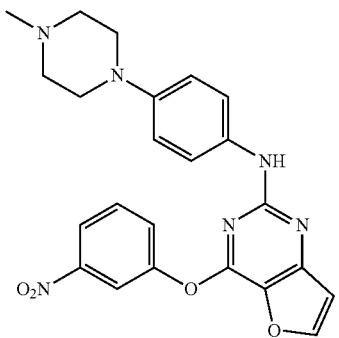 [SMILES: CN1CCN(c2ccc(Nc3nc(Oc4cccc([N+](=O)[O-])c4)c4occc4n3)cc2)CC1]

2.5 g (8.6 mmol) of the compound obtained in the Step 1) was dissolved in 50 ml of 2-butanol, and 2.0 g (10.3 mmol) of 4-(4-methyl-piperazin-1-yl)aniline and 1.5 mL (8.6 mmol) of trifluoroacetic acid were added thereto. The reaction mixture was stirred for 12 hours at 100° C., upon the completion of the reaction, diluted with dichloromethane and washed with a saturated aqueous solution of sodium bicarbonate. The organic layer was separated, dried over anhydrous Na$_2$SO$_4$, and filtered and distilled under a reduced pressure and dried over. The resulting residue was separated by column chromatography (dichloromethane:methanol=20:1 (v/v)) to obtain 2.0 g of the title compound (yield: 53%).

$^1$H-NMR (300 MHz, CDCl$_3$) δ 8.20 (s, 2H), 7.85 (s, 1H), 7.64 (s, 2H), 7.30 (s, 1H), 6.79 (m, 4H), 3.14 (m, 4H), 2.60 (m, 4H), 2.37 (s, 3H);

Step 3) Preparation of 4-(3-aminophenoxy)-N-[4-(4-methyl-piperazin-1-yl)-phenyl]-furo[3,2-d]pyrimidin-2-amine

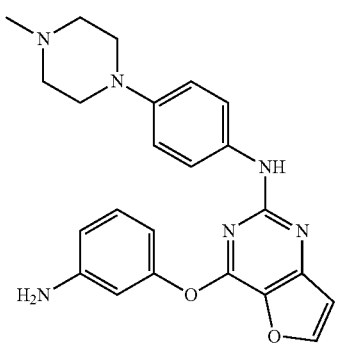

1.3 g (22.4 mmol) of Iron and 2 mL of 12 N aqueous hydrochloric acid were diluted in 10 mL of 50% aqueous ethanol and stirred for 10 minutes at 100° C. 2.0 g (4.5 mmol) of the compound obtained in the Step 2) was dissolved in 10 ml of 50% aqueous ethanol, added to flask where the iron was activated, and stirred for 1 hour at 100° C. Upon the completion of the reaction, the resulting mixture was filtered over a short bed of Celite filter to remove Iron, and distilled under a reduced pressure. The resulting residue was diluted with dichloromethane and washed with a saturated aqueous solution of sodium bicarbonate. The organic layer was separated, dried over anhydrous Na$_2$SO$_4$, and filtered and distilled under a reduced pressure to obtain 1.8 g of the title compound (yield: 97%).

$^1$H-NMR (300 MHz, CDCl$_3$) δ 7.79 (s, 1H), 7.32 (d, 2H), 7.24 (m, 1H), 6.84 (m, 2H), 6.75 (s, 1H), 6.65 (m, 3H), 3.22 (m, 4H), 2.60 (m, 4H), 2.36 (s, 3H);

Step 4) Preparation of N-(3-{2-[4-(4-methyl-piperazin-1-yl)-phenylamino]-furo[3,2-d]pyrimidin-4-yloxy}-phenyl)-acrylamide 1.8 g (4.3 mmol) of the compound obtained in the Step 3) and 1.1 g (23.0 mmol) of sodium bicarbonate were diluted with 20 ml of tetrahydrofuran and 5 mL of distilled water, and 0.4 mL (4.3 mmol) of acryloyl chloride was slowly added thereto at 0° C., and stirred for 30 minutes. Upon the completion of the reaction, the resulting mixture was diluted with dichloromethane and washed with a saturated aqueous solution of sodium bicarbonate. The organic layer was separated, dried over anhydrous Na$_2$SO$_4$, and filtered and distilled under a reduced pressure and dried over. The resulting residue was separated by column chromatography (chloroform:methanol=20:1 (v/v)) to obtain 940 mg of the desired compound (yield: 46%).

$^1$H-NMR (300 MHz, CD$_3$OD) δ 8.04 (s, 1H), 7.68 (d, 2H), 7.45 (t, 1H), 7.32 (d, 2H), 7.03 (d, 1H), 6.78 (m, 3H), 6.45 (m, 2H), 5.80 (d, 1H), 3.08 (m, 4H), 2.61 (m, 4H), 2.35 (s, 3H);

MS (ESI$^+$): m/z=470.2 [M+H]$^+$.

The procedure of Example 228 or a similar procedure was repeated except for using various amine derivatives of Z—NH$_2$ (Z has the same meaning as defined in the present invention), instead of 4-(4-methylpiperazin-1-yl)benzeneamine in step 2) of Example 228, to obtain the title compounds of Examples 229 to 237 as shown in Tables 9a and 9b.

TABLE 9a

| Example | Structure | Analysis data |
|---------|-----------|---------------|
| 229 | 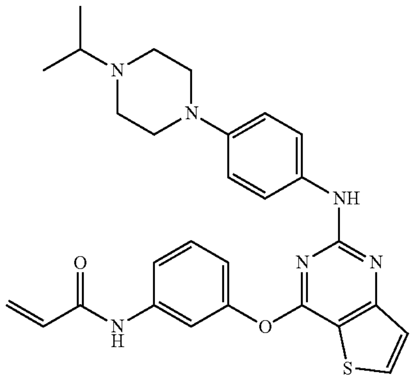 | $^1$H-NMR (300 MHz, CD$_3$OD) δ 8.04 (s, 1H), 7.67 (d, 2H), 7.45 (t, 1H), 7.31 (d, 2H), 7.04 (d, 1H), 6.78 (m, 3H), 6.40 (m, 2H), 5.79 (d, 1H), 3.23 (m, 4H), 2.76 (m, 5H), 1.15 (d, 6H); MS (ESI$^+$): m/z = 498.2 [M + H]$^+$. |
| 230 | 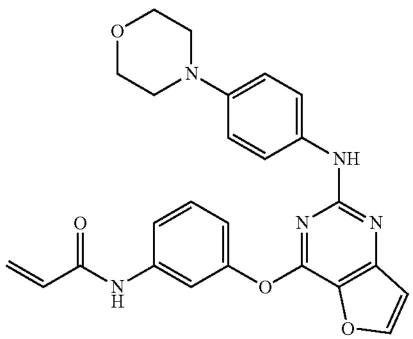 | $^1$H-NMR (300 MHz, CD$_3$OD) δ 8.03 (s, 1H), 7.73 (s, 2H), 7.45 (m, 1H), 7.31 (d, 2H), 7.04 (m, 1H), 6.82 (s, 3H), 6.49 (m, 2H), 5.80 (d, 1H), 3.81 (m, 4H), 3.01 (m, 4H); MS (ESI$^+$): m/z = 457.1 [M + H]$^+$. |
| 231 | 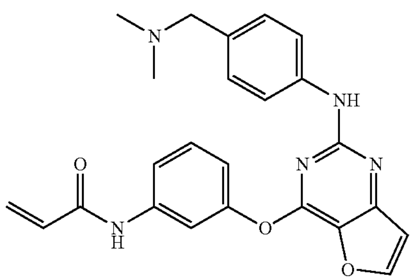 [SMILES: C=CC(=O)Nc1cccc(Oc2nc(Nc3ccc(CN(C)C)cc3)nc3ccoc23)c1] | $^1$H-NMR (300 MHz, CD$_3$OD) δ 8.14 (s, 1H), 7.83 (s, 2H), 7.70 (s, 1H), 7.50 (m, 2H), 7.33 (m, 1H), 7.11 (d, 2H), 6.87 (s, 1H), 6.47 (m, 2H), 5.83 (d, 1H), 3.66 (s, 2H), 2.16 (s, 6H); MS (ESI$^+$): m/z = 429.1 [M + H]$^+$. |
| 232 | 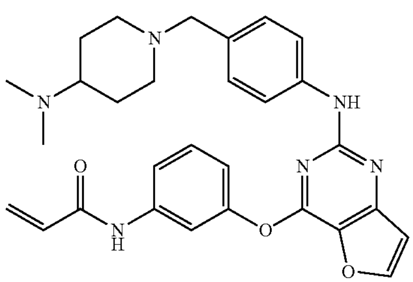 [SMILES: C=CC(=O)Nc1cccc(Oc2nc(Nc3ccc(CN4CCC(N(C)C)CC4)cc3)nc3ccoc23)c1] | $^1$H-NMR (300 MHz, CD$_3$OD) δ 8.03 (s, 1H), 7.70 (s, 1H), 7.60 (d, 1H), 7.40 (m, 3H), 7.02 (d, 3H), 6.79 (s, 1H), 6.40 (m, 2H), 5.76 (d, 1H), 3.30 (m, 2H), 2.90 (d, 2H), 2.25 (d, 6H), 2.15 (m, 1H), 2.00 (m, 2H), 1.80 (m, 2H), 1.50 (m, 2H); MS (ESI$^+$): m/z = 512.2 [M + H]$^+$. |
| 233 | 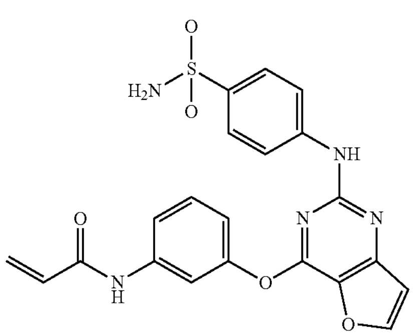 | $^1$H-NMR (300 MHz, CD$_3$OD) δ 8.13 (s, 1H), 7.70 (s, 1H), 7.60 (m, 3H), 7.45 (m, 2H), 7.05 (m, 1H), 6.89 (s, 1H), 6.69 (m, 1H), 6.38 (m, 2H), 5.77 (d, 1H); MS (ESI$^+$): m/z = 451.1 [M + H]$^+$. |

TABLE 9a-continued

| Example | Structure | Analysis data |
|---|---|---|
| 234 | 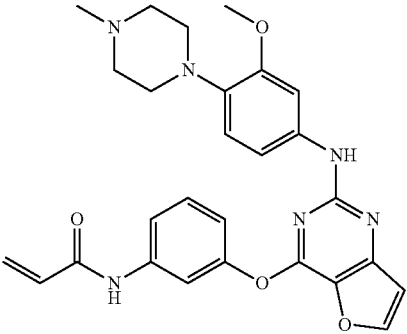 [SMILES: C=CC(=O)Nc1cccc(Oc2nc(Nc3ccc(N4CCN(C)CC4)c(OC)c3)nc3ccoc23)c1] | ¹H-NMR (300 MHz, CDCl₃) δ 7.96 (s, 1H), 7.64 (brs, 1H), 7.58-7.52 (m, 2H), 7.40-7.37 (m, 1H), 7.12 (m, 1H), 7.04 (m, 1H), 6.94-6.92 (m, 2H), 6.80-6.74 (m, 2H), 6.40 (m, 1H), 6.29-6.25 (m, 1H), 5.79-5.75 (m, 1H), 3.79 (s, 3H), 3.48 (s, 3H), 3.02 (m, 4H), 2.61 (m, 4H), 2.35 (s, 3H);<br>MS (ESI⁺): m/z = 501.2 [M + H]⁺. |
| 235 | 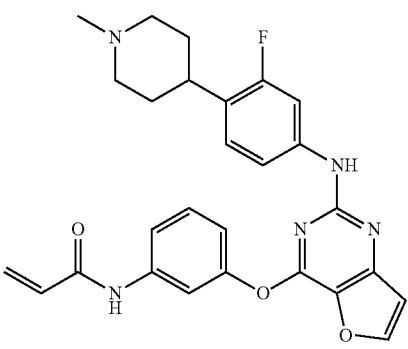 | ¹H-NMR (300 MHz, CD₃OD) δ 8.07 (s, 1H), 7.75 (s, 1H), 7.47 (m, 1H), 7.41 (m, 2H), 7.04 (m, 3H), 6.83 (s, 1H), 6.38 (m, 2H), 5.77 (d, 1H), 2.99 (d, 2H), 2.71 (m, 1H), 2.32 (s, 3H), 2.15 (m, 2H), 1.76 (m, 4H);<br>MS (ESI⁺): m/z = 487.2 [M + H]⁺. |

TABLE 9b

| Example | Structure | Analysis data |
|---|---|---|
| 236 | 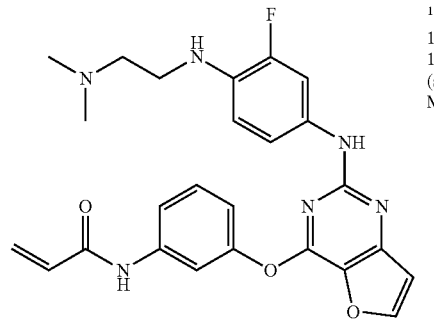 | ¹H-NMR (300 MHz, CD₃OD) δ 8.01 (s, 1H), 7.73 (s, 1H), 7.58 (d, 1H), 7.43 (m, 2H), 7.28 (q, 1H), 7.02 (m, 2H), 6.77 (s, 1H), 6.57 (t, 1H), 6.40 (m, 2H), 5.77 (q, 1H), 3.21 (m, 2H), 2.60 (m, 2H), 2.32 (s, 6H);<br>MS (ESI⁺): m/z = 476.2 [M + H]⁺. |
| 237 | 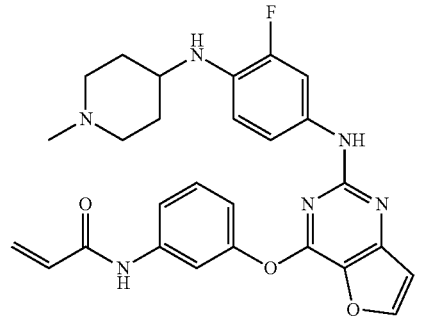 | ¹H-NMR (300 MHz, CD₃OD) δ 8.04 (s, 1H), 7.70 (s, 1H), 7.60 (d, 1H), 7.43 (t, 1H), 7.26 (d, 1H), 7.04 (m, 2H), 6.79 (s, 1H), 6.62 (t, 1H), 6.40 (m, 2H), 5.77 (d, 1H), 3.30 (s, 1H), 2.85 (d, 2H), 2.31 (s, 3H), 2.16 (m, 2H), 1.90 (m, 2H), 1.48 (m, 2H);<br>MS (ESI⁺): m/z = 502.2 [M + H]⁺. |

Preparation Example 1

Tablets for oral administration comprising each of the compounds of formula (I) obtained in Examples 1 to 237 as an active ingredient were prepared by the conventional method based on the recipe of Table 10.

TABLE 10

| Ingredient | Amount/tablet |
| --- | --- |
| Active Ingredient | 100 mg |
| Corn Starch | 80 mg |
| Lactose | 80 mg |
| Magnesium Stearate | 5 mg |

Preparation Example 2

Hard gelatin capsules for oral administration comprising each of the compounds of formula (I) obtained in Examples 1 to 237 as an active ingredient were prepared by the conventional method based on the recipe of Table 11.

TABLE 11

| Ingredient | Amount/tablet |
| --- | --- |
| Active Ingredient | 100 mg |
| Corn Starch | 40 mg |
| Lactose | 80 mg |
| Crystalline Cellulose | 80 mg |
| Magnesium Stearate | 5 mg |

Preparation Example 3

Injection formulations comprising each of the compounds of formula (I) obtained in Examples 1 to 237 as an active ingredient were prepared by the conventional method based on the recipe of Table 12, wherein when a salt of the compound of formula (I) was used, the pH value was not manipulated.

TABLE 12

| Ingredient | Amount/tablet |
| --- | --- |
| Active Ingredient | 20 mg |
| 5% Glucose solution | 10 ml |
| HCl (1N) | adjusted to pH 4 |

Preparation Example 4

Injection formulations comprising each of the compounds of formula (I) obtained in Examples 1 to 237 as an active ingredient were prepared by the conventional method based on the recipe of Table 13.

TABLE 13

| Ingredient | Amount/tablet |
| --- | --- |
| Active Ingredient | 20 mg |
| Polyethylene Glycol 400 | 2 ml |
| Sterile Water | 8 ml |

Test Example 1

Inhibition Test for Growth of Cancer Cell Expressing EGFR

In order to identify that the inventive compounds obtained in Examples 1 to 237 selectively inhibit on the growth of the cancer cell expressing EGFR mutants compared than EGFR WT, the inhibiting test of the inventive compounds on the cancer cell growth was conducted as follow. For the test, a skin cancer cell line, A431 overexpressing EGFR wild-type (WT), a lung cancer cell line, HCC827 whose in-frame is deleted at position 19 exon in EGFR tyrosine kinase, and NCI-H1975 expressing EGFR L858R/T790M mutant which have resistance to the approved EGFR inhibitors such as Gefitinib or Erlotinib were employed.

The inhibiting test of the inventive compounds on the cancer cell growth was conducted in A431 (ATCC CRL-1555), HCC827 (ATCC CRL-2868) and NCI-H1975 (ATCC CRL-5908) cell lines.

A431 cell line was incubated in a high-glucose DMEM (Dulbecco's Modified Eagle's Medium) supplemented with 10% fetal bovine serum (FBS) and 1% penicillin/streptomycin (Gibco BRL), and HCC827 and NCI-H1975 cell lines were incubated in an RPMI medium supplemented with 10% FBS, 1% penicillin/streptomycin and 1% sodium pyruvate.

The cancer cell lines stored in a liquid nitrogen tank were each quickly thawed at 37° C., and centrifuged to remove the medium. The resulting cell pellet was mixed with a culture medium, incubated in a culture flask at 37° C. under 5% $CO_2$ for 2 to 3 days, and the medium was removed. The remaining cells were washed with DPBS (Dulbecco's Phosphate Buffered Saline) and separated from the flask by using Tripsin-EDTA. The separated cells were diluted with a culture medium to a concentration of $1\times10^5$ A431 cells/ml, except that in case of HCC827 and NCI-H1975 cells, the dilution was carried out to $5\times10^4$ cells/ml. 100 μl of the diluted cell solution was added to each well of a 96-well plate, and incubated at 37° C. under 5% $CO_2$ for 1 day. NCI-H1975 cells were starved in a RPMI-1640 medium containing 0.1% FBS and 1% penicillin/streptomycin to maximize the reacting activities of the cell on the test compounds on the following day.

The compounds obtained in Examples 1 to 237 were each dissolved in 99.5% dimethylsulfoxide (DMSO) to a concentration of 25 mM. In case that the test compound was not soluble in DMSO, 1% HCl was added thereto and treated in a 40° C. water bath for 30 mins until a complete dissolution was attained. The DMSO solution containing test compound was diluted with a culture medium to a final concentration of 100 μM, and then diluted 10 times serially to $10^{-6}$ μM (a final concentration of DMSO was less than 1%).

The medium was removed from each well of the 96-well plate. And then, 100 μl of a test compound solution was added to each well holding the cultured cells, and the plate was incubated at 37° C. under 5% $CO_2$ for 72 hours (except that NCI-H1975 cells were incubated for 48 hours). After removing the medium from the plate, 50 μl of 10% trichloroacetic acid was added to each well, and the plate was kept at 4° C. for 1 hour to fix the cells to the bottom of the plate. The added 10% trichloroacetic acid solution was removed from each well, the plate was dried, 100 μl of an SRB (Sulforhodamine-B) dye solution at a concentration of 0.4% dissolved in 1% acetic acid was added thereto, and the resulting mixture was reacted for 10 mins at room temperature. After removing the dye solution, the plate was washed with water, and well dried.

When the dye solution was not effectively removed by water, 1% acetic acid was used. 150 µl of 10 mM trisma base was added to each well, and the absorbance at 540 nm wavelength was determined with a microplate reader. In case of NCI-H1975, the cell viabilities were determined as the absorbance at 490 nm wavelength using Celltiter 96 Aqueous One solution (MTS, promega).

$GI_{50}$, the concentration at which 50% inhibition occurs, was evaluated based on the difference between the final density of the test cells and the initial density of the cells incubated in a well not-treated with the test compound which was regarded as 100%. The calculation of $GI_{50}$ and the result analysis were carried out by using Microsoft Excel, and the results are shown in Tables 14a to 14f. Wherein, A means that $GI_{50} \leq 50$ nM, B means that $GI_{50}$ is 50-100 nM, C means that $GI_{50}$ is 100-1,000 nM, and D means that $GI_{50} \geq 1,000$ nM.

TABLE 14a

| | $GI_{50}$ | | |
|---|---|---|---|
| Example | HCC827 EGFR DelE746__A750 | NCI-H1975 EGFR L858R/T790M | A431 EGFR WT |
| 1 | A | A | D |
| 2 | B | B | D |
| 3 | A | A | D |
| 4 | B | B | D |
| 6 | B | A | — |
| 7 | A | A | — |
| 8 | A | A | D |
| 9 | A | A | — |
| 10 | A | A | C |
| 11 | A | A | C |
| 12 | A | A | — |
| 13 | A | A | C |
| 14 | A | B | — |
| 15 | A | A | — |
| 16 | B | A | — |
| 17 | A | A | — |
| 18 | A | A | — |
| 22 | A | B | — |
| 23 | B | A | D |
| 24 | A | B | D |
| 25 | B | B | — |
| 26 | A | A | D |
| 27 | A | A | — |
| 28 | B | A | — |
| 29 | B | A | D |
| 30 | C | A | D |
| 31 | A | A | D |
| 32 | A | A | D |
| 35 | A | A | — |
| 36 | B | A | — |

TABLE 14b

| | $GI_{50}$ | | |
|---|---|---|---|
| Example | HCC827 EGFR DelE746__A750 | NCI-H1975 EGFR L858R/T790M | A431 EGFR WT |
| 37 | C | A | D |
| 38 | A | A | — |
| 40 | A | B | |
| 41 | A | A | — |
| 42 | A | A | D |
| 45 | A | A | — |
| 46 | A | A | — |
| 47 | A | A | — |
| 48 | A | A | D |
| 49 | A | A | — |
| 50 | A | C | D |
| 51 | A | A | D |
| 52 | A | A | D |

TABLE 14b-continued

| | $GI_{50}$ | | |
|---|---|---|---|
| Example | HCC827 EGFR DelE746__A750 | NCI-H1975 EGFR L858R/T790M | A431 EGFR WT |
| 53 | A | A | D |
| 54 | A | A | D |
| 55 | A | A | — |
| 56 | B | A | — |
| 57 | A | C | — |
| 59 | A | C | — |
| 60 | C | C | — |
| 61 | B | A | — |
| 62 | A | A | D |
| 65 | A | A | D |
| 66 | A | A | D |
| 69 | B | A | — |
| 71 | B | A | — |
| 72 | A | A | — |
| 76 | A | B | D |
| 77 | A | A | — |
| 78 | B | B | — |
| 79 | A | C | — |
| 80 | A | A | D |

TABLE 14c

| | $GI_{50}$ | | |
|---|---|---|---|
| Example | HCC827 EGFR DelE746__A750 | NCI-H1975 EGFR L858R/T790M | A431 EGFR WT |
| 82 | A | A | D |
| 83 | A | A | C |
| 84 | B | B | — |
| 90 | A | A | D |
| 92 | A | A | — |
| 93 | B | B | — |
| 94 | A | A | D |
| 95 | A | A | — |
| 97 | B | A | — |
| 98 | A | A | — |
| 99 | B | A | D |
| 100 | A | A | D |
| 102 | A | B | — |
| 103 | C | A | — |
| 106 | B | A | — |
| 107 | A | A | D |
| 108 | B | B | — |
| 109 | A | A | — |
| 111 | B | A | — |
| 112 | A | A | D |
| 114 | B | A | — |
| 115 | A | A | — |
| 116 | A | A | — |
| 117 | A | B | — |
| 118 | A | B | — |
| 119 | A | A | — |
| 120 | A | A | D |
| 121 | B | A | — |
| 122 | A | A | D |
| 123 | B | B | — |
| 124 | A | A | — |
| 125 | A | A | D |

TABLE 14d

| | $GI_{50}$ | | |
|---|---|---|---|
| Example | HCC827 EGFR DelE746__A750 | NCI-H1975 EGFR L858R/T790M | A431 EGFR WT |
| 126 | A | A | — |
| 127 | A | A | — |
| 128 | A | A | D |

TABLE 14d-continued

| | GI$_{50}$ | | |
|---|---|---|---|
| Example | HCC827 EGFR DelE746_A750 | NCI-H1975 EGFR L858R/T790M | A431 EGFR WT |
| 129 | A | A | D |
| 130 | A | A | — |
| 131 | B | A | — |
| 132 | A | A | — |
| 133 | A | A | — |
| 134 | A | A | — |
| 135 | B | A | — |
| 136 | A | A | — |
| 138 | A | A | — |
| 139 | A | A | — |
| 140 | B | B | — |
| 142 | A | A | D |
| 143 | B | A | — |
| 144 | A | B | — |
| 148 | A | A | — |
| 154 | B | B | — |
| 156 | A | B | — |
| 158 | A | C | D |
| 159 | A | A | D |
| 160 | A | A | — |
| 165 | A | A | D |
| 167 | A | A | D |
| 168 | A | A | D |
| 169 | A | B | — |
| 172 | B | A | — |
| 173 | A | A | C |
| 174 | A | A | — |
| 175 | A | A | — |
| 176 | A | A | D |

TABLE 14e

| | GI$_{50}$ | | |
|---|---|---|---|
| Example | HCC827 EGFR DelE746_A750 | NCI-H1975 EGFR L858R/T790M | A431 EGFR WT |
| 178 | A | A | D |
| 180 | A | A | D |
| 181 | A | A | D |
| 182 | A | A | D |
| 183 | A | A | D |
| 184 | A | A | D |
| 185 | A | A | D |
| 186 | A | A | D |
| 187 | B | A | D |
| 189 | A | A | D |
| 190 | A | A | — |
| 191 | A | A | — |
| 196 | A | B | — |
| 197 | A | A | — |
| 199 | A | A | D |
| 201 | A | B | — |
| 202 | B | A | — |
| 203 | A | A | D |
| 205 | A | A | — |
| 206 | A | A | D |
| 207 | A | A | — |
| 208 | A | A | — |
| 209 | A | A | — |
| 210 | A | A | — |
| 211 | A | A | — |
| 212 | B | B | — |
| 213 | B | A | — |
| 214 | B | A | — |
| 215 | A | A | — |
| 216 | A | A | — |
| 217 | A | B | — |
| 218 | A | B | D |

TABLE 14f

| | GI$_{50}$ | | |
|---|---|---|---|
| Example | HCC827 EGFR DelE746_A750 | NCI-H1975 EGFR L858R/T790M | A431 EGFR WT |
| 219 | A | A | D |
| 220 | A | A | — |
| 221 | A | A | — |
| 222 | B | B | — |
| 223 | A | A | D |
| 224 | A | A | — |
| 225 | A | A | — |
| 228 | A | A | C |
| 229 | A | A | C |
| 232 | B | B | — |
| 234 | A | A | D |
| 235 | A | A | — |
| 237 | A | A | D |
| Erlotinib | A | D | B |
| Lapatinib | C | D | B |
| BIBW2992 | A | A | A |

As shown in Tables 14a to 14f, almost of the inventive compounds showed an excellent anticancer activity by selectively inhibiting the growth of the HCC827 and NCI-H1975 non-small cell lung cancer (NSCLC) cells expressing EGFR mutants (GI$_{50}$=A or B), with no anticancer activity on A431 cell expressing EGFR WT (GI$_{50}$=D). Such the inhibition mechanisms of the inventive compounds are very different from those of the commercially marketable EGFR tyrosine kinases (e.g., Erlotinib and Lapatinib) or the being developed material (BIBW2992).

As shown in Table 14f, Erlotinib as the first generation EGFR inhibitor was very effective in inhibiting the growth of NSCLC cell lines expressing EGFR mutants (HCC827, GI$_{50}$=A), while it provided no inhibition activity against NSCLC cell lines expressing EGFR T790M point mutation (NCI-H1975, GI$_{50}$=D). Also, the currently marketable Lapatinib which inhibits both EGFR and HER-2 showed a weak inhibition activity (HCC827, GI$_{50}$=C) or no inhibition activity (NCI-H1975, GI$_{50}$=D) against NSCLC cell lines. Further, the irreversible inhibitor having quinazoline structure, BIBW2992 (Boehringer Ingelheim, currently in the phase III stage, exhibited a strong inhibition activity against pan-HER and effectively inhibited all the cancer cell lines disclosed in Tables 14a to 14f including A431 cell line (GI$_{50}$=A). However, such irreversible inhibitor having the quinazoline structure may cause serious adverse side effects (e.g., diarrhea, skin rash and weight loss) when treated in an amount for inhibiting EGFR T790M, and therefore, there still has been a need to develop a safe drug for overcoming the problems of the resistance development of EGFR T790M. Therefore, the inventive compounds showed a highly improved inhibition activity against EGFR mutants including EGFR T790M, with no inhibition activity against EGFR WT expressed in normal cell, which suggests that the inventive compounds can be used as more effective and safe anticancer drugs to NSCLC patients.

Test Example 2

Inhibition Test for Activities of EGFR WT and L858R/T790M Kinase

The inhibiting activities of the inventive compounds obtained in Examples 1 to 237 against EGFR WT and EGFR L858R/T790M kinase were determined using z-lyte kinase assay kit (Invitrogen, PV3191). The kinases used in the test were purchased from Invitrogen.

The compounds obtained in Examples 1 to 237 were each prepared to 10 mM DMSO solution, and a solution containing 4% DMSO were prepared therefrom and diluted to a concentration of 1 µM to 0.0001 µM. Then, an approximate Kd value of each kinase was calculated, and diluted using a kinase buffer (50 mM HEPES (PH 7.4), 10 mM MgCl$_2$, 1 mM EGTA and 0.01% BRIJ-35) to 1 to 100 ng/assay concentration. The test was conducted in a 384 well polystyrene flat-bottomed plates. 5 µl of the diluted solution of each compound was added to each well, and 10 µl of a mixture of peptide substrate and kinase in a suitable concentration and 5 µl of 5-300 µM ATP solution were successively added thereto and the plate was incubated in a stirrer at room temperature for 60 minutes. After 60 mins, 10 µl of coloring reagent was added to the resulting mixture to initiate a fluorescence reaction of peptide substrate and a terminating solution was added thereto for terminating the reaction. A fluorescence value of each well was determined with a fluorescence meter (Molecular Device) at 400 nm (excitation filter) and 520 nm (emission filter). The inhibiting activity of the test compounds against the kinases was determined as a phosphorylation percentage (%) compared with control group, according to the kit protocol, and measured for IC$_{50}$, the concentration of x-axis at which 50% inhibition was observed. The calculation of IC$_{50}$ and the result analysis were carried out by using Microsoft Excel. The results are shown in Table 15. Wherein, A means that IC$_{50}$≤50 nM, B means that IC$_{50}$ is 50-100 nM, C means that IC$_{50}$ is 100-1,000 nM, and D means that IC$_{50}$≥1,000 nM.

TABLE 15

| Example | IC$_{50}$ | |
|---|---|---|
| | EGFR WT | EGFR L858R/T790M |
| 1 | C | A |
| 2 | D | A |
| 48 | C | A |
| 115 | D | A |
| 122 | D | A |
| 206 | C | A |
| 215 | D | A |
| Erlotinib | A | C |
| Lapatinib | B | D |
| BIBW2992 | A | A |

As shown in Table 15, the inventive compounds showed a relatively low inhibition activity against EGFR WT related with the adverse effects (IC$_{50}$=C or D), while it showed an excellent inhibition activity against EGFR L858R/T790M mutants having a resistance to the commercially marketable EGFR inhibitors (IC$_{50}$=A). Like the results from Test Example 1, such the inhibition mechanisms of the inventive compounds are very different from those of the commercially marketable EGFR tyrosine kinases (e.g., Erlotinib and Lapatinib) or the being developed material (BIBW2992) which strongly inhibit EGFR WT (IC$_{50}$=A or B). Therefore, the inventive compounds are effective and safe drug employable to NSCLC patients by showing an effectively excellent inhibition activity against EGFR mutants including EGFR T790M with no inhibition activity against EGFR WT expressed in normal cell.

Test Example 3

Inhibition Test for Activities of BTK and JAK3 Kinase

The inhibiting activities of the inventive compounds obtained in Examples 1 to 237 against BTK and JAK3 kinases were determined, respectively. The procedure of Test Example 2 was repeated except that BTK and JAK3 kinases (Invitrogen) were employed instead of using the EGFR kinase. The results are shown in Tables 16a to 16c. Wherein, A means that IC$_{50}$≤50 nM, B means that IC$_{50}$ is 50-100 nM, C means that IC$_{50}$ is 100-1,000 nM, and D means that IC$_{50}$≥1,000 nM.

TABLE 16a

| Example | IC$_{50}$ | |
|---|---|---|
| | BTK | JAK3 |
| 1 | A | A |
| 3 | A | B |
| 7 | A | B |
| 9 | A | A |
| 11 | A | A |
| 21 | A | B |
| 28 | A | A |
| 29 | A | A |
| 36 | B | B |
| 40 | B | B |
| 41 | B | B |
| 42 | A | B |
| 44 | B | B |
| 47 | B | B |
| 48 | A | A |
| 50 | A | B |
| 51 | A | B |
| 53 | A | A |
| 55 | B | A |
| 57 | A | B |
| 59 | A | B |
| 62 | A | A |
| 66 | A | B |
| 67 | A | A |
| 68 | B | A |
| 70 | A | A |
| 72 | A | A |
| 73 | A | B |
| 74 | A | B |
| 79 | A | A |

TABLE 16b

| Example | IC$_{50}$ | |
|---|---|---|
| | BTK | JAK3 |
| 82 | A | A |
| 83 | A | A |
| 85 | A | A |
| 88 | B | B |
| 89 | A | B |
| 91 | A | B |
| 95 | B | B |
| 99 | A | B |
| 103 | A | A |
| 104 | A | A |
| 105 | B | A |
| 125 | A | A |
| 127 | B | B |
| 129 | A | A |
| 130 | B | A |
| 141 | A | B |
| 142 | A | A |
| 145 | A | A |
| 146 | B | B |
| 148 | A | B |
| 151 | B | B |
| 152 | A | B |
| 154 | A | B |
| 169 | A | B |
| 173 | A | A |
| 174 | A | B |
| 177 | A | A |

TABLE 16b-continued

| | $IC_{50}$ | |
|---|---|---|
| Example | BTK | JAK3 |
| 179 | A | A |
| 180 | A | A |
| 181 | A | A |

TABLE 16c

| | $IC_{50}$ | |
|---|---|---|
| Example | BTK | JAK3 |
| 182 | A | B |
| 183 | B | B |
| 187 | B | B |
| 199 | A | A |
| 203 | A | B |
| 219 | A | A |
| 223 | A | A |
| 228 | A | A |
| 229 | A | A |
| 232 | A | A |
| 233 | A | A |
| 237 | A | A |

As shown in Tables 16a to 16c, the inventive compound showed an excellent inhibition activity against BTK and JAK kinases ($IC_{50}$=A or B).

Test Example 4

Inhibition Test for Activities of BMX, ITX and RLK Kinases

The compound obtained in Example 1 was measured for its inhibitory activity on TEC family kinases, i.e., BMX, ITK, TEX and RLK. The measurement was carried out in the same process as in Example 2, except for using BMX, ITK, TEC and RLK enzymes (Invitrogen) instead of EGFR enzyme. The results are shown in Table 17. The letter 'A' in the table means $IC_{50}$≤50 nM, 'B' means $IC_{50}$=50-100 nM, 'C' means $IC_{50}$=100-1,000 nM, and 'D' means $IC_{50}$≥1,000 nM.

TABLE 17

| | $IC_{50}$ | | |
|---|---|---|---|
| Example | BMX | ITK | RLK |
| 1 | A | B | A |

As shown in Table 17, the compound of Example 1 according to the present invention effectively inhibited TEC family kinases such as BTK, BMX, ITK, and RLK kinases ($IC_{50}$=A or B).

Test Example 5

Anticancer Efficacy Test in Nude Mice Xenografted with NCI-H1975 Cancer Cells

The compound according to the present invention (Example 2) was tested for its anticancer effect and toxicity in nude mice xenografted with NCI-H1975 cancer cells which shows resistance to Erlotinib previously approved for the treatment of non-small cell lung cancer, due to the acquisition of EGFR T790M point mutation. In order to evaluate the anticancer efficacy and toxicity of the compound according to the present invention, BIBW2992 (Boehringer Ingelheim), which currently exhibits excellent activity to resistant non-small cell lung cancer and is actively under development, was also used in the test.

NCI-H1975 cell (lung cancer cell) was purchased from American Type Culture Collection (ATCC). After formation of tumor by subcutaneous injection with $1\times10^8$ cells/0.3 mL of tumor cell suspension on the back of mice, passages were carried out and tumor in at least third generation was used in the test.

Figure 2:
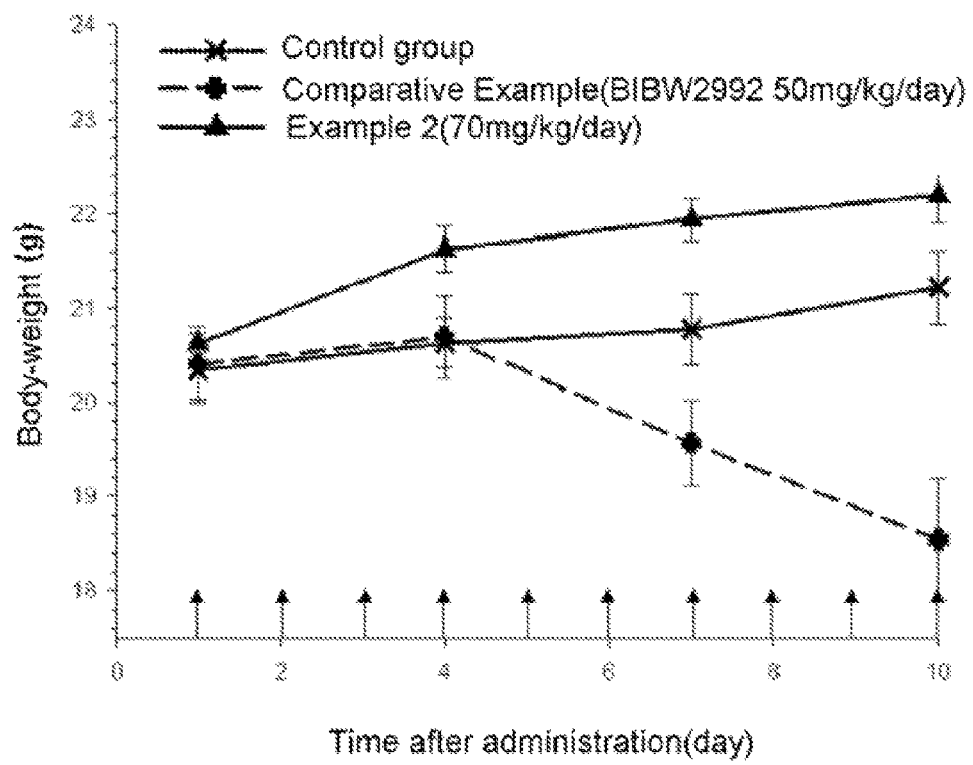
FIG. 2: body-weight change by oral administration of the compound obtained in Example 2 in nude mice xenografted with NCI-H1975 cancer cells.

In the test, a tumor in the sixth generation isolated from an individual was cut into a size of 30 mg, and transplanted subcutaneously into right flanks of mice using a 12-gauge trocar. The volume of tumor (V) is calculated from following equation 1 after measuring a long diameter (L) and a short diameter (S) using a vernier caliper twice a week for 18 days of test. All test materials were orally administered one time a day for total 10 days, and the tumor growth inhibition rate (IR: tumor growth inhibition rate (%) calculated based on a vehicle-treated control) and the maximum body weight loss (mBWL: maximum body weight loss calculated based on the body weight just before administration) were calculated using following equations 2 and 3. The results are shown in Table 6 and FIGS. 1 and 2.

$$V = L \times S^2 / 2 \quad \text{<Equation 1>}$$

wherein, L is a long diameter and S is a short diameter.

$$IR\ (\%) = (1 - (RTG\ \text{of the treatment group of test material})/(RTG\ \text{of the control group})) \times 100 \quad \text{<Equation 2>}$$

wherein, RTG is a relative tumor growth, which is the mean tumor volume on a particular day based on daily mean tumor volume.

$$mBWL\ (\%) = (1 - (\text{mean body weight on day x/mean body weight just before administration})) \times 100 \quad \text{<Equation 3>}$$

wherein, day x is a day on which the body weight loss is largest during the test.

Following Table 18 is the results of IR and mBWL in an NCI-H1975 in vivo model.

TABLE 18

| Compound | BIBW2992 | Example 2 |
|---|---|---|
| Dose | 50 mg/kg | 70 mg/kg |
| IR[1] | 77% | 75% |
| mBWL[2] | 9.1% | -7.6% |

[1] measured on 16th day after administration;
[2] measured on 10th day after administration.

The compound of the present invention did not inhibit EGFR WT and exhibited an excellent activity on EGFR mutant specific to non-small cell lung cancer (active mutant: EGFR DelR746_A750, EGFR L858R; acquired mutation: EGFR T790M). As shown in Table 18 and FIGS. 1 and 2, EGFR inhibitors exhibited comparable efficacies to BIBW2992 in NCI-H1975, an animal model which is the most difficult to show the efficacy (IR=77% vs 75%), while it did not exhibit any adverse side effects resulted from the pharmacological actions such as dermatologic diseases and body weight loss (BIBW2992: 9.1% of weight loss, Example 2: 7.6% of weight gain in therapeutically equivalent dose). These experimental results show that the compounds according to the present invention selectively and effectively inhibit the growth of cancer and the resistance to drug caused by the mutation of EGFR while showing no adverse side effects.

Test Example 6

Inhibition on Collagen-Induced Arthritis in Mice

In order to evaluate the efficacy of the compound according to the present invention for rheumatoid arthritis, the compound was subjected to arthritis inhibition test in a collagen-induced arthritis (CIA) model. The CIA model is a widely used, representative autoimmune arthritis model, arthritis of which is induced by injecting a mixture of type II collagen and an immunologic adjuvant to a specific mouse strain having major histocompatability complex (MHC) class II with $H$-$2^q$ or $H$-$2^r$ and thus CD4+ T cells and B-cells specifically responsive to the type II collagen are abnormally activated.

Male DBA/1J mice (8 weeks old) were first immunized by intradermal injection of 0.7 mL of a suspension liquid in which an equal volume of 2 mg/mL of type II collagen is emulsified in 4 mg/mL of complete Freund's adjuvant supplemented with bacteria tuberculosis. After 21 days, the mice were second immunized by the injection as above, except for using a suspension liquid in which an equal volume of 2 mg/mL of type II collagen is emulsified in incomplete Freund's adjuvant containing no bacteria tuberculosis. After 1 week of second immunization, mice were evaluated for clinical scores based on Table 19 and seven animals were grouped such that the average of experimental group is between 1 and 2. Test samples and vehicle of given concentrations were orally administered in an amount of 10 mL per body weight for 14 days everyday by using a Sonde. The clinical scores of arthritis (David D Brand et al., Nature Protocol. 2(5), 1269, 2007) were evaluated three times a day.

Figure 3:
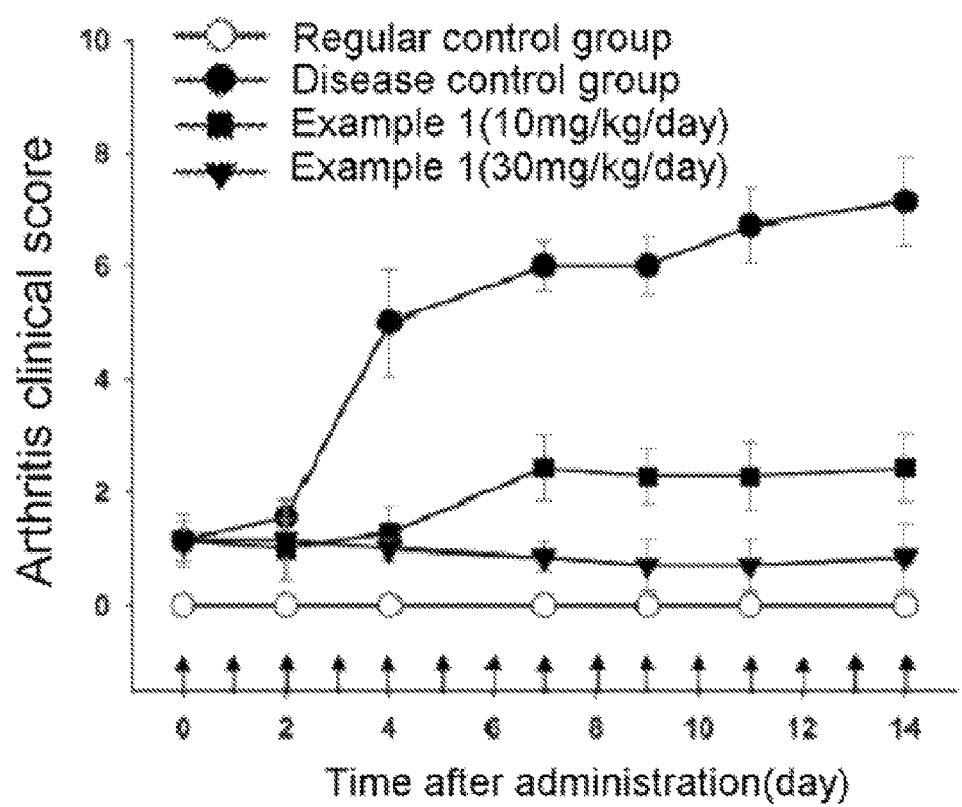
FIG. 3: change in an arthritis clinical score by oral administration of the compound obtained in Example 1 in a collagen-induced arthritis (CIA) model.

The compound of Example 1 reduced edema and flare until the last day (14 days) of the test in 10 mg/kg and 30 mg/kg groups compared to a control group, and significantly reduced edema, inflammation and flare in a 30 mg/kg group (FIG. 3).

As shown in Tables 16a, 16b and 16c and FIG. 3, the compound according to the present invention inhibited the activities of BTK and JAK3 kinases, and the inhibitions reduced edema, inflammation and flare as well as anti-collagen antibody values in a CIA model of autoimmune arthritis, compared to a control group, and also reduced the formation of pannus in histopathologic testing. The above results in a rodent model of arthritis suggest that the compound according to the present invention may provide clinical effects for patients with rheumatoid arthritis.

In addition, the compound according to the present invention significantly reduced the secretion of interleukin-6 (IL-6) and TNF-α in human peripheral blood mononuclear cells (PBMCs) and mouse splenocytes abundant in T-lymphocytes, B-lymphocytes, Cytes and macrophages after treatment of phorbol-12-myristate-13-acetate (PMA), phytohemagglutinin (PHA), Ionomycin, and others which stimulate lymphocytes, compared to a control group. This demonstrates that the compound according to the present invention inhibits the activation of lymphocytes.

TABLE 19

Evaluation of clinical scores of arthritis

| Rate | Characteristics |
|---|---|
| 0 | No edema and flare in paws, ankles, and ankle joints |
| 1 | Flare and mild edema in ankles or ankle joints |
| 2 | Flare and mild edema generally from ankle joints to ankles |
| 3 | Flare and edema from ankle joints to toe joints |
| 4 | Severe edema or spastic tetraplegia in overall joints, paws and toes |

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I) or a pharmaceutically acceptable salt thereof:

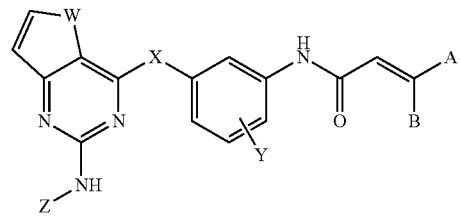

(I)

wherein,
W is O;
X is O, NH, S, SO or $SO_2$;
Y is hydrogen atom, halogen atom, $C_{1-6}$alkyl or $C_{1-6}$alkoxy;
A and B are each independently hydrogen atom, halogen atom, or di($C_{1-6}$alkyl)aminomethyl;
Z is selected from the group consisting of formulae Z1 to Z203:

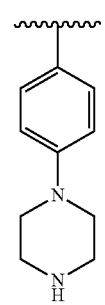

Z1

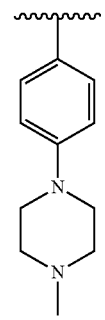

Z2

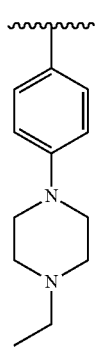 Z3
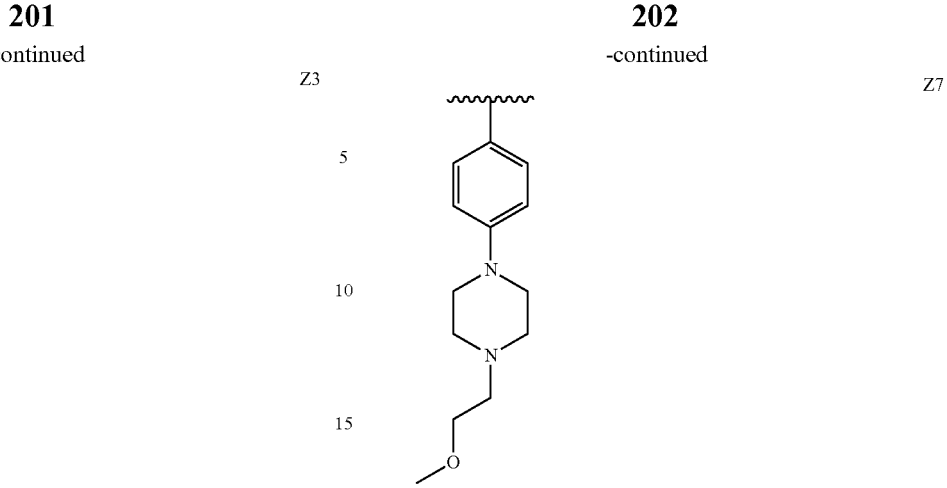 Z7
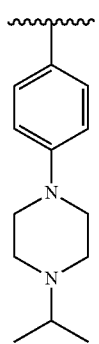 Z4
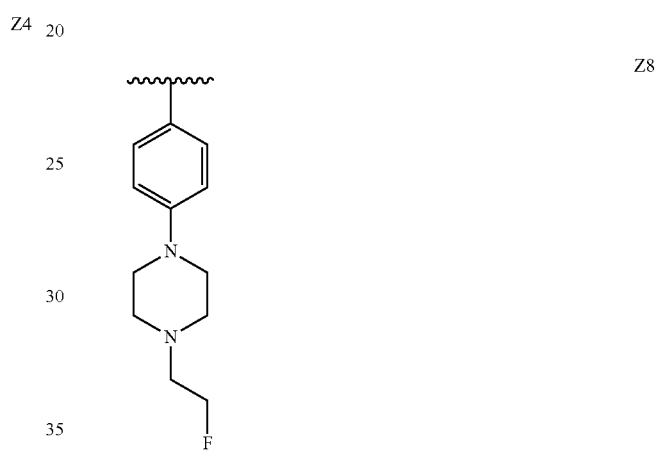 Z8
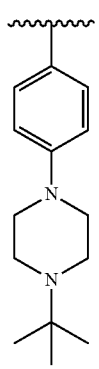 Z5
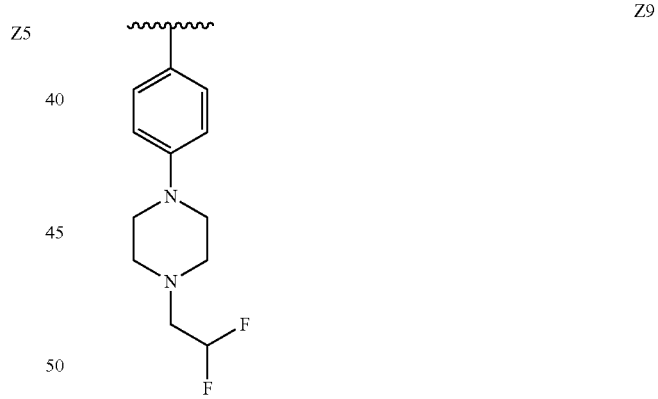 Z9
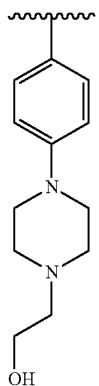 Z6
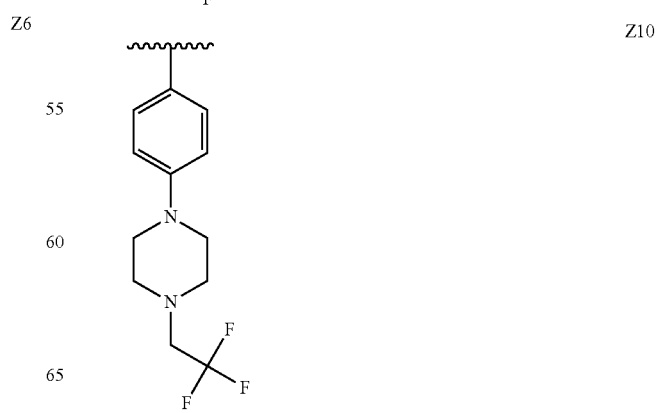 Z10

| Z11 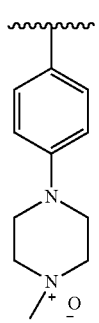 | Z15 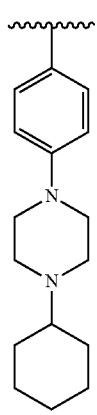 |
| Z12 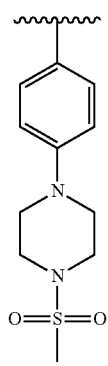 | Z16 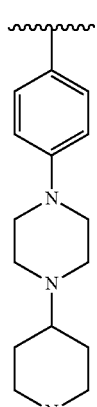 |
| Z13 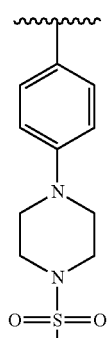 | Z17 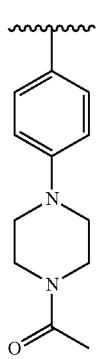 |
| Z14 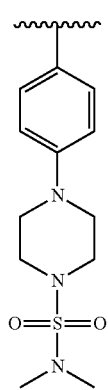 | Z18 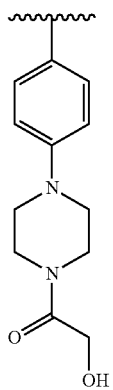 |

205
-continued
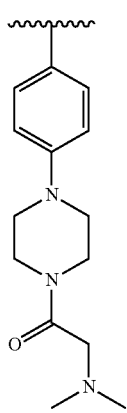
Z19
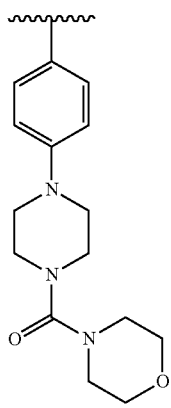
Z20
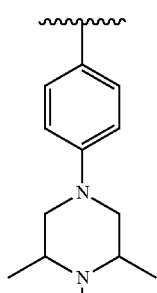
Z21
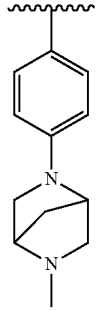
Z22
206
-continued
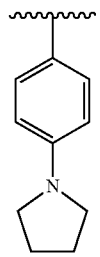
Z23
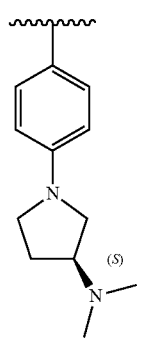
Z24
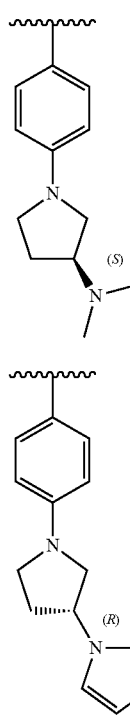
Z25
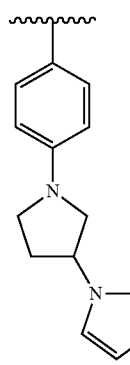
Z26
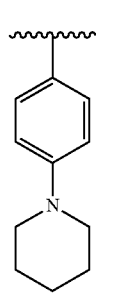
Z27

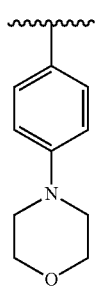 Z28
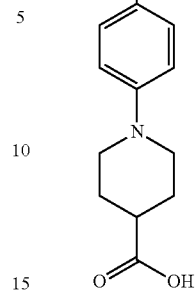 Z33
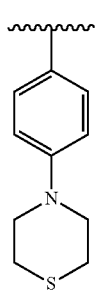 Z29
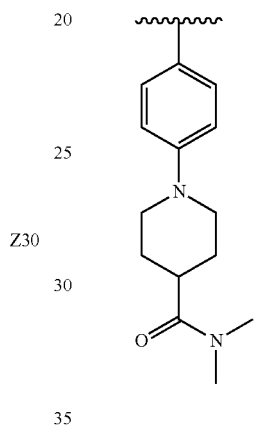 Z34
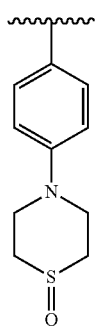 Z30
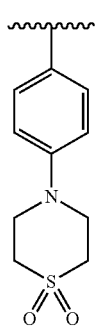 Z31
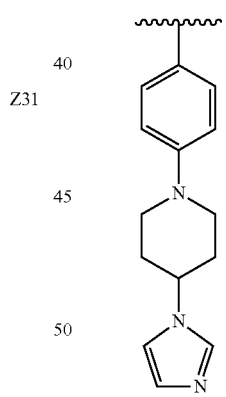 Z35
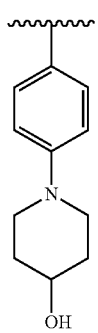 Z32
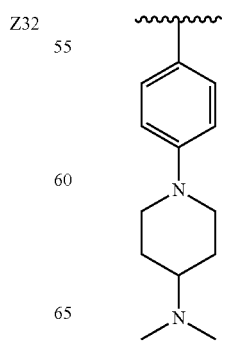 Z36

Z37 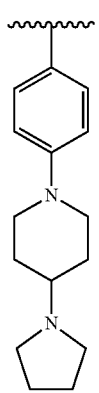
Z38 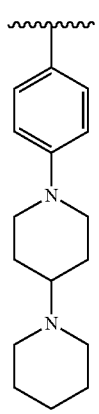
Z39 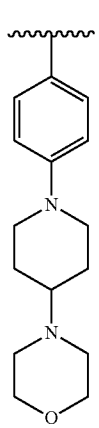
Z40 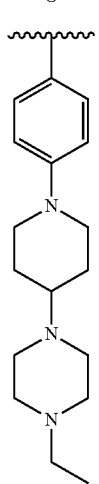
Z41 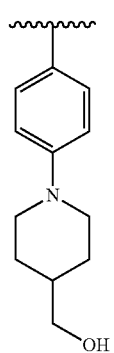
Z42 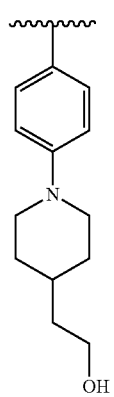
Z43 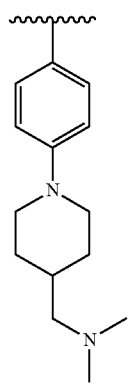
Z44 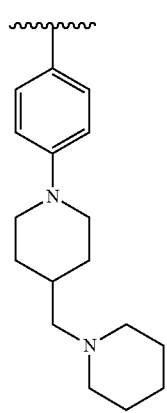

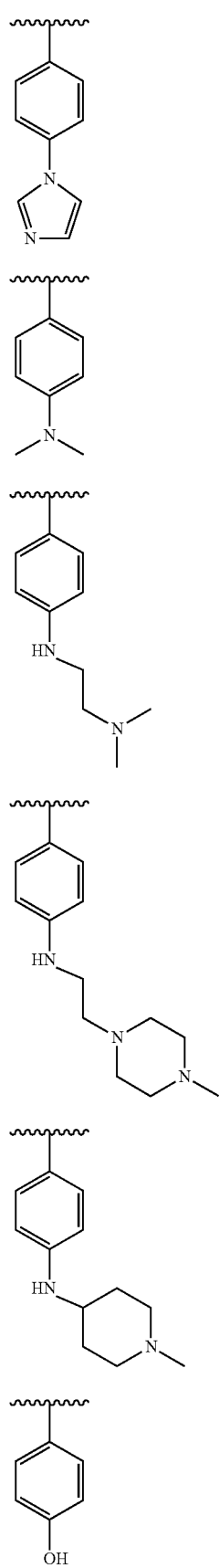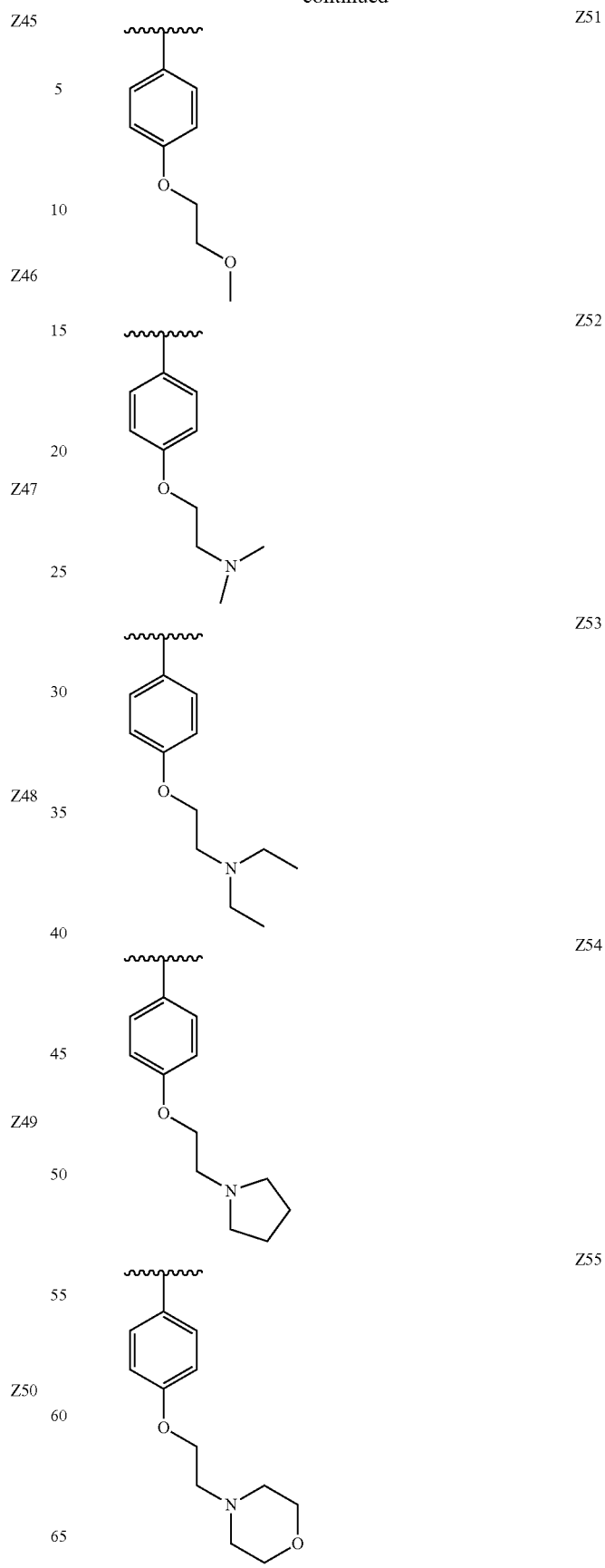

213
-continued
Z56 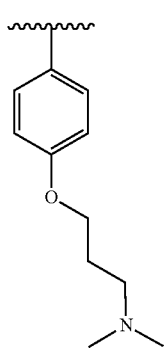
Z57 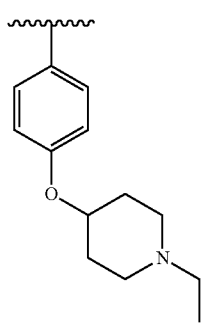
Z58 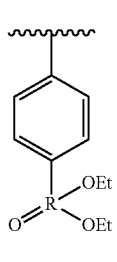
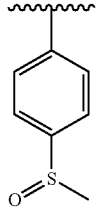
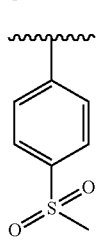
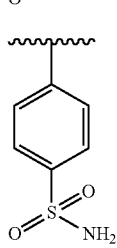
214
-continued
Z62 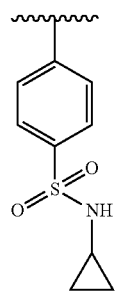
Z63 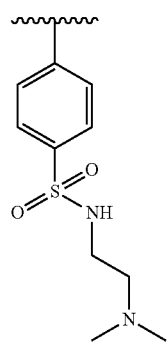
Z64
Z65 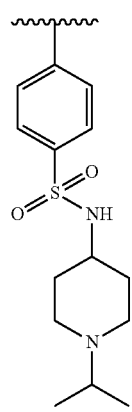

-continued
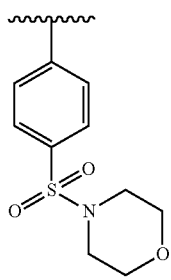
Z66
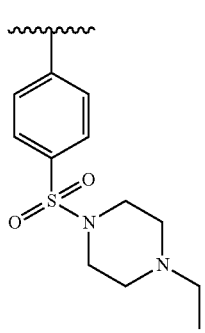
Z67
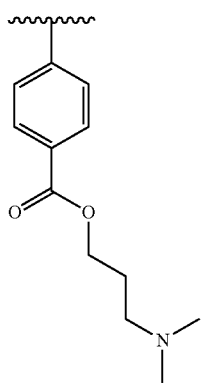
Z68
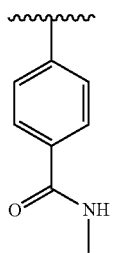
Z69
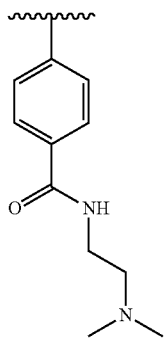
Z70
-continued
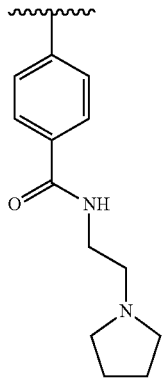
Z71
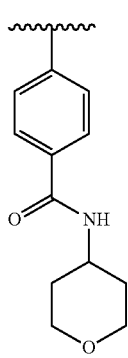
Z72
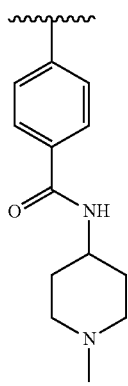
Z73
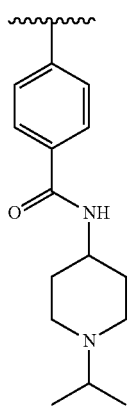
Z74

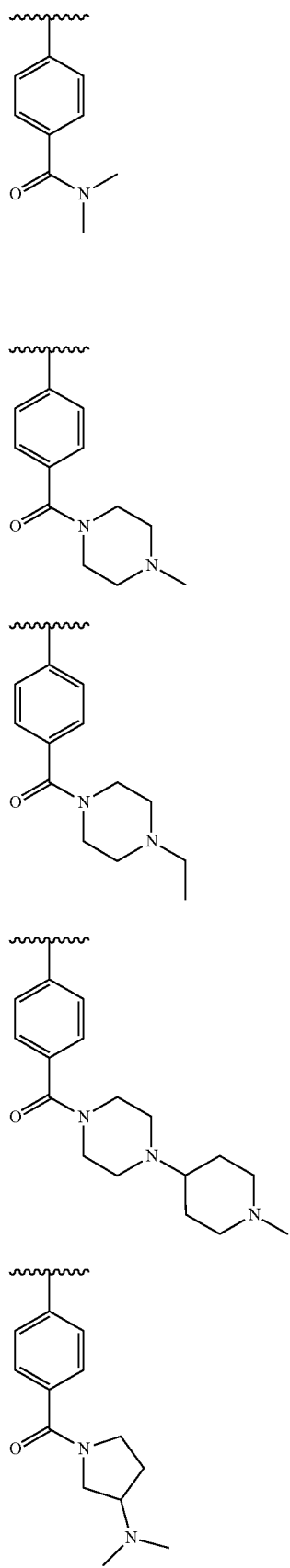
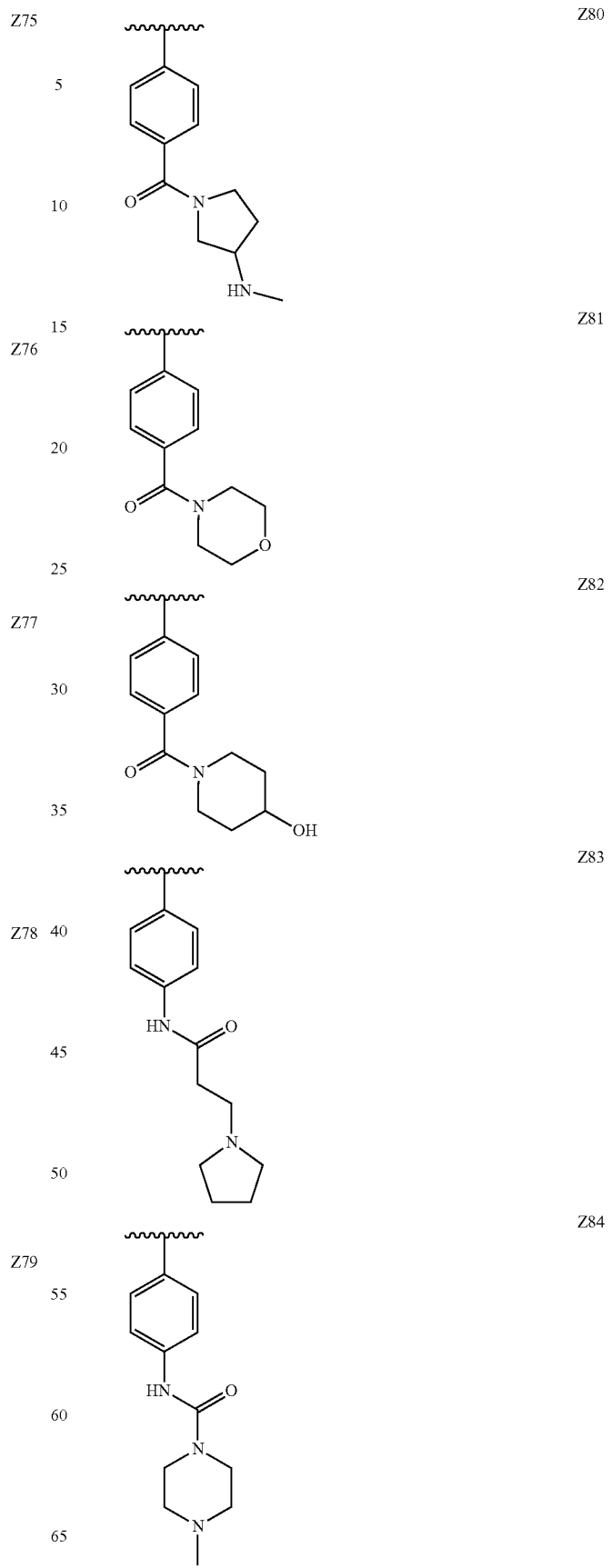

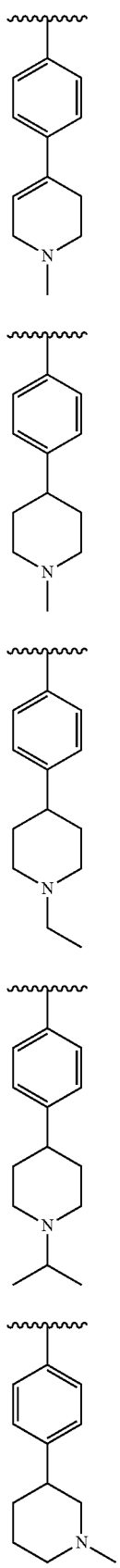
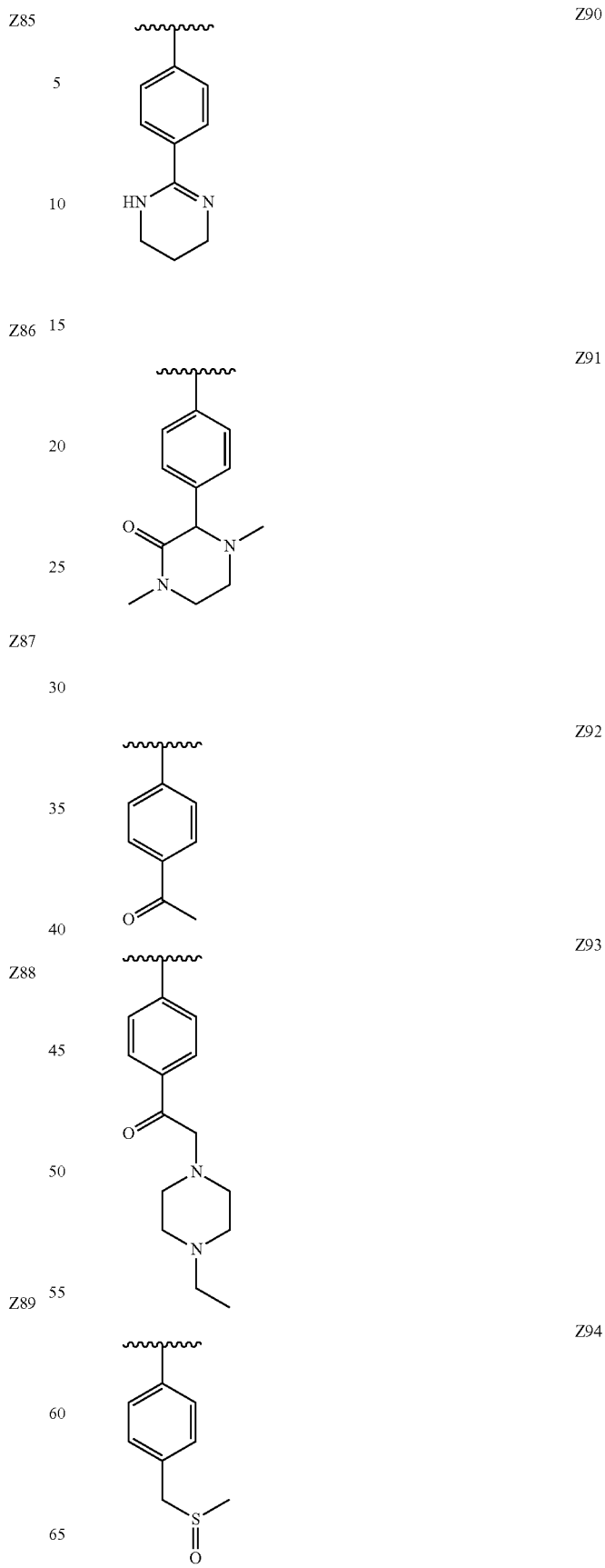

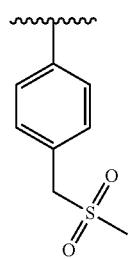 Z95
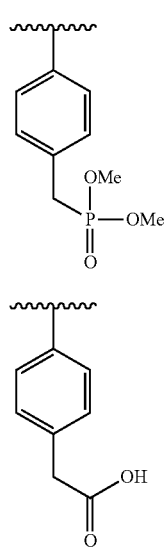
Z96
Z97
Z98
Z99
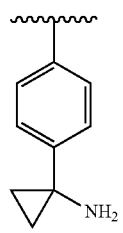
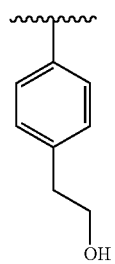
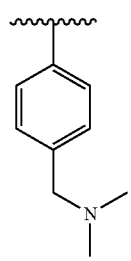
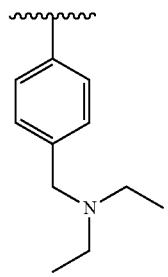 Z101
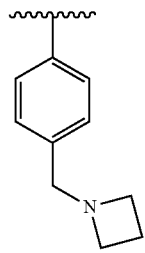 Z102
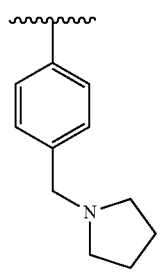 Z103
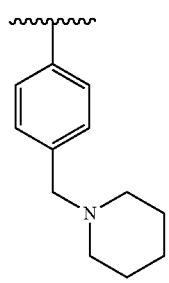 Z104
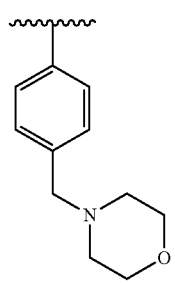 Z105
Z100
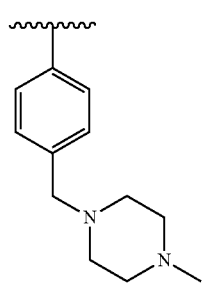 Z106

Z107 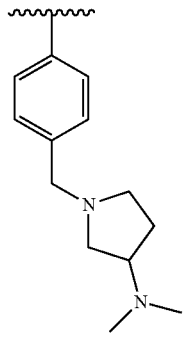
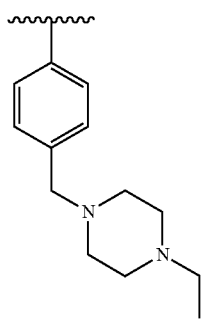
Z108 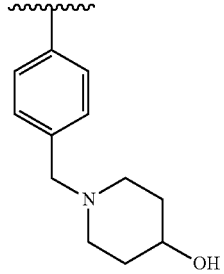
Z109 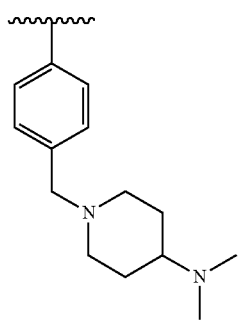
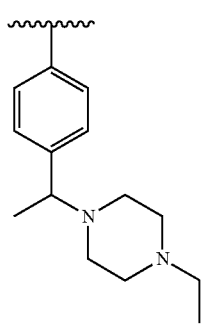
Z110 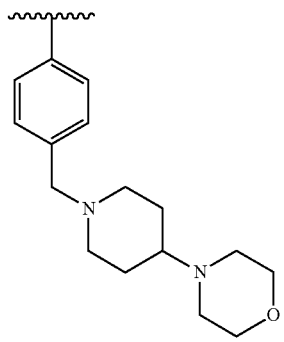
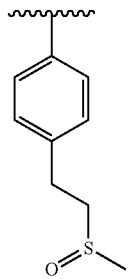

225
-continued
Z116 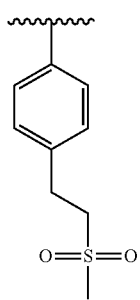
Z117 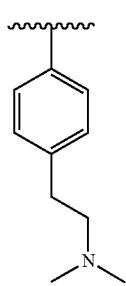
Z118 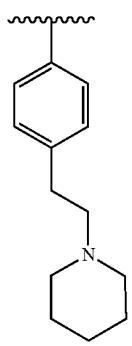
Z119 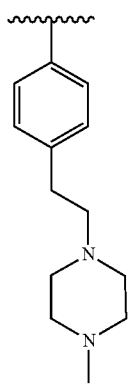
226
-continued
Z120 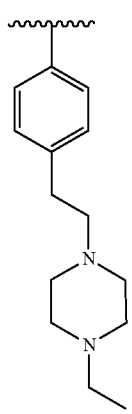
Z121 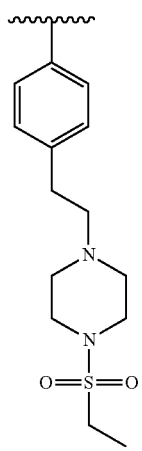
Z122 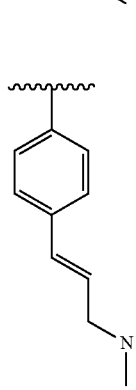
Z123 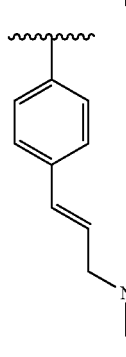

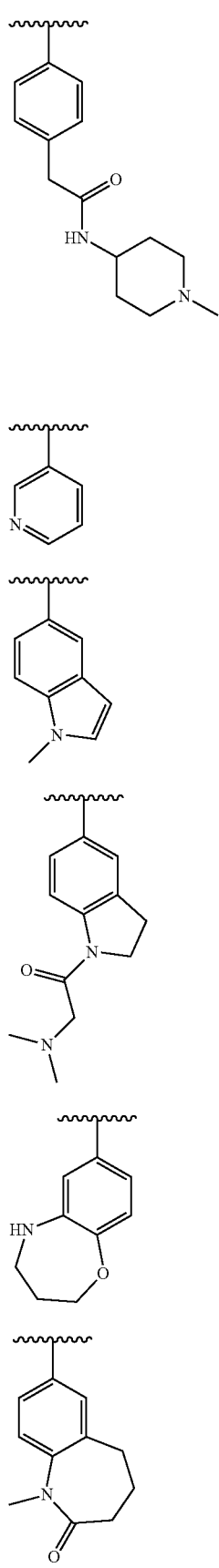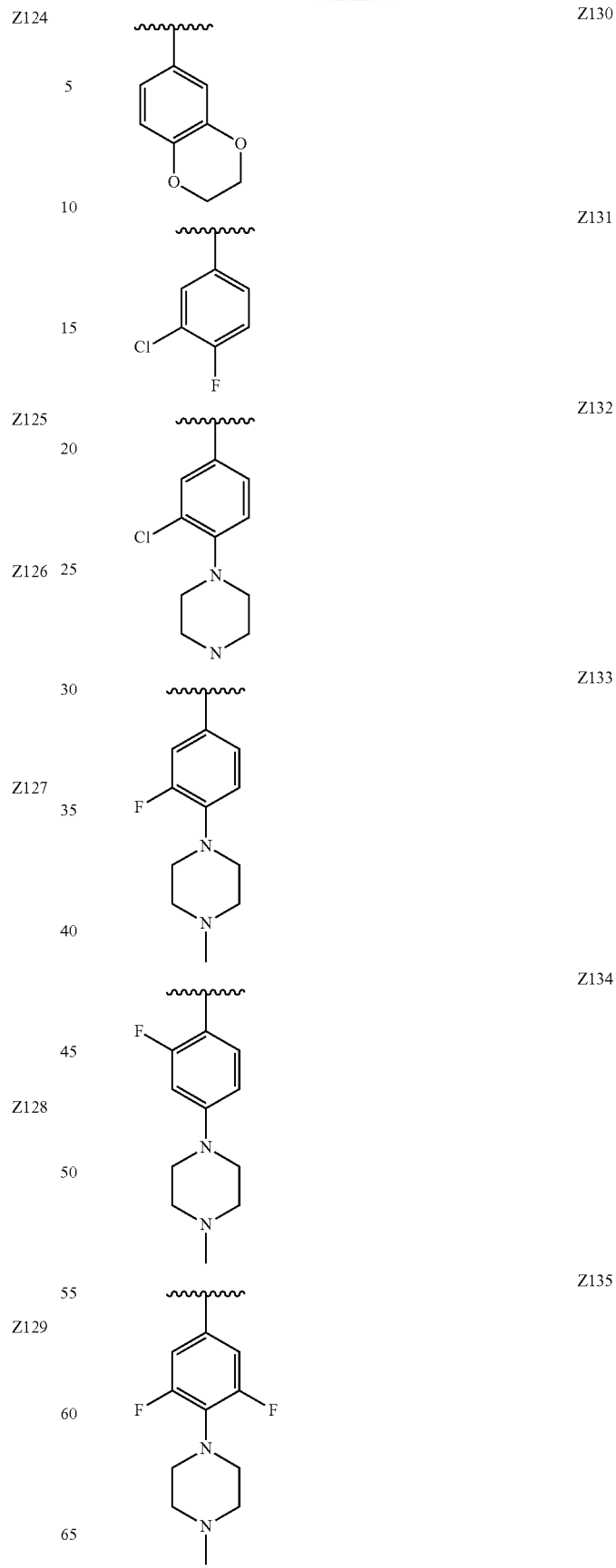

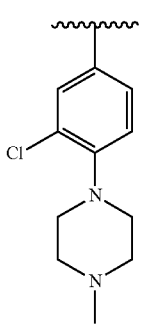
Z136
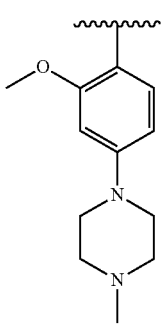
Z137
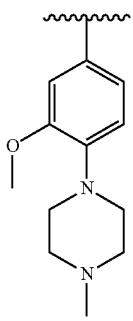
Z138
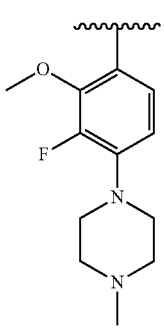
Z139
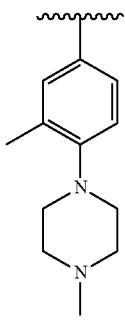
Z140
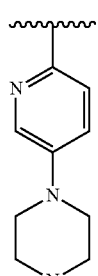
Z141
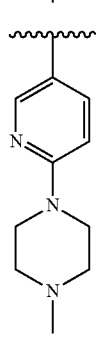
Z142
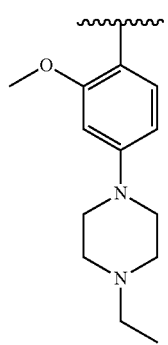
Z143
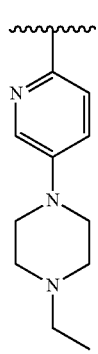
Z144
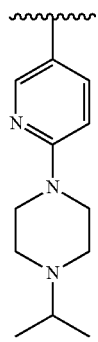
Z145

-continued
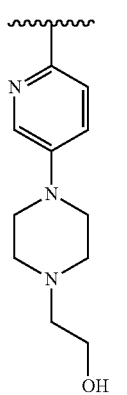
Z146
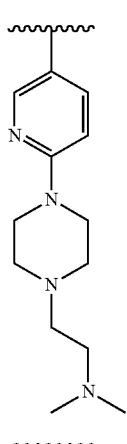
Z147
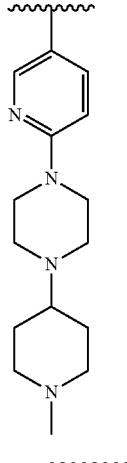
Z148
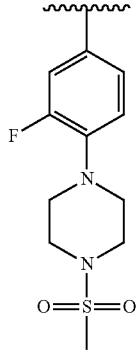
Z149
-continued
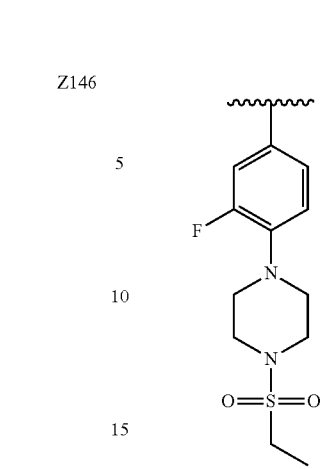
Z150
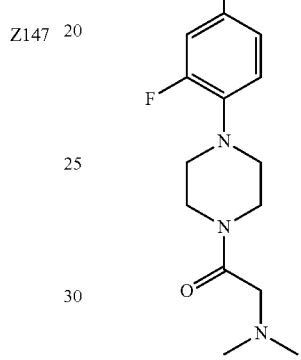
Z151
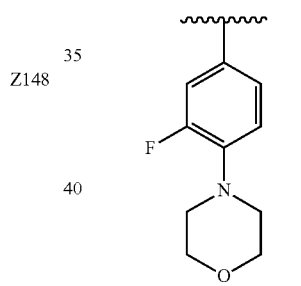
Z152
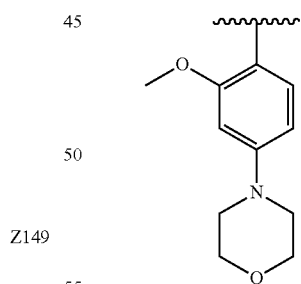
Z153
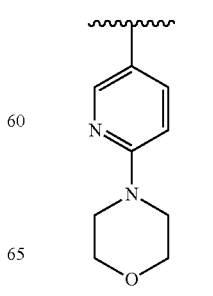
Z154

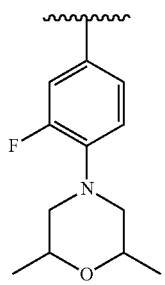 Z155
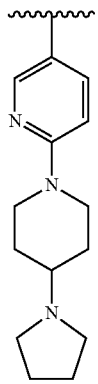 Z159
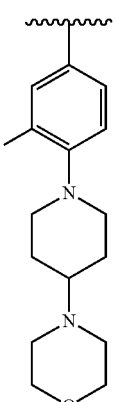 Z156
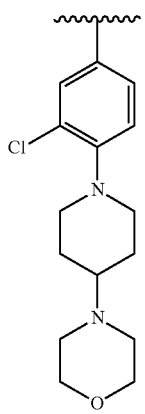 Z160
Z157
Z161
Z158
Z162

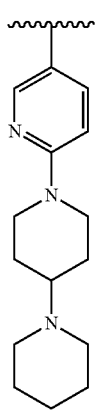
Z163
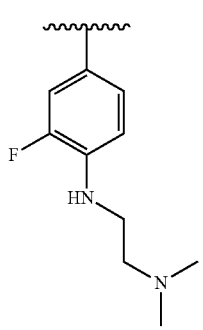
Z164
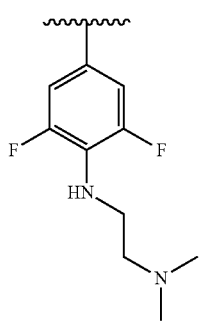
Z165
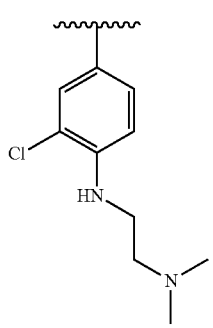
Z166
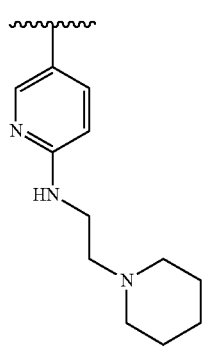
Z167
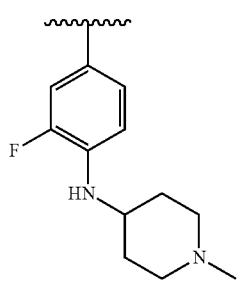
Z168
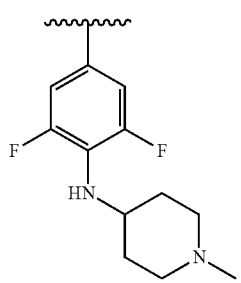
Z169
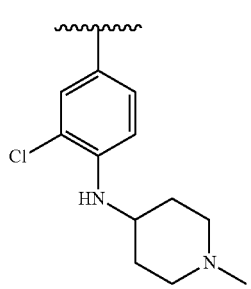
Z170
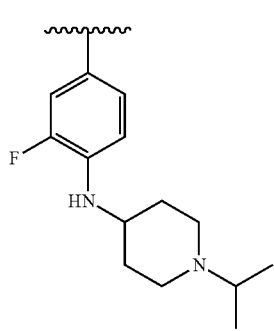
Z171

Z172 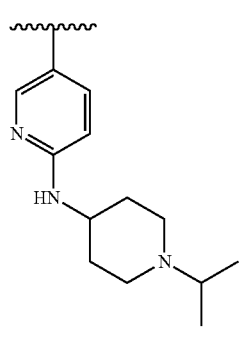
Z173 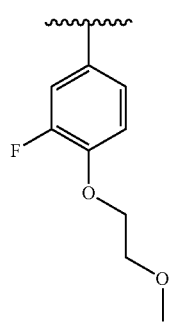
Z174 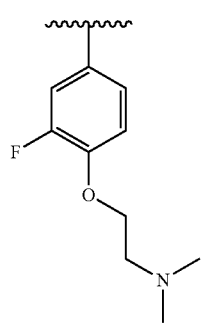
Z175 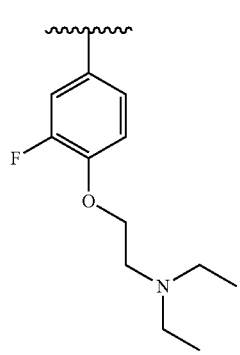
Z176 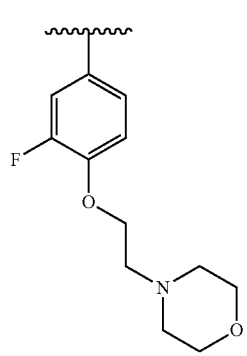
Z177 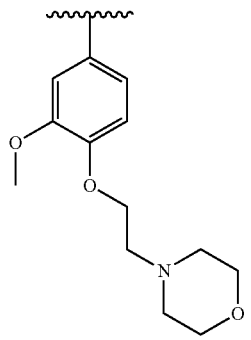
Z178 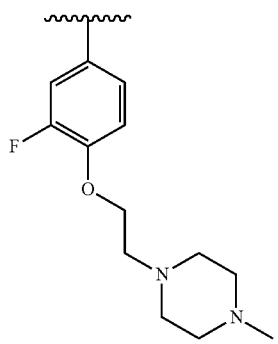
Z179
Z180
Z181

Z182 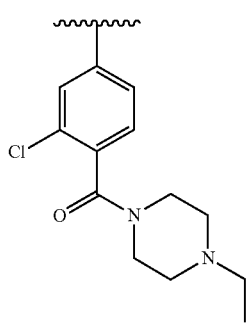
Z183 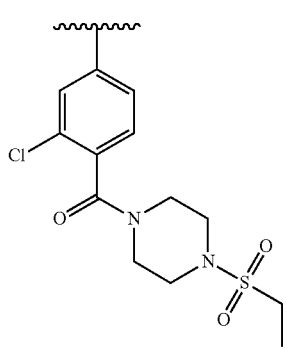
Z184 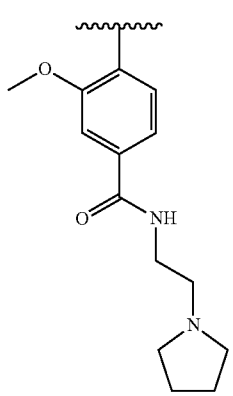
Z185 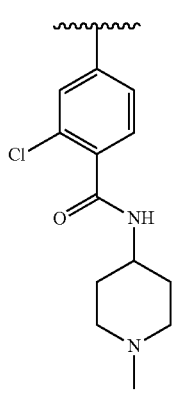
Z186 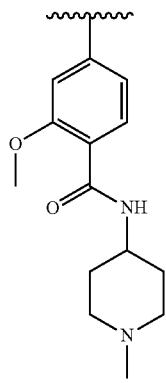
Z187 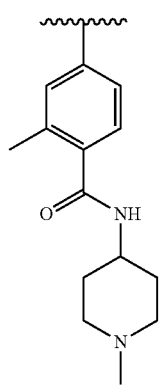
Z188 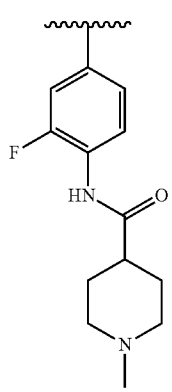
Z189

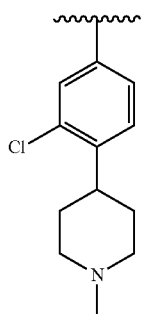 Z190
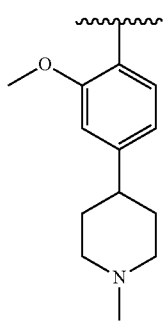 Z191
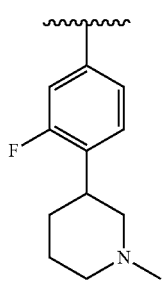 Z192
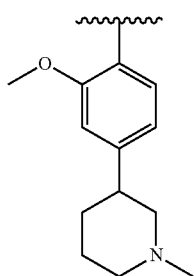 Z193
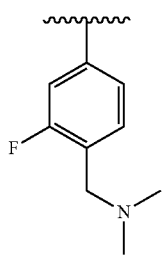 Z194
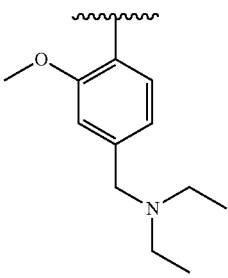 Z195
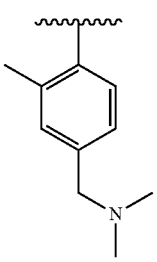 Z196
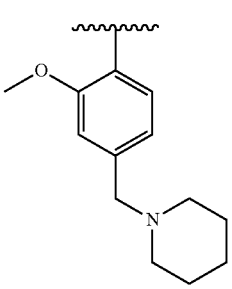 Z197
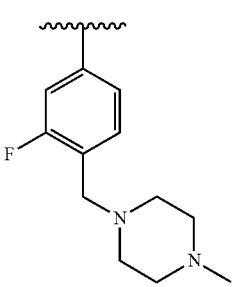 Z198
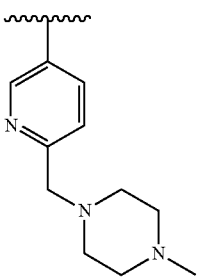 Z199

-continued

Z200
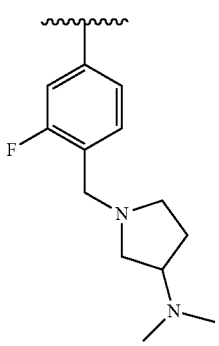

Z201
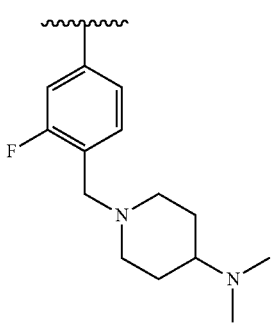

Z202
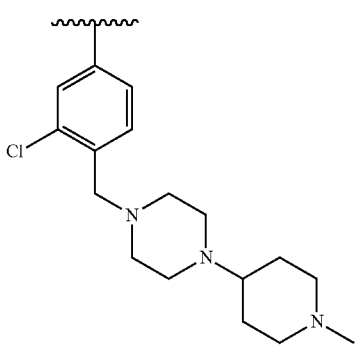

Z203
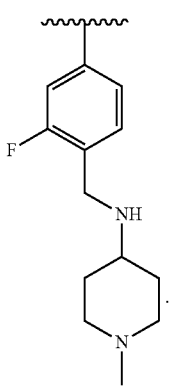

2. The compound of claim 1, or a pharmaceutically acceptable salt thereof, wherein, W is O; X is O; Y is hydrogen; and A and B are each independently hydrogen.

3. A compound of formula (I) or a pharmaceutically acceptable salt thereof:

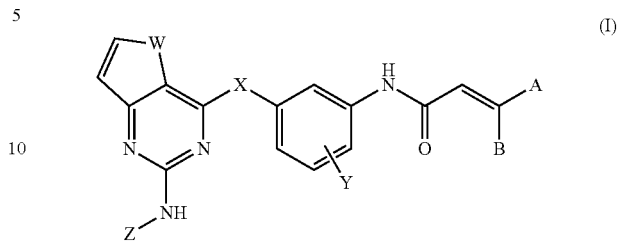

(I)

wherein,

W is O;

X is O;

Y is hydrogen;

A and B are each independently hydrogen; and

Z is selected from the group consisting of formulae Z2, Z4, Z28, Z61, Z100, Z113, Z138, Z164, Z168 and Z189:

Z2
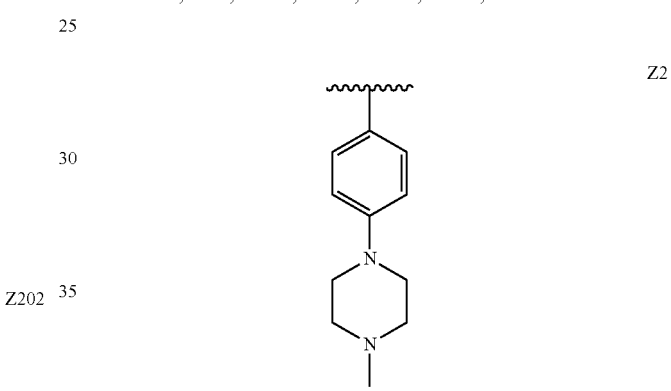

Z4
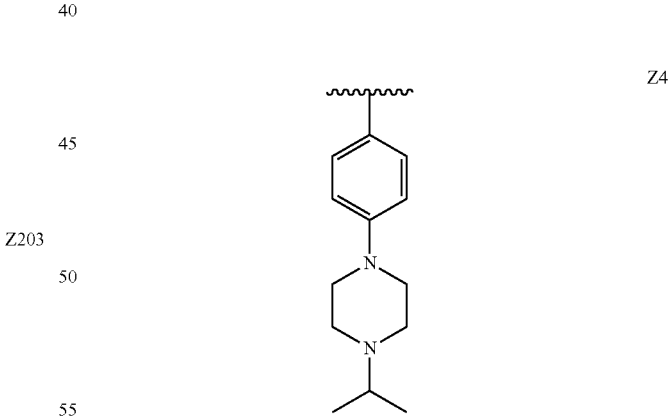

Z28
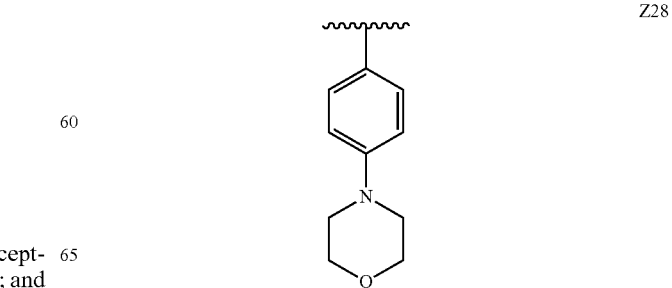

-continued
Z61 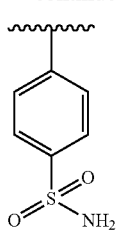
Z100 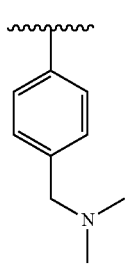
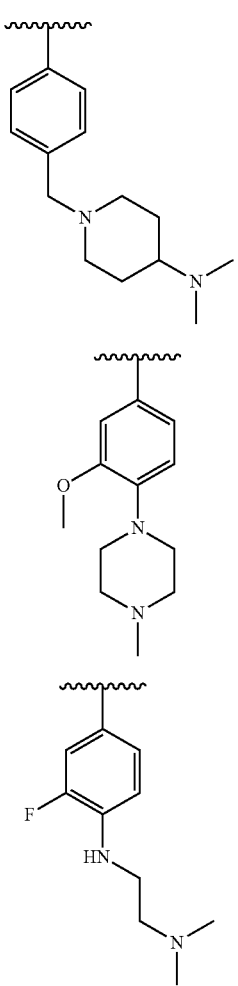
Z113
Z138
Z164
-continued
Z168 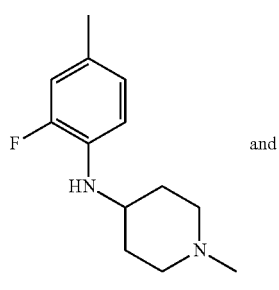
and
Z189 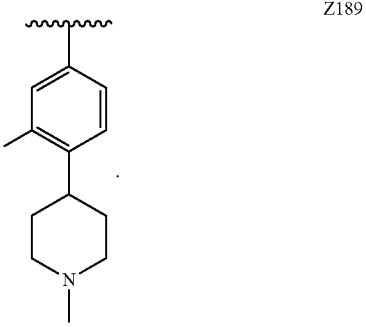
4. A compound selected from the group consisting of:
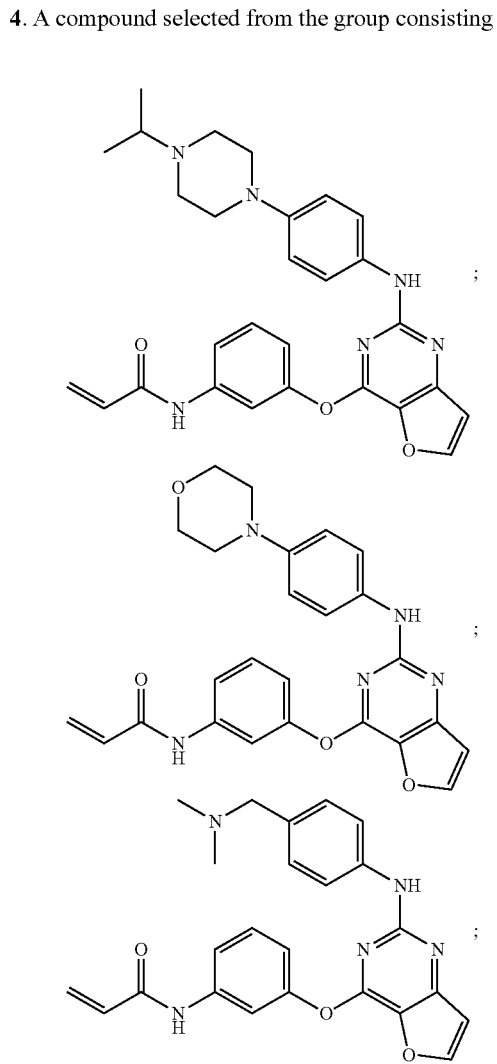

-continued

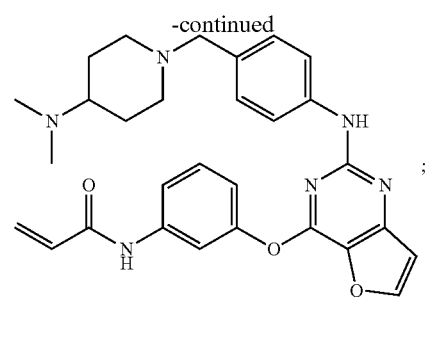

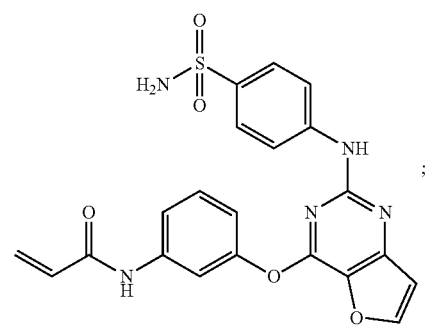

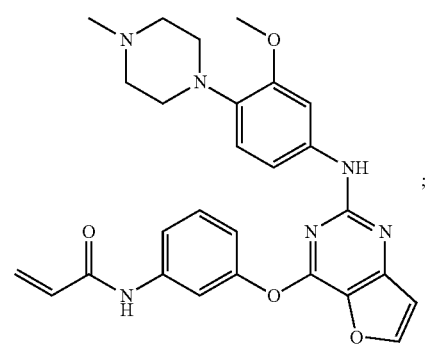

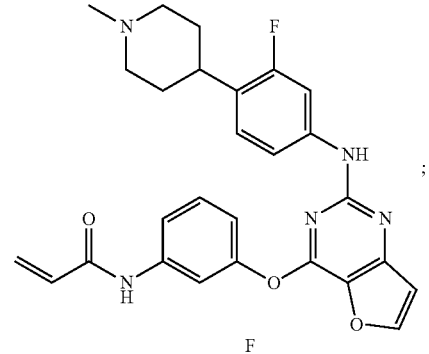

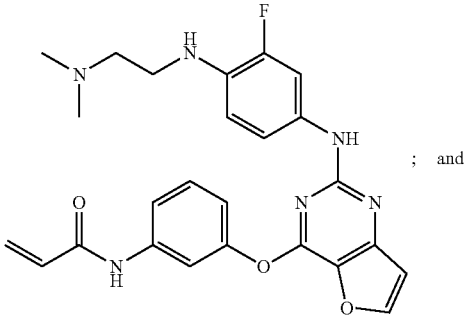

; and

-continued

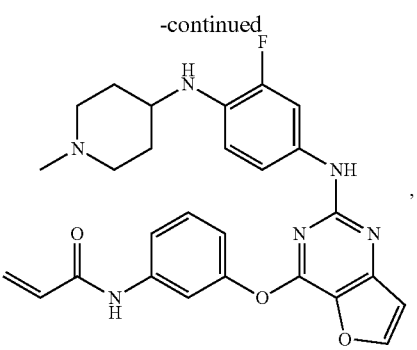

or a pharmaceutically acceptable salt thereof.

5. A compound of the formula:

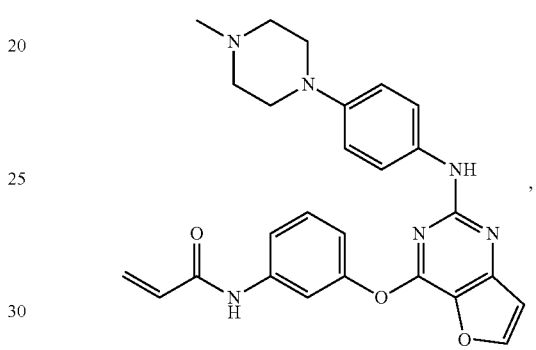

or a pharmaceutically acceptable salt thereof.

6. A compound of the formula:

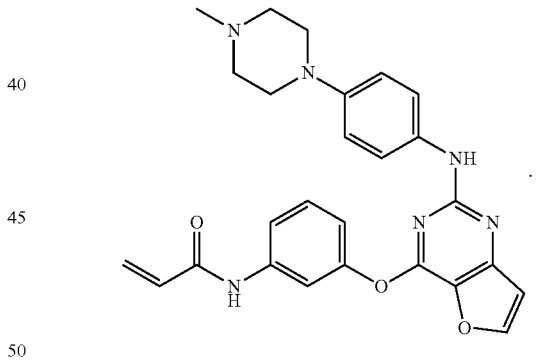

7. A method of inhibiting epidermal growth factor receptor (EGFR) tyrosine kinase, Bruton's tyrosine kinase (BTK), EGFR L858R/T790M mutant, janus kinase 3 (JAK3), interleukin-2 inducing T-cell kinase (ITK), resting lymphocyte kinase (RLK), and/or bone marrow tyrosine kinase (BMX), comprising administering to a mammal in need thereof a therapeutically effective amount of a compound of formula (I) or its pharmaceutically acceptable salt of claim 1, wherein the mammal is suffering from cancer, tumor, inflammatory disease, autoimmune disease, or immunologically mediated disease.

8. A method of inhibiting epidermal growth factor receptor (EGFR) tyrosine kinase, Bruton's tyrosine kinase (BTK), EGFR L858R/T790M mutant, janus kinase 3 (JAK3), interleukin-2 inducing T-cell kinase (ITK), resting lymphocyte kinase (RLK), and/or bone marrow tyrosine kinase (BMX), comprising administering to a mammal in need thereof a therapeutically effective amount of a compound of formula (I) or its pharmaceutically acceptable salt of claim 2, wherein the mammal is suffering from cancer, tumor, inflammatory disease, autoimmune disease, or immunologically mediated disease.

9. A method of inhibiting epidermal growth factor receptor (EGFR) tyrosine kinase, Bruton's tyrosine kinase (BTK), EGFR L858R/T790M mutant, janus kinase 3 (JAK3), interleukin-2 inducing T-cell kinase (ITK), resting lymphocyte kinase (RLK), and/or bone marrow tyrosine kinase (BMX), comprising administering to a mammal in need thereof a therapeutically effective amount of a compound of formula (I) or its pharmaceutically acceptable salt of claim 3, wherein the mammal is suffering from cancer, tumor, inflammatory disease, autoimmune disease, or immunologically mediated disease.

10. The method according to claim 7, wherein the cancer or tumor is induced by EGFR tyrosine kinase or EGFR L858R/T790M mutant.

11. The method of claim 7, wherein the mammal in need thereof suffers from cancer, tumor, inflammatory disease, autoimmune disease, or immunologically mediated disease that is mediated by at least one kinase selected from the group consisting of BTK, JAK3, ITK, RLK, and BMX.

12. The method of claim 7, wherein the mammal in need thereof suffers from cancer, tumor, inflammatory disease, autoimmune disease, or immunologically mediated disease that is mediated by abnormally activated B-lymphocytes, T-lymphocytes or both.

13. The method of claim 7, wherein the inflammatory disease, autoimmune disease, or immunologically mediated disease is arthritis, rheumatoid arthritis, spondyloarthropathy, gouty arthritis, osteoarthritis, juvenile arthritis, other arthritic condition, lupus, systemic lupus erythematosus (SLE), skin-related disease, psoriasis, eczema, dermatitis, atopic dermatitis, pain, pulmonary disorder, lung inflammation, adult respiratoty distress syndrome (ARDS), pulmonary sarcoidosis, chronic pulmonary inflammatory disease, chronic obstructive pulmonary disease (COPD), cardiovascular disease, artherosclerosis, myocardial infarction, congestive heart failure, cardiac reperfusion injury, inflammatory bowel disease, Crohn's disease, ulcerative colitis, irritable bowel syndrome, asthma, sjogren syndrome, autoimmunity thyroid disease, urticaria (cnidosis), multiple sclerosis, scleroderma, organ transplantation rejection, heteroplastic graft, idiopathic thrombocytopenic purpura (ITP), Parkinson's disease, Alzheimer's disease, diabetic associated disease, inflammation, pelvic inflammatory disease, allergic rhinitis, allergic bronchitis, allergic sinusitis, leukemia, lymphoma, B-cell lymphoma, T-cell lymphoma, myeloma, acute lymphoid leukemia (ALL), chronic lymphoid leukemia (CLL), acute myeloid leukemia (AML), chronic myeloid leukemia (CML), hairy cell leukemia, Hodgkin's disease, non-Hodgkin's lymphoma, multiple myeloma, myelodysplastic syndrome (MDS), myeloproliferative neoplasms (MPN), diffuse large B-cell lymphoma, or follicular lymphoma.

14. The method of claim 7, wherein the compound of formula (I) or its pharmaceutically acceptable salt is administered in combination with an anticancer agent selected from the group consisting of: cell signal transduction inhibitors, mitosis inhibitors, alkylating agents, intercalating anticancer agents, topoisomerase inhibitors, immunotherapic agents, antihormonal agents, and a mixture thereof.

15. The method of claim 7, wherein the compound of formula (I) or its pharmaceutically acceptable salt is administered in combination with a therapeutic agent selected from the group consisting of: steroid drugs, methotrexates, leflunomides, anti-TNFα agents, calcineurin inhibitors, antihistaminic drugs, and a mixture thereof.

16. The method according to claim 8, wherein the cancers or tumors are induced by EGFR tyrosine kinase or EGFR L858R/T790M mutant.

17. The method of claim 8, wherein the mammal in need thereof suffers from cancer, tumor, inflammatory disease, autoimmune disease, or immunologically mediated disease that is mediated by at least one kinase selected from the group consisting of BTK, JAK3, ITK, RLK, and BMX.

18. The method of claim 8, wherein the mammal in need thereof suffers from cancer, tumor, inflammatory disease, autoimmune disease, or immunologically mediated disease that is mediated by abnormally activated B-lymphocytes, T-lymphocytes or both.

19. The method of claim 8, wherein the inflammatory disease, autoimmune disease, or immunologically mediated disease is arthritis, rheumatoid arthritis, spondyloarthropathy, gouty arthritis, osteoarthritis, juvenile arthritis, other arthritic condition, lupus, systemic lupus erythematosus (SLE), skin-related disease, psoriasis, eczema, dermatitis, atopic dermatitis, pain, pulmonary disorder, lung inflammation, adult respiratoty distress syndrome (ARDS), pulmonary sarcoidosis, chronic pulmonary inflammatory disease, chronic obstructive pulmonary disease (COPD), cardiovascular disease, artherosclerosis, myocardial infarction, congestive heart failure, cardiac reperfusion injury, inflammatory bowel disease, Crohn's disease, ulcerative colitis, irritable bowel syndrome, asthma, sjogren syndrome, autoimmunity thyroid disease, urticaria (cnidosis), multiple sclerosis, scleroderma, organ transplantation rejection, heteroplastic graft, idiopathic thrombocytopenic purpura (ITP), Parkinson's disease, Alzheimer's disease, diabetic associated disease, inflammation, pelvic inflammatory disease, allergic rhinitis, allergic bronchitis, allergic sinusitis, leukemia, lymphoma, B-cell lymphoma, T-cell lymphoma, myeloma, acute lymphoid leukemia (ALL), chronic lymphoid leukemia (CLL), acute myeloid leukemia (AML), chronic myeloid leukemia (CML), hairy cell leukemia, Hodgkin's disease, non-Hodgkin's lymphoma, multiple myeloma, myelodysplastic syndrome (MDS), myeloproliferative neoplasms (MPN), diffuse large B-cell lymphoma, or follicular lymphoma.

20. The method of claim 8, wherein the compound of formula (I) or its pharmaceutically acceptable salt is administered in combination with an anticancer agent selected from the group consisting of: cell signal transduction inhibitors, mitosis inhibitors, alkylating agents, intercalating anticancer agents, topoisomerase inhibitors, immunotherapic agents, antihormonal agents, and a mixture thereof.

21. The method of claim 8, wherein the compound of formula (I) or its pharmaceutically acceptable salt is administered in combination with a therapeutic agent selected from the group consisting of: steroid drugs, methotrexates, leflunomides, anti-TNFα agents, calcineurin inhibitors, antihistaminic drugs, and a mixture thereof.

22. The method according to claim 9, wherein the cancer or tumor is induced by EGFR tyrosine kinase or EGFR L858R/T790M mutant.

23. The method of claim 9, wherein the mammal in need thereof suffers from cancer, tumor, inflammatory disease, autoimmune disease, or immunologically mediated disease that is mediated by at least one kinase selected from the group consisting of BTK, JAK3, ITK, RLK, and BMX.

24. The method of claim 9, wherein the mammal in need thereof suffers from cancer, tumor, inflammatory disease, autoimmune disease, or immunologically mediated disease that is mediated by abnormally activated B-lymphocytes, T-lymphocytes or both.

25. The method of claim 9, wherein the inflammatory disease, autoimmune disease, or immunologically mediated disease is arthritis, rheumatoid arthritis, spondyloarthropathy, gouty arthritis, osteoarthritis, juvenile arthritis, other arthritic condition, lupus, systemic lupus erythematosus (SLE), skin-related disease, psoriasis, eczema, dermatitis, atopic dermatitis, pain, pulmonary disorder, lung inflammation, adult respiratoty distress syndrome (ARDS), pulmonary sarcoidosis, chronic pulmonary inflammatory disease, chronic obstructive pulmonary disease (COPD), cardiovascular disease, atherosclerosis, myocardial infarction, congestive heart failure, cardiac reperfusion injury, inflammatory bowl disease, Crohn's disease, ulcerative colitis, irritable bowl syndrome, asthma, sjogren syndrome, autoimmunity thyroid disease, urticaria (cnidosis), multiple sclerosis, scleroderma, organ transplantation rejection, heteroplastic graft, idiopathic thrombocytopenic purpura (ITP), Parkinson's disease, Alzheimer's disease, diabetic associated disease, inflammation, pelvic inflammatory disease, allergic rhinitis, allergic bronchitis, allergic sinusitis, leukemia, lymphoma, B-cell lymphoma, T-cell lymphoma, myeloma, acute lymphoid leukemia (ALL), chronic lymphoid leukemia (CLL), acute myeloid leukemia (AML), chronic myeloid leukemia (CML), hairy cell leukemia, Hodgkin's disease, non-Hodgkin's lymphoma, multiple myeloma, myelodysplastic syndrome (MDS), myeloproliferative neoplasms (MPN), diffuse large B-cell lymphoma, or follicular lymphoma.

26. The method of claim 9, wherein the compound of formula (I) or its pharmaceutically acceptable salt is administered in combination with an anticancer agent selected from the group consisting of: cell signal transduction inhibitors, mitosis inhibitors, alkylating agents, intercalating anticancer agents, topoisomerase inhibitors, immunotherapic agents, antihormonal agents, and a mixture thereof.

27. The method of claim 9, wherein the compound of formula (I) or its pharmaceutically acceptable salt is administered in combination with a therapeutic agent selected from the group consisting of: steroid drugs, methotrexates, leflunomides, anti-TNFα agents, calcineurin inhibitors, antihistaminic drugs, and a mixture thereof.

28. A pharmaceutical composition comprising a compound of any one of claims 1-4 and a pharmaceutical carrier.

29. A pharmaceutical composition comprising a compound of the formula:

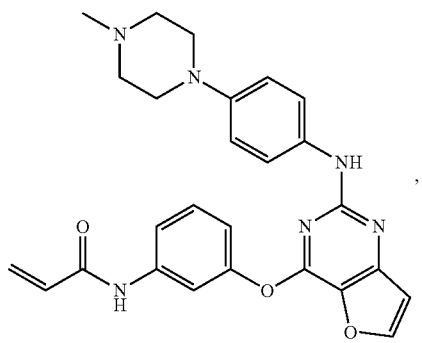 [SMILES: C=CC(=O)Nc1cccc(Oc2nc(Nc3ccc(N4CCN(C)CC4)cc3)nc3ccoc23)c1]

or a pharmaceutically acceptable salt thereof, and a pharmaceutical carrier.

30. A method of treating rheumatoid arthritis comprising administering to a mammal in need thereof a therapeutically effective amount of a compound of the formula:

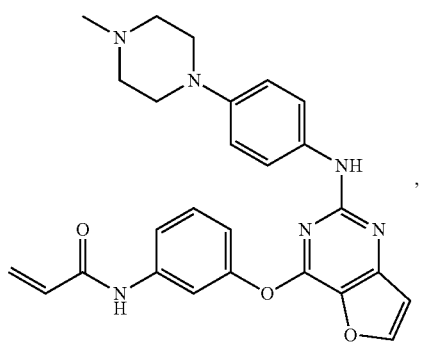 [SMILES: C=CC(=O)Nc1cccc(Oc2nc(Nc3ccc(N4CCN(C)CC4)cc3)nc3ccoc23)c1]

or a pharmaceutically acceptable salt thereof.

31. A method of treating sjogren syndrome comprising administering to a mammal in need thereof a therapeutically effective amount of a compound of the formula:

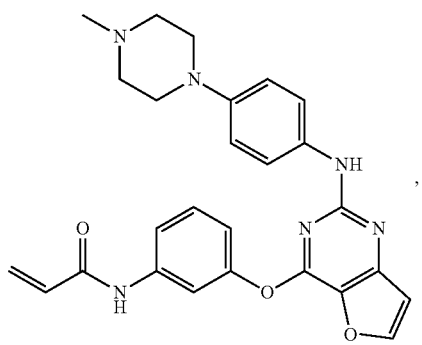 [SMILES: C=CC(=O)Nc1cccc(Oc2nc(Nc3ccc(N4CCN(C)CC4)cc3)nc3ccoc23)c1]

or a pharmaceutically acceptable salt thereof.

* * * * *